US011826399B2

(12) United States Patent
McGonigle et al.

(10) Patent No.: US 11,826,399 B2
(45) Date of Patent: Nov. 28, 2023

(54) CHLOROTOXIN AGENTS AND USES THEREOF

(71) Applicant: Eisai Inc., Nutley, NJ (US)

(72) Inventors: Sharon McGonigle, Andover, MA (US); Utpal Majumder, Tewksbury, MA (US); Maarten H. D. Postema, Dublin, NH (US)

(73) Assignee: Eisai Inc., Nutley, NJ (US)

( * ) Notice: Subject to any disclaimer, the term of this patent is extended or adjusted under 35 U.S.C. 154(b) by 0 days.

(21) Appl. No.: 16/646,998

(22) PCT Filed: Sep. 14, 2018

(86) PCT No.: PCT/US2018/051165
§ 371 (c)(1),
(2) Date: Mar. 12, 2020

(87) PCT Pub. No.: WO2019/055840
PCT Pub. Date: Mar. 21, 2019

(65) Prior Publication Data
US 2020/0206312 A1    Jul. 2, 2020

Related U.S. Application Data

(60) Provisional application No. 62/559,432, filed on Sep. 15, 2017.

(51) Int. Cl.
| | |
|---|---|
| *A61K 38/17* | (2006.01) |
| *A61K 47/68* | (2017.01) |
| *A61P 35/00* | (2006.01) |
| *A61K 31/337* | (2006.01) |
| *A61K 45/06* | (2006.01) |
| *A61K 49/00* | (2006.01) |

(52) U.S. Cl.
CPC ........ *A61K 38/1767* (2013.01); *A61K 31/337* (2013.01); *A61K 45/06* (2013.01); *A61K 47/6817* (2017.08); *A61K 49/0019* (2013.01); *A61K 49/0026* (2013.01); *A61K 49/0065* (2013.01); *A61P 35/00* (2018.01)

(58) Field of Classification Search
None
See application file for complete search history.

(56) References Cited

U.S. PATENT DOCUMENTS

| | | |
|---|---|---|
| 5,905,027 A | 5/1999 | Ullrich et al. |
| 6,028,174 A | 2/2000 | Ullrich et al. |
| 6,319,891 B1 | 11/2001 | Sontheimer et al. |
| 6,429,187 B1 | 8/2002 | Sontheimer et al. |
| 6,667,156 B2 | 12/2003 | Lyons et al. |
| 6,870,029 B2 | 3/2005 | Sontheimer et al. |
| 9,018,347 B2 | 4/2015 | Sentissi et al. |
| 2003/0021810 A1* | 1/2003 | Sontheimer ............ A61K 38/57 424/236.1 |
| 2006/0166892 A1 | 7/2006 | Alvarez et al. |
| 2008/0153746 A1 | 6/2008 | Alvarez et al. |
| 2013/0195760 A1 | 8/2013 | Olson |
| 2017/0304342 A1 | 10/2017 | Cox et al. |

FOREIGN PATENT DOCUMENTS

| | | |
|---|---|---|
| EP | 2182004 A1 | 5/2010 |
| WO | WO-1997/24619 A1 | 7/1997 |
| WO | WO-2000/62807 A1 | 10/2000 |
| WO | WO-2003/101474 A1 | 12/2003 |
| WO | WO-2003/101475 A1 | 12/2003 |
| WO | WO-2005/099774 A2 | 10/2005 |
| WO | WO-2007/117467 A2 | 10/2007 |
| WO | WO-2009/021136 A1 | 2/2009 |
| WO | WO-2009/049184 A2 | 4/2009 |
| WO | WO-2009/117018 A1 | 9/2009 |
| WO | WO-2009/140599 A1 | 11/2009 |
| WO | WO-2011/097533 A1 | 8/2011 |
| WO | WO-2011/142858 A2 | 11/2011 |
| WO | WO-2013/003507 A1 | 1/2013 |
| WO | WO-2017/136769 A1 | 8/2017 |
| WO | WO-2019/055840 A1 | 3/2019 |

OTHER PUBLICATIONS

Fiveash et al. Tumor Specific Targeting of Intravenous 131I-chlorotoxin (TM-601) in patients with Recurrent Glioma. International Journal of Radiation Oncology Biology Physics. Poster Viewing Presentation. vol. 69, Issue 3, Supplement, S257-S258 Nov. 1, 2007.*
DeBin et al Am. J. Physiol. 264 (Cell Physiol. 33): C361-C369, 1993.*
McGonigle et al. Cell Commun Signal 17, 67 (2019) pp. 1-14.*
Benson, A. B. et al, Neuropilin 1 may be Prognostic and Identify a Subgroup of Patients with Metastatic Colorectal Cancer who Benefit from from Tivozanib+mFOLFOX6 Compared to Bevacizumab+mFOLFOX6, powerpoint,(dated Jul. 3, 2015).
Haspel, N. et al., Binding of a C-end rule peptide to neuropilin-1 receptor: A molecular modeling approach, Biochemistry, 50(10): 1755-1762 (2011).
Huys, I. et al. Structure-function study of a chlorotoxin-chimer and its activity on Kvl.3 Channels, J. Chromatogr., 803:67-73 (2004).

(Continued)

*Primary Examiner* — Oluwatosin A Ogunbiyi
(74) *Attorney, Agent, or Firm* — Choate, Hall & Stewart LLP; Brenda Herschbach Jarrell; Dustin K. Goncharoff

(57) ABSTRACT

The present invention provides, among other things, compositions and methods relating to detection and/or treatment cancer (e.g., one or more tumors) that expresses Neuropilin 1 (NRP1). The present invention provides methods of treating cancer that include administering a chlorotoxin agent to a subject (e.g., to a subject suffering from or susceptible to the cancer which may, in some embodiments, be a cancer that expresses NRP1). In some embodiments, a chlorotoxin agent for use in accordance with the present invention can be or comprise a chlorotoxin polypeptide and a payload moiety (e.g., as a covalent conjugate).

15 Claims, 61 Drawing Sheets

Specification includes a Sequence Listing.

(56) References Cited

OTHER PUBLICATIONS

International Search Report for PCT/US18/51165 (Chlorotoxin Agents and Uses Thereof, filed Sep. 14, 2018), issued by ISA/US, 4 pages (dated Dec. 26, 2018).

Interntional Search Report for PCT/US2011/023797, 6 pages (dated Nov. 18, 2011).

Jacoby, D. B. et al., Potent pleiotropic anti-angiogenic effects ofCTX, a synthetic chlorotoxin peptide. *Anticancer Res.*, 30:39-46 (2010).

Lin, J. et al., Circulating neuropilin-1 as a potential biomarker of progression-free survival benefit for tivozanib in metastatic clear cell renal cell carcinoma (RCC): post-hoc biomarker analysis of tivozanib RCC trials, AVEO Oncology (dated 2015). Presented at the 17th Annual Symposium on Anti-Angiogenesis and Immune Therapies for Cancer: Recent Advances and Future Directions in Basic and Clinical Cancer Research; Feb. 19-21, 2015; La Jolla, CA.

Lyons, S. A. et al., Chlorotoxin, a scorpion—derived peptide, specifically binds to gliomas and tumors of neuroectodermal origin, Glia 39:162-173 (2002).

Miyauchi, J. T. et al, Ablation of Neuropilin 1 from glioma-associated microglia and macrophages slows tumor progression, Oncotarget, 7(9): 9801-9814 (2016).

Pan, Q. et al., Blocking Neuropilin-1 Function Has an Additive Effect with Anti-VEGF to Inhibit Tumor Growth. *Cancer Cell*, I I:53-67 (2007).

Silva, R. L. E. et al., Agents that bind annexin A2 suppress ocular neovascularization. *J Cell Physiol.*, 225(3):855-64 (2010).

Teesalu, T. et al., C-end rule peptides mediate neuropilin-1-dependent cell, vascular, and tissue penetration, 106(38):16157-16162 (2009).

Wang, H. B. et al., Neuropilin 1 is an entry factor that promotes EBV infection of nasopharyngeal epithelial cells, Nature Communications, 6:6240 (2015).

Weekes, C. D. et al., A Phase I study of the human monocloncal anti-NRP1 antibody MNRP1685A in patients with advanced solid tumors, Invest New Drugs, 32:653-660 (2014).

Written Opinion for PCT/US18/51165 (Chlorotoxin Agents and Uses Thereof, filed Sep. 14, 2018), issued by ISA/US, 11 pages (Dec. 26, 2018).

Written Opinion for PCT/US2011/023797, 5 pages (dated Nov. 18, 2011).

Ellis, L. M., The role of neuropilins in cancer, Mol Cancer Ther., 5(5):1-9 (2006).

Tse, B. et al., Neuropilin-I is upregulated in the adaptive response of prostate tumors to androgen-targeted therapies and is prognosis of metastatic progression and patient mortality, Oncogene, 36:3417-3427 (2017).

\* cited by examiner

FIG. 11

| Peptide | Source | NRP1 Binding $K_D$ |
|---|---|---|
| TM601-Lys27 Biotin (full length) | Synthetic (UM-1438-112-2) ER-1166728 | ns ns ns ns |
| TM601-N-terminal Biotin (full length) | Synthetic (UM-1438-113) | ns ns |
| TM601-Lys23 Biotin (full length) | Synthetic (UM-1438-112-1) | ns ns |
| TM601-Multi-Biotin (full length) | Synthetic (UM-1438-112-3) | ns |
| TM601-Lys27 Biotin (full length); cysteine residues reduced with TCEP and capped with iodoacetamide | Synthetic (UM-1438-86) | ns ns |
| 1 NH₂-M-C-M-P-C-F-T-T-D-H-Q-M-A-R-COOH<br>2 NH₂-G-K(Biotin)-C-Y-G-P-Q-C-L-C-R-COOH<br>3 NH₂-K-C-D-D-C-C-G-G-K-COOH | From trypsin digestion of Lys-27 biotinylated TM601 (UM-1438-118) | 112 nM 187 nM |
| 1 NH₂-M-C-M-P-C-F-T-T-D-H-Q-M-A-R-COOH (Biotin)<br>2 NH₂-C-Y-G-P-Q-C-L-C-R-COOH<br>3 NH₂-K-C-D-D-C-C-G-G-K-COOH | From trypsin digestion of N-terminal biotinylated TM601 (UM-1438-127-1) | 173 nM 70 nM |
| 1 NH₂-M-C-M-P-C-F-T-T-D-H-Q-M-A-R-COOH<br>2 NH₂-C-Y-G-P-Q-C-L-C-R-COOH<br>3 NH₂-C-D-D-C-C-G-G-K-COOH | From trypsin digestion of N-terminal biotinylated TM601 (UM-1438-127-2) | 126 nM 129 nM |

FIG. 11 Continued

| Peptide | Source | NRP1 Binding K$_D$ |
|---|---|---|
| NH$_2$-M-C-M-P-C-F-T-T-D-H-Q-M-A-R-COOH (with S-S bridge, Biotin) | From trypsin digestion of N-terminal or multi-site biotinylated TM601 (UM-1438-127-3) ER-1166735 (UM-1438-100-2) | 255 nM<br>175 nM<br>114 nM<br>118 nM<br>173 nM<br>*167 nM (avg.)* |
| NH$_2$-M-C-M-P-C-F-T-T-D-H-Q-M-A-R-COOH (Capped Capped, Biotin) | Peptide synthesis ER-1183034 | 169 nM |
| NH$_2$-M-C-M-P-C-F-T-T-D-H-Q-M-A-R-K-COOH (Capped Capped, Biotin) | Peptide synthesis (ER-1178320) | ns<br>ns |
| NH$_2$-K-C-D-D-C-C-G-G-K-G-R-G-K-COOH (Capped Capped, Biotin) | Peptide synthesis (ER-1174687) | ns<br>ns |
| NH$_2$-K-C-D-C-C-G-G-K-COOH (Capped) | Peptide synthesis (ER-1174706) | ns |
| NH$_2$-D-C-C-G-G-K-COOH (Capped, Biotin) | Peptide synthesis (ER-1178115) | ns |
| NH$_2$-C-Y-G-P-Q-C-L-C-R-COOH (Capped Capped, Biotin) | Peptide synthesis (ER-1174836) | 153 nM<br>335 nM |

FIG. 11 Continued

| Peptide | Source | NRP1 Binding $K_D$ |
|---|---|---|
| NH₂-C-Y-G-P-Q-C-L-C-R-COOH (S-S, Capped, Biotin) | Peptide synthesis (ER-1174837) | 410 nM<br>ns |
| NH₂-Y-G-P-Q-C-L-C-R-COOH (Biotin, Capped) | Peptide synthesis UM-1637-067 (ER-1174688) | 300 nM<br>294 nM |
| NH-G-P-Q-C-L-COOH (Capped, Biotin) | Peptide synthesis (ER-1177939) | ns |
| NH₂-C-Y-G-P-Q-COOH (Capped, Biotin) | Peptide synthesis (ER-1177941) | ns |
| NH₂-C-L-C-R-COOH (Capped, Biotin, Capped) | Peptide synthesis (ER-1174991) | 335 nM |
| VEGF-165-Biotin | ACRO Biosystems | 43 nM<br>26 nM<br>75 nM<br>98 nM<br>18 nM<br>26 nM |

FIG. 54

| Peptide | Scan # | Modifications | RT (min) | Intensity (Precursor Counts) |
|---|---|---|---|---|
| MCMPCFTTDHQMARKCDDCCGGKGRGKC | | | 14.6 | 549341 |
| YGPQCLCR | 1 | 36 Carbamidomethyl C(8),Amidation C-TERM(1) | | |
| MCMPCFTTDHQMARKCDDCCGGKGRGKC | 1 | 35 Deamidation Q(1),Carbamidomethyl C(2),Oxidation M(2) | 16 | 106490 |
| YGPQCLC | 1 | 36 Carbamidomethyl C(8),Amidation C-TERM(1),Oxidation M(1) | 14.7 | 30424 |
| MCMPCFTTDHQMARKCDDCCGGKGRGKC | | Deamidation Q(2),Carbamidomethyl C(6),Amidation C- | | |
| YGPQCLCR | 1 | 36 TERM(1),Oxidation M(1) | 10.2 | 18926 |
| CMPCFTTDHQMARKCDDCCGGKGRGK | 2 | 27 Oxidation M(1) | 4.1 | 16527 |
| TTDHQMARKCDDCCGGKGRGKCYG | 7 | 30 Deamidation Q(1),Oxidation M(1) | 4.1 | 15372 |
| MCMPCFTTDHQMARKCDDCCGGKGRGKC | | | | |
| YGPQCLCR | 1 | 36 Carbamidomethyl C(8),Amidation C-TERM(1),Oxidation M(1) | 14 | 14664 |
| MCMPCFTTDHQMARKCDDCCGGKGRGKC | | | | |
| YGPQCLCR | 1 | 36 Oxidation M(3), C-term Arg-COOH | 15.9 | 13403 |
| MCMPCFTTDHQMARKCDDCCGGKGRGKC | | Deamidation Q(1),Carbamidomethyl C(8),Oxidation M(1),C- | | |
| YGPQCLCR | 1 | 36 term Arg-COOH | 8.7 | 13323 |
| MCMPCFTTDHQMARKCDDCCGGKGRGKC | | Deamidation Q(2),Carbamidomethyl C(7),Oxidation M(1),C- | | |
| YGPQCLCR | 1 | 36 TERM(1),Oxidation M(1) | 8.6 | 10048 |
| CGGKGRGKCYGPQ | 19 | 32 | 15.5 | 9481 |
| MCMPCFTTDHQMARKCDDCCGGKGRGKC | | | | |
| YGPQCLCR | 1 | 36 Carbamidomethyl C(8),Oxidation M(1), C-term Arg-COOH | 13 | 8168 |
| DCCGGKGR | 18 | 25 C-term Arg-COOH | 4.6 | 6145 |
| MCMPCFTTDHQMARKCDDCCGGKGRGKC | | | | |
| YGPQCLCR | 1 | 36 term Arg-COOH | 10.1 | 5172 |
| YGPQCL | 1 | 34 Carbamidomethyl C(3),Oxidation M(2) | 14.6 | 4293 |
| ARKCDDCCGGKGRGKCYGPQC | 13 | 33 Deamidation Q(1) | 11.6 | 3920 |
| TDHQMARKCDDCCGGKGRGK | 8 | 27 Carbamidomethyl C(3) | 4.1 | 3750 |
| MCMPCFTTDHQMARKCDDCCGG | | 22 Carbamidomethyl C(3),Oxidation M(1) | 16.6 | 3161 |
| MCMPCFTTDHQMARKCDDC | 1 | 19 Carbamidomethyl C(2),Oxidation M(1) | 23.3 | 2400 |
| CGGKGRGKCYGPQC | 20 | 33 Carbamidomethyl C(1) | 15.4 | 2373 |

FIG. 55

| Peptide | Start | End | Modifications | RT (min) | Intensity (counts) |
|---|---|---|---|---|---|
| MCMPCFTTDHQMARKCDDCCGGKGRGKCYG | | | | | |
| PQCLCR | 1 | 36 | Carbamidomethyl C(8),Amidation C-TERM(1) | 14.7 | 278677 |
| QMARKCDDCCGGKGRGKCYGPQ | 11 | 32 | Carbamidomethyl C(4) | 4.1 | 68718 |
| CFTTDHQMARKCDDCCGGKGR | 5 | 25 | C-term Arg-COOH | 4.2 | 44798 |
| MCMPCFTTDHQMARKCDDCCGGKGRGKCYG | | | Deamidation Q(2),Carbamidomethyl C(8),Amidation C- | | |
| PQCLCR | 1 | 36 | TERM(1),Oxidation M(1) | 10.3 | 42742 |
| TDHQMARKCDDCLGGKGRGK | 8 | 27 | Deamidation Q(1),Carbamidomethyl C(3) | 4.4 | 25956 |
| GGKGRGKCYGPQCC | 21 | 33 | Carbamidomethyl C(2) | 4.1 | 24465 |
| FTTDHQMARKCDDCCGGKGRGKCYGPQCL | 6 | 34 | Carbamidomethyl C(3),Oxidation M(1) | 4.1 | 23581 |
| MCMPCFTTDHQMARKCDDCCGGKGRGKCYG | | | | | |
| PQCLC | 1 | 35 | Deamidation Q(2),Carbamidomethyl C(1),Oxidation M(1) | 24.1 | 22297 |
| MCMPCFTTDHQMAR | 1 | 14 | Deamidation Q(1),Carbamidomethyl C(2),Oxidation M(2) | 16.3 | 21423 |
| PCFTTDHQMAR | 4 | 14 | Deamidation Q(1), C-term Arg-COOH | 4.6 | 18433 |
| QMARKCDDCCGGKGRGKCYGPQ | 11 | 32 | Carbamidomethyl C(2),Oxidation M(1) | 4.4 | 15072 |
| QMARKCDDCCGGKGRGKCYGP | 11 | 31 | Carbamidomethyl C(2) | 24.2 | 13155 |
| DCCGGKGRGK | 18 | 27 | | 24.1 | 13142 |
| QMARKCDDCCGGKGRGKCYGPQCLCR | 11 | 36 | Deamidation Q(1),Carbamidomethyl C(2), C-term Arg-COOH | 4.9 | 12581 |
| MCMPCFTTDHQMARKCDDCCGGKGRGKCYG | | | Deamidation Q(2),Carbamidomethyl C(7),Oxidation M(1), C- | | |
| PQCLCR | 1 | 36 | term Arg-COOH | 8.9 | 11115 |
| CMPCFTTDHQMARKCDDCCGGKGRGKCYGP | 2 | 31 | Carbamidomethyl C(2) | 4.5 | 10548 |
| ARKCDCCGGKGRGKCY | 13 | 29 | | 4.4 | 9016 |
| CMPCFTTDHQMARKCDDCCGGKGR GKCYGPQ | | | Deamidation Q(1),Carbamidomethyl C(1),Oxidation M(1), C- | | |
| CLCR | 2 | 36 | term Arg-COOH | 14.8 | 8088 |
| CMPCFTTDHQMARKCDDCCGGKGRGK | 2 | 27 | Oxidation M(1) | 4.5 | 6459 |
| TDHQMARKCDDCCGGKGRGKCYGPQCL | 8 | 34 | Oxidation M(1) | 24 | 6339 |

FIG. 56

| Sequence | Spectral Count | Modifications | Mass Error | Score |
|---|---|---|---|---|
| MCMPCFTTDHQMARKCDDCCGGKGRGKCYGP QCLCR | 1 | 36 Carbamidomethyl C(8),Amidation C-TERM(1) | 14.6 | 358622 |
| MCMPCFTTDHQMARKCDDCLGGKGRGKCYGP QCLCR | | | | |
| QCLC | 1 | 35 Deamidation Q(1),Carbamidomethyl C(2),Oxidation M(2) | 16.2 | 78349 |
| MCMPCFTTDHQMARKCDDCCGGKGRGKCYGP QCLCR | 1 | Deamidation Q(2),Carbamidomethyl C(6),Amidation C-TERM(1),Oxidation | | |
| QCLCR | 1 | 36 M(1) | 10.2 | 44099 |
| TTDHQMARKCDDCCGGKGRGKCYG | 7 | 30 | 4.1 | 27841 |
| CMPCFTTDHQMARKCDDCCGGKGRGKCYGPQ | 2 | 32 Deamidation Q(1),Carbamidomethyl C(6) | 4.1 | 13299 |
| DHQMARKCDDCCGGKGRGKCYGPQCL | 9 | 34 Carbamidomethyl C(2) | 23.9 | 12799 |
| TDHQMARKCDDCCGGKGRGK | 8 | 27 Carbamidomethyl C(3),Oxidation M(1) | 24 | 12007 |
| PCFTTDHQMAR | 4 | 14 C-term Arg-COOH | 4.6 | 11279 |
| MCMPCFTTDHQMARKCDDCLGGKGRGKCYGP QCLCR | 1 | 36 Carbamidomethyl C(8),Oxidation M(1), C-term Arg-COOH | 13.1 | 10007 |
| MCMPCFTTDHQMARKCDDCCGGKGRGKCYGP QCLC | 1 | 36 Carbamidomethyl C(8),Amidation C-TERM(1),Oxidation M(1) | 14.5 | 9888 |
| QCLC | 1 | 35 Carbamidomethyl C(1),Oxidation M(2) | 23.9 | 9706 |
| CMPCFTTDHQMARKCDDCCGGKGRGKCYGPQ | | Deamidation Q(1),Carbamidomethyl C(1),Oxidation M(1), C-term Arg- | | |
| CLCR | 2 | 36 COOH | 14.7 | 9387 |
| MCMPCFTTDHQMARKCDDCCGGKGRGKCYG | 1 | 30 Carbamidomethyl C(5) | 10.6 | 8439 |
| TTDHQMARKCDDCCGGKGRGKCYGPQCLC | 7 | 35 Deamidation Q(1),Carbamidomethyl C(1),Oxidation M(1) | 4.2 | 7725 |
| MCMPCFTTDHQMARKCDDCLGGKGRGKCYGP QCLC | 1 | Deamidation Q(2),Carbamidomethyl C(7),Oxidation M(1), C-term Arg-36 COOH | 8.8 | 7549 |
| MCMPCFTTDHQMARKCDDCCG5KG | 1 | 24 Carbamidomethyl C(5),Oxidation M(2) | 23.9 | 6992 |
| TTDHQMARKCD | 7 | 17 Oxidation M(1) | 4.1 | 6969 |
| MCMPCFTTDHQMARKCDDCL | 1 | 20 Oxidation M(1) | 23.9 | 6794 |
| MCMPCFTTDHQMARKCDDCCGGKGRG | 1 | 26 Carbamidomethyl C(1),Oxidation M(1) | 24.1 | 6434 |
| MPCFTTDHQMARKC | 3 | 16 Deamidation Q(1),Carbamidomethyl C(1),Oxidation M(1) | 4.2 | 6066 |

| sequences |
|---|
| MARKCDDCCGGKGRGKCYGPQCLCR |
| ARKCDDCCGGKGRGKCYGPQCLCR |
| RKCDDCCGGKGRGKCYGPQCLCR |
| KCDDCCGGKGRGKCYGPQCLCR |
| CDDCCGGKGRGKCYGPQCLCR |
| DDCCGGKGRGKCYGPQCLCR |
| DCCGGKGRGKCYGPQCLCR |
| CCGGKGRGKCYGPQCLCR |
| CGGKGRGKCYGPQCLCR |
| GGKGRGKCYGPQCLCR |
| GKGRGKCYGPQCLCR |
| KGRGKCYGPQCLCR |
| GRGKCYGPQCLCR |
| RGKCYGPQCLCR |
| GKCYGPQCLCR |
| KCYGPQCLCR |
| CYGPQCLCR |
| YGPQCLCR |
| GPQCLCR |
| PQCLCR |
| QCLCR |

| | |
|---|---|
| | MARKCDDCCGGKGRGKCYGPQCLCR |
| | ARKCDDCCGGKGRGKCYGPQCLCR |
| | RKCDDCCGGKGRGKCYGPQCLCR |
| | KCDDCCGGKGRGKCYGPQCLCR |
| | CDDCCGGKGRGKCYGPQCLCR |
| | DDCCGGKGRGKCYGPQCLCR |
| | DCCGGKGRGKCYGPQCLCR |
| | CCGGKGRGKCYGPQCLCR |
| | CGGKGRGKCYGPQCLCR |
| | GGKGRGKCYGPQCLCR |
| | GKGRGKCYGPQCLCR |
| | KGRGKCYGPQCLCR |
| | GRGKCYGPQCLCR |
| | RGKCYGPQCLCR |
| | GKCYGPQCLCR |
| | KCYGPQCLCR |
| | CYGPQCLCR |
| | YGPQCLCR |
| | GPQCLCR |
| | PQCLCR |
| | QCLCR |

FIG. 58

SEQUENCE LISTING

```
<160> NUMBER OF SEQ ID NOS: 251

<210> SEQ ID NO 1
<211> LENGTH: 36
<212> TYPE: PRT
<213> ORGANISM: Leiurius quinquestriatus

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Met Cys Met Pro Cys Phe Thr Thr Asp His Gln Met Ala Arg Cys Asp
1               5                   10                  15

Asp Cys Cys Gly Gly Gly Arg Gly Cys Tyr Gly Pro Gln Cys Leu Cys
                20                  25                  30

Arg

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Met Cys Met Pro Cys Phe Thr Thr Asp His Gln Met Ala Arg Cys
1               5                   10                  15

Asp Asp Cys Cys Gly Gly Gly Arg Gly Cys Tyr Gly Pro Gln Cys Leu
                20                  25                  30

Cys Arg

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Cys Met Pro Cys Phe Thr Thr Asp His Gln Met Ala Arg Cys Asp
1               5                   10                  15

Asp Cys Cys Gly Gly Gly Arg Gly Cys Tyr Gly Pro Gln Cys Leu Cys
                20                  25                  30

Arg Lys

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Cys Met Pro Cys Phe Thr Thr Asp His Gln Met Ala Arg Ala Cys
1               5                   10                  15

Asp Asp Cys Cys Gly Gly Ala Gly Arg Gly Ala Cys Tyr Gly Pro Gln
                20                  25                  30

Cys Leu Cys Arg
        35

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Met Cys Met Pro Cys Phe Thr Thr Asp His Gln Met Ala Arg Arg Cys
1               5                   10                  15

Asp Asp Cys Cys Gly Gly Arg Gly Arg Gly Arg Cys Tyr Gly Pro Gln
            20                  25                  30

Cys Leu Cys Arg
        35
```

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Lys Met Cys Met Pro Cys Phe Thr Thr Asp His Gln Met Ala Arg Ala
1               5                   10                  15

Cys Asp Asp Cys Cys Gly Gly Ala Gly Arg Gly Ala Cys Tyr Gly Pro
            20                  25                  30

Gln Cys Leu Cys Arg
        35
```

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Lys Met Cys Met Pro Cys Phe Thr Thr Asp His Gln Met Ala Arg Arg
1               5                   10                  15

Cys Asp Asp Cys Cys Gly Gly Arg Gly Arg Gly Arg Cys Tyr Gly Pro
            20                  25                  30

Gln Cys Leu Cys Arg
        35
```

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Cys Met Pro Cys Phe Thr Thr Asp His Gln Met Ala Arg Ala Cys
1               5                   10                  15

Asp Asp Cys Cys Gly Gly Ala Gly Arg Gly Ala Cys Tyr Gly Pro Gln
            20                  25                  30

Cys Leu Cys Arg Lys
        35
```

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Cys Met Pro Cys Phe Thr Thr Asp His Gln Met Ala Arg Arg Cys
1               5                   10                  15

Asp Asp Cys Cys Gly Gly Arg Gly Gly Arg Cys Tyr Gly Pro Gln
            20                  25                  30

Cys Leu Cys Arg Lys
        35

<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Cys Met Pro Cys Phe Thr Thr Asp His Gln Met Ala Arg Cys Asp
1               5                   10                  15

Asp Cys Cys Gly Gly Lys Gly Arg Gly Lys Cys Tyr Gly Pro Gln Cys
            20                  25                  30

Leu Cys Arg
        35

<210> SEQ ID NO 12
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Cys Met Pro Cys Phe Thr Thr Asp His Gln Met Ala Arg Lys Cys
1               5                   10                  15

Asp Asp Cys Cys Gly Gly Gly Arg Gly Lys Cys Tyr Gly Pro Gln Cys
            20                  25                  30

Leu Cys Arg
        35

<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Cys Met Pro Cys Phe Thr Thr Asp His Gln Met Ala Arg Lys Cys
1               5                   10                  15

Asp Asp Cys Cys Gly Gly Lys Gly Arg Gly Cys Tyr Gly Pro Gln Cys
            20                  25                  30

Leu Cys Arg
        35

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 14

Met Cys Met Pro Cys Phe Thr Thr Asp His Gln Met Ala Arg Cys Asp
1               5                   10                  15

Asp Cys Cys Gly Gly Gly Arg Gly Lys Cys Tyr Gly Pro Gln Cys Leu
            20                  25                  30

Cys Arg

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Cys Met Pro Cys Phe Thr Thr Asp His Gln Met Ala Arg Cys Asp
1               5                   10                  15

Asp Cys Cys Gly Gly Lys Gly Arg Gly Cys Tyr Gly Pro Gln Cys Leu
            20                  25                  30

Cys Arg

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Cys Met Pro Cys Phe Thr Thr Asp His Gln Met Ala Arg Lys Cys
1               5                   10                  15

Asp Asp Cys Cys Gly Gly Gly Arg Gly Cys Tyr Gly Pro Gln Cys Leu
            20                  25                  30

Cys Arg

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Cys Met Pro Cys Phe Thr Thr Asp His Gln Met Ala Arg Ala Cys
1               5                   10                  15

Asp Asp Cys Cys Gly Gly Ala Gly Arg Gly Lys Cys Tyr Gly Pro Gln
            20                  25                  30

Cys Leu Cys Arg
        35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Met Cys Met Pro Cys Phe Thr Thr Asp His Gln Met Ala Arg Ala Cys
1               5                   10                  15

Asp Asp Cys Cys Gly Gly Lys Gly Arg Gly Ala Cys Tyr Gly Pro Gln
            20                  25                  30

Cys Leu Cys Arg
        35
```

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Cys Met Pro Cys Phe Thr Thr Asp His Gln Met Ala Arg Lys Cys
1               5                   10                  15

Asp Asp Cys Cys Gly Gly Ala Gly Arg Gly Ala Cys Tyr Gly Pro Gln
            20                  25                  30

Cys Leu Cys Arg
        35
```

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Cys Met Pro Cys Phe Thr Thr Asp His Gln Met Ala Arg Arg Cys
1               5                   10                  15

Asp Asp Cys Cys Gly Gly Arg Gly Arg Gly Lys Cys Tyr Gly Pro Gln
            20                  25                  30

Cys Leu Cys Arg
        35
```

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Cys Met Pro Cys Phe Thr Thr Asp His Gln Met Ala Arg Arg Cys
1               5                   10                  15

Asp Asp Cys Cys Gly Gly Lys Gly Arg Gly Arg Cys Tyr Gly Pro Gln
            20                  25                  30

Cys Leu Cys Arg
        35
```

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Cys Met Pro Cys Phe Thr Thr Asp His Gln Met Ala Arg Lys Cys
1               5                   10                  15

Asp Asp Cys Cys Gly Gly Arg Gly Arg Gly Arg Cys Tyr Gly Pro Gln
            20                  25                  30

Cys Leu Cys Arg
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Cys Met Pro Cys Phe Thr Thr Asp His Gln Met Ala Arg Arg Cys
1               5                   10                  15

Asp Asp Cys Cys Gly Gly Lys Gly Arg Gly Ala Cys Tyr Gly Pro Gln
            20                  25                  30

Cys Leu Cys Arg
        35

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Cys Met Pro Cys Phe Thr Thr Asp His Gln Met Ala Arg Cys Asp
1               5                   10                  15

Asp Cys Cys Gly Gly Ala Gly Arg Gly Ala Cys Tyr Gly Pro Gln Cys
            20                  25                  30

Leu Cys Arg
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Cys Met Pro Cys Phe Thr Thr Asp His Gln Met Ala Arg Ala Cys
1               5                   10                  15

Asp Asp Cys Cys Gly Gly Gly Arg Gly Ala Cys Tyr Gly Pro Gln Cys
            20                  25                  30

Leu Cys Arg
        35

<210> SEQ ID NO 26
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 26

Met Cys Met Pro Cys Phe Thr Thr Asp His Gln Met Ala Arg Arg Cys
1               5                   10                  15

Asp Asp Cys Cys Gly Gly Arg Gly Arg Gly Cys Tyr Gly Pro Gln Cys
            20                  25                  30

Leu Cys Arg
        35

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Met Cys Met Pro Cys Phe Thr Thr Asp His Gln Met Ala Arg Lys
1               5                   10                  15

Cys Asp Asp Cys Cys Gly Gly Lys Gly Arg Gly Lys Cys Tyr Gly Pro
            20                  25                  30

Gln Cys Leu Cys Arg
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Lys
        35

<210> SEQ ID NO 29

<400> SEQUENCE: 29

000

<210> SEQ ID NO 30
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Cys Met Pro Cys Phe Thr Thr Asp His Gln Met Ala Arg Lys Cys Asp
1               5                   10                  15

Asp Cys Cys Gly Gly Lys Gly Arg Gly Lys Cys Tyr Gly Pro Gln Cys
            20                  25                  30

Leu Cys Arg
        35
```

```
<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Pro Cys Phe Thr Thr Asp His Gln Met Ala Arg Lys Cys Asp Asp
1               5                   10                  15

Cys Cys Gly Gly Lys Gly Arg Gly Lys Cys Tyr Gly Pro Gln Cys Leu
            20                  25                  30

Cys Arg

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Cys Phe Thr Thr Asp His Gln Met Ala Arg Lys Cys Asp Asp Cys
1               5                   10                  15

Cys Gly Gly Lys Gly Arg Gly Lys Cys Tyr Gly Pro Gln Cys Leu Cys
            20                  25                  30

Arg

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Cys Phe Thr Thr Asp His Gln Met Ala Arg Lys Cys Asp Asp Cys Cys
1               5                   10                  15

Gly Gly Lys Gly Arg Gly Lys Cys Tyr Gly Pro Gln Cys Leu Cys Arg
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Phe Thr Thr Asp His Gln Met Ala Arg Lys Cys Asp Asp Cys Cys Gly
1               5                   10                  15

Gly Lys Gly Arg Gly Lys Cys Tyr Gly Pro Gln Cys Leu Cys Arg
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 35

Thr Thr Asp His Gln Met Ala Arg Lys Cys Asp Asp Cys Cys Gly Gly
1               5                   10                  15

Lys Gly Arg Gly Lys Cys Tyr Gly Pro Gln Cys Leu Cys Arg
            20                  25                  30

<210> SEQ ID NO 36
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Asp His Gln Met Ala Arg Lys Cys Asp Asp Cys Cys Gly Gly Lys
1               5                   10                  15

Gly Arg Gly Lys Cys Tyr Gly Pro Gln Cys Leu Cys Arg
            20                  25

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp His Gln Met Ala Arg Lys Cys Asp Asp Cys Cys Gly Gly Lys Gly
1               5                   10                  15

Arg Gly Lys Cys Tyr Gly Pro Gln Cys Leu Cys Arg
            20                  25

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Gln Met Ala Arg Lys Cys Asp Asp Cys Cys Gly Gly Lys Gly Arg
1               5                   10                  15

Gly Lys Cys Tyr Gly Pro Gln Cys Leu Cys Arg
            20                  25

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Met Ala Arg Lys Cys Asp Asp Cys Cys Gly Gly Lys Gly Arg Gly
1               5                   10                  15

Lys Cys Tyr Gly Pro Gln Cys Leu Cys Arg
            20                  25

<210> SEQ ID NO 40
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Ala Arg Lys Cys Asp Asp Cys Cys Gly Gly Lys Gly Arg Gly Lys
1               5                   10                  15

Cys Tyr Gly Pro Gln Cys Leu Cys Arg
            20                  25

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Arg Lys Cys Asp Asp Cys Cys Gly Gly Lys Gly Arg Gly Lys Cys
1               5                   10                  15

Tyr Gly Pro Gln Cys Leu Cys Arg
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Lys Cys Asp Asp Cys Cys Gly Gly Lys Gly Arg Gly Lys Cys Tyr
1               5                   10                  15

Gly Pro Gln Cys Leu Cys Arg
            20

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Cys Asp Asp Cys Cys Gly Gly Lys Gly Arg Gly Lys Cys Tyr Gly
1               5                   10                  15

Pro Gln Cys Leu Cys Arg
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Asp Asp Cys Cys Gly Gly Lys Gly Arg Gly Lys Cys Tyr Gly Pro
1               5                   10                  15
```

```
Gln Cys Leu Cys Arg
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Cys Cys Gly Gly Lys Gly Arg Gly Lys Cys Tyr Gly Pro Gln
1               5                   10                  15

Cys Leu Cys Arg
            20

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Cys Cys Gly Gly Lys Gly Arg Gly Lys Cys Tyr Gly Pro Gln Cys
1               5                   10                  15

Leu Cys Arg

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Cys Gly Gly Lys Gly Arg Gly Lys Cys Tyr Gly Pro Gln Cys Leu
1               5                   10                  15

Cys Arg

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Gly Gly Lys Gly Arg Gly Lys Cys Tyr Gly Pro Gln Cys Leu Cys
1               5                   10                  15

Arg

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

```
Gly Gly Lys Gly Arg Gly Lys Cys Tyr Gly Pro Gln Cys Leu Cys Arg
1               5                   10                  15
```

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Gly Lys Gly Arg Gly Lys Cys Tyr Gly Pro Gln Cys Leu Cys Arg
1               5                   10                  15
```

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Lys Gly Arg Gly Lys Cys Tyr Gly Pro Gln Cys Leu Cys Arg
1               5                   10
```

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Gly Arg Gly Lys Cys Tyr Gly Pro Gln Cys Leu Cys Arg
1               5                   10
```

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Arg Gly Lys Cys Tyr Gly Pro Gln Cys Leu Cys Arg
1               5                   10
```

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Gly Lys Cys Tyr Gly Pro Gln Cys Leu Cys Arg
1               5                   10
```

<210> SEQ ID NO 55
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 55

Lys Cys Tyr Gly Pro Gln Cys Leu Cys Arg
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Tyr Gly Pro Gln Cys Leu Cys Arg
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Gly Pro Gln Cys Leu Cys Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Pro Gln Cys Leu Cys Arg
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Gln Cys Leu Cys Arg
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Cys Leu Cys Arg
1               5
```

<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Cys Met Pro Cys Phe Thr Thr Asp His Gln Met Ala Arg Lys Cys
1               5                   10                  15

Asp Asp Cys Cys Gly Gly Lys Gly Arg
            20                  25

<210> SEQ ID NO 62
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Met Pro Cys Phe Thr Thr Asp His Gln Met Ala Arg Lys Cys Asp
1               5                   10                  15

Asp Cys Cys Gly Gly Lys Gly Arg
            20

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Pro Cys Phe Thr Thr Asp His Gln Met Ala Arg Lys Cys Asp Asp
1               5                   10                  15

Cys Cys Gly Gly Lys Gly Arg
            20

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Cys Phe Thr Thr Asp His Gln Met Ala Arg Lys Cys Asp Asp Cys
1               5                   10                  15

Cys Gly Gly Lys Gly Arg
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Cys Phe Thr Thr Asp His Gln Met Ala Arg Lys Cys Asp Asp Cys Cys
1               5                   10                  15

Gly Gly Lys Gly Arg
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Thr Thr Asp His Gln Met Ala Arg Lys Cys Asp Asp Cys Cys Gly
1               5                   10                  15

Gly Lys Gly Arg
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Thr Asp His Gln Met Ala Arg Lys Cys Asp Asp Cys Cys Gly Gly
1               5                   10                  15

Lys Gly Arg

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Asp His Gln Met Ala Arg Lys Cys Asp Asp Cys Cys Gly Gly Lys
1               5                   10                  15

Gly Arg

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp His Gln Met Ala Arg Lys Cys Asp Asp Cys Cys Gly Gly Lys Gly
1               5                   10                  15

Arg

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 70

His Gln Met Ala Arg Lys Cys Asp Asp Cys Cys Gly Gly Lys Gly Arg
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Met Ala Arg Lys Cys Asp Asp Cys Cys Gly Gly Lys Gly Arg
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Ala Arg Lys Cys Asp Asp Cys Cys Gly Gly Lys Gly Arg
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Lys Cys Asp Asp Cys Cys Gly Gly Lys Gly Arg
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Lys Cys Asp Asp Cys Cys Gly Gly Lys Gly Arg
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Cys Asp Asp Cys Cys Gly Gly Lys Gly Arg
1               5                   10

<210> SEQ ID NO 76
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Asp Asp Cys Cys Gly Gly Lys Gly Arg
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Asp Cys Cys Gly Gly Lys Gly Arg
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Cys Cys Gly Gly Lys Gly Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Cys Gly Gly Lys Gly Arg
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Gly Gly Lys Gly Arg
1               5

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Met Cys Met Pro Cys Phe Thr Thr Asp His Gln Met Ala Arg
```

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Met Pro Cys Phe Thr Thr Asp His Gln Met Ala Arg
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Pro Cys Phe Thr Thr Asp His Gln Met Ala Arg
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Cys Phe Thr Thr Asp His Gln Met Ala Arg
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Phe Thr Thr Asp His Gln Met Ala Arg
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Phe Thr Thr Asp His Gln Met Ala Arg
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic

```
                           peptide

<400> SEQUENCE: 87

Thr Thr Asp His Gln Met Ala Arg
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Asp His Gln Met Ala Arg
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp His Gln Met Ala Arg
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

His Gln Met Ala Arg
1               5

<210> SEQ ID NO 91
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Cys Met Pro Cys Phe Thr Thr Asp His Gln Met Ala Arg Ala Cys Asp
1               5                   10                  15

Asp Cys Cys Gly Gly Ala Gly Arg Gly Lys Cys Tyr Gly Pro Gln Cys
            20                  25                  30

Leu Cys Arg
        35

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92
```

```
Met Pro Cys Phe Thr Thr Asp His Gln Met Ala Arg Ala Cys Asp Asp
1               5                   10                  15

Cys Cys Gly Gly Ala Gly Arg Gly Lys Cys Tyr Gly Pro Gln Cys Leu
            20                  25                  30

Cys Arg

<210> SEQ ID NO 93
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Pro Cys Phe Thr Thr Asp His Gln Met Ala Arg Ala Cys Asp Asp Cys
1               5                   10                  15

Cys Gly Gly Ala Gly Arg Gly Lys Cys Tyr Gly Pro Gln Cys Leu Cys
            20                  25                  30

Arg

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Cys Phe Thr Thr Asp His Gln Met Ala Arg Ala Cys Asp Asp Cys Cys
1               5                   10                  15

Gly Gly Ala Gly Arg Gly Lys Cys Tyr Gly Pro Gln Cys Leu Cys Arg
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Phe Thr Thr Asp His Gln Met Ala Arg Ala Cys Asp Asp Cys Cys Gly
1               5                   10                  15

Gly Ala Gly Arg Gly Lys Cys Tyr Gly Pro Gln Cys Leu Cys Arg
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Thr Thr Asp His Gln Met Ala Arg Ala Cys Asp Asp Cys Cys Gly Gly
1               5                   10                  15

Ala Gly Arg Gly Lys Cys Tyr Gly Pro Gln Cys Leu Cys Arg
            20                  25                  30
```

<210> SEQ ID NO 97
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Asp His Gln Met Ala Arg Ala Cys Asp Asp Cys Cys Gly Gly Ala
1               5                   10                  15

Gly Arg Gly Lys Cys Tyr Gly Pro Gln Cys Leu Cys Arg
            20                  25

<210> SEQ ID NO 98
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp His Gln Met Ala Arg Ala Cys Asp Asp Cys Cys Gly Gly Ala Gly
1               5                   10                  15

Arg Gly Lys Cys Tyr Gly Pro Gln Cys Leu Cys Arg
            20                  25

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

His Gln Met Ala Arg Ala Cys Asp Asp Cys Cys Gly Gly Ala Gly Arg
1               5                   10                  15

Gly Lys Cys Tyr Gly Pro Gln Cys Leu Cys Arg
            20                  25

<210> SEQ ID NO 100
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Met Ala Arg Ala Cys Asp Asp Cys Cys Gly Gly Ala Gly Arg Gly
1               5                   10                  15

Lys Cys Tyr Gly Pro Gln Cys Leu Cys Arg
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Met Ala Arg Ala Cys Asp Asp Cys Cys Gly Gly Ala Gly Arg Gly Lys
1               5                   10                  15

Cys Tyr Gly Pro Gln Cys Leu Cys Arg
            20                  25

<210> SEQ ID NO 102
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Arg Ala Cys Asp Asp Cys Cys Gly Gly Ala Gly Arg Gly Lys Cys
1               5                   10                  15

Tyr Gly Pro Gln Cys Leu Cys Arg
            20

<210> SEQ ID NO 103
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Cys Asp Asp Cys Cys Gly Gly Ala Gly Arg Gly Lys Cys Tyr
1               5                   10                  15

Gly Pro Gln Cys Leu Cys Arg
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Cys Asp Asp Cys Cys Gly Gly Ala Gly Arg Gly Lys Cys Tyr Gly
1               5                   10                  15

Pro Gln Cys Leu Cys Arg
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Asp Asp Cys Cys Gly Gly Ala Gly Arg Gly Lys Cys Tyr Gly Pro
1               5                   10                  15

Gln Cys Leu Cys Arg
            20

<210> SEQ ID NO 106
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 106

Asp Asp Cys Cys Gly Gly Ala Gly Arg Gly Lys Cys Tyr Gly Pro Gln
1               5                   10                  15

Cys Leu Cys Arg
            20

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Cys Cys Gly Gly Ala Gly Arg Gly Lys Cys Tyr Gly Pro Gln Cys
1               5                   10                  15

Leu Cys Arg

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Cys Gly Gly Ala Gly Arg Gly Lys Cys Tyr Gly Pro Gln Cys Leu
1               5                   10                  15

Cys Arg

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Gly Gly Ala Gly Arg Gly Lys Cys Tyr Gly Pro Gln Cys Leu Cys
1               5                   10                  15

Arg

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Gly Ala Gly Arg Gly Lys Cys Tyr Gly Pro Gln Cys Leu Cys Arg
1               5                   10                  15

<210> SEQ ID NO 111
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 111

Gly Ala Gly Arg Gly Lys Cys Tyr Gly Pro Gln Cys Leu Cys Arg
1               5                   10                  15

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Gly Arg Gly Lys Cys Tyr Gly Pro Gln Cys Leu Cys Arg
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Arg Gly Lys Cys Tyr Gly Pro Gln Cys Leu Cys Arg
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Gly Lys Cys Tyr Gly Pro Gln Cys Leu Cys Arg
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Lys Cys Tyr Gly Pro Gln Cys Leu Cys Arg
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Cys Tyr Gly Pro Gln Cys Leu Cys Arg
1               5                   10
```

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Tyr Gly Pro Gln Cys Leu Cys Arg
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Tyr Gly Pro Gln Cys Leu Cys Arg
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Pro Gln Cys Leu Cys Arg
1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Pro Gln Cys Leu Cys Arg
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Cys Leu Cys Arg
1               5

<210> SEQ ID NO 122
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 122

Met Cys Met Pro Cys Phe Thr Thr Asp His Gln Met Ala Arg Ala Cys
1               5                   10                  15

Asp Asp Cys Cys Gly Gly Ala Gly Arg
            20                  25

<210> SEQ ID NO 123
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys Met Pro Cys Phe Thr Thr Asp His Gln Met Ala Arg Ala Cys Asp
1               5                   10                  15

Asp Cys Cys Gly Gly Ala Gly Arg
            20

<210> SEQ ID NO 124
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Met Pro Cys Phe Thr Thr Asp His Gln Met Ala Arg Ala Cys Asp Asp
1               5                   10                  15

Cys Cys Gly Gly Ala Gly Arg
            20

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Pro Cys Phe Thr Thr Asp His Gln Met Ala Arg Ala Cys Asp Asp Cys
1               5                   10                  15

Cys Gly Gly Ala Gly Arg
            20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Phe Thr Thr Asp His Gln Met Ala Arg Ala Cys Asp Asp Cys Cys
1               5                   10                  15

Gly Gly Ala Gly Arg
            20

<210> SEQ ID NO 127
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Phe Thr Thr Asp His Gln Met Ala Arg Ala Cys Asp Asp Cys Cys Gly
1               5                   10                  15

Gly Ala Gly Arg
            20

<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Thr Thr Asp His Gln Met Ala Arg Ala Cys Asp Asp Cys Cys Gly Gly
1               5                   10                  15

Ala Gly Arg

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Asp His Gln Met Ala Arg Ala Cys Asp Asp Cys Cys Gly Gly Ala
1               5                   10                  15

Gly Arg

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp His Gln Met Ala Arg Ala Cys Asp Asp Cys Cys Gly Gly Ala Gly
1               5                   10                  15

Arg

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

His Gln Met Ala Arg Ala Cys Asp Asp Cys Cys Gly Gly Ala Gly Arg
1               5                   10                  15

<210> SEQ ID NO 132
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Met Ala Arg Ala Cys Asp Asp Cys Cys Gly Gly Ala Gly Arg
1               5                   10                  15

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Met Ala Arg Ala Cys Asp Asp Cys Cys Gly Gly Ala Gly Arg
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Arg Ala Cys Asp Asp Cys Cys Gly Gly Ala Gly Arg
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Ala Cys Asp Asp Cys Cys Gly Gly Ala Gly Arg
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Cys Asp Asp Cys Cys Gly Gly Ala Gly Arg
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Asp Asp Cys Cys Gly Gly Ala Gly Arg
```

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Asp Cys Cys Gly Gly Ala Gly Arg
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Cys Cys Gly Gly Ala Gly Arg
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Cys Cys Gly Gly Ala Gly Arg
1               5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Gly Gly Ala Gly Arg
1               5

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Met Cys Met Pro Cys Phe Thr Thr Asp His Gln Met Ala Arg
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Cys Met Pro Cys Phe Thr Thr Asp His Gln Met Ala Arg
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Pro Cys Phe Thr Thr Asp His Gln Met Ala Arg
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Cys Phe Thr Thr Asp His Gln Met Ala Arg
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Phe Thr Thr Asp His Gln Met Ala Arg
1               5                   10

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Phe Thr Thr Asp His Gln Met Ala Arg
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Thr Asp His Gln Met Ala Arg
1               5

<210> SEQ ID NO 149

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Asp His Gln Met Ala Arg
1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp His Gln Met Ala Arg
1               5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

His Gln Met Ala Arg
1               5

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157
```

000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

```
<210> SEQ ID NO 180
<400> SEQUENCE: 180
000

<210> SEQ ID NO 181
<400> SEQUENCE: 181
000

<210> SEQ ID NO 182
<400> SEQUENCE: 182
000

<210> SEQ ID NO 183
<400> SEQUENCE: 183
000

<210> SEQ ID NO 184
<400> SEQUENCE: 184
000

<210> SEQ ID NO 185
<400> SEQUENCE: 185
000

<210> SEQ ID NO 186
<400> SEQUENCE: 186
000

<210> SEQ ID NO 187
<400> SEQUENCE: 187
000

<210> SEQ ID NO 188
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191
```

```
<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Cys Met Pro Cys Phe Thr Thr Asp His Gln Met Ala Arg Lys Cys Asp
1               5                   10                  15

Asp Cys Cys Gly Gly Lys Gly Arg Gly Lys Cys Tyr Gly Pro Gln Cys
            20                  25                  30

Leu Cys Arg
        35

<210> SEQ ID NO 200
<211> LENGTH: 24
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 200

Cys Met Pro Cys Phe Thr Thr Asp His Gln Met Ala Arg Lys Cys Asp
1               5                   10                  15

Asp Cys Cys Gly Gly Lys Gly Arg
            20

<210> SEQ ID NO 201
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Pro Cys Phe Thr Thr Asp His Gln Met Ala Arg Lys Cys Asp Asp Cys
1               5                   10                  15

Cys Gly Gly Lys Gly Arg Gly Lys Cys Tyr Gly Pro Gln Cys Leu Cys
            20                  25                  30

Arg

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (8)..(8)
<223> OTHER INFORMATION: Asp or Glu

<400> SEQUENCE: 202

Cys Arg Gly Asp Xaa Gly Pro Xaa Cys
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Arg

<400> SEQUENCE: 203

Cys Arg Gly Asp Xaa
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 204

Lys Cys Asp Asp Cys Cys Gly Gly Lys
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Asp Asp Cys Cys Gly Gly Lys
1               5

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Met Cys Met Pro Cys Phe Thr Thr Asp His Gln Met Ala Arg Lys
1               5                   10                  15

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Lys Cys Asp Asp Cys Cys Gly Gly Lys Gly Arg Gly Lys
1               5                   10

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asp Cys Cys Gly Gly Lys
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Pro Gln Cys Leu
1               5

<210> SEQ ID NO 210
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 210

Cys Tyr Gly Pro Gln
1               5

<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Cys Leu Cys Arg
1

<210> SEQ ID NO 212
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys
        35

<210> SEQ ID NO 213
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Met Pro Cys Phe Thr Thr Asp His Gln Met Ala Arg Lys Cys Asp
1               5                   10                  15

Asp Cys Cys Gly Gly Lys Gly Arg Gly Lys
            20                  25

<210> SEQ ID NO 214
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Thr Asp His Gln Met Ala Arg Lys Cys Asp Asp Cys Cys Gly Gly
1               5                   10                  15

Lys Gly Arg Gly Lys Cys Tyr Gly
            20
```

```
<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Cys Cys Gly Gly Lys Gly Arg Gly Lys Cys Tyr Gly Pro Gln
1               5                   10

<210> SEQ ID NO 216
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu

<210> SEQ ID NO 217
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Arg Lys Cys Asp Asp Cys Cys Gly Gly Lys Gly Arg Gly Lys Cys
1               5                   10                  15

Tyr Gly Pro Gln Cys
            20

<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Thr Asp His Gln Met Ala Arg Lys Cys Asp Asp Cys Cys Gly Gly Lys
1               5                   10                  15

Gly Arg Gly Lys
            20

<210> SEQ ID NO 219
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Met Cys Met Pro Cys Phe Thr Thr Asp His Gln Met Ala Arg Lys Cys
1               5                   10                  15
```

Asp Asp Cys Cys Gly Gly
            20

<210> SEQ ID NO 220
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Met Cys Met Pro Cys Phe Thr Thr Asp His Gln Met Ala Arg Lys Cys
1               5                   10                  15

Asp Asp Cys

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Cys Gly Gly Lys Gly Arg Gly Lys Cys Tyr Gly Pro Gln Cys
1               5                   10

<210> SEQ ID NO 222
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Met Ala Arg Lys Cys Asp Asp Cys Cys Gly Gly Lys Gly Arg Gly
1               5                   10                  15

Lys Cys Tyr Gly Pro Gln
            20

<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Lys Gly Arg Gly Lys Cys Tyr Gly Pro Gln Cys
1               5                   10

<210> SEQ ID NO 224
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Phe Thr Thr Asp His Gln Met Ala Arg Lys Cys Asp Asp Cys Cys Gly
1               5                   10                  15

Gly Lys Gly Arg Gly Lys Cys Tyr Gly Pro Gln Cys Leu
            20                  25

<210> SEQ ID NO 225
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Met Ala Arg Lys Cys Asp Asp Cys Cys Gly Gly Lys Gly Arg Gly
1               5                   10                  15

Lys Cys Tyr Gly Pro
            20

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Cys Cys Gly Gly Lys Gly Arg Gly Lys
1               5                   10

<210> SEQ ID NO 227
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Cys Met Pro Cys Phe Thr Thr Asp His Gln Met Ala Arg Lys Cys Asp
1               5                   10                  15

Asp Cys Cys Gly Gly Lys Gly Arg Gly Lys Cys Tyr Gly Pro
            20                  25                  30

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Arg Lys Cys Asp Asp Cys Cys Gly Gly Lys Gly Arg Gly Lys Cys
1               5                   10                  15

Tyr

<210> SEQ ID NO 229
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Thr Asp His Gln Met Ala Arg Lys Cys Asp Asp Cys Cys Gly Gly Lys

```
                1               5                  10                 15
Gly Arg Gly Lys Cys Tyr Gly Pro Gln Cys Leu
            20                  25
```

<210> SEQ ID NO 230
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

```
Met Cys Met Pro Cys Phe Thr Thr Asp His Gln Met Ala Arg Lys Cys
1               5                   10                  15
Asp Asp Asp Cys Gly Gly Lys Gly Arg Gly Lys Cys Tyr Gly Pro Gln
            20                  25                  30
Cys Leu Cys Arg
        35
```

<210> SEQ ID NO 231
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

```
Cys Met Pro Cys Phe Thr Thr Asp His Gln Met Ala Arg Lys Cys Asp
1               5                   10                  15
Asp Cys Cys Gly Gly Lys Gly Arg Gly Lys Tyr Gly Pro Gln
            20                  25                  30
```

<210> SEQ ID NO 232
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

```
Asp His Gln Met Ala Arg Lys Cys Asp Asp Cys Cys Gly Gly Lys Gly
1               5                   10                  15
Arg Gly Lys Cys Tyr Gly Pro Gln Cys Leu
            20                  25
```

<210> SEQ ID NO 233
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

```
Met Cys Met Pro Cys Phe Thr Thr Asp His Gln Met Ala Arg Lys Cys
1               5                   10                  15
Asp Asp Cys Cys Gly Gly Lys Gly Arg Gly Lys Cys Tyr Gly
            20                  25                  30
```

<210> SEQ ID NO 234
<211> LENGTH: 29

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Thr Asp His Gln Met Ala Arg Lys Cys Asp Asp Cys Cys Gly Gly
1               5                   10                  15

Lys Gly Arg Gly Lys Cys Tyr Gly Pro Gln Cys Leu Cys
            20                  25

<210> SEQ ID NO 235
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Met Cys Met Pro Cys Phe Thr Thr Asp His Gln Met Ala Lys Cys
1               5                   10                  15

Asp Asp Cys Cys Gly Gly Lys Gly
            20

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Thr Thr Asp His Gln Met Ala Arg Lys Cys Asp
1               5                   10

<210> SEQ ID NO 237
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Met Cys Met Pro Cys Phe Thr Thr Asp His Gln Met Ala Arg Lys Cys
1               5                   10                  15

Asp Asp Cys Cys
            20

<210> SEQ ID NO 238
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Met Cys Met Pro Cys Phe Thr Thr Asp His Gln Met Ala Arg Lys Cys
1               5                   10                  15

Asp Asp Cys Cys Gly Gly Lys Gly Arg Gly
            20                  25
```

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Met Pro Cys Phe Thr Thr Asp His Gln Met Ala Arg Lys Cys
1               5                   10

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Lys Gly Arg
1               5

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Met Pro Cys Phe Thr Thr Asp His Gln Met Ala Arg Lys
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Met Pro Cys Phe Thr Thr Asp His Gln Met Ala Arg Lys
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Pro Cys Phe Thr Thr Asp His Gln Met Ala Arg Lys
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 244

Cys Phe Thr Thr Asp His Gln Met Ala Arg Lys
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Phe Thr Thr Asp His Gln Met Ala Arg Lys
1               5                   10

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Thr Asp His Gln Met Ala Arg Lys
1               5

<210> SEQ ID NO 247
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Asp His Gln Met Ala Arg Lys
1               5

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp His Gln Met Ala Arg Lys
1               5

<210> SEQ ID NO 249
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

His Gln Met Ala Arg Lys
1               5

<210> SEQ ID NO 250
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 250

Gln Met Ala Arg Lys
1               5

<210> SEQ ID NO 251
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: R or K
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: R or K

<400> SEQUENCE: 251

Xaa Xaa Xaa Xaa
1
```

CHLOROTOXIN AGENTS AND USES THEREOF

RELATED APPLICATIONS

This application is a U.S. National Stage Application based on International Application No. PCT/US18/51165, filed Sep. 14, 2018, which claims the benefit of U.S. Provisional Application No. 62/559,432, filed Sep. 15, 2017, each of which is herein incorporated by reference in its entirety.

SEQUENCE LISTING

In accordance with 37 CFR 1.52(e)(5), a Sequence Listing in the form of a text file (entitled "2006636-0265_Sequence_Listing", created on Jan. 14, 2022, and having a size of 66,924 bytes) is hereby incorporated by reference in its entirety.

BACKGROUND

Chlorotoxin is a peptide component of venom from the scorpion *Leiurius quinquestriatus*. Chlorotoxin has been shown to bind specifically to tumor cells. Chlorotoxin has been used as a targeting moiety to deliver payload (e.g., therapeutic and/or detectable) agents to various tumors, including metastatic tumors and brain tumors. Various chlorotoxin-payload complexes and conjugates are known and may be used, for example, to detect (e.g., to image) and/or to treat cancer.

SUMMARY

The present invention provides, among other things, compositions and methods relating to detection and/or treatment of cancer (e.g., one or more tumors) that expresses Neuropilin 1 (NRP1). The present invention provides methods of treating cancer that include administering a chlorotoxin agent to a subject (e.g., to a subject suffering from or susceptible to the cancer which can, in some embodiments, be a cancer that expresses NRP1). In some embodiments, a chlorotoxin agent for use in accordance with the present invention can be or include a chlorotoxin polypeptide and a payload moiety (e.g., as a covalent conjugate).

In certain embodiments, a chlorotoxin agent as described in one or more of WO 2007/117467; WO 2005/099774; WO 2003/101474; WO 03/101475; WO 97/24619; WO 00/62807; WO 2009/021136; WO 2009/049184; WO 2009/117018; WO 2009/140599; WO 2011/097533 (see also, e.g., U.S. Pat. No. 9,018,347); WO 2011/142858; and WO 2013/003507, each of which is herein incorporated by reference in its entirety, is utilized in accordance with the present invention.

In some embodiments, a chlorotoxin agent for use in accordance with the present invention is, includes, or is prepared from (e.g., by conjugation of), a chlorotoxin polypeptide whose amino acid sequence includes a C-terminal arginine residue (a "C-terminal arginine chlorotoxin polypeptide"), a chlorotoxin polypeptide that includes zero, one, or two lysine residues available for conjugation (a "reduced-lysine chlorotoxin polypeptide"), or both (a reduced-lysine C-terminal arginine chlorotoxin polypeptide).

In some embodiments, a chlorotoxin polypeptide for use in accordance with the present invention has an amino acid sequence that shows at least 85% identity with an appropriate reference polypeptide (e.g., the polypeptide of SEQ ID NO: 1), or a relevant fragment thereof; in certain such embodiments, the chlorotoxin polypeptide has an amino acid sequence that differs from that of the reference polypeptide, or relevant fragment thereof. In some embodiments, a chlorotoxin polypeptide is or includes a C-terminal arginine chlorotoxin polypeptide, a reduced-lysine chlorotoxin polypeptide, or a reduced-lysine C-terminal arginine chlorotoxin polypeptide. In some embodiments, a chlorotoxin polypeptide that has not more than one lysine available for conjugation has a lysine at a position corresponding to a position selected from the group including position 15 of SEQ ID NO: 1, position 23 of SEQ ID NO: 1, and position 27 of SEQ ID NO: 1. In particular embodiments, the lysine can be at a position corresponding to position 27 of SEQ ID NO: 1. In some embodiments, at least one of the amino acid residues corresponding to positions 15, 23, and 27 of SEQ ID NO: 1 can be not a lysine. For instance, in certain embodiments, at least one amino acid residue corresponding to positions 15, 23, and 27 of SEQ ID NO: 1 can be an alanine or at least one amino acid residue corresponding to positions 15, 23, and 27 of SEQ ID NO: 1 can be an arginine. In some instances, the chlorotoxin polypeptide lacks at least one amino acid corresponding to position 15, 23, or 27 of SEQ ID NO: 1. In various instances, the chlorotoxin polypeptide includes a single lysine residue, or the chlorotoxin polypeptide has no lysine residues. In some embodiments, a chlorotoxin polypeptide has a length within a range of 24 to 48 amino acids. In some embodiments a chlorotoxin polypeptide has a length of 33 to 39 amino acids, e.g., 36 amino acids. In some embodiments, a chlorotoxin polypeptide a length less than 36 amino acids.

In some embodiments, a chlorotoxin polypeptide includes one or more pendant moieties. In certain embodiments, the chlorotoxin polypeptide is associated with one or more amino acid side chains at the polypeptide's N-terminus, at the polypeptide's C-terminus, at an internal residue, or any combination thereof. In various embodiments described herein, a chlorotoxin polypeptide includes at least one pendant moiety selected from a PEG (polyethylene glycol); a PEG di-acid thiol-acid; maleimide-acid; a dipeptide; an amide; a di-methyl group; a tri-methyl group; an alkyl group; a butyl group; a propyl group; and an ethyl group. A pendant moiety can be covalently linked to one or more amino acid side chains of a chlorotoxin polypeptide, at the polypeptide's N-terminus, at the polypeptide's C-terminus, or any combination thereof The present invention provides a method that includes a step of: administering to a subject having a cancer (e.g., one or more tumors) that expresses Neuropilin 1 a chlorotoxin agent (e.g., a chlorotoxin polypeptide such as a C-terminal arginine chlorotoxin polypeptide, a reduced-lysine chlorotoxin polypeptide, or a reduced-lysine C-terminal arginine chlorotoxin polypeptide) alone or in association (e.g., conjugated to) a payload moiety (e.g., a detectable (e.g., imageable), therapeutic, or targeting moiety).

Definitions

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" can encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system, for example to achieve delivery of an agent that is, is included in, or is otherwise delivered by, the composition.

Agent: In general, the term "agent", as used herein, is used to refer to an entity (e.g., for example, a lipid, metal, nucleic acid, polypeptide, polysaccharide, small molecule, etc., or complex, combination, mixture or system, or phenomenon (e.g., heat, electric current or field, magnetic force or field, etc.). A "chlorotoxin agent", as that term is used herein, is any agent that includes a chlorotoxin polypeptide.

Amelioration: as used herein, refers to the prevention, reduction or palliation of a state, or improvement of the state of a subject. Amelioration includes, but does not require complete recovery or complete prevention of a disease, disorder or condition (e.g., radiation injury).

Amino acid: in its broadest sense, as used herein, refers to any compound and/or substance that can be incorporated into a polypeptide chain, e.g., through formation of one or more peptide bonds. In some embodiments, an amino acid has the general structure $H_2N$—$C(H)(R)$—$COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with a typical or canonical amino acid structure. For example, in some embodiments, an amino acid can be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification can, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" can be used to refer to a free amino acid; in some embodiments it can be used to refer to an amino acid residue of a polypeptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. In certain embodiments, any polypeptide or complex of polypeptides that includes sufficient immunoglobulin domain sequences, e.g., as found in natural antibodies, can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in certain embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); camelid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; TransBodies®; Affibodies®; TrimerX®; MicroProteins; Fynomers®, Centyrins®; and KALBITOR®s. In some embodiments, an antibody can lack a covalent modification (e.g., association with a glycan) otherwise characteristic of antibodies produced naturally. In some embodiments, an antibody can contain a covalent modification.

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent can include one or more constant region sequences that are characteristic of mouse, rabbit, primate, or human antibodies. In some embodiments, an antibody agent can include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof, single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; TransBodies®; Affibodies®; TrimerX®; MicroProteins; Fynomers®, Centyrins®; and KALBITOR®s. In some embodiments, an antibody can lack a covalent modification (e.g., association with a glycan) that it would have if produced naturally. In some embodiments, an antibody can contain a covalent modification (e.g., association with a glycan, or other pendant group (e.g., poly-ethylene glycol, etc.)). In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody fragment: As used herein, an "antibody fragment" refers to a portion of an antibody or antibody agent as described herein, and typically refers to a portion that includes an antigen-binding portion or variable region thereof. An antibody fragment can be produced by any means. For example, in some embodiments, an antibody fragment can be enzymatically or chemically produced by fragmentation of an intact antibody or antibody agent. Alternatively, in some embodiments, an antibody fragment can be recombinantly produced (i.e., by expression of an engineered nucleic acid sequence. In some embodiments, an antibody fragment can be wholly or partially synthetically produced. In some embodiments, an antibody fragment (particularly an antigen-binding antibody fragment) can have a length of at least about 50, 60, 70, 80, 90, 100, 110, 120, 130, 140, 150, 160, 170, 180, 190 amino acids or more, in some embodiments at least about 200 amino acids.

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Binding: It will be understood that the term "binding", as used herein, typically refers to a non-covalent association between or among two or more entities. "Direct" binding involves physical contact between moieties; indirect binding involves physical interaction by way of physical contact with one or more intermediate entities. Binding between two or more entities can typically be assessed in any of a variety of contexts—including where interacting moieties are studied in isolation or in the context of more complex systems (e.g., while covalently or otherwise associated with a carrier entity and/or in a biological system or cell).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample can be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semipermeable membrane. Such a "processed sample" can comprise, for example nucleic acids or proteins extracted from a sample or obtained by subjecting a primary sample to techniques such as amplification or reverse transcription of mRNA, isolation and/or purification of certain components, etc.

Biomarker: The term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker can be or comprise a marker for a particular disease state, or for likelihood that a particular disease, disorder or condition can develop, occur, or reoccur. In some embodiments, a biomarker can be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker can be an entity of any chemical class. For example, in some embodiments, a biomarker can be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc.

Cancer: As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In some embodiments, a cancer can be characterized by one or more tumors. In some embodiments, a cancer can be or comprise cells that are precancerous (e.g., benign), malignant, pre-metastatic, metastatic, and/or non-metastatic. In some embodiments, a relevant cancer can be characterized by a solid tumor. In some embodiments, a relevant cancer can be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Characteristic portion: As used herein, the term "characteristic portion", in the broadest sense, refers to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 25, 30, 35, or more amino acids. In general, a characteristic portion of a substance (e.g., of a protein, antibody, etc.) is one that, in addition to the sequence and/or structural identity specified herein, shares at least one functional characteristic with the relevant intact substance. In some embodiments, a characteristic portion can be biologically active.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Chemotherapeutic moiety: The term "chemotherapeutic moiety", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic moieties are useful in the treatment of cancer. In some embodiments, a chemotherapeutic moiety can be or include one or more alkylating agents, one or more anthracyclines, one or more cytoskeletal disruptors (e.g. microtubule targeting moieties such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhihitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic moiety can be or include one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic moiety can be utilized in the context of an antibody-drug conjugate. In some embodiments, a chemotherapeutic moiety is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic moiety can be or comprise one or more of farnesyl-thiosalicylic acid (FTS), 4-(4-Chloro-2-methylphenoxy)-N-hydroxybutanamide (CMH), estradiol (E2), tetramethoxystilbene (TMS), 6-tocatrienol, salinomycin, or curcumin.

Chlorotoxin Conjugate: As used herein, the term "chlorotoxin conjugate" refers to an entity that includes a chlorotoxin polypeptide in association with a payload moiety. In some embodiments, a payload moiety is or includes a detectable (e.g., imageable) moiety, a therapeutic moiety, a targeting moiety, or a combination thereof.

Chlorotoxin Polypeptide: As used herein, the term "chlorotoxin polypeptide" refers to a polypeptide whose amino acid sequence shows at least 45% identity with that of an appropriate reference chlorotoxin (e.g. that of SEQ ID NO: 1, or a relevant fragment thereof. In some embodiments, a chlorotoxin polypeptide has an amino acid sequence that shows at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identity with SEQ ID NO: 1 or a relevant fragment thereof. In some embodiments, a chlorotoxin polypeptide has an amino acid sequence that is identical to that of SEQ ID NO: 1. In some embodiments, a chlorotoxin polypeptide is a chlorotoxin variant in that it has an amino acid sequence that is different from that of SEQ ID NO: 1, or a relevant fragment thereof. In some embodiments, a chlorotoxin variant has an amino acid sequence that differs at not more than 1, 2, 3, 4, 5, 6, 7, 8, 9, or 10 positions relative to SEQ ID NO: 1, or a relevant fragment thereof. In some embodiments, a relevant fragment of SEQ ID NO: 1 includes at least 5 contiguous residues of SEQ ID NO: 1. In some embodiments, a relevant fragment of SEQ ID NO: 1 includes a span of 5 to 25 amino acids having at least 45% sequence identity with a corresponding span of SEQ ID NO: 1.

Combination therapy: As used herein, the term "combination therapy" refers to those situations in which a subject is simultaneously exposed to two or more therapeutic regimens (e.g., two or more therapeutic moieties). In some embodiments, the two or more regimens can be administered simultaneously; in some embodiments, such regimens can be administered sequentially (e.g., all "doses" of a first regimen are administered prior to administration of any doses of a second regimen); in some embodiments, such agents are administered in overlapping dosing regimens. In some embodiments, "administration" of combination therapy can involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, can be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions can reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition", as used herein, can be used to refer to a discrete physical entity that comprises one or more specified components. In general, unless otherwise specified, a composition can be of any form—e.g., gas, gel, liquid, solid, etc.

Comprising: A composition or method described herein as "comprising" one or more named elements or steps is open-ended, meaning that the named elements or steps are essential to a particular aspect or embodiment, but other elements or steps can be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and can also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step can be substituted for that element or step.

Corresponding to: As used herein, the term "corresponding to" can be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) can be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Detectable moiety: The term "detectable moiety" as used herein refers to any element, molecule, functional group, compound, fragment or moiety that is detectable. In some embodiments, a detectable moiety is provided or utilized alone. In some embodiments, a detectable moiety is provided and/or utilized in association with (e.g., joined to) another agent. Examples of detectable moieties include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$ $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.), nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Dosing regimen: Those skilled in the art will appreciate that the term "dosing regimen" can be used to refer to a set of unit doses (typically more than one) that are administered individually to a subject, typically separated by periods of time. In some embodiments, a given therapeutic moiety has a recommended dosing regimen, which can involve one or more doses. In some embodiments, a dosing regimen comprises a plurality of doses each of which is separated in time from other doses. In some embodiments, individual doses are separated from one another by a time period of the same length; in some embodiments, a dosing regimen includes a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Engineered. In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments described herein, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Fragment: A "fragment" of a material or entity as described herein has a structure that includes a discrete portion of a reference whole material or entity, but lacks one or more moieties found in the reference whole. In some embodiments, a fragment consists of such a discrete portion. In some embodiments, a fragment consists of or comprises a characteristic structural element or moiety found in the reference whole. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in a reference whole polymer. A reference whole material or entity can in some embodiments be referred to as the "parent" of the fragment.

In some instances a fragment is generated by physical fragmentation of a reference whole or parent material or entity. In some instances, a fragment is not generated by physical fragmentation of a reference whole or parent material or entity. Thus, in some instances, a fragment is produced by de novo synthesis or another means that does not require physical fragmentation of a reference whole or parent material or entity. For instance, a fragment of a polypeptide can be a polypeptide that that comprises or consists of an amino acid sequence having at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more identity to an amino acid sequence of a reference whole or parent polypeptide, and may, or may not, be generated by physical fragmentation of a reference whole or parent polypeptide.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene can include both coding (e.g., exonic) and non-coding (e.g., intronic) sequences. In some embodiments, a gene can include one or more regulatory elements that, for example, can control or impact one or more aspects of gene expression (e.g., cell-type-specific expression, inducible expression, etc.).

Genotype: As used herein, the term "genotype" refers to the diploid combination of alleles at a given genetic locus, or set of related loci, in a given cell or organism. A homozygous subject carries two copies of the same allele and a heterozygous subject carries two distinct alleles.

Genotyping: As used herein, the term "genotyping" refers to an experimental, computational, or observational protocol for distinguishing an individual's genotype at one or more well-defined loci. Those skilled in the art will be aware of a variety of technologies that can usefully and effectively perform genotyping. In some embodiments, genotyping involves direct detection of a nucleic acid or nucleic acid sequence. In some embodiments, genotyping involves indirect detection of a nucleic acid or nucleic acid sequence, for example through detection or analysis of a proxy marker or event that correlates with presence of the nucleic acid or nucleic acid sequence.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known in the art. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. The comparison of sequences and determination of percent identity between two sequences can be accomplished using a mathematical algorithm, such as BLAST (basic local alignment search tool).

Marker: A marker, as used herein, refers to an entity or moiety whose presence or level is a characteristic of a particular state or event. In some embodiments, presence or level of a particular marker can be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that can be characteristic of a particular class of tumors. The statistical significance of the presence or absence of a marker can vary depending upon the particular marker. In some embodiments, detection of a marker is highly specific in that it reflects a high probability that the tumor is of a particular subclass. Such specificity can come at the cost of sensitivity (i.e., a negative result can occur even if the tumor is a tumor that would be expected to express the marker). Conversely, markers with a high degree of sensitivity can be less specific that those with lower sensitivity. According to the present invention a useful marker need not distinguish tumors of a particular subclass with 100% accuracy.

Non-natural amino acid: The phrase "non-natural amino acid" refers to an entity having the chemical structure of an amino acid

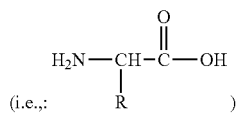

(i.e.,:  H$_2$N—CH(R)—C(=O)—OH )

and therefore being capable of participating in at least two peptide bonds, but having an R group that differs from those found in nature. In some embodiments, non-natural amino acids can also have a second R group rather than a hydrogen, and/or can have one or more other substitutions on the amino or carboxylic acid moieties.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is or includes of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are provided herein. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving predetermined therapeutic effects when administered to a relevant population. In some embodiments, a pharmaceutical composition can be specially formulated for administration in a particular form (e.g., in a solid form or a liquid form), and/or can be specifically adapted for, for example: oral administration (for example, as a drench (aqueous or non-aqueous solutions or suspensions), tablet, capsule, bolus, powder, granule, paste, etc, which can be formulated specifically for example for buccal, sublingual, or systemic absorption); parenteral administration (for example, by subcutaneous, intramuscular, intravenous or epidural injection as, for example, a sterile solution or suspension, or sustained-release formulation, etc); topical application (for example, as a cream, ointment, patch or spray applied for example to skin, lungs, or oral cavity); intravaginal or intrarectal administration (for example, as a pessary, suppository, cream, or foam); ocular administration; nasal or pulmonary administration, etc.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide can comprise or consist of natural amino acids, non-natural amino acids, or both. In some embodiments, a polypeptide can comprise or consist of only natural amino acids or only non-natural amino acids. In some embodiments, a polypeptide can comprise D-amino acids, L-amino acids, or both. In some embodiments, a polypeptide can comprise only D-amino acids. In some embodiments, a polypeptide can comprise only L-amino acids. In some embodiments, a polypeptide can include one or more pendant groups or other modifications, e.g., modifying or associated with one or more amino acid side chains, at the polypeptide's N-terminus, at the polypeptide's C-terminus, or any combination thereof. In some embodiments, such pendant groups or modifications can be selected from the group consisting of acetylation, amidation, lipidation, methylation, pegylation, etc., including combinations thereof. In some embodiments, a polypeptide can be cyclic, and/or can comprise a cyclic portion. In some embodiments, a polypeptide is not cyclic and/or does not comprise any cyclic portion. In some embodiments, a polypeptide is linear. In some embodiments, a polypeptide can be or comprise a stapled polypeptide. In some embodiments, the term "polypeptide" can be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that can in some embodiments be or comprise a characteristic sequence element) that shows very high sequence identity, often greater than 90% or even 95%, 96%, 97%, 98%, or 99%. Such a conserved region usually encompasses at least 3-4 and in some instances up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide can comprise or consist of a fragment of a parent polypeptide.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention can be considered complete when onset of a disease, disorder or condition has been delayed for a predefined period of time.

Protein: As used herein, the term "protein" refers to a polypeptide (i.e., a string of at least two amino acids linked to one another by peptide bonds). Proteins can include moieties other than amino acids (e.g., can be glycoproteins, proteoglycans, etc.) and/or can be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides can contain L-amino acids, D-amino acids, or both and can contain any of a variety of amino acid modifications or analogs known in the art. Useful modifications include, e.g., terminal acetylation, amidation, methylation, etc. In some embodiments, proteins can comprise natural amino acids, non-natural amino acids, synthetic amino acids, and combinations thereof. In some embodiments, proteins are antibodies, antibody fragments, biologically active portions thereof, and/or characteristic portions thereof.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Refractory: The term "refractory" as used herein, refers to any subject or condition that does not respond with an expected clinical efficacy following the administration of provided compositions as normally observed by practicing medical personnel.

Risk: as will be understood from context, "risk" of a disease, disorder, and/or condition refers to a likelihood that a particular individual will develop the disease, disorder, and/or condition. In some embodiments, risk is expressed as a percentage. In some embodiments, a risk is a percentage likelihood that is equal to or greater than 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is increased or decreased in comparison to the reference sample by a factor of 0, 1, 2, 3, 4, 5, 6, 7, 8, 9, 10, or more.

Sample: As used herein, the term "sample" typically refers to an aliquot of material obtained or derived from a source of interest, as described herein. In some embodiments, a source of interest is a biological or environmental source. In some embodiments, a source of interest can be or comprise a cell or an organism, such as a microbe, a plant, or an animal (e.g., a human). In some embodiments, a source of interest is or comprises biological tissue or fluid. In some embodiments, a biological tissue or fluid can be or comprise amniotic fluid, aqueous humor, ascites, bile, bone marrow, blood, breast milk, one or more cancer cells, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, one or more tumor cells, urine, vaginal secretions, vitreous humour, vomit, and/or combinations or component(s) thereof. In some embodiments, a biological fluid can be or comprise an intracellular fluid, an extracellular fluid, an intravascular fluid (blood plasma), an interstitial fluid, a lymphatic fluid, and/or a transcellular fluid. In some embodiments, a biological fluid can be or comprise a plant exudate. In some embodiments, a biological tissue or sample can be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semipermeable membrane. Such a "processed sample" can comprise, for example nucleic acids or proteins extracted from a sample or obtained by subjecting a primary sample to one or more techniques such as amplification or reverse transcription of nucleic acid, isolation and/or purification of certain components, etc.

Solid Tumor: As used herein, the term "solid tumor" refers to an abnormal mass of tissue that usually does not contain cysts or liquid areas. In some embodiments, a solid tumor can be benign; in some embodiments, a solid tumor can be malignant. Those skilled in the art will appreciate that different types of solid tumors are typically named for the type of cells that form them. Examples of solid tumors are carcinomas, lymphomas, and sarcomas. In some embodiments, solid tumors can be or comprise adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Stage of cancer: As used herein, the term "stage of cancer" refers to a qualitative or quantitative assessment of the level of advancement of a cancer. In some embodiments, criteria used to determine the stage of a cancer can include, but are not limited to, one or more of where the cancer is located in a body, tumor size, whether the cancer has spread to lymph nodes, whether the cancer has spread to one or more different parts of the body, etc. In some embodiments, cancer can be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer can be referred to as Stage 0 (abnormal cells are present but have not spread to nearby tissue, also called carcinoma in situ, or CIS; CIS is not cancer, but it can become cancer), Stage I-III (cancer is present; the higher the number, the larger the tumor and the more it has spread into nearby tissues), or Stage IV (the cancer has spread to distant parts of the body). In some embodiments, a cancer can be assigned to a stage selected from the group consisting of: in situ (abnormal cells are present but have not spread to nearby tissue); localized (cancer is limited to the place where it started, with no sign that it has spread); regional (cancer has spread to nearby lymph nodes, tissues, or organs): distant (cancer has spread to distant parts of the body); and unknown (there is not enough information to identify cancer stage).

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Subject: As used herein, the term "subject" refers to an organism, typically a mammal (e.g., a human). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic moiety: As used herein, the phrase "therapeutic moiety" in general refers to any agent that elicits a desired pharmacological effect when administered to an organism. In some embodiments, an agent is considered to be a therapeutic moiety if it demonstrates a statistically significant effect across an appropriate population. In some embodiments, the appropriate population can be a population of model organisms. In some embodiments, an appropriate population can be defined by various criteria, such as a certain age group, gender, genetic background, preexisting clinical conditions, etc. In some embodiments, a therapeutic moiety is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic moiety" is an agent that has been or is required to be approved by a government agency before it can be marketed for administration to humans. In some embodiments, a "therapeutic moiety" is an agent for which a medical prescription is required for administration to humans.

Therapeutically effective amount: As used herein, the term "therapeutically effective amount" refers to an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount can be that amount that provides a particular desired pharmacological response in a significant number of subjects when administered to patients in need of such treatment. In some embodiments, reference to a therapeutically effective amount can be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy can be formulated and/or administered in a single dose. In some embodiments, a therapeutically effective agent can be formulated and/or administered in a plurality of doses, for example, as part of a dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, and/or condition, or is administered for the purpose of achieving any such result. In some embodiments, such treatment can be of a subject who does not exhibit signs of the relevant disease, disorder and/or condition and/or of a subject who exhibits only early signs of the disease, disorder, and/or condition. Alternatively or additionally, such treatment can be of a subject who exhibits one or more established signs of the relevant disease, disorder and/or condition. In some embodiments, treatment can be of a subject who has been diagnosed as suffering from the relevant disease, disorder, and/or condition. In some embodiments, treatment can be of a subject known to have one or more susceptibility factors that are statistically correlated with increased risk of development of the relevant disease, disorder, and/or condition. In various examples, treatment is of a cancer. Tumor: As used herein, the term "tumor" refers to an abnormal growth of cells or tissue. In some embodiments, a tumor can comprise cells that are precancerous (e.g., benign), malignant, pre-metastatic, metastatic, and/or non-metastatic. In some embodiments, a tumor is associated with, or is a manifestation of, a cancer. In some embodiments, a tumor can be a disperse tumor or a liquid tumor. In some embodiments, a tumor can be a solid tumor.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose can be, for example, a volume of liquid (e.g., an acceptable carrier) containing a predetermined quantity of one or more therapeutic moieties, a predetermined amount of one or more therapeutic moieties in solid form, a sustained release formulation or drug delivery device containing a predetermined amount of one or more therapeutic moieties, etc. It will be appreciated that a unit dose can be present in a formulation that includes any of a variety of components in addition to the therapeutic moiety(s). For example, acceptable carriers (e.g., pharmaceutically acceptable carriers), diluents, stabilizers, buffers, preservatives, etc., can be included as described infra. It will be appreciated by those skilled in the art, in many embodiments, a total appropriate daily dosage of a particular therapeutic moiety can comprise a portion, or a plurality, of unit doses, and can be decided, for example, by the attending physician within the scope of sound medical judgment. In some embodiments, the specific effective dose level for any particular subject or organism can depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule can have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc) within the core, a polypeptide can have a characteristic sequence element comprised of a plurality of amino acids having designated positions relative to one another in linear or three-dimensional space and/or contributing to a particular biological function, a nucleic acid can have a characteristic sequence element comprised of a plurality of nucleotide residues having designated positions relative to on another in linear or three-dimensional space. For example, a variant polypeptide can differ from a reference polypeptide as a result of one or more differences in amino acid sequence (an "amino acid variant") and/or one or more differences in chemical moieties (e.g., carbohydrates, lipids, other pendant moieties, etc) covalently associated with the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. In some embodiments, a variant has 10, 9, 8, 7, 6, 5, 4, 3, 2, or 1 substituted residue as compared with a parent. In some embodiments, a variant has not more than 5, 4, 3, 2, or 1 additions or deletions, or has no additions or deletions, as compared with the parent. In various embodiments, the number of additions or deletions is fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature.

BRIEF DESCRIPTION OF THE DRAWING

FIG. 9 includes SEQ ID NOs: 81, 56, 204, 81, 81, 56, and 205, respectively, in order of appearance from top to bottom and left to right.

FIG. 10 includes SEQ ID NOs: 81 and 56, respectively, in order of appearance from left to right.

FIG. 11 is a table showing selected peptides, the source of each as used in Example 8, and NRP1 binding of each as measured in Example 8. FIG. 11 includes SEQ ID NOs: 81, 54, 204, 81, 56, 204, 81, 56, 205, 81, 81, 206, 207, 204, 208, 56, 56, 57, and 209-211, respectively, in order of appearance from top to bottom.

FIG. 54 is a table showing selected CTX-related peptides unique to tumor lysates from CTX-treated mice. FIG. 54 includes SEQ ID NOs: 1, 212, 1, 1, 213, 214, 1, 1, 1, 1, 215, 1, 78, 1, and 216-221, respectively, in order of appearance from top to bottom.

FIG. 55 is a table showing selected CTX-related peptides unique to tumor lysates from CTX-treated mice. FIG. 55 includes SEQ ID NOs: 1, 222, 65, 1, 218, 223, 224, 212, 212, 84, 222, 225, 226, 39, 1, 227, 228, 30, 213, and 229, respectively, in order of appearance from top to bottom.

FIG. 56 is a table showing selected CTX-related peptides unique to tumor lysates from CTX-treated mice. FIG. 56 includes SEQ ID NOs: 230, 212, 1, 214, 231, 232, 218, 84, 1, 1, 212, 30, 233, 234, 1, and 235-239, respectively, in order of appearance from top to bottom.

FIG. 58 is a table showing selected CTX peptides identified in tumor lysates of CTX-treated mice. FIG. 58 includes SEQ ID NOs: 40-60 in the left column and SEQ ID NOs: 40-60 in the right column, respectively, in order of appearance from top to bottom.

FIG. 59 includes SEQ ID NOs: 61-80 and 240 in the left column and SEQ ID NOs: 81-90, 206, and 241-250 in the right column, respectively, in order of appearance from top to bottom.

DETAILED DESCRIPTION

Figure 1:
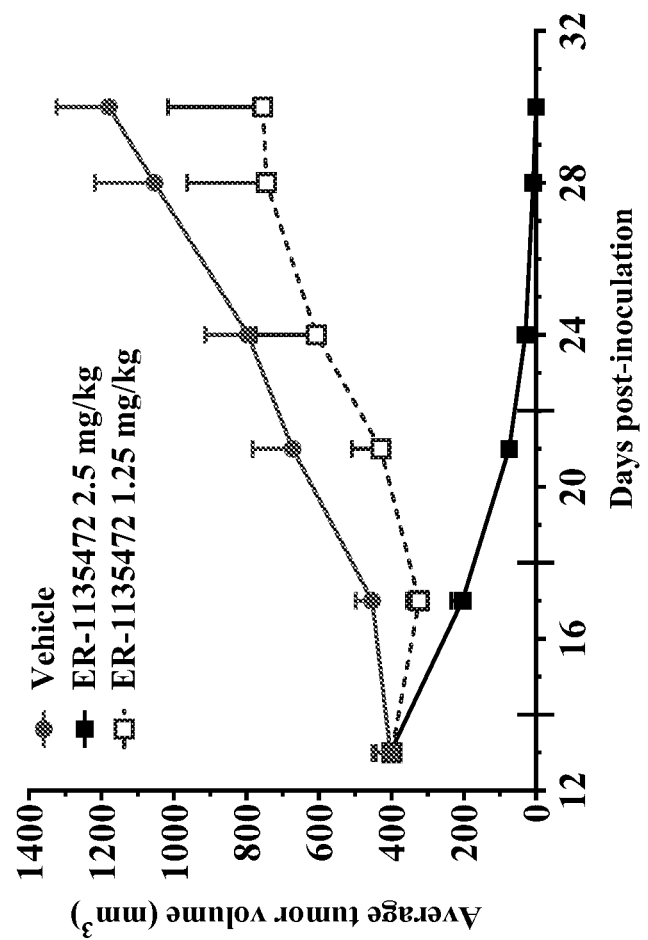
FIG. 1 is a chart showing the average tumor volume of MIA PaCa-2 human pancreatic cancer cell xenograft mouse tumor following treatment with a dosage of 1.25 mg/kg CTX-Cryptophycin, a dosage of 2.5 mg/kg CTX-Cryptophycin, or vehicle control mice by intravenous administration every four days for three treatments (Q4Dx3 schedule).

The present invention encompasses the discovery that certain cancers, including certain cancers characterized by expression of NRP1, can be detected (e.g., imaged, characterized, or diagnosed) and/or treated by administration of a chlorotoxin agent, in some embodiments with greater efficacy than certain cancers characterized by low or absent (i.e., undetected) expression of NRP1.

The present invention also includes the discovery of certain chlorotoxin agents that are particularly useful to detect and/or treat cancer, and/or bind NRP1. For example, the present invention includes the discovery that certain particularly useful chlorotoxin agents are, include, or are prepared from a chlorotoxin polypeptide having an amino acid sequence that includes a C-terminal arginine residue, e.g., a C-terminal arginine residue including a carboxyl group. In some embodiments, particularly useful chlorotoxin agents may or may not include an (R/K)XX(R/K) motif (SEQ ID NO: 251). In certain embodiments, a chlorotoxin agent utilized in accordance with the present invention does not include an (R/K)XX(R/K) motif (SEQ ID NO: 251). In certain embodiments, a chlorotoxin agent utilized in accordance with the present invention comprises a chlorotoxin polypeptide conjugated (e.g., covalently linked) to a payload moiety. In certain embodiments, a chlorotoxin agent utilized in accordance with the invention is a C-terminal arginine chlorotoxin agent, a reduced lysine chlorotoxin agent, or both (i.e., is a reduced lysine C-terminal arginine chlorotoxin agent) that is conjugated (e.g., covalently linked) to or used in combination therapy with a payload moiety (e.g., to a detectable moiety, a therapeutic moiety, a targeting moiety, or a combination thereof). Further, without wishing to be bound by any particular scientific theory, chlorotoxin polypeptide (e.g., chlorotoxin polypeptide that does not include a C-terminal arginine residue) may be metabolized to expose an internal or cryptic arginine residue, which exposed internal or cryptic arginine residue can be a carboxylated arginine residue.

Without wishing to be bound by any particular scientific theory, the present disclosure proposes that certain chlorotoxin agents, upon administration to a subject, can be digested by proteases present in the subject. Such protease digestion generates fragments of chlorotoxin polypeptide from administered chlorotoxin agent. Certain such chlorotoxin polypeptide fragments include a C-terminal arginine residue. Certain such chlorotoxin polypeptide fragments, including certain chlorotoxin polypeptide fragments that have a C-terminal arginine residue, are substrates for Neuropilin 1 (NRP1). Interaction of a relevant chlorotoxin polypeptide fragment with NRP1 can enhance uptake of the chlorotoxin polypeptide fragment (and any associated payload moiety, if present) into NRP1-expressing cells. Interaction of a fragment with NRP1 is, in certain instances, facilitated by the presence of carboxyl group on a C-terminal arginine residue of the fragment. Treatment, detection, or targeting of cancer by chlorotoxin agents, under this theory, is particularly efficacious with respect to cancer expressing NRP1. Treatment, detection, or targeting of cancer by certain chlorotoxin agents, under this theory, is particularly efficacious where the chlorotoxin agent is, includes, or is prepared from a chlorotoxin polypeptide having an amino acid sequence that includes a C-terminal arginine residue, e.g., where the C-terminal arginine residue includes a carboxyl group.

Neuropilin 1

Neuropilin 1 (NRP1) is a transmembrane glycoprotein that acts as a co-receptor for a number of extracellular ligands including class III/IV semaphorins, certain isoforms of vascular endothelial growth factor, and transforming growth factor beta. Its ability to bind or modulate the activity of a number of other extracellular ligands, such as class 3 semaphorins, TGF-β, HGF, FGF, and PDGF, has suggested the involvement of NRP1 in a variety of physiological and pathological processes. NRP1 has been implicated in axon guidance, angiogenesis, and immune responses. NRP1 is also expressed in a variety of cancers (prostate, lung, pancreatic, or colon carcinoma, melanoma, astrocytoma, glioblastoma, and neuroblastoma), suggesting a critical role in tumor progression. Moreover, evidence suggests that NRP1 might display important functions independently of other VEGF receptors. In particular, in the absence of VEGFR-1/2, NRP1 promotes melanoma invasiveness, through the activation of selected integrins, by stimulating VEGF-A and metalloproteinases secretion and modulating specific signal transduction pathways. As a therapeutic target, NRP1 allows targeting of, e.g., NRP1-expressing tumor vasculature, $NRP1^+$ regulatory T cells (Tregs), and pDCs. With the development of anti-NRP1 monoclonal antibodies and cell-penetrating peptides, NRP1 represents a promising new target for cancer therapies.

NRP1 is expressed in tumor-associated vessels and in a variety of cancers, suggesting a role in cancer progression. Increased levels of NRP1 correlate with cancer aggressiveness, advanced disease stage, and poor prognosis. NRP1 up-regulation appears to be associated with the cancer invasive behavior and metastatic potential, for instance in melanoma and breast cancer. NRP1 has been implicated in mediating the effects of VEGF-A and semaphorins on the proliferation, survival, and migration of cancer cells. NRP1 is also expressed by various stromal cells, including fibroblasts, endothelial and immune cells, which can be activated by growth factors different from VEGF-A and contribute to cancer progression. Cancer promoting effects of NRP1 are, in certain instances, attributed to an enhancement of VEGF receptors (VEGFR)-2 activation in response to VEGF-A. However, certain cancers express NRP1 but neither VEGFR-1 nor VEGFR-2. A large number of human melanoma cell lines, derived from primary and metastatic lesions, secrete VEGF-A and express its receptors, including NRP1. NRP1 enhances the activation of a VEGF-A/VEGFR-2 autocrine loop, which promotes the invasion of melanoma cells into the extracellular matrix, e.g., through the up-regulation of VEGF-A and metalloproteinases secretion. NRP1 over-expression provides human melanoma cells with an increased in vivo growth rate. NRP1 might be also involved in the effects of P1GF on melanoma cells. It has been recently demonstrated that NRP1 expression in melanoma cells increases their aggressiveness and ability to form tubule-like structures. NRP1 has been indicated as a promoter of epithelial-mesenchymal transition, a critical step in cancer invasion and disease progression. A similar process of phenotype switching has been reported in melanoma and implicated in promotion to a metastatic state, providing further evidence of NRP1 involvement in multiple oncogenic functions. Without wishing to be bound by any particular scientific theory, this evidence supports a hypothesis that NRP1 might represent a suitable target, e.g., for anti-melanoma therapy.

The human NRP1 gene encodes a human neuropilin having specific protein domains which allow participation in several different types of signaling pathways that control, among other things, cell migration. Neuropilins contain a large N-terminal extracellular domain, made up of complement-binding, coagulation factor V/VIII, and meprin domains. Neuropilins also include a short membrane-spanning domain and a small cytoplasmic domain. Neuropilins bind many ligands and various types of co-receptors; they affect cell survival, migration, and attraction. Several alternatively spliced transcript variants that encode different protein isoforms have been described.

One canonical human NRP1 protein is a 923 amino acid protein found in UniProtKB/Swiss-Prot accession 014786.1. As used herein, NRP1 includes proteins having at least 70% sequence identity with NRP1 protein sequence (UniProtKB/

Swiss-Prot accession O14786.1), e.g., at least 75% identity, at least 80% identity, at least 85% identity, at least 90% identity, at least 95% identity, at least 96% identity, at least 97% identity, at least 98% identity, or at least 99% identity. NRP1 as described herein includes known variants such as 014786.2 (UniParc—UPI00001F9122; 642-644: EFP/GIK, 645-923: deleted; soluble) and 014786.3 (UniParc—UPI000013EECB; 587-621: deleted; 642-644: EFP/GIK; 645-923: deleted). As used herein, NRP1 includes proteins having at least 70% sequence identity with UniProtKB/Swiss-Prot accession 014786.2 or 014786.3, e.g., at least 75% identity, at least 80% identity, at least 85% identity, at least 90% identity, at least 95% identity, at least 96% identity, at least 97% identity, at least 98% identity, or at least 99% identity. Various NRP1 proteins encompassed by the present invention can include any of one or more of the following known variations, and/or other variations: K26E; D219G; D749H; D855E; V179A; F561L; V733I; 587-621: deleted; 642-644: EFP/GIK; 645-923: deleted.

Both NRP1 and its homolog NRP2 are glycoproteins encoded by genes that are alternatively spliced into full-length transmembrane receptors and shorter soluble forms. As used herein, NRP1 refers to NRP1 transmembrane receptor. The NRP1 transmembrane form includes an extracellular domain, a single-pass transmembrane domain and an amino acid cytoplasmic domain. The extracellular NRP1 part consists of two domains called a1 and a2, which resemble the CUB (complement, Uegf, BMP) domain present in complement components. They are followed by the b1 and b2 domains, which are similar to coagulation factor V/VIII domains. The c domain, with homology to a MAM (meprin/antigen 5/receptor tyrosine phosphatase domain), separates the other extracellular domains from the transmembrane region. The short intracellular (cytoplasmic) domain is catalytically inactive, but contains a C-terminal SEA (serine-glutamine-alanine) motif that interacts with intracellular proteins containing a PDZ domain.

Chlorotoxin Agents

Chlorotoxin agents for use in accordance with the present invention include peptides and conjugates that include a chlorotoxin polypeptide (whether full-length or a chlorotoxin polypeptide fragment). In certain embodiments, a chlorotoxin agent includes a chlorotoxin polypeptide associated with a payload.

Chlorotoxin Polypeptides

Chlorotoxin is a 36-amino acid peptide (SEQ ID NO: 1) having three lysine residues, which lysine residues are located at positions 15, 23, and 27 of SEQ ID NO: 1. A chlorotoxin polypeptide having a sequence that differs from that of SEQ ID NO: 1 can be referred to, in some instances, as a "variant."

In some embodiments, a chlorotoxin polypeptide is and/or includes 24, 25, 26, 27, 28, 29, 30, 31, 32, 33, 34, 35, 36, 37, 38, 39, 40, 41, 42, 43, 44, 45, 46, 47, or 48 consecutive amino acids having at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% overall sequence identity with the sequence of chlorotoxin (SEQ ID NO: 1) or a relevant fragment thereof. In certain instances, a chlorotoxin polypeptide is a polypeptide having a length of between twenty-four and forty amino acid residues, inclusive, and having at least 45% overall sequence identity with SEQ ID NO: 1 or a relevant fragment thereof.

In certain instances, at least one difference from SEQ ID NO: 1 will include a substitution or deletion of Lys 15, Lys 23, or Lys 27 as compared to SEQ ID NO: 1. In certain instances, at least two differences from SEQ ID NO: 1 will be selected from the group consisting of substitution or deletion of Lys 15, substitution or deletion of Lys 23, and substitution or deletion of Lys 27 as compared to SEQ ID NO: 1.

In certain embodiments, a chlorotoxin polypeptide as described herein includes a C-terminal arginine residue. In certain embodiments, the C-terminal residue of a chlorotoxin polypeptide as described herein is not amidated. In certain embodiments, the C-terminal residue of a chlorotoxin polypeptide as described herein is carboxylated. In certain embodiments, the C-terminal residue of a chlorotoxin polypeptide as described herein is an arginine that is not amidated. In certain embodiments, the C-terminal residue of a chlorotoxin polypeptide as described herein is an arginine residue that is carboxylated.

In some embodiments, a chlorotoxin polypeptide is a reduced lysine chlorotoxin polypeptide in that it includes a reduced number of lysine residues as compared to SEQ ID NO: 1, e.g., 0, 1, or 2 lysine residues rather than 3 lysine residues as found in SEQ ID NO: 1.

In some embodiments, a reduced lysine chlorotoxin polypeptide includes only one lysine residue (a "monolysine chlorotoxin polypeptide"). In some embodiments, such a chlorotoxin polypeptide has a lysine residue where a lysine residue is normally present in chlorotoxin, e.g., at a position corresponding to position 15, 23, or 27 of SEQ ID NO: 1 (See, e.g., SEQ ID NOs: 14-23 for non-limiting examples). In some embodiments, a monolysine chlorotoxin polypeptide does not have any lysine residues where a lysine residue is normally present in chlorotoxin (i.e., positions corresponding to positions 15, 23, and 27 of SEQ ID NO: 1), but has a lysine residue at a position that does not correspond to any of positions 15, 23, and 27 of SEQ ID NO: 1. As with chlorotoxin polypeptides having no lysines at all, monolysine chlorotoxin polypeptides can be missing amino acids at one or more positions corresponding to positions 15, 23 and 27 of SEQ ID NO: 1, and/or can have an amino acid or amino acid derivative substitution at one or more positions corresponding to positions 15, 23 and 27 of SEQ ID NO: 1 as compared to SEQ ID NO: 1.

In certain embodiments, a reduced lysine chlorotoxin polypeptide has not more than one lysine available as a site for conjugation. In some such embodiments, one lysine is available and the available lysine is at a position within the chlorotoxin polypeptide that corresponds to a position where a lysine is present in chlorotoxin (i.e., a position corresponding to position 15, 23 or 27 of SEQ ID NO: 1). In some embodiments, the single lysine that is available is at a position corresponding to position 15 of SEQ ID NO: 1. In some embodiments, the single lysine that is available is at a position corresponding to position 23 of SEQ ID NO: 1. In some embodiments, the single lysine that is available is at a position corresponding to position 27 of SEQ ID NO: 1.

In certain embodiments, a reduced lysine chlorotoxin polypeptide lacks at least one amino acid residue corresponding to position 15, 23, or 27 of SEQ ID NO: 1.

In certain embodiments, a reduced lysine chlorotoxin polypeptide lacks an amino acid or lysine residue at any position corresponding to any of positions 15, 23, or 27 of SEQ ID NO: 1. Thus, in certain embodiments, a reduced lysine chlorotoxin polypeptide lacks lysine residues entirely (See, e.g., SEQ ID NOs: 2, 5, 6, 24, 25 and 26).

In some embodiments, a single lysine is present in a reduced lysine chlorotoxin polypeptide as used in the present invention at a position corresponding to a site in chlorotoxin that does not contain a lysine residue (i.e., not at a position corresponding to any of positions 15, 23 or 27 of SEQ ID NO: 1). Thus, in some embodiments, a reduced lysine chlorotoxin polypeptide does not have any lysine residues where a lysine residue is normally present in chlorotoxin (i.e., positions corresponding to positions 15, 23, and 27 of SEQ ID NO: 1), but has a lysine residue at a position that does not correspond to any of positions 15, 23, and 27 of SEQ ID NO: 1.

In some embodiments in which a reduced lysine chlorotoxin polypeptide lacks lysine residues entirely, one terminus or both termini (i.e., the N- and/or C-terminus) of the reduced lysine chlorotoxin polypeptide can serve as a site for conjugation, e.g., to a therapeutic, targeting, or detectable (e.g., imagable) moiety, e.g., by chemical conjugation. In certain instances, availability of the terminus or termini can depend on the particular conjugation chemistry employed. In some embodiments in which a reduced lysine chlorotoxin polypeptide lacks lysine residues entirely, only the alpha amino group at the N-terminus is available as a site for conjugation.

In any instance in which a chlorotoxin polypeptide includes a reduced number of lysine residues, each of one or more lysine residues present in SEQ ID NO: 1 can be substituted or deleted as compared to SEQ ID NO: 1. Thus, in some embodiments, an amino acid is missing where a lysine residue is normally found in chlorotoxin. In some embodiments, one or more lysine residues normally found in chlorotoxin is/are replaced by another (non-lysine) amino acid residue and/or by an amino acid derivative. In other words, at least one amino acid residue in the reduced lysine chlorotoxin polypeptide corresponding to positions 15, 23 or 27 of SEQ ID NO: 1 is not a lysine.

In some embodiments residue of a chlorotoxin polypeptide (e.g., one or more lysine residues) can be substituted. In some embodiments, a residue of a chlorotoxin polypeptide can be substituted with a natural amino acid. In some embodiments a residue of a chlorotoxin polypeptide can be substituted with a non-natural amino acid. In some embodiments, substitution of a residue of a chlorotoxin polypeptide can be conservative. In some embodiments, substitution of a residue of a chlorotoxin polypeptide is not conservative.

In some embodiments, one or more lysine residues is/are replaced by arginine and/or alanine.

In certain embodiments in which more than one residue, e.g., more than one lysine residue, is substituted as compared to SEQ ID NO: 1, each substituted residue can be substituted by the same or different amino acid residue(s) or amino acid derivative(s). See, e.g., SEQ ID NOs: 17-22 for non-limiting examples in which the same amino acid residue has been used to replace lysine residues and SEQ ID NO: 23 for a non-limiting example in which different amino acid residues have been used to replace lysine residues.

Table 1 depicts the sequence of chlorotoxin and sequences of certain reduced lysine chlorotoxin polypeptides. Table 1 is not intended to be limiting. Table 1 illustrates certain exemplary reduced lysine chlorotoxin polypeptides that may, in some embodiments, be utilized in accordance with the present invention.

TABLE 1

Sequences of Chlorotoxin and of Exemplary Reduced Lysine Chlorotoxin Polypeptides

| SEQ ID NO: | Comment | Sequence (N-terminus to C-terminus) |
|---|---|---|
| | | Chlorotoxin |
| 1 | Full length chlorotoxin | MCMPC FTTDH QMARK CDDCC GGKGR GKCYG PQCLC R<br>     5       10      15      20      25      30      35 |
| | | Exemplary reduced lysine polypeptides |
| 2 | No lysines | MCMPC FTTDH QMARC DDCCG GGRGC YGPQC LCR<br>     5       10      15      20      25      30 |
| 3 | No lysines at positions 15, 23, or 27 of SEQ ID NO: 1; lysine at N-terminus | KMCMP CFTTD HQMAR CDDCC GGGRG CYGPQ CLCR<br>     5       10      15      20      25      30 |
| 4 | No lysines at positions 15, 23, or 27 of SEQ ID NO: 1; lysine at C-terminus | MCMPC FTTDH QMARC DDCCG GGRGC YGPQC LCRK<br>     5       10      15      20      25      30 |
| 5 | Lysines at positions 15, 23, and 27 of SEQ ID NO: 1 replaced by alanine | MCMPC FTTDH QMARA CDDCC GGAGR GACTG PQCLC R<br>     5       10      15      20      25      30      35 |

TABLE 1-continued

Sequences of Chlorotoxin and of Exemplary
Reduced Lysine Chlorotoxin Polypeptides

| SEQ ID NO: | Comment | Sequence (N-terminus to C-terminus) |
|---|---|---|
| 6 | Lysines at positions 15, 23, and 27 of SEQ ID NO: 1 replaced by arginine | MCMPC FTTDH QMARR CDDCC GGRGR GRCYG PQCLC R<br>         5    10    15    20    25    30    35 |
| 7 | Lysines at positions 15, 23, and 27 of SEQ ID NO: 1 replaced by alanine; lysine at N-terminus | KMCMP CFTTD HQMAR ACDDC CGGAG RGACY GPQCL CR<br>         5    10    15    20    25    30    35 |
| 8 | Lysines at positions 15, 23, and 27 of SEQ ID NO: 1 replaced by arginine; lysine at N-terminus | KMCMP CFTTD HQMAR RCDDC CGGRG RGACY GPQCL CR<br>         5    10    15    20    25    30    35 |
| 9 | Lysines at positions 15, 23, and 27 of SEQ ID NO: 1 replaced by alanine; lysine at C-terminus | MCMPC FTTDH QMARA CDDCC GGAGR GACYG PQCLC RK<br>         5    10    15    20    25    30    35 |
| 10 | Lysines at positions 15, 23, and 27 of SEQ ID NO: 1 replaced by arginine; lysine at C-terminus | MCMPC FTTDH QMARR CDDCC GGRGR GRCYG PQCLC RK<br>         5    10    15    20    25    30    35 |
| 11 | No lysine at position 15 of SEQ ID NO: 1 | MCMPC FTTDH QMARC DDCCG GKGRG KCYGP QCLCR<br>         5    10    15    20    25    30    35 |
| 12 | No lysine at position 23 of SEQ ID NO: 1 | MCMPC FTTDH QMARK CDDCC GGGRG KCYGP QCLCR<br>         5    10    15    20    25    30    35 |
| 13 | No lysine at position 27 of SEQ ID NO: 1 | MCMPC FTTDH QMARK CDDCC GGKGR GCYGP QCLCR<br>         5    10    15    20    25    30    35 |
| 14 | No lysines at positions 15 and 23 of SEQ ID NO: 1 | MCMPC FTTDH QMARC DDCCG GGRGK CYGPQ CLCR<br>         5    10    15    20    25    30 |
| 15 | No lysines at positions 15 and 27 of SEQ ID NO: 1 | MCMPC FTTDH QMARC DDCCG GKGRG CYGPQ CLCR<br>         5    10    15    20    25    30 |

TABLE 1-continued

Sequences of Chlorotoxin and of Exemplary
Reduced Lysine Chlorotoxin Polypeptides

| SEQ ID NO: | Comment | Sequence (N-terminus to C-terminus) |
|---|---|---|
| 16 | No lysines at positions 23 and 27 of SEQ ID NO: 1 | MCMPC FTTDH QMARK CDDCC GGGRG CYGPQ CLCR<br>     5        10      15      20      25      30 |
| 17 | Lysines at positions 15 and 23 of SEQ ID NO: 1 replaced by alanine | MCMPC FTTDH QMARA CDDCC GGAGR GKCYG PQCLC R<br>     5        10      15      20      25      30      35 |
| 18 | Lysines at positions 15 and 27 of SEQ ID NO: 1 replaced by alanine | MCMPC FTTDH QMARA CDDCC GGKGR GACYG PQCLC R<br>     5        10      15      20      25      30      35 |
| 19 | Lysines at positions 23 and 27 of SEQ ID NO: 1 replaced by alanine | MCMPC FTTDH QMARK CDDCC GGAGR GACYG PQCLC R<br>     5        10      15      20      25      30      35 |
| 20 | Lysines at positions 15 and 23 of SEQ ID NO: 1 replaced by arginine | MCMPC FTTDH QMARR CDDCC GGRGR GKCYG PQCLC R<br>     5        10      15      20      25      30      35 |
| 21 | Lysines at positions 15 and 27 of SEQ ID NO: 1 replaced by arginine | MCMPC FTTDH QMARR CDDCC GGKGR GKCYG PQCLC R<br>     5        10      15      20      25      30      35 |
| 22 | Lysines at positions 23 and 27 of SEQ ID NO: 1 replaced by arginine | MCMPC FTTDH QMARK CDDCC GGRGR GRCYG PQCLC R<br>     5        10      15      20      25      30      35 |
| 23 | Lysine at position 15 of SEQ ID NO: 1 replaced by arginine; lysine at position 27 of SEQ ID NO: 1 replaced by alanine | MCMPC FTTDH QMARR CDDCC GGKGR GACYG PQCLC R<br>     5        10      15      20      25      30      35 |
| 24 | No lysine at position 15 of SEQ ID NO: 1; lysines at positions 23 | MCMPC FTTDH QMARC DDCCG GAGRG ACYGP QCLCR<br>     5        10      15      20      25      30      35 |

TABLE 1-continued

Sequences of Chlorotoxin and of Exemplary
Reduced Lysine Chlorotoxin Polypeptides

| SEQ ID NO: | Comment | Sequence (N-terminus to C-terminus) |
|---|---|---|
|  | and 27 of SEQ ID NO: 1 replaced by arginine |  |
| 25 | No lysine at position 23 of SEQ ID NO: 1; lysines at positions 15 and 27 replaced by arginine | MCMPC FTTDH QMARA CDDCC GGGRG ACYGP QCLCR<br>    5      10     15     20     25     30     35 |
| 26 | No lysine at position 27 of SEQ ID NO: 1; lysines at positions 15 and 23 replaced by arginine | MCMPC FTTDH QMARR CDDCC GGRGR GCYGP QCLCR<br>    5      10     15     20     25     30     35 |

In some embodiments, a reduced lysine chlorotoxin polypeptide has an amino acid sequence that includes one or more than one lysine residues, e.g., three lysine residues, but nonetheless has a reduced number of lysines available for conjugation as compared with chlorotoxin (SEQ ID NO: 1). In some embodiments, one or more lysine residues in a reduced lysine chlorotoxin polypeptide provided herein is/are made unavailable as a site for conjugation though they are present in the chlorotoxin polypeptide. For example, one or more lysine residue(s) can be covalently or non-covalently associated with a pendant moiety such that the one or more lysine residue(s) is/are blocked from participating in a chemical conjugation reaction, leaving fewer than 3, 2 or 1 (i.e., "reduced" lysine) lysine residue(s) available as a site for conjugation. Non-limiting examples of pendant moieties that can be covalently associated to lysine residues that could be employed in this manner include pegylation (i.e., association with a polyethylene glycol polymer), methylation (including di- and tri-methylation), and association with other alkyl group(s). In certain embodiments, one or more lysine residues is/are associated with a pendant moiety at the epsilon $NH_2$ group. For example, if a given R group (e.g., butyl, propyl, or ethyl group) is used to covalently associate a pendant moiety with a lysine residue, the epsilon $NH_2$ group can be modified to an $NR_2$ or $NR_3$ group.

Table 2 presents some non-limiting examples of schemes that produce reduced lysine chlorotoxin polypeptides.

TABLE 2

Exemplary modification schemes

| SEQ ID NO: | Core sequence (N-terminus to C-terminus) | Position(s) of lysine residue(s) |
|---|---|---|
| 1 | MCMPC FTTDH QMARK CDDCC GGKGR GKCYG PQCLC R<br>    5      10     15     20     25     30     35 | 15, 23 and 27<br>15 and 23<br>15 and 27<br>23 and 27 |
| 11 | MCMPC FTTDH QMARC DDCCG GKGRG KCYGP QCLCR<br>    5      10     15     20     25     30     35 | 22 and 26<br>22<br>26 |
| 12 | MCMPC FTTDH QMARK CDDCC GGGRG KCYGP QCLCR<br>    5      10     15     20     25     30     35 | 15 and 26<br>15<br>26 |
| 13 | MCMPC FTTDH QMARK CDDCC GGKGR GCYGP QCLCR<br>    5      10     15     20     25     30     35 | 15 and 23<br>15<br>23 |

TABLE 2-continued

Exemplary modification schemes

| SEQ ID NO: | Core sequence (N-terminus to C-terminus) | Position(s) of lysine residue(s) |
|---|---|---|
| 27 (lysine added to N-term) | KMCMP CFTTD HQMAR KCDDC CGGKG RGKCY GPQCL CR<br>5    10    15    20    25    30    35 | 16, 24 and 28 |
| 28 (lysine added to C-term) | MCMPC FTTDH QMARK CDDCC GGKGR GKCYG PQCLC RK<br>5    10    15    20    25    30    35 | 15, 23 and 27 |

In certain embodiments, blocking of particular lysine residue is achieved by incorporating a blocked lysine (in which sites that would otherwise be available for conjugation are already blocked) during the appropriate step during synthesis of the reduced lysine chlorotoxin polypeptide. Blocked lysine residues are readily available commercially and can be synthesized by routine methods known in the art. Non-limiting examples of blocked lysines that can be used in this manner include, but are not limited to, di-substituted lysine or tri-substituted lysines (e.g., N,N—$R_2$-lysine or N,N,N—$R_3$-lysine, where R is the blocking group) and lysines with short PEG molecules associated with them. R can be any group that when covalently associated with the lysine would serve to block the lysine residue from participating in a chemical conjugation reaction. For example, alkyl groups (e.g., butyl, methyl, and ethyl) can serve as blocking groups. For example, N,N-dimethyl-lysine and/or N,N,N-trimethyl-lysine be used during synthesis.

In certain embodiments, one terminus or both termini (i.e., the N- and/or C-terminus) of the reduced lysine chlorotoxin polypeptide is/are blocked so as to prevent the terminus/termini from participating in a chemical conjugation reaction. For example, in some embodiments, a conjugation chemistry is used in which at least one terminus would participate, or would be available to participate, in the conjugation reaction if it were not blocked. A variety of methods of blocking N- and/or C-termini of polypeptides are known in the art, including, but not limited to, covalent addition of alkyl groups (e.g., methylation) at amines.

Methods of synthesizing reduced lysine chlorotoxin polypeptides as described herein are known in the art. In some peptide synthesis methods, an amino group of one amino acid (or amino acid derivative) is linked to a carboxyl group of another amino acid (or amino acid derivative) that has been activated by reacting it with a reagent such as dicyclohexylcarbodiimide (DCC). When the free amino group attacks the activated carboxyl group, a peptide bond is formed and dicyclohexylurea is released. In such methods, other potentially reactive groups (such as the ca-amino group of the N-terminal amino acid or amino acid derivative and the carboxyl group of the C-terminal amino acid or amino acid derivative) can be blocked ("protected") from participating in the chemical reaction. Thus, only particular active groups react such that the desired product is formed. Blocking groups useful for this purpose include for example tertbutoxycarbonyl groups (t-Boc) and benzoyloxycarbonyl groups to protect amine groups; and simple esters (such as methyl and ethyl groups) and benzyl esters to protect carboxyl groups. Blocking groups can typically be subsequently removed with a treatment that leaves peptide bonds intact (for example, treatment with dilute acid). This process of protecting reacting groups that should not react, coupling to form a peptide bond, and de-protecting reactive groups can be repeated. A peptide can be synthesized by sequentially adding amino acids to a growing peptide chain. Both liquid-phase and solid phase peptide synthesis methods are suitable for use in accordance with the invention. In solid-phase peptide synthesis methods, the growing peptide chain is typically linked to an insoluble matrix (such as, for example, polystyrene beads) by linking the carboxyterminal amino acid to the matrix. At the end of synthesis, the peptide can be released from the matrix using a cleaving reagent that does not disrupt peptide bonds, such as hydrofluoric acid (HF). Protecting groups are also typically removed at this time. Automated, high throughput, and/or parallel peptide synthesis methods can also be used in accordance with the invention. For more information about peptide synthesis methods, see, e.g., Merrifield (1969) "Solid-phase peptide synthesis," *Adv Enzymol Relat Areas Mol Biol,* 32:221-96; Fridkin et al. (1974) *Annu Rev Biochem.,* 43 (0):419-43; Merrifield (1997) "Concept and Early Development of Solid Phase Peptide Synthesis," *Methods in Enzymology,* 289:3-13; Sabatino et al. (2009) "Advances in automatic, manual and microwave-assisted solid-phase peptide synthesis," *Curr Opin Drug Discov Devel,* 11(6):762-70, the entire contents of each of which are herein incorporated by reference.

In some embodiments, association of pendant moieties to block lysine residues are used in combination with other means as described herein (e.g., replacement of a lysine residue with another amino acid or amino acid derivative and/or lack of a lysine residue where one is normally found in chlorotoxin).

In some embodiments, the protecting group in the N-terminus is not removed at the end of synthesis. Leaving the protecting group on may, for example, serve to generate a reduced lysine chlorotoxin polypeptide with a blocked N-terminus, thus limiting the sites available for conjugation in a particular chemical conjugation scheme.

In various of embodiments, a chlorotoxin polypeptide as described herein includes a C-terminal arginine residue. In various embodiments, the C-terminal residue of a chlorotoxin polypeptide as described herein is not amidated. In various embodiments, the C-terminal residue of a chlorotoxin polypeptide as described herein is carboxylated. In various embodiments, the C-terminal residue of a chlorotoxin polypeptide as described herein is an arginine that is not amidated. In various embodiments, the C-terminal residue of a chlorotoxin polypeptide as described herein is an arginine residue that is carboxylated.

Chlorotoxin Polypeptide Fragments In some embodiments, a chlorotoxin polypeptide fragment for use in accordance with the present invention is chlorotoxin polypeptides having fewer amino acid residues than SEQ ID NO: 1. In some embodiments, a chlorotoxin polypeptide fragment may be or comprise a polypeptide having a length of at least 5 to about 25 amino acids and that includes at least 5 consecutive amino acids having at least at least 45% sequence identity with SEQ ID NO: 1. Thus, a chlorotoxin polypeptide fragment can include 5, 6, 7, 8, 9, 10, 11, 12, 13, 14, 15, 16, 17, 18, 19, 20, 21, 22, 23, 24, or 25 amino acids having at least at least 45% sequence identity with SEQ ID NO: 1, e.g., at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% overall sequence identity with SEQ ID NO: 1. In certain embodiments, a chlorotoxin polypeptide fragment as described herein includes a C-terminal arginine residue. In certain embodiments, the C-terminal residue of a chlorotoxin polypeptide fragment as described herein is not amidated. In certain embodiments, the C-terminal residue of a chlorotoxin polypeptide fragment as described herein is carboxylated. In certain embodiments, the C-terminal residue of a chlorotoxin polypeptide fragment as described herein is an arginine that is not amidated. In certain embodiments, the C-terminal residue of a chlorotoxin polypeptide fragment as described herein is an arginine residue that is carboxylated.

In certain instances, a chlorotoxin polypeptide fragment can include 5 to 20 amino acid residues, 5 to 18 amino acid residues, 5 to 16 amino acid residues, 5 to 14 amino acid residues, 5 to 12 amino acid residues, 5 to 10 amino acid residues, 5 to 8 amino acid residues, 6 to 20 amino acid residues, 6 to 18 amino acid residues, 6 to 16 amino acid residues, 6 to 14 amino acid residues, 6 to 12 amino acid residues, 6 to 10 amino acid residues, 6 to 8 amino acid residues, 8 to 20 amino acid residues, 8 to 18 amino acid residues, 8 to 16 amino acid residues, 8 to 14 amino acid residues, 8 to 12 amino acid residues, 8 to 10 amino acid residues, 10 to 20 amino acid residues, 10 to 18 amino acid residues, 10 to 16 amino acid residues, 10 to 14 amino acid residues, 10 to 12 amino acid residues, 12 to 20 amino acid residues, 12 to 16 amino acid residues, 12 to 14 amino acid residues, 14 to 20 amino acid residues, 14 to 18 amino acid residues, or 14 to 16 amino acid residues having at least at least 45% sequence identity with SEQ ID NO: 1, e.g., at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% overall sequence identity with SEQ ID NO: 1. Thus, in certain embodiments, a chlorotoxin polypeptide fragment can be identical with SEQ ID NO: 1 at positions corresponding to 5, 6, 7, 8, 9, 10, 11, 12, 13, 14, 15, 16, 17, 18, 19, 20, 21, 22, 23, 24, or 25 positions of SEQ ID NO: 1. In certain embodiments, a chlorotoxin polypeptide fragment as described herein includes a C-terminal arginine residue. In certain embodiments, the C-terminal residue of a chlorotoxin polypeptide fragment as described herein is not amidated. In certain embodiments, the C-terminal residue of a chlorotoxin polypeptide fragment as described herein is carboxylated. In certain embodiments, the C-terminal residue of a chlorotoxin polypeptide fragment as described herein is an arginine that is not amidated. In certain embodiments, the C-terminal residue of a chlorotoxin polypeptide fragment as described herein is an arginine residue that is carboxylated.

In certain instances, a chlorotoxin polypeptide fragment is a peptide having a length of between five and twenty-five amino acid residues, inclusive, e.g., 5, 6, 7, 8, 9, 10, 11, 12, 13, 14, 15, 16, 17, 18, 19, 20, 21, 22, 23, 24, or 25 amino acid residues. In certain instances, a chlorotoxin polypeptide fragment is a peptide having a length of 5 to 20 amino acid residues, 5 to 18 amino acid residues, 5 to 16 amino acid residues, 5 to 14 amino acid residues, 5 to 12 amino acid residues, 5 to 10 amino acid residues, 5 to 8 amino acid residues, 6 to 20 amino acid residues, 6 to 18 amino acid residues, 6 to 16 amino acid residues, 6 to 14 amino acid residues, 6 to 12 amino acid residues, 6 to 10 amino acid residues, 6 to 8 amino acid residues, 8 to 20 amino acid residues, 8 to 18 amino acid residues, 8 to 16 amino acid residues, 8 to 14 amino acid residues, 8 to 12 amino acid residues, 8 to 10 amino acid residues, 10 to 20 amino acid residues, 10 to 18 amino acid residues, 10 to 16 amino acid residues, 10 to 14 amino acid residues, 10 to 12 amino acid residues, 12 to 20 amino acid residues, 12 to 16 amino acid residues, 12 to 14 amino acid residues, 14 to 20 amino acid residues, 14 to 18 amino acid residues, or 14 to 16 amino acid residues.

In some embodiments, a chlorotoxin polypeptide fragment is a fragment of a reduced lysine chlorotoxin polypeptide and/or otherwise contains fewer lysine residues than an appropriate reference chlorotoxin polypeptide or chlorotoxin polypeptide fragment; such a fragment may be referred to herein as a "Reduced Lysine Ctx Ppt Fragment."

TABLE 3

Example Chlorotoxin polypeptide fragments

| SEQ ID NO: | Sequence |
|---|---|
| 30 | CMPCFTTDHQMARKCDDCCGGKGRGKCYGPQCLCR |
| 31 | MPCFTTDHQMARKCDDCCGGKGRGKCYGPQCLCR |
| 32 | PCFTTDHQMARKCDDCCGGKGRGKCYGPQCLCR |
| 33 | CFTTDHQMARKCDDCCGGKGRGKCYGPQCLCR |
| 34 | FTTDHQMARKCDDCCGGKGRGKCYGPQCLCR |
| 35 | TTDHQMARKCDDCCGGKGRGKCYGPQCLCR |
| 36 | TDHQMARKCDDCCGGKGRGKCYGPQCLCR |
| 37 | DHQMARKCDDCCGGKGRGKCYGPQCLCR |
| 38 | HQMARKCDDCCGGKGRGKCYGPQCLCR |
| 39 | QMARKCDDCCGGKGRGKCYGPQCLCR |
| 40 | MARKCDDCCGGKGRGKCYGPQCLCR |
| 41 | ARKCDDCCGGKGRGKCYGPQCLCR |
| 42 | RKCDDCCGGKGRGKCYGPQCLCR |
| 43 | KCDDCCGGKGRGKCYGPQCLCR |
| 44 | CDDCCGGKGRGKCYGPQCLCR |
| 45 | DDCCGGKGRGKCYGPQCLCR |
| 46 | DCCGGKGRGKCYGPQCLCR |

TABLE 3-continued

Example Chlorotoxin polypeptide fragments

| SEQ ID NO: | Sequence |
|---|---|
| 47 | CCGGKGRGKCYGPQCLCR |
| 48 | CGGKGRGKCYGPQCLCR |
| 49 | GGKGRGKCYGPQCLCR |
| 50 | GKGRGKCYGPQCLCR |
| 51 | KGRGKCYGPQCLCR |
| 52 | GRGKCYGPQCLCR |
| 53 | RGKCYGPQCLCR |
| 54 | GKCYGPQCLCR |
| 55 | KCYGPQCLCR |
| 56 | CYGPQCLCR |
| 57 | YGPQCLCR |
| 58 | GPQCLCR |
| 59 | PQCLCR |
| 60 | QCLCR |
| 61 | MCMPCFTTDHQMARKCDDCCGGKGR |
| 62 | CMPCFTTDHQMARKCDDCCGGKGR |
| 63 | MPCFTTDHQMARKCDDCCGGKGR |
| 64 | PCFTTDHQMARKCDDCCGGKGR |
| 65 | CFTTDHQMARKCDDCCGGKGR |
| 66 | FTTDHQMARKCDDCCGGKGR |
| 67 | TTDHQMARKCDDCCGGKGR |
| 68 | TDHQMARKCDDCCGGKGR |
| 69 | DHQMARKCDDCCGGKGR |
| 70 | HQMARKCDDCCGGKGR |
| 71 | QMARKCDDCCGGKGR |
| 72 | MARKCDDCCGGKGR |
| 73 | ARKCDDCCGGKGR |
| 74 | RKCDDCCGGKGR |
| 75 | KCDDCCGGKGR |
| 76 | CDDCCGGKGR |
| 77 | DDCCGGKGR |
| 78 | DCCGGKGR |
| 79 | CCGGKGR |
| 80 | CGGKGR |
| 81 | MCMPCFTTDHQMAR |
| 82 | CMPCFTTDHQMAR |
| 83 | MPCFTTDHQMAR |
| 84 | PCFTTDHQMAR |
| 85 | CFTTDHQMAR |
| 86 | FTTDHQMAR |
| 87 | TTDHQMAR |
| 88 | TDHQMAR |
| 89 | DHQMAR |
| 90 | HQMAR |
| 91 | CMPCFTTDHQMARACDDCCGGAGRGKCYGPQCLCR |
| 92 | MPCFTTDHQMARACDDCCGGAGRGKCYGPQCLCR |
| 93 | PCFTTDHQMARACDDCCGGAGRGKCYGPQCLCR |
| 94 | CFTTDHQMARACDDCCGGAGRGKCYGPQCLCR |
| 95 | FTTDHQMARACDDCCGGAGRGKCYGPQCLCR |
| 96 | TTDHQMARACDDCCGGAGRGKCYGPQCLCR |
| 97 | TDHQMARACDDCCGGAGRGKCYGPQCLCR |
| 98 | DHQMARACDDCCGGAGRGKCYGPQCLCR |
| 99 | HQMARACDDCCGGAGRGKCYGPQCLCR |
| 100 | QMARACDDCCGGAGRGKCYGPQCLCR |
| 101 | MARACDDCCGGAGRGKCYGPQCLCR |
| 102 | ARACDDCCGGAGRGKCYGPQCLCR |
| 103 | RACDDCCGGAGRGKCYGPQCLCR |
| 104 | KCDDCCGGAGRGKCYGPQCLCR |
| 105 | CDDCCGGAGRGKCYGPQCLCR |
| 106 | DDCCGGAGRGKCYGPQCLCR |
| 107 | DCCGGAGRGKCYGPQCLCR |
| 108 | CCGGAGRGKCYGPQCLCR |
| 109 | CGGAGRGKCYGPQCLCR |
| 110 | GGAGRGKCYGPQCLCR |
| 111 | GAGRGKCYGPQCLCR |
| 112 | KGRGKCYGPQCLCR |
| 113 | GRGKCYGPQCLCR |
| 114 | RGKCYGPQCLCR |
| 115 | GKCYGPQCLCR |
| 116 | KCYGPQCLCR |
| 117 | CYGPQCLCR |
| 118 | YGPQCLCR |
| 119 | GPQCLCR |
| 120 | PQCLCR |

TABLE 3-continued

Example Chlorotoxin polypeptide fragments

| SEQ ID NO: | Sequence |
|---|---|
| 121 | QCLCR |
| 122 | MCMPCFTTDHQMARACDDCCGGAGR |
| 123 | CMPCFTTDHQMARACDDCCGGAGR |
| 124 | MPCFTTDHQMARACDDCCGGAGR |
| 125 | PCFTTDHQMARACDDCCGGAGR |
| 126 | CFTTDHQMARACDDCCGGAGR |
| 127 | FTTDHQMARACDDCCGGAGR |
| 128 | TTDHQMARACDDCCGGAGR |
| 129 | TDHQMARACDDCCGGAGR |
| 130 | DHQMARACDDCCGGAGR |
| 131 | HQMARACDDCCGGAGR |
| 132 | QMARACDDCCGGAGR |
| 133 | MARACDDCCGGAGR |
| 134 | ARACDDCCGGAGR |
| 135 | RACDDCCGGAGR |
| 136 | KCDDCCGGAGR |
| 137 | CDDCCGGAGR |
| 138 | DDCCGGAGR |
| 139 | DCCGGAGR |
| 140 | CCGGAGR |
| 141 | CGGAGR |
| 142 | MCMPCFTTDHQMAR |
| 143 | CMPCFTTDHQMAR |
| 144 | MPCFTTDHQMAR |
| 145 | PCFTTDHQMAR |
| 146 | CFTTDHQMAR |
| 147 | FTTDHQMAR |
| 148 | TTDHQMAR |
| 149 | TDHQMAR |
| 150 | DHQMAR |
| 151 | HQMAR |

Payload-Containing Agents

In some embodiments, a chlorotoxin agent for use in accordance with the present invention may be or comprise a chlorotoxin polypeptide (including a chlorotoxin fragment, e.g., as described herein) in association with a payload moiety such as a detectable, therapeutic, or targeting moiety. In some embodiments, a chlorotoxin polypeptide is associated with a plurality of moieties. In some embodiments, such association is or comprises a covalent bond, so that the agent may be or comprise a conjugate.

A. Payload

As is noted herein, in certain embodiments, a chlorotoxin agent for use in the present invention includes one or more non-chlorotoxin moieties (i.e., a payload), which payload can include, e.g., detectable, therapeutic, and/or targeting moieties. Any of a variety of such moieties can be employed. In certain embodiments, a playload includes an agent. In certain embodiments a payload includes an agent and a moiety, modification, or other feature for conjugation of payload to chlorotoxin agent.

1. Therapeutic Moieties

In certain embodiments, chlorotoxin agents for use in the present invention include one or more therapeutic entities or moieties, as described below. In certain embodiments, a chlorotoxin agent as described in one or more of WO 2011/097533 (see also, e.g., U.S. Pat. No. 9,018,347) and WO 2011/142858 (see also, e.g., US 2013/0195760), each of which is incorporated by reference in its entirety, is utilized in accordance with the present invention.

a. Anti-Cancer Agents

In various embodiments, a therapeutic entity or moiety for use in the present invention is or includes an anti-cancer agent. Suitable anti-cancer agents include any of a large variety of substances, molecules, compounds, agents or factors that are directly or indirectly toxic or detrimental to cancer cells, including, for example, cytotoxic agents. Anti-cancer agents include any of a wide variety of agents known to treat cancer in a subject, reduce the size or amount of cancer in a subject, inhibit the growth of cancer in a subject, reduce the occurrence or likelihood of cancer in a subject, prevent cancer in a subject, inhibit metastasis of cancer in a subject, reduce metastasis of cancer in a subject, prevent metastasis of cancer in a subject, or improve the prognosis of a subject that has cancer. Anti-cancer agents suitable for use in the practice of the invention can be synthetic or natural. Anticancer agents can include a single molecule or a complex, set, series, or regimen of different molecules.

Suitable anti-cancer agents can belong to any of various classes of compounds including, but not limited to, small molecules, peptides, saccharides, steroids, antibodies, fusion proteins, antisense polynucleotides, ribozymes, small interfering RNAs, peptidomimetics, and the like. Similarly, suitable anti-cancer agents can be found among any of a variety of classes of anti-cancer agents including, but not limited to, alkylating agents, anti-metabolite drugs, anti-mitotic antibiotics, alkaloidal anti-cancer agents, hormones and anti-hormones, interferons, nonsteroidal anti-inflammatory drugs, and various other anti-cancer agents.

In certain instances, particularly suitable anti-cancer agents are agents that cause undesirable side effects due to poor selectivity/specificity for cancer cells; agents that undergo no or poor cellular uptake and/or retention; agents that are associated with cellular drug resistance; and agents that cannot be readily formulated for administration to cancer patients due to poor water solubility, aggregation, and the like.

In certain instances, the therapeutic moiety can be a member of the group including radioisotopes, enzymes, prodrug activating enzymes, radiosensitizers, nucleic acid molecules, interfering RNAs, superantigens, anti-angiogenic agents, alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. In certain embodiments, the nucleic acid molecules are or include DNA, enzymatic RNA, RNA:DNA hybrid, triplexed DNA, ssRNA, dsRNA, tRNA, mRNA, rRNA, or any combination thereof.

Examples of suitable anti-cancer agents that can be used in or with chlorotoxin agents for use in the present invention are described in more detail below. In certain embodiments, a chlorotoxin conjugate as described in one or more of WO 2011/097533 (see also, e.g., U.S. Pat. No. 9,018,347) and WO 2011/142858 (see also, e.g., US 2013/0195760), each of which is incorporated by reference in its entirety, is utilized in accordance with the present invention.

i. Poorly Water Soluble Anti-Cancer Agents

In certain embodiments, an anti-cancer agent within an inventive chlorotoxin agent is a poorly water soluble compound. As will be recognized by one skilled in the art, a wide variety of poorly water soluble anti-cancer agents are suitable for use in the present invention.

For example, an anti-cancer agent can be selected among taxanes, which are recognized as effective agents in the treatment of many solid tumors that are refractory to other anti-neoplastic agents. Two currently approved taxanes are paclitaxel (TAXOL™) and docetaxel (TAXOTERE™). Paclitaxel, docetaxel, and other taxanes act by enhancing the polymerization of tubulin, an essential protein in the formation of spindle microtubules. Polymerization of tubulin results in the formation of very stable, nonfunctional tubules, which inhibits cell replication and leads to cell death.

Paclitaxel is very poorly water soluble, and therefore, cannot be practically formulated with water for intravenous administration. Some formulations of TAXOL™ for injection or intravenous infusion have been developed using CREMOPHOR EL™ (polyoxyethylated castor oil) as a drug carrier. However, CREMOPHOREL™ is itself toxic, and is considered to be, at least in part, responsible for the hypersensitivity reactions (severe skin rashes, hives, flushing, dyspnea, tacchycardia and others) associated with administration of such preparations. To avoid such side effects, premedication is often prescribed along with paclitaxel formulations containing CREMOPHOR™. Docetaxel, which is an analog of paclitaxel, is like paclitaxel poorly soluble in water. The currently most preferred solvent used to dissolve docetaxel for pharmaceutical use is polysorbate 80 (TWEEN 80). In addition to causing hypersensitivity reactions in patients, TWEEN 80 cannot be used with PVC delivery apparatus, because of its tendency to leach diethylhexyl phthalate, which is highly toxic.

In certain embodiments, a chlorotoxin agent according to the present invention that includes a taxane and a chlorotoxin polypeptide can be used as an improved delivery method to avoids the use of solvents and carriers that induce adverse reactions in patients.

In some embodiments, an anti-cancer agent of a chlorotoxin agent can belong to the enediyne family of antibiotics. As a family, the enediyne antibiotics are particularly potent anti-cancer agents. Some members are 1000 times more potent than adriamycin, one of the most effective, clinically used anti-cancer antibiotics (Y. S. Zhen et al., *J. Antibiot.*, 1989, 42: 1294-1298). For example, an anti-cancer agent within a chlorotoxin agent can be a member of the enediyne family of calicheamicins. Originally isolated from a broth extract of the soil microorganism *Micromonospora echinospora* ssp. calichensis, the calicheamicins were detected in a screen for potent DNA damaging agents (M. D. Lee et al., *J. Am. Chem. Soc.,* 1987, 109: 3464-3466; M. D. Lee et al., *J. Am. Chem. Soc.,* 1987, 109: 3466-3468; W. M. Maiese et al., *J. Antibiot.,* 1989, 42: 558-563; M. D. Lee et al., *J. Antibiot.,* 1989, 42: 1070-1087).

Calicheamicins are characterized by a complex, rigid bicyclic enediyne allylic trisulfide core structure linked through glycosyl bonds to an oligosaccharide chain. The oligosaccharide portion contains a number of substituted sugar derivatives, and a substituted tetrahydropyran ring. The enediyne containing core (or aglycone) and carbohydrate portions of calicheamicins have been reported to carry out different roles in the biological activity of these molecules. It is generally believed that the core portion cleaves DNA, whereas the oligosaccharide portion of the calicheamicins serves as a recognition and delivery system and guides the drug to a double-stranded DNA minor groove in which the drug anchors itself ("Enediyne Antibiotics as Antitumor Agents," Doyle and Borders, 1995, Marcel-Dekker: New York). Double-stranded DNA cleavage is a type of damage that is usually non-repairable or non-easily repairable for the cell and is most often lethal.

Because of their chemical and biological properties, several analogues of the calicheamicins have been tested in preclinical models as potential anti-cancer agents. Their development as single agent therapies has not been pursued because of delayed toxicities that limit the therapeutic dose range for treatment. However, their potency makes them particularly useful for targeted chemotherapy.

Other examples of suitable poorly water soluble anti-cancer agents include tamoxifen and BCNU. Tamoxifen has been used with varying degrees of success to treat, among other things, a variety of estrogen receptor positive carcinomas such as breast cancer, endometrial carcinoma, prostate carcinoma, ovarian carcinoma, renal carcinoma, melanoma, colorectal tumors, desmoid tumors, pancreatic carcinoma, and pituitary tumors. In addition to being limited by poor water solubility, chemotherapy using tamoxifen can cause side effects such as cellular drug resistance. BCNU (1,3-bis(2-chloroethyl)-1-nitrosourea) is well known for its anti-cancer properties and, since 1972, it has been charted by the National Cancer Institute for use against brain cancer (e.g., brain tumors), colon cancer, Hodgkin's Disease, lung cancer and multiple myeloma. However, the efficient use of this anti-cancer drug is also compromised by its low solubility.

ii. Anti-Cancer Agents Associated with Drug Resistance

In certain embodiments described herein, a chlorotoxin agent includes an anti-cancer agent associated with drug resistance. As used herein, the term "anti-cancer agent associated with drug resistance" refers to any chemotherapeutic to which cancer cells are or can become resistant. As already mentioned herein, resistance to an anti-cancer agent can be due to many factors and can operate by different mechanisms. Administration of a chlorotoxin agent for use in the present invention including a chlorotoxin polypeptide and an anti-cancer agent associated with drug resistance can enhance cellular uptake of the anti-cancer agent and carry it into cancer cells, e.g., resistant tumor cells.

Any of a wide variety of anti-cancer agents associated with drug resistance are suitable for use in the present invention. For example, the anti-cancer agent associated with drug resistance can be methotrexate. Methotrexate, a widely used cancer drug, is an analogue of folic acid and blocks important steps in the synthesis of tetrahydrofolic acid which itself is a critical source of compounds utilized in the synthesis of thymidylate, a building block that is specific and therefore especially critical for DNA synthesis. Methotrexate-induced drug resistance is linked to a deficiency in cellular uptake of that drug.

Other examples of suitable anti-cancer agents include purine and pyrimidine analogs that are associated with drug resistance due to inadequate intracellular activation of the drug through loss of enzymatic activity. An example of such a purine analog is 6-mercaptopurine (6-MP). A common cause of cancer cell resistance to 6-MP is the loss of the enzyme hypoxanthine guanine phosphoribosyl transferase (HGPRT) which activates 6-MP into its corresponding nucleotide, 6-mercaptophosphoribosylpurine (6-MPRP), the lethal form of the drug. Without being held to theory, it is postulated that resistance could be overcome if 6-MPRP itself could be introduced into the cell. Although this compound is commercially available, it has not yet been used therapeutically in cancer treatment because it is not adequately transported into living cells. Association of 6-MPRP to a reduced lysine chlorotoxin polypeptide according to the present invention would dramatically increase its ability to cross the cell membrane. Thioguanine is another example of anti-cancer agent that is associated with drug resistance due to lack of the enzyme HGPRT.

Examples of pyrimidine analogs that are associated with drug resistance due to inadequate intracellular activation include cytosine arabinoside and adenosine arabinoside which are activated by the enzyme deoxycytidine kinase (DOCK) to the lethal forms cytosine diphosphate and adenosine diphosphate, respectively. A chlorotoxin polypeptide can be coupled to the activated form of such pyrimidine analogs to enhance their cellular uptake and overcome cellular drug resistance.

Other examples of anti-cancer agents associated with drug resistance include, but are not limited to, 5-fluorouracil, fluorodeoxyuridine, cytosine, arabinoside, vinblastin, vincristin, daunorubicin, doxorubicin, actinomycin, and bleomycin.

iii. Other Anti-Cancer Agents

In some embodiments, an anti-cancer agent is selected from the group consisting of alkylating drugs (e.g., mechlorethamine, chlorambucil, cyclophosphamide, melphalan, ifosfamide), antimetabolites (e.g., methotrexate), purine antagonists and pyrimidine antagonists (e.g., 6-mercaptopurine, 5-fluorouracil, cytarabile, gemcitabine), spindle poisons (e.g., vinblastine, vincristine, vinorelbine, paclitaxel), podophyllotoxins (e.g., etoposide, irinotecan, topotecan), antibiotics (e.g., doxorubicin, bleomycin, mitomycin), nitrosoureas (e.g., carmustine, lomustine), inorganic ions (e.g., cisplatin, carboplatin), enzymes (e.g., asparaginase), and hormones (e.g., tamoxifen, leuprolide, flutamide, and megestrol), to name a few. For a more comprehensive discussion of updated cancer therapies see <www.cancer.gov/about-cancer/treatment/drugs> and The Merck Manual, Seventeenth Ed. 1999, the entire contents of which are hereby incorporated by reference.

iv. Nucleic Acid Agents

In certain embodiments, a chlorotoxin agent include a nucleic acid agent.

Numerous cancers and tumors have been shown to be associated with varying degrees of genetic impairment, such as point mutations, gene deletions, or duplications. Many new strategies for the treatment of cancer, such as those that have been termed "antisense," "antigene" and "RNA interference" have been developed to modulate the expression of genes (A. Kalota et al., *Cancer Biol. Ther.*, 2004, 3: 4-12; Y. Nakata et al., *Crit. Rev. Eukaryot. Gene Expr.*, 2005, 15: 163-182; V. Wacheck and U. Zangmeister-Wittke, *Crit. Rev. Oncol. Hematol.*, 2006, 59: 65-73; A. Kolata et al., *Handb. Exp. Pharmacol.*, 2006, 173: 173-196). These approaches utilize, for example, antisense nucleic acids, ribozymes, triplex agents, or short interfering RNAs (siRNAs) to block the transcription or translation of a specific mRNA or DNA of a target gene, either by masking that mRNA with an antisense nucleic acid or DNA with a triplex agent, by cleaving the nucleotide sequence with a ribozyme, or by destruction of the mRNA, through a mechanism of RNA-interference. In many of these strategies, mainly oligonucleotides are used as active agents, although small molecules and other structures have also been applied. While oligonucleotide-based strategies for modulating gene expression have a huge potential for the treatment of some cancers, pharmacological applications of oligonucleotides have been hindered mainly by ineffective delivery of these compounds to their sites of action within cancer cells. (P. Herdewijn et al., *Antisense Nucleic Acids Drug Dev.*, 2000, 10: 297-310; Y. Shoji and H. Nakashima, Curr. Charm. Des., 2004, 10: 785-796; A. W Tong et al., *Curr. Opin. Mol. Ther.*, 2005, 7: 114-124).

In certain embodiments, provided chlorotoxin agents include a chlorotoxin polypeptide and a nucleic acid molecule that is useful as a therapeutic (e.g., anti-cancer) agent. A variety of chemical types and structural forms of nucleic acid can be suitable for such strategies. These include, by way of non-limiting example, DNA, including single-stranded (ssDNA) and double-stranded (dsDNA); RNA, including, but not limited to ssRNA, dsRNA, tRNA, mRNA, rRNA, enzymatic RNA; RNA:DNA hybrids, triplexed DNA (e.g., dsDNA in association with a short oligonucleotide), and the like.

In some embodiments, the nucleic acid agent is between about 5 and 2000 nucleotides long. In some embodiments, the nucleic acid agent is at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. In some embodiments, the nucleic acid agent is less than about 2000, 1900, 1800, 1700, 1600, 1500, 1400, 1300, 1200, 1100, 1000, 900, 800, 700, 600, 500, 450, 400, 350, 300, 250, 200, 150, 100, 50, 45, 40, 35, 30, 25, 20 or fewer nucleotides long.

In some embodiments, the nucleic acid agent includes a promoter and/or other sequences that regulate transcription. In some embodiments, the nucleic acid agent includes an origin of replication and/or other sequences that regulate replication. In some embodiments, the nucleic acid agent does not include a promoter and/or an origin of replication.

Nucleic acid anti-cancer agents suitable for use in the practice of an invention described herein include those agents that target genes associated with tumorigenesis and cell growth or cell transformation (e.g., proto-oncogenes, which code for proteins that stimulate cell division), angiogenic/anti-angiogenic genes, cancer suppressor genes (which code for proteins that suppress cell division), genes encoding proteins associated with cancer growth and/or cancer migration, and suicide genes (which induce apoptosis or other forms of cell death), especially suicide genes that are most active in rapidly dividing cells.

Examples of genes associated with tumorigenesis and/or cell transformation include MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed genes such as multidrug resistance genes; cyclins; beta-Catenin; telomerase genes; c-myc, n-myc, Bcl-2, Erb-B1 and Erb-B2; and mutated genes such as Ras, Mos, Raf, and Met. Examples of cancer suppressor genes include, but are not limited to, p53, p21, RB 1, WT 1, NF 1, VHL, APC, DAP kinase, p16, ARF, Neurofibromin, and PTEN. Examples of genes that can be targeted by nucleic acid agents useful in anti-cancer therapy include genes encoding proteins associated with cancer migration such as integrins, selectins, and metalloproteinases; anti-angiogenic genes encoding proteins that promote formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor (α-FGF and β-FGF), insulin-like growth factor (e.g., IGF-1 and IGF-2), Platelet-derived growth factor (PDGF), tumor necrosis factor (TNF), Transforming Growth Factor (e.g., TGF-α and TGF-β), Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like. As will be recognized by one skilled in the art, the foregoing examples are not exclusive.

Nucleic acid agents suitable for use in the invention can have any of a variety of uses including, for example, use as anti-cancer or other therapeutic moieties, probes, primers, etc. Nucleic acid agents can have enzymatic activity (e.g., ribozyme activity), gene expression inhibitory activity (e.g., as antisense or siRNA agents, etc), and/or other activities. Nucleic acids agents can be active themselves or can be vectors that deliver active nucleic acid agents (e.g., through replication and/or transcription of a delivered nucleic acid). For purposes of the present specification, such vector nucleic acids are considered "therapeutic moieties" if they encode or otherwise deliver a therapeutically active agent, even if they do not themselves have therapeutic activity.

In certain embodiments, chlorotoxin agents include a nucleic acid therapeutic moiety that includes or encodes an antisense compound. The terms "antisense compound or agent," "antisense oligomer," "antisense oligonucleotide," and "antisense oligonucleotide analog" are used herein interchangeably, and refer to a sequence of nucleotide bases and a subunit-to-subunit backbone that allows the antisense compound to hybridize to a target sequence in an RNA by Watson-Crick base pairing to form an RNA oligomer heteroduplex within the target sequence. The oligomer can have exact sequence complementarity within the target sequence or near complementarity. Such antisense oligomers can block or inhibit translation of the mRNA containing the target sequence, or inhibit gene transcription. Antisense oligomers can bind to double-stranded or single-stranded sequences.

Examples of antisense oligonucleotides suitable for use in the practice of the present invention include, for example, those mentioned in the following reviews: R. A Stahel et al., Lung Cancer, 2003, 41: S81-S88; K. F. Pirollo et al., Pharmacol. Ther., 2003, 99: 55-77; A. C. Stephens and R. P. Rivers, Curr. Opin. Mol. Ther., 2003, 5: 118-122; N. M. Dean and C. F. Bennett, Oncogene, 2003, 22: 9087-9096; N. Schiavone et al., Curr. Pharm. Des., 2004, 10: 769-784; L. Vidal et al., Eur. J. Cancer, 2005, 41: 2812-2818; T. Aboul-Fadi, Curr. Med. Chem., 2005, 12: 2193-2214; M. E. Gleave and B. P. Monia, Nat. Rev. Cancer, 2005, 5: 468-479; Y. S. Cho-Chung, Curr. Pharm. Des., 2005, 11: 2811-2823; E. Rayburn et al., Lett. Drug Design & Discov., 2005, 2: 1-18; E. R. Rayburn et al., Expert Opin. Emerg. Drugs, 2006, 11: 337-352; I. Tamm and M. Wagner, Mol. Biotechnol., 2006, 33: 221-238 (each of which is incorporated herein by reference in its entirety).

Examples of suitable antisense oligonucleotides include, for example oblimersen sodium (also known as Genasense™ or G31239, developed by Genta, Inc., Berkeley Heights, N.J.), a phosphorothioate oligomer targeted towards the initiation codon region of the bcl-2 mRNA. Bcl-2 is a potent inhibitor of apoptosis and is overexpressed in many cancer including follicular lymphomas, breast cancer, colon cancer, prostate cancer, and intermediate/high-grade lymphomas (C. A. Stein et al., Semin. Oncol., 2005, 32: 563-573; S. R. Frankel, Semin. Oncol., 2003, 30: 300-304). Other suitable antisense oligonucleotides include GEM-231 (HYB0165, Hybridon, Inc., Cambridge, Mass.), which is a mixed backbone oligonucleotide directed against cAMP-dependent protein kinase A (PKA) (S. Goel et al., Clin. Cancer Res., 203, 9: 4069-4076); Affinitak (ISIS 3521 or aprinocarsen, ISIS pharmaceuticals, Inc., Carlsbad, Calif.), an antisense inhibitor of PKCalpha; OGX-011 (Isis 112989, Isis Pharmaceuticals, Inc.), a 2'-methoxyethyl modified antisense oligonucleotide against clusterin, a glycoprotein implicated in the regulation of the cell cycle, tissue remodeling, lipid transport, and cell death and which is overexpressed in cancers of breast, prostate and colon; ISIS 5132 (Isis 112989, Isis Pharmaceuticals, Inc.), a phosphorothioate oligonucleotide complementary to a sequence of the 3'-unstranslated region of the c-raf-1 mRNA (S. P. Henry et al., Anticancer Drug Des., 1997, 12: 409-420; B. P. Monia et al., Proc. Natl. Acad. Sci. USA, 1996, 93: 15481-15484; C. M. Rudin et al., Clin. Cancer Res., 2001, 7: 1214-1220); ISIS 2503 (Isis Pharmaceuticals, Inc.), a phosphorothioate oligonucleotide antisense inhibitor of human H-ras mRNA expression (J. Kurreck, Eur. J Biochem., 2003, 270: 1628-1644); oligonucleotides targeting the X-linked inhibitor of apoptosis protein (XIAP), which blocks a substantial portion of the apoptosis pathway, such as GEM 640 (AEG 35156, Aegera Therapeutics Inc. and Hybridon, Inc.) or targeting survivin, an inhibitor of apoptosis protein (IAP), such as ISIS 23722 (Isis Pharmaceuticals, Inc.), a 2'-O-methoxyethyl chimeric oligonucleotide; MG98, which targets DNA methyl transferase; and GTI-2040 (Lorus Therapeutics, Inc. Toronto, Canada), a 20-mer oligonucleotide that is complementary to a coding region in the mRNA of the R2 small subunit component of human ribonucleotide reductase.

Other suitable antisense oligonucleotides include antisense oligonucleotides that are being developed against Her-2/neu, c-Myb, c-Myc, and c-Raf (see, for example, A. Biroccio et al., Oncogene, 2003, 22: 6579-6588; Y. Lee et al., Cancer Res., 2003, 63: 2802-2811; B. Lu et al., Cancer Res., 2004, 64: 2840-2845; K. F. Pirollo et al., Pharmacol. Ther., 2003, 99: 55-77; and A. Rait et al., Ann. N.Y. Acad. Sci., 2003, 1002: 78-89).

In certain embodiments, chlorotoxin agents for use in the present invention include a nucleic acid anti-cancer agent that includes or encodes an interfering RNA molecule. The terms "interfering RNA" and "interfering RNA molecule" are used herein interchangeably, and refer to an RNA molecule that can inhibit or downregulate gene expression or silence a gene in a sequence-specific manner, for example by mediating RNA interference (RNAi). RNA interference (RNAi) is an evolutionarily conserved, sequence-specific mechanism triggered by double-stranded RNA (dsRNA) that induces degradation of complementary target single-stranded mRNA and "silencing" of the corresponding translated sequences (McManus and Sharp, 2002, Nature Rev. Genet., 2002, 3: 737). RNAi functions by enzymatic cleavage of longer dsRNA strands into biologically active "short-interfering RNA" (siRNA) sequences of about 21-23 nucleotides in length (Elbashir et al., Genes Dev., 2001, 15: 188). RNA interference has emerged as a promising approach for therapy of cancer.

An interfering RNA suitable for use in the practice of an invention described herein can be provided in any of several forms. For example, an interfering RNA can be provided as one or more of an isolated short interfering RNA (siRNA), double-stranded RNA (dsRNA), micro-RNA (miRNA), or short hairpin RNA (shRNA).

Examples of interfering RNA molecules suitable for use in the present invention include, for example, the iRNAs cited in the following reviews: 0. Milhavet et al., *Pharmacol. Rev.*, 2003, 55: 629-648; F. Bi et al., *Curr. Gene. Ther.*, 2003, 3: 411-417; P. Y. Lu et al., *Curr. Opin. Mol. Ther.*, 2003, 5: 225-234; I. Friedrich et al., *Semin. Cancer Biol.*, 2004, 14: 223-230; M. Izquierdo, Cancer *Gene Ther.*, 2005, 12: 217-227; P. Y. Lu et al., *Adv. Genet.*, 2005, 54: 117-142; G. R. Devi, Cancer *Gene Ther.*, 2006, 13: 819-829; M. A. Behlke, *Mol. Ther.*, 2006, 13: 644-670; and L. N. Putral et al., *Drug News Perspect.*, 2006, 19: 317-324 (the contents of each of which are incorporated herein by reference in its entirety).

Other examples of suitable interfering RNA molecules include, but are not limited to, p53 interfering RNAs (e.g., T. R. Brummelkamp et al., *Science*, 2002, 296: 550-553; M. T. Hemman et al., *Nat. Genet.*, 2003, 33: 396-400); interfering RNAs that target the bcr-abl fusion, which is associated with development of chronic myeloid leukemia and acute lymphoblastic leukemia (e.g., M. Scherr et al., *Blood*, 2003, 101: 1566-1569; M. J. Li et al., *Oligonucleotides*, 2003, 13: 401-409), interfering RNAs that inhibit expression of NPM-ALK, a protein that is found in 75% of anaplastic large cell lymphomas and leads to expression of a constitutively active kinase associated with cancer formation (U. Ritter et al., *Oligonucleotides*, 2003, 13: 365-373); interfering RNAs that target oncogenes, such as Raf-1 (T. F. Lou et al., *Oligonucleotides*, 2003, 13: 313-324), K-Ras (T. R. Brummelkamp et al., *Cancer Cell*, 2002, 2: 243-247), erbB-2 (G. Yang et al., *J. Biol. Chem.*, 2004, 279: 4339-4345); interfering RNAs that target b-catenin protein, whose over-expression leads to transactivation of the T-cell factor target genes, which is thought to be the main transforming event in colorectal cancer (M. van de Wetering et al., *EMBO Rep.*, 2003, 4: 609-615).

In certain embodiments, chlorotoxin agents include a nucleic acid therapeutic moiety that is a ribozyme. As used herein, the term "ribozyme" refers to a catalytic RNA molecule that can cleave other RNA molecules in a target-specific manner Ribozymes can be used to down-regulate the expression of any undesirable products of genes of interest. Examples of ribozymes that can be used in the practice of an invention described herein include, but are not limited to, ANGIOZYME™ (RPI.4610, Sima Therapeutics, Boulder, Colo.), a ribozyme targeting the conserved region of human, mouse, and rat vascular endothelial growth factor receptor (VEGFR)-1 mRNA, and Herzyme (Sima Therapeutics).

v. Photosensitizers

In certain embodiments, moieties within chlorotoxin agents include a photosensitizer used in photodynamic therapy (PDT). In PDT, local or systemic administration of a photosensitizer to a patient is followed by irradiation with light that is absorbed by the photosensitizer in the tissue or organ to be treated. Light absorption by the photosensitizer generates reactive species (e.g., radicals) that are detrimental to cells. For maximal efficacy, a photosensitizer typically is in a form suitable for administration, and also in a form that can readily undergo cellular internalization at the target site, often with some degree of selectivity over normal tissues.

While some photosensitizers (e.g., Photofrin®, QLT, Inc., Vancouver, BC, Canada) have been delivered successfully as part of a simple aqueous solution, such aqueous solutions may not be suitable for hydrophobic photosensitizer drugs, such as those that have a tetra- or poly-pyrrole-based structure. These drugs have an inherent tendency to aggregate by molecular stacking, which results in a significant reduction in the efficacy of the photosensitization processes (Siggel et al., *J. Phys. Chem.*, 1996, 100: 2070-2075). Approaches to minimize aggregation include liposomal formulations (e.g., for benzoporphyrin derivative monoacid A, BPDMA, Verteporfin®, QLT, Inc., Vancouver, Canada; and zinc phthalocyanine, CIBA-Geigy, Ltd., Basel, Switzerland), and conjugation of photosensitizers to biocompatible block copolymers (Peterson et al., *Cancer Res.*, 1996, 56: 3980-3985) and/or antibodies (Omelyanenko et al., *Int. J. Cancer,* 1998, 75: 600-608).

Chlorotoxin agents including a chlorotoxin polypeptide associated with a photosensitizer can be used as new delivery systems in PDT. In addition to reducing photosensitizer aggregation, delivery of photosensitizers according to the present invention exhibits other advantages such as increased specificity for target tissues/organ and cellular internalization of the photosensitizer.

Photosensitizers suitable for use in the present invention include any of a variety of synthetic and naturally occurring molecules that have photosensitizing properties useful in PDT. In certain embodiments, the absorption spectrum of the photosensitizer is in the visible range, typically between 350 nm and 1200 nm, preferably between 400 nm and 900 nm, e.g., between 600 nm and 900 nm. Suitable photosensitizers that can be coupled to toxins according to the present invention include, but are not limited to, porphyrins and porphyrin derivatives (e.g., chlorins, bacteriochlorins, isobacteriochlorins, phthalocyanines, and naphthalocyanines); metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid (R. W. Redmond and J. N. Gamlin, *Photochem. Photobiol.*, 1999, 70: 391-475).

Exemplary photosensitizers suitable for use in the present invention include those described in U.S. Pat. Nos. 5,171,741; 5,171,749; 5,173,504; 5,308,608; 5,405,957; 5,512,675; 5,726,304; 5,831,088; 5,929,105; and 5,880,145 (the contents of each of which are incorporated herein by reference in their entirety).

vi. Radiosensitizers

In certain embodiments, chlorotoxin agents include a radiosensitizer. As used herein, the term "radiosensitizer" refers to a molecule, compound or agent that makes cancer cells more sensitive to radiation therapy. Administration of a radiosensitizer to a patient receiving radiation therapy generally results in enhancement of the effects of radiation therapy. Ideally, a radiosensitizer exerts its function only on target cells. For ease of use, a radiosensitizer should also be able to find target cells even if it is administered systemically. However, currently available radiosensitizers are typically not selective for tumors, and they are distributed by diffusion in a mammalian body. Chlorotoxin agents for use in the present invention can be used as a new delivery system for radiosensitizers.

A variety of radiosensitizers are known in the art. Examples of radiosensitizers suitable for use in the present invention include, but are not limited to, paclitaxel (TAXOL®), carboplatin, cisplatin, and oxaliplatin (Amorino et al, *Radiat. Oncol. Investig.*, 1999; 7: 343-352; Choy, *Oncology*, 1999, 13: 22-38; Safran et al., *Cancer Invest.*, 2001, 19: 1-7; Dionet et al., *Anticancer Res.*, 2002, 22: 721-725; Cividalli et al., *Radiat. Oncol. Biol. Phys.*, 2002, 52: 1092-1098); gemcitabine (Gemzar®) (Choy, *Oncology*, 2000, 14: 7-14; Mornex and Girard, Annals of Oncology, 2006, 17: 1743-1747); etanidazole (Nitrolmidazole®) (Inanami et al., *Int. J. Radiat. Biol.*, 2002, 78: 267-274); misonidazole (Tamulevicius et al., *Br. J. Radiology*, 1981, 54: 318-324; Palcic et al., *Radiat. Res.*, 1984, 100: 340-347), tirapazamine (Masunaga et al., *Br. J. Radiol.*, 2006, 79: 991-998; Rischin et al., *J. Clin. Oncol.*, 2001, 19: 535-542; Shulman et al., *Int. J. Radiat. Oncol. Biol. Phys.*, 1999, 44: 349-353); and nucleic acid base derivatives, e.g., halogenated purines or pyrimidines, such as 5-fluorodeoxyuridine (Buchholz et al., *Int. J. Radiat. Oncol. Biol. Phys.*, 1995, 32: 1053-1058).

vii. Radioisotopes

In certain embodiments, chlorotoxin agents include a radioisotope. Examples of suitable radioisotopes include any α-, β- or γ-emitter, which, when localized at a cancer site, results in cell destruction (S. E. Order, "Analysis, Results, and Future Prospective of the Therapeutic Use of Radiolabeled Antibody in Cancer Therapy," Monoclonal Antibodies for Cancer Detection and Therapy, R. W. Baldwin et al. (Eds.), Academic Press, 1985). Examples of such radioisotopes include, but are not limited to, iodine-131 ($^{131}$I), iodine-125 ($^{125}$I), bismuth-212 ($^{212}$Bi), bismuth-213 ($^{213}$Bi), astatine-211 ($^{211}$At), rhenium-186 ($^{186}$Re), rhenium-188 ($^{88}$Re), phosphorus-32 ($^{32}$P), yttrium-90 ($^{90}$Y), samarium-153 ($^{153}$Sm), and lutetium-177 ($^{77}$Lu). viii. Superantigens In certain embodiments, chlorotoxin agents include a superantigen or biologically active portion thereof. Superantigens constitute a group of bacterial and viral proteins that are extremely efficient in activating a large fraction of the T-cell population. Superantigens bind directly to the major histocompatibility complex (MHC) without being processed. In fact, superantigens bind unprocessed outside the antigen-binding groove on the MHC class II molecules, thereby avoiding most of the polymorphism in the conventional peptide-binding site.

A superantigen-based cancer therapeutic approach can be useful in the treatment of solid tumors. In this approach, a targeting moiety, for example, an antibody or antibody fragment, is conjugated to a superantigen, providing a targeted superantigen. If the antibody, or antibody fragment, recognizes a cancer-associated antigen, the targeted superantigen, bound to cancer cells, can trigger superantigen-activated cytotoxic T-cells to kill the cancer cells directly by superantigen-dependent cell mediated cytotoxicity. (See, e.g., Sogaard et al. (1996) "Antibody-targeted superantigens in cancer immunotherapy," *Immunotechnology*, 2(3): 151-162, the entire contents of which are herein incorporated by reference.)

Superantigen-based cancer therapeutics have had some success. For example, fusion proteins with wild-type staphylococcal enterotoxin A (SEA) have been investigated in clinical trials of colorectal and pancreatic cancer (Giantonio et al., *J. Clin. Oncol.*, 1997, 15: 1994-2007; Alpaugh et al., *Clin. Cancer Res.*, 1998, 4: 1903-1914; Cheng et al., *J. Clin. Oncol.*, 2004, 22: 602-609; the entire contents of each of which are herein incorporated by reference); staphylococcal superantigens of the enterotoxin gene cluster (egc) have been studied for the treatment of non-small cell lung cancer (Terman et al., *Clin. Chest Med.*, 2006, 27: 321-324, the entire contents of which are herein incorporated by reference), and staphylococcal enterotoxin B has been evaluated for the intravesical immunotherapy of superficial bladder cancer (Perabo et al., *Int. J. Cancer*, 2005, 115: 591-598, the entire contents of which are herein incorporated by reference).

A superantigen, or a biologically active portion thereof, can be associated with a chlorotoxin polypeptide to form a chlorotoxin agent according to the present invention and used in a therapy, e.g., an anti-cancer therapy, as described herein.

Examples of superantigens suitable for use in the present invention include, but are not limited to, staphylococcal enterotoxin (SE) (e.g., staphylococcal enterotoxin A (SEA) or staphylococcal enterotoxin E (SEE)), *Streptococcus pyogenes* exotoxin (SPE), *Staphylococcus aureus* toxic shock-syndrome toxin (TSST-1), streptococcal mitogenic exotoxin (SME), streptococcal superantigen (SSA), and staphylococcal superantigens of the enterotoxin gene cluster. As known to one skilled in the art, the three-dimensional structures of the listed superantigens can be obtained from the Protein Data Bank. Similarly, the nucleic acid sequences and the amino acid sequences of the listed superantigens and other superantigens can be obtained from GenBank.

ix. Prodrug Activating Enzymes

In certain embodiments, a chlorotoxin agent for use in the present invention can be used in directed enzyme prodrug therapy. In a directed enzyme prodrug therapy approach, a directed/targeted enzyme and a prodrug are administered to a subject, wherein the targeted enzyme is specifically localized to a portion of the subject's body where it converts the prodrug into an active drug. The prodrug can be converted to an active drug in one step (by the targeted enzyme) or in more than one step. For example, the prodrug can be converted to a precursor of an active drug by the targeted enzyme. The precursor can then be converted into the active drug by, for example, the catalytic activity of one or more additional targeted enzymes, one or more non-targeted enzymes administered to the subject, one or more enzymes naturally present in the subject or at the target site in the subject (e.g., a protease, phosphatase, kinase or polymerase), by an agent that is administered to the subject, and/or by a chemical process that is not enzymatically catalyzed (e.g., oxidation, hydrolysis, isomerization, epimerization, etc.).

Different approaches have been used to direct/target the enzyme to the site of interest. For example, in ADEPT (antibody-directed enzyme prodrug therapy), an antibody designed/developed against a cancer antigen is linked to an enzyme and injected in a subject, resulting in selective binding of the enzyme to the cancer. When the discrimination between cancer and normal tissue enzyme levels is sufficient, a prodrug is administered to the subject. The prodrug is converted to its active form by the enzyme only within the cancer. Selectivity is achieved by the cancer specificity of the antibody and by delaying prodrug administration until there is a large differential between cancer and normal tissue enzyme levels. Early clinical trials are promising and indicate that ADEPT can become an effective treatment for all solid cancers for which cancer-associated or cancer-specific antibodies are known. Cancers have also been targeted with the genes encoding for prodrug activating enzymes. This approach has been called virus-directed enzyme prodrug therapy (VDEPT) or more generally GDEPT (gene-directed enzyme prodrug therapy, and has shown good results in laboratory systems. Other versions of directed enzyme prodrug therapy include PDEPT (polymer-directed enzyme prodrug therapy), LEAPT (lectin-directed enzyme-activated prodrug therapy), and CDEPT (clostridial-directed enzyme prodrug therapy). A chlorotoxin agent according to the present invention, which includes a prodrug activating enzyme associated with a chlorotoxin polypeptide, can be used in a similar way.

Non-limiting examples of enzyme/prodrug/active drug combinations suitable for use in the present invention are described, for example, in Bagshawe et al., *Current Opinions in Immunology,* 1999, 11: 579-583; Wilman, "Prodrugs in Cancer Therapy," *Biochemical Society Transactions,* 14: 375-382, 615$^{th}$ Meeting, Belfast, 1986; Stella et al., "Prodrugs: A Chemical Approach To Targeted Drug Delivery," in "Directed Drug Delivery," Borchardt et al., (Eds), pp. 247-267 (Humana Press, 1985). Non-limiting examples of enzyme/prodrug/active anti-cancer drug combinations are described, for example, in Rooseboom et al., *Pharmacol. Reviews,* 2004, 56: 53-102.

Examples of prodrug activating enzymes include, but are not limited to, nitroreductase, cytochrome P450, purine-nucleoside phosphorylase, thymidine kinase, alkaline phosphatase, β-glucuronidase, carboxypeptidase, penicillin amidase, β-lactamase, cytosine deaminase, and methionine .gamma.-lyase.

Examples of anti-cancer drugs that can be formed in vivo by activation of a prodrug by a prodrug activating enzyme include, but are not limited to, 5-(aziridin-1-yl)-4-hydroxyl-amino-2-nitro-benzamide, isophosphoramide mustard, phosphoramide mustard, 2-fluoro adenine, 6-methylpurine, ganciclovir-triphosphate nucleotide, etoposide, mitomycin C, p-[N,N-bis(2-chloroethyl)amino]phenol (POM), doxorubicin, oxazolidinone, 9-aminocamptothecin, mustard, methotrexate, benzoic acid mustard, doxorubicin, adriamycin, daunomycin, caminomycin, bleomycins, esperamicins, melphalan, palytoxin, 4-desacetylvinblastine-3-carboxylic acid hydrazide, phenylenediamine mustard, 4'-carboxyphthalato(1,2-cyclohexane-diamine) platinum, taxol, 5-fluorouracil, methylselenol, and carbonothionic difluoride.

b. Anti-Angiogenic Agents

In certain embodiments, a therapeutic (e.g., anti-cancer) agent within a chlorotoxin agent for use in the present invention includes an anti-angiogenic agent. Antiangiogenic agents suitable for use in the present invention include any molecule, compound, or factor that blocks, inhibits, slows down, or reduces the process of angiogenesis, or the process by which new blood vessels form by developing from preexisting vessels. Such a molecule, compound, or factor can block angiogenesis by blocking, inhibiting, slowing down, or reducing any of the steps involved in angiogenesis, including (but not limited to) steps of (1) dissolution of the membrane of the originating vessel, (2) migration and proliferation of endothelial cells, and (3) formation of new vasculature by migrating cells.

Examples of anti-angiogenic agents include, but are not limited to, bevacizumab (AVASTIN®), celecoxib (CELEBREX®) endostatin, thalidomide, EMD121974 (Cilengitide), TNP-470, squalamine, combretastatin A4, interferon-α, anti-VEGF antibody, SU5416, SU6668, PTK787/2K 22584, Marimistal, AG3340, COL-3, Neovastat, and BMS-275291.

Anti-angiogenic agents can be used in a variety of therapeutic contexts, including, but not limited to, anti-cancer therapies and therapies for macular degeneration.

As will be recognized by one skilled in the art, the specific examples of therapeutic moieties cited herein represent only a very small number of the therapeutic moieties that are suitable for use in the practice of an invention described herein.

2. Detectable Moieties

In certain embodiments, provided chlorotoxin agents include one or more detectable moieties, i.e., a chlorotoxin polypeptide is "labeled" with one or more such moieties. In some such embodiments, such a chlorotoxin polypeptide is useful in diagnostic or imaging applications.

Any of a wide variety of detectable moieties can be used in embodiments described herein. Suitable detectable moieties include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

a. Radioactive and/or Paramagnetic Isotopes or Ions

In certain embodiments, a chlorotoxin polypeptide is labeled with a radioactive and/or paramagnetic isotope or ion. For example, a chlorotoxin polypeptide can be isotopically-labeled (i.e., can contain one or more atoms that have been replaced by an atom having an atomic mass or mass number different from the atomic mass or mass number usually found in nature) or an isotope can be associated with the chlorotoxin polypeptide. Non-limiting examples of isotopes that can be incorporated into a chlorotoxin polypeptide include isotopes of hydrogen, carbon, fluorine, phosphorous, copper, gallium, yttrium, technetium, indium, iodine, rhenium, thallium, bismuth, astatine, samarium, and lutetium (i.e., $^{3}$H, $^{13}$C, $^{14}$C, $^{18}$F, $^{32}$P, $^{35}$S, $^{64}$CU, $^{67}$Ga, $^{90}$Y, $^{99}$MTc, $^{111}$In, $^{125}$I, $^{123}$I, $^{129}$I, $^{131}$I, $^{135}$I, $^{186}$Re, $^{187}$Re, $^{201}$Tl, $^{212}$Bi, $^{211}$At, $^{153}$Sm, $^{177}$Lu).

In certain embodiments, a chlorotoxin polypeptide includes a radioisotope that is detectable by Single Photon Emission Computed Tomography (SPECT) or Position Emission Tomography (PET). Examples of such radionuclides include, but are not limited to, iodine-131 ($^{131}$I), iodine 125 ($^{125}$I), bismuth-212 ($^{212}$Bi), bismuth-213 ($^{213}$Bi), astatine-221 ($^{221}$At), copper-67 ($^{67}$Cu), copper-64 ($^{64}$Cu), rhenium-186 ($^{186}$Re) rhenium-188 ($^{88}$Re), phosphorus-32 ($^{32}$P), samarium-153 ($^{153}$Sm), lutetium-177 ($^{177}$Lu), technetium-99m ($^{99m}$Tc), gallium-67 ($^{67}$Ga), indium-111, ($^{111}$In), and thallium-201 ($^{201}$Tl).

In certain embodiments, a chlorotoxin polypeptide is labeled with a radioisotope that is detectable by Gamma camera. Examples of such radioisotopes include, but are not limited to, iodine-131 ($^{131}$I), and technetium-99m ($^{99m}$Tc).

In certain embodiments, a chlorotoxin polypeptide is labeled with a paramagnetic metal ion that is a good contrast enhancer in Magnetic Resonance Imaging (MRI). Examples of such paramagnetic metal ions include, but are not limited to, gadolinium III (Gd3+), chromium III (Cr3+), dysprosium III (Dy3+), iron III (Fe3+), manganese II (Mn2+), and ytterbium III (Yb3+). In certain embodiments, the labeling moieties includes gadolinium III (Gd3+). Gadolinium is an FDA-approved contrast agent for MRI, which accumulates in abnormal tissues causing these abnormal areas to become very bright (enhanced) on the magnetic resonance image. Gadolinium is known to provide great contrast between normal and abnormal tissues in different areas of the body, in particular in the brain.

In certain embodiments, a chlorotoxin polypeptide is labeled with a stable paramagnetic isotope detectable by nuclear magnetic resonance spectroscopy (MRS). Examples of suitable stable paramagnetic isotopes include, but are not limited to, carbon-13 ($^{13}C$) and fluorine-19 ($^{19}F$).

In some embodiments, metal isotopes are non-covalently associated with a chlorotoxin polypeptide by chelation. Examples of chelation include chelation of a metal isotope to a poly-His region fused to a chlorotoxin polypeptide.

In some embodiments, a metal such as gadolinium (Gd) is incorporated into a chlorotoxin polypeptide through covalent bonding or through chelation, as described herein.

b. Fluorescent Dyes

In certain embodiments, a chlorotoxin polypeptide is labeled with a fluorescent dye. Numerous known fluorescent dyes of a wide variety of chemical structures and physical characteristics are suitable for use in the practice of an invention described herein. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products," 9$^{th}$ Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

c. Targeting Moieties

In certain embodiments, a chlorotoxin agent for use in the present invention includes a chlorotoxin polypeptide associated with one or more targeting moieties.

In certain embodiments, one or more targeting moieties is an antibody. An antibody can be an antibody that binds a cancer cell. An antibody can be an antibody that binds a biomarker of cancer. Biomarkers of cancer include, e.g., proteins and genes involved in cell cycle regulation, DNA replication, transcription, signal transduction, cell proliferation, invasion, proteolysis, or metastasis. Biomarkers of cancer include, e.g., the following proteins: Alpha-fetoprotein, Carcinoembryonic antigen, Epidermal growth factor receptor, Kallikrein 3 (prostate specific antigen), Vascular endothelial growth factor A, VEGF, Albumin, CA 125, Calcitonin, Chromogranin A (parathyroid secretory protein 1), Corticotropin-lipotropin contains ACTH, Estrogen receptor 1, Gastrin, Progesterone receptor, Prolactin, S100 alpha chain, Somatostatin, Thyroglobulin, V-erb-b2, Her2/neu, Antigen identified by monoclonal antibody Ki-67, B-cell CLL/lymphoma 2, BCL2-associated X protein, Beta-2-microglobulin, Breast cancer 1 early onset, CA 15.3, CA 19.9, Cadherin 1 type 1 E-cadherin (epithelial), Caspase 3, CD44 antigen, Cellular tumor antigen p53, Coagulation factor II, prothrombin, Colony stimulating factor 2 (granulocyte-macrophage), Colony stimulating factor 3 (granulocyte), C-reactive protein, Cyclin D1, Cyclin-dependent kinase inhibitor 1, p21, Erythropoietin, Fibrinogen alpha/alpha-E chain, Follicle-stimulating hormone, Gamma enolase, Insulin, Interferon gamma, Interleukin 2, Interleukin 6, k-ras, Neprilysin, CD10, Transferrin, Trypsin, Tumor necrosis factor (TNF-alpha), Tumor necrosis factor receptor superfamily member 6, fas, Von Willebrand Factor, Chemokine ligand 5 (CCL5), Chitinase-3 like protein 1, YKL-40, Choriogonadotropin beta chain, Colony stimulating factor 1 (macrophage), Haptoglobin-1, Hepatocyte growth factor, Inhibin, Interferon-alpha/beta receptor alpha chain, Interferon-alpha/beta receptor beta chain, Kallikrein 10, Kallikrein 11, Kallikrein 6, Matrix metalloproteinase 3, Small inducible cytokine A21 (CCL21), soluble IL-2R alpha, Somatotropin growth factor, growth hormone, Breast cancer 2 early onset, Catenin Beta 1, Cathepsin D, CD15, Desmin, DNA-(apurinic or apyrimidinic site) lyase, APEX, Lutropin beta chain, Luteinizing hormone, Parathyroid Hormone, Proliferating cell nuclear antigen, Tumor necrosis factor ligand superfamily member 8 (CD30 ligand), V-myc myelocytomatosis viral oncogene homolog (avian), Tumor necrosis factor ligand superfamily member 8 (CD30), 17beta-Hydroxysteroid dehydrogenase type 1 (17HSD1), Acid phosphatase prostate, Adrenomedullin, Aldolase A, Alkaline phosphatase bone-specific, Alkaline phosphatase, placental type, Alpha-1-acid glycoprotein 1, orosomucoid, Alpha-1-antitrypsin, alpha-2-HS-glycoprotein, Alpha-2-macroglobulin, Alpha-lactalbumin, Angiogenin ribonuclease RNase A family 5, Angiopoietin 1, Angiopoietin 2, Antileukoproteinase 1, SLPI, Apolipoprotein A1, Apolipoprotein A-II, Apolipoprotein C-I, Apolipoprotein C-III, Bone sialoprotein II, Brain-derived neurotrophic factor, Breast cancer metastasis-suppressor 1, CA 27.29, CA 72-4, Cathepsin B, CC chemokine 4, HCC-4, CD44 variant V5 soluble, Ceruloplasmin, Cervical cancer 1 protooncogene protein p40, Chemokine (C—C motif) ligand 4 Small inducible cytokine A4 (CCL4), MIP-1-beta, Claudin-3, Claudin-4, Clusterin, Coagulation factor III, Coagulation factor XIII A chain, Coagulation factor XIII B chain, Collagen I c-terminal telopeptide, Complement component 3, Complement component 4, Complement component 7, Complement factor H related protein, Cyclin-dependent kinase 6, Cyclooxygenase-2, Cystatin A, Cystatin B, Cystatin C, Cytokeratin 8, Diazepam binding inhibitor, Endoglin, Endothelin 1, Epidermal growth factor, E-selectin, Ferritin H, Ferritin, L, Fibroblast growth factor 2 (basic), Fibronectin 1, Flt-3 ligand, Fms-related tyrosine kinase 1, VEGFR1, Follistatin, Fructose-bisphosphate aldolase B, Fructose-bisphosphate aldolase C, Geminin, Glucose-6-phosphate isomerase, Glypican-3, n-terminal, Growth arrest and DNA-damage-inducible alpha, Immunosuppressive acidic protein, Insulin-like growth factor 1 (somatomedin C), Insulin-like growth factor 2 (somatomedin A), Insulin-like growth factor binding protein 1, Insulin-like growth factor binding protein 2, Insulin-like growth factor binding protein 3, Intercellular Adhesion Molecule 1, Interferon alpha 1, Interleukin 1 alpha, Interleukin 1 beta, Interleukin 10, Interleukin 12A, Interleukin 16, Interleukin 5, Interleukin 6 receptor, Interleukin 6 signal transducer, Interleukin 7, Interleukin 8, Interleukin 9, Interleukin-1 receptor antagonist protein, IRAP, Kallikrein 14 (hK14), Kallikrein 2 prostatic, Kallikrein 5, Kallikrein 7, Kallikrein 8, Keratin 18, Keratin, type I cytoskeletal 19, cytokeratin 19, Kit ligand, Lactotransferrin, Leptin, L-selectin, Luteinizing hormone-releasing hormone receptor, Mac-2 Binding Protein 90K, Mammaglobin B, Mammary Serum Antigen, Mast/stem cell growth factor receptor, Matrix metalloproteinase 2, Matrix metalloproteinase 9, Melanoma-inhibiting activity, Membrane cofactor protein, CD46 antigen, Mesothelin, Midkine, MK-1 protein, Ep-CAM, Myoblast determination protein 1, Nerve growth factor beta, Netrin-1, Neuroendocrine secretory protein-55, Neutrophil defensin 1, Neutrophil defensin 3, Nm23-H1, OVX1, OX40, p65 oncofetal protein, Pancreatic secretory trypsin inhibitor, TATI, Parathyroid hormone-related protein, Pcaf, P300/CBP-associated factor, Pepsinogen-1, Placental specific tissue protein 12, Plasma retinol-binding protein, Plasminogen (Contains Angiostatin), Platelet endothelial cell adhesion molecule, PECAM-1, Platelet factor 4, Platelet-derived growth factor beta polypeptide, Platelet-derived growth factor receptor alpha polypeptide, Pregnancy zone protein, Pregnancy-associated plasma protein-A, Prostate secretory protein PSP94, P-selectin, PSP94 binding protein, Pyruvate kinase, isozymes M1/M2, Riboflavin carrier protein, S100 beta chain, Secreted phosphoprotein 1, osteopontin, Serine (or cysteine) proteinase inhibitor clade B, maspin, Serine (or cysteine) proteinase inhibitor clade E, PAI-1, Serum amyloid alpha-1, Serum paraoxonase/arylesterase 1, Small inducible cytokine A14 CCL14, Small inducible cytokine A18(CCL18), MIP-4, Small inducible cytokine A2(CCL2), Small inducible cytokine A3(CCL3), Macrophage inflammatory protein 1-alpha, Small inducible cytokine B5(CXCL5), Squamous cell carcinoma antigen 1, Squamous cell carcinoma antigen 2, Survivin, Syndecan-1, synuclein-gamma, TEK tyrosine kinase endothelial, Tie-2, Tenascin, Tetranectin, TGF-beta receptor type III, Thioredoxin reductase 1, cytoplasmic, Thrombopoietin, Thrombospondin 1, Thymidine kinase, cytosolic, Tissue inhibitor of metalloproteinase 1, Tissue inhibitor of metalloproteinase 2, Tissue-type plasminogen activator, tPA, Transferrin receptor (p90 CD71), Transforming growth factor alpha, Transforming growth factor beta 1, transthyretin, Tropomyosin 1 alpha chain (Alpha-tropomyosin), Tumor necrosis factor (ligand) superfamily member 5, CD154, Tumor necrosis factor (ligand) superfamily member 6, Fas ligand, Tumor necrosis factor ligand superfamily member 13B, TALL-1, Tumor necrosis factor receptor superfamily member 11B, osteoprotegerin, Tumor necrosis factor receptor superfamily member 1A p60 TNF-RI p55 CD120a, TNFR1, Tumor necrosis factor receptor superfamily member 1B, TNFR2, Urokinase plasminogen activator surface receptor, U-PAR, Vascular cell adhesion molecule 1, Vascular endothelial growth factor receptor 2, Vasoactive intestinal peptide, VEGF(165)b, Vitamin K dependent protein C, Vitronectin, X box binding protein-1 (for a list of cancer biomarkers, see Polanski and Anderson 2006 *Biomarker Insights* 1: 1-48, which is herein incorporated by reference in its entirety).

In certain embodiments, one or more targeting moieties is a polypeptide. In certain embodiments, a polypeptide targeting moiety is polypeptide selected or designed to bind a cancer biomarker. In certain embodiments a polypeptide targeting moiety is a receptor. In certain embodiments a polypeptide targeting moiety is a ligand.

In certain embodiments, one or more targeting moieties is a saccharide. In some instances, the saccharide is a carbohydrate drug. A number of FDA-approved prescription drugs are or include carbohydrate moieties. Carbohydrate drugs can be divided, in some instances into five categories: Monosaccharide conjugates, disaccharides and disaccharide conjugates, trisaccharides, oligosaccharides and polysaccharides, and macrolides. monosaccharide conjugates include, among other members: anthracycline antibiotics and agents (e.g., doxorubicin, daunorubicin, epirubicin, idarubicin), Nucleotides and nucleosides and their analogs (fludarabine phosphate, stavudine, adenosine, gemcitabine, ribavirin, acadesine), polyenes (amphotericin b), and other agents such as etoposide, lincomycin, clindamycin and pentostatin. (see, e.g., Klyosov, Anatole. "Carbohydrates and Drug Design." Glycobiology and Drug Design. American Chemical Society, 2012. Pages 3-22, which is herein incorporated by reference in its entirety.)

In certain embodiments, one or more targeting moieties is a nucleic acid. In certain embodiments, a nucleic acid targeting moiety is a nucleic acid aptamer. Aptamers include small RNA and/or DNA molecules that form secondary and tertiary structures capable of specifically binding proteins or other cellular targets. In certain embodiments, a nucleic acid targeting moiety is a nucleic acid aptamer that binds a cancer biomarker. In certain embodiments, a starting point for the generation of an aptamer is the synthesis of a nucleic acid library (RNA, DNA, or modified RNA) of large sequence complexity followed by the selection for oligonucleotides able to bind with high affinity and specificity to a target molecule, using a simple procedure called 'systematic evolution of ligands by exponential enrichment' (SELEX). Examples of aptamers that inhibit or target cancer-related proteins are known in the art (see, e.g., Cerchia et al. 2002 *FEBS Letters* 1-3: 12-16).

d. Enzymes Moieties

In certain embodiments, a chlorotoxin polypeptide is associated with an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme can be conjugated to a chlorotoxin polypeptide using a linker group such as a carbodiimide, a diisocyanate, a glutaraldehyde, and the like.

It will be recognized by those of ordinary skill in the art that in some embodiments, a particular non-chlorotoxin entity or moiety can serve more than one purpose. For example, a moiety can have both a therapeutic purpose and a detection purpose (e.g., imaging or diagnosis). To give but one example, radioactive iodine such as $^{131}$I has been used as both a radiolabel and a cytotoxic therapeutic moiety within a chlorotoxin agent in the detection and/or treatment of a variety of cancers including malignant glioma. Radioactive or paramagnetic isotopes or ions are examples of moieties that can have both a therapeutic purpose and a detection purpose (e.g., imaging or diagnosis).

B. Conjugation

In some embodiments, one or more moieties (e.g., one or more detectable (e.g., imagable), therapeutic, or targeting moieties; i.e., a "payload") is/are associated with a chlorotoxin polypeptide. In some instances the payload is associated with the chlorotoxin polypeptide via a lysine residue and/or via a terminus of the chlorotoxin polypeptide. In certain such embodiments, the position(s) where moieties can be associated with a chlorotoxin polypeptide is limited by the number of lysine residues available as a site for conjugation. For example, moieties can be associated at the single available lysine residue in a chlorotoxin polypeptide having a single lysine residue ("monolysine").

In certain instances, a chlorotoxin polypeptide is directly associated with a payload moiety. In certain instances, a chlorotoxin polypeptide is indirectly associated with a payload moiety. In certain instances, a chlorotoxin polypeptide is covalently associated with a payload moiety. In certain instances, a chlorotoxin polypeptide is noncovalently associated with a payload moiety. In certain instances, a chlorotoxin polypeptide is associated with a payload moiety via a linker.

In certain instances, a chlorotoxin polypeptide is associated with a payload moiety via the C-terminus of the chlorotoxin polypeptide. In certain instances, a chlorotoxin polypeptide is associated with a payload moiety via a linker covalently or noncovalently associated with the C-terminus of the chlorotoxin polypeptide. In certain instances, a chlorotoxin polypeptide is covalently associated with a payload moiety via the C-terminus of the chlorotoxin polypeptide. In certain instances, a chlorotoxin polypeptide is noncovalently associated with a payload moiety via the C-terminus of the chlorotoxin polypeptide. In certain instances, a chlorotoxin polypeptide is directly associated with a payload moiety via the C-terminus of the chlorotoxin polypeptide. In certain instances, a chlorotoxin polypeptide is indirectly associated with a payload moiety via the C-terminus of the chlorotoxin polypeptide. In certain instances the C-terminal residue of the chlorotoxin polypeptide is the same amino acid as found in a corresponding position of SEQ ID NO: 1. In certain instances the C-terminal residue of the chlorotoxin polypeptide differs from an amino acid as found in a corresponding position of SEQ ID NO: 1.

In certain instances, a chlorotoxin polypeptide is associated with a payload moiety via the N-terminus of the chlorotoxin polypeptide. In certain instances, a chlorotoxin polypeptide is associated with a payload moiety via a linker covalently or noncovalently associated with the N-terminus of the chlorotoxin polypeptide. In certain instances, a chlorotoxin polypeptide is covalently associated with a payload moiety via the N-terminus of the chlorotoxin polypeptide. In certain instances, a chlorotoxin polypeptide is noncovalently associated with a payload moiety via the N-terminus of the chlorotoxin polypeptide. In certain instances, a chlorotoxin polypeptide is directly associated with a payload moiety via the N-terminus of the chlorotoxin polypeptide. In certain instances, a chlorotoxin polypeptide is indirectly associated with a payload moiety via the N-terminus of the chlorotoxin polypeptide. In certain instances the N-terminal residue of the chlorotoxin polypeptide is the same amino acid as found in a corresponding position of SEQ ID NO: 1. In certain instances the N-terminal residue of the chlorotoxin polypeptide differs from an amino acid as found in a corresponding position of SEQ ID NO: 1.

In certain instances, a chlorotoxin polypeptide is associated with a payload moiety via a lysine residue of the chlorotoxin polypeptide. In certain instances, a chlorotoxin polypeptide is associated with a payload moiety via a linker covalently or noncovalently associated with a lysine residue of the chlorotoxin polypeptide. In certain instances, a chlorotoxin polypeptide is covalently associated with a payload moiety via a lysine residue of the chlorotoxin polypeptide. In certain instances, a chlorotoxin polypeptide is noncovalently associated with a payload moiety via a lysine residue of the chlorotoxin polypeptide. In certain instances, a chlorotoxin polypeptide is directly associated with a payload moiety via a lysine residue of the chlorotoxin polypeptide. In certain instances, a chlorotoxin polypeptide is indirectly associated with a payload moiety via a lysine residue of the chlorotoxin polypeptide. In certain instances association is via a lysine residue of the chlorotoxin polypeptide that is in position that corresponds to the position of a lysine residue of SEQ ID NO: 1. In certain instances association is via a lysine residue of the chlorotoxin polypeptide that is not in a position that corresponds to the position of a lysine residue of SEQ ID NO: 1. In certain instances, a chlorotoxin polypeptide is associated with a payload moiety via a lysine residue of the chlorotoxin polypeptide selected from a lysine residue corresponding to Lys 15, Lys 23, or Lys 27 of SEQ ID NO: 1.

A variety of conjugation chemistries are known in the art and can be used in a chlorotoxin agent for use in the present invention. In certain embodiments, one or more entity/entities or moiety/moieties are associated with the epsilon amino group of a lysine residue of a chlorotoxin polypeptide. In some embodiments, the conjugation chemistry is based on NHS(N-hydroxysuccinimide)/EDC (1-ethyl-3-[3-dimethylaminopropyl]carbodiimide hydrochloride) chemistry. In some embodiments, the conjugation chemistry is based on thiolation chemistry, i.e., using a thiolating agent such as Traut's reagent and/or 2-Iminothiolane.

Direct covalent binding can be achieved in any of a variety of ways, for example, via amide, ester, carbon-carbon, disulfide, carbamate, ether, thioether, urea, amine, or carbonate bonds. Covalent binding can be achieved, for example, by taking advantage of function groups present on the entity/entities or moiety/moieties and/or on a chlorotoxin polypeptide. Suitable functional groups that can be used include, but are not limited to, amines, anhydrides, hydroxyl groups, carboxyl groups, thiols, and the like. In certain embodiments, a functional group of one part of the future conjugate is activated for coupling to the other part of the future conjugate. For example, an activating agent, such as a carbodiimide, can be used to effect such a coupling. A wide variety of activating agents are known in the art and are suitable for forming a conjugate or other chlorotoxin agent as described herein.

Examples of non-covalent associations include, but are not limited to, hydrophobic interactions, electrostatic interactions, dipole interactions, van der Waals interactions, and hydrogen bonding.

In some embodiments, a chlorotoxin polypeptide and one or more entity/entities or moiety/moieties are indirectly covalently linked to each other via a linker group. Such indirect covalent linkage can be accomplished by using any of a number of stable bifunctional agents well known in the art, including homofunctional and heterofunctional agents. For non-limiting examples of such agents, see, e.g., Pierce Catalog and Handbook. Use of a bifunctional agent differs from use of an activating agent in that the former results in a linking moiety being present in the resulting conjugate, whereas the latter results in a direct coupling between two moieties involved in the reaction. A role of the bifunctional agent can be to allow a reaction between two otherwise inert moieties. Alternatively or additionally, the bifunctional agent, which becomes part of the reaction product, can be selected such that in confers some degree of conformational flexibility to the conjugate. For example, the bifunctional agent can include a straight alkyl chain containing several atoms, for example, between 2 and 10 carbon atoms. Alternatively or additionally, the bifunctional agent can be selected such that the linkage formed between a chlorotoxin polypeptide and the one or more entity/entities or moiety/moieties is cleavable, e.g., hydrolysable. (For non-limiting examples of such linkers, see, e.g., U.S. Pat. Nos. 5,773,001; 5,739,116 and 5,877,296, the contents of each of which are incorporated herein by reference.) Such linkers may, for example, be used when the entity or moiety being conjugated to a chlorotoxin polypeptide is a therapeutic moiety that is observed to have a higher activity after hydrolysis from a chlorotoxin polypeptide. Exemplary mechanisms to achieve cleavage include hydrolysis in the acidic pH of lysosomes (hydrazones, acetals, and cis-aconitate-like amides), peptide cleavage by lysosomal enzymes (e.g., cathepsins and other lysosomal enzymes), and reduction of disulfides. Additional cleavage mechanisms include hydrolysis at physiological pH extra- or intracellularly. This mechanism can be applied when the crosslinker used to couple the one or more entity/entities or moiety/moieties to a chlorotoxin polypeptide is a biodegradeable/bioerodible entity, such as polydextran and the like.

For example, for conjugates including one or more therapeutic moieties, hydrazone-containing conjugates can be made with introduced carbonyl groups that provide the desired drug-release properties. Conjugates can also be made with a linker that includes an alkyl chain with a disulfide group at one end and a hydrazine derivative at the other end.

Linkers containing functional groups other than hydrazones also have the potential to be cleaved in the acidic milieu of lysosomes. For example, conjugates can be made from thiol-reactive linkers that contain a group other than a hydrazone that is cleavable intracellularly, such as esters, amides, and acetals/ketals. Ketals made from a 5 to 7 member ring ketone that has one of the oxygen atoms associated with the entity or moiety and the other associated with a linker for association with a chlorotoxin polypeptide can also be used.

A further example of class pH-sensitive linkers are the cis-aconitates, which have a carboxylic acid group juxtaposed to an amide group. The carboxylic acid accelerates amide hydrolysis in the acidic lysosomes. Linkers that achieve a similar type of hydrolysis rate acceleration with several other types of structures can also be used.

Enzymatic hydrolysis of peptides by lysosomal enzymes can also be used to release moieties from chlorotoxin agents. For example, a chlorotoxin polypeptide can be associated via an amide bond to para-aminobenzyl alcohol and then a carbamate or carbonate can be made between the benzyl alcohol and the entity or moiety. Cleavage of a chlorotoxin polypeptide leads to collapse of the amino benzyle carabamate or carbonate, and release of the entity or moiety. As a further example, a phenol can be cleaved by collapse of the linker instead of the carbamate. As a yet further example, disulfide reaction is used to initiate collapse of a para-meraptobenzyl carbamate or carbonate.

Many therapeutic moieties, in particular anti-cancer agents, have little, if any, solubility in water, which limits drug loading on a chlorotoxin agent due to aggregation of the therapeutic moiety. One approach to overcoming this is to add solubilizing groups to the linker. Chlorotoxin agents made with a linker consisting of PEG (polyethylene glycol) and a dipeptide can be used, including, for example, those having a PEG di-acid thiol-acid, or maleimide-acid associated with the chlorotoxin polypeptide, a dipeptide, and an amide bound to the entity or moiety. Approaches that incorporate PEG groups can be beneficial in overcoming aggregation and limits in drug loading.

In embodiments in which an entity or moiety within a chlorotoxin agent includes a moiety that is a protein, polypeptide, or peptide, the chlorotoxin agent can be a fusion protein. A fusion protein is a molecule including two or more proteins, polypeptides, or peptides linked by a covalent bond via their individual peptide backbones. For example, a fusion protein can include a chlorotoxin polypeptide linked by a covalent bond to a payload moiety that is a protein, polypeptide, or peptide. Fusion proteins for use in the present invention can be produced by any suitable method known in the art. For example, they can be produced by direct protein synthetic methods using a polypeptide synthesizer. Alternatively, PCR amplification of gene fragments can be carried out using anchor primers which give rise to complementary overhangs between two consecutive gene fragments that can subsequently be annealed and re-amplified to generate a chimeric gene sequence. Fusion proteins can be obtained by standard recombinant methods (See, for example, Maniatis et al. "Molecular Cloning: A Laboratory Manual," $2^{nd}$ Ed., 1989, Cold Spring Harbor Laboratory, Cold Spring, N.Y., the entire contents of which is herein incorporated by reference). Such methods can include (1) construction of a nucleic acid molecule that encodes the desired fusion protein; (2) insertion of the nucleic acid molecule into a recombinant expression vector; (3) transformation of a suitable host cell with the expression vector; and (4) expression of the fusion protein in the host cell. Fusion protein chlorotoxin agents produced by such methods can be recovered and isolated, either directly from the culture medium or by lysis of the cells, as known in the art. Many methods for purifying proteins produced by transformed host cells are well-known in the art. These include, but are not limited to, precipitation, centrifugation, gel filtration, and column chromatography (e.g., ion exchange, reverse-phase, and affinity). Other purification methods have been described (See, for example, Deutscher et al. "Guide to Protein Purification" in *Methods in Enzymology*, 1990, vol. 192, Academic Press, the entire contents of which are herein incorporated by reference).

Irrespective of the nature of the association between the chlorotoxin polypeptide and detectable (e.g. imagable), therapeutic, or targeting moiety, the association is typically selective, specific, and strong enough so that a chlorotoxin agent does not dissociate before or during transport to and/or into tumor microenvironment and/or cells. Association between a reduced lysine chlorotoxin polypeptide and one or more moieties can be achieved using any chemical, biochemical, enzymatic, or genetic coupling known to one skilled in the art.

As can readily be appreciated by those skilled in the art, a chlorotoxin agent for use in the present invention can include any number of chlorotoxin polypeptides and any number of payload moieties, associated with one another by any number of different ways. The design of a chlorotoxin agent will be influenced by its intended purpose(s) and the properties that are desirable in the particular context of its use. Selection of a method to associate or bind a chlorotoxin polypeptide to an moiety to form a chlorotoxin agent is within the knowledge of one skilled in the art and will generally depend on the nature of the association desired (e.g., covalent vs. non-covalent and/or cleavable vs. non-cleavable), the nature of the chlorotoxin polypeptide and the moiety, the presence and nature of functional chemical groups, and the like.

In certain embodiments, a chlorotoxin conjugate or payload as described in one or more of WO 2011/097533 (see also, e.g., U.S. Pat. No. 9,018,347) and WO 2011/142858

(see also, e.g., US 2013/0195760), each of which is incorporated by reference in its entirety, is utilized in accordance with the present invention.

Pharmaceutical Compositions

Chlorotoxin agents described herein can be administered per se and/or in the form of a pharmaceutical composition. In some embodiments, pharmaceutical compositions for use in the present invention include an effective amount of at least one chlorotoxin agent and at least one pharmaceutically acceptable carrier.

A chlorotoxin agent (e.g., a chlorotoxin polypeptide), or a pharmaceutical composition thereof, can be administered according to the present invention in such amounts and for such a time as is necessary or sufficient to achieve at least one desired result. For example, a chlorotoxin polypeptide, or pharmaceutical composition thereof, can be administered in such amounts and for such a time that it kills cancer cells, reduces tumor size, inhibits tumor growth or metastasis, treats various leukemias, and/or prolongs the survival time of mammals (including humans) with those diseases, or otherwise yields clinical benefit.

Pharmaceutical compositions for use in the present invention can be administered using any amount and any route of administration effective for achieving the desired therapeutic effect.

The exact amount of pharmaceutical composition to be administered will vary from subject to subject, depending on the species, age, and general condition of the subject, the severity of the condition, and the like (see below).

The optimal pharmaceutical formulation can be varied depending upon the route of administration and desired dosage. Such formulations can influence the physical state, stability, rate of in vivo release, and rate of in vivo clearance of the administered compounds.

Pharmaceutical compositions for use in the present invention can be formulated in dosage unit form for ease of administration and uniformity of dosage. The expression "unit dosage form," as used herein, refers to a physically discrete unit of chlorotoxin agent (with or without one or more additional agents) for the patient to be treated. It will be understood, however, that the total daily usage of compositions in the present invention will be decided by the attending physician within the scope of sound medical judgment.

After formulation with one or more appropriate physiologically acceptable carrier(s) or excipient(s) in a desired dosage, pharmaceutical compositions for use in the present invention can be administered to humans or other mammals by any suitable route. Various delivery systems are known and can be used to administer such compositions, including, tablets, capsules, injectable solutions, etc. Methods of administration include, but are not limited to, dermal, intradermal, intramuscular, intraperitoneal, intravenous, subcutaneous, intranasal, pulmonary, epidural, ocular, and oral routes. A composition can be administered by any convenient or otherwise appropriate route, for example, by infusion or bolus injection, by absorption through epithelial or mucocutaneous linings (e.g., oral, mucosa, rectal and intestinal mucosa, etc) and can be administered together with other biologically active agents. Administration can be systemic and/or local.

Injectable preparations, for example, sterile injectable aqueous or oleaginous suspensions, can be formulated according to the known art using suitable dispersing or wetting agents, and suspending agents. A sterile injectable preparation can also be a sterile injectable solution, suspension or emulsion in a non-toxic parenterally acceptable diluent or solvent, for example, as a solution in 2,3-butanediol. Among the acceptable vehicles and solvents that can be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid can also be used in the preparation of injectable formulations. Sterile liquid carriers are useful in sterile liquid from compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection can be via single push or by gradual infusion (e.g., 30 minute intravenous infusion). Where necessary, the composition can include a local anesthetic to ease pain at the site of injection.

In order to prolong an effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming micro-encapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes (also known as lipid vesicles) or microemulsions that are compatible with body tissues.

Liquid dosage forms for oral administration include, but are not limited to, pharmaceutically acceptable emulsions, microemulsions, solutions, suspensions, syrups, elixirs, and pressurized compositions. In addition to the active ingredient (i.e., conjugate), the liquid dosage form can contain inert diluents commonly used in the art such as, for example, water or other solvent, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, suspending agents, preservatives, sweetening, flavoring, and perfuming agents, thickening agents, colors, viscosity regulators, stabilizers or osmoregulators. Suitable examples of liquid carriers for oral administration include water (partially containing additives; e.g., cellulose derivatives, such as sodium caboxymethyl cellulose solution), alcohols (including monohydric alcohols and polyhydric alcohols such as glycols) and their derivatives, and oils (e.g., fractionated coconut oil and arachis oil)).

Solid dosage forms for oral administration include, for example, capsules, tablets, pills, powders, and granules. In such solid dosage forms, the active ingredient is mixed with at least one inert, physiologically acceptable excipient or carrier such as sodium citrate or dicalcium phosphate and one or more of: (a) fillers or extenders such as starches, lactose, sucrose, glucose, mannitol, and silicic acid; (b) binders such as, for example, carboxymethylcellulose, alginates, gelatin, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulfate, and mixtures thereof. Additional or alternative excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form can also include buffering agents. The amount of solid carrier per solid dosage form will vary widely. In some embodiments, the amount of solid carrier per solid dosage form is from about 25 mg to about 1 g.

Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

In certain embodiments, it can be desirable to administer an inventive composition locally to an area in need of diagnosis and/or treatment. This can be achieved, for example, by local infusion during surgery, topically application, by injection, by means of a catheter, by means of suppository, or by means of a skin patch or stent or other implant, among other ways.

Some compositions for topical administration can be formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurate (5%) in water, or sodium lauryl sulfate (5%) in water. Other materials such as antioxidants, humectants, viscosity stabilizers, and similar agents can be added as necessary. Percutaneous penetration enhancers such as Azone can also be included.

In addition, in certain instances, compositions can be disposed within transdermal devices placed upon, in, or under the skin. Such devices include patches, implants, and injections which release the compound onto the skin, by either passive or active release mechanisms. Transdermal administrations include all administrations across the surface of the body and the inner linings of bodily passage including epithelial and mucosal tissues. Such administrations can be carried out using the present compositions in lotions, creams, foams, patches, suspensions, solutions, and suppositories (rectal and vaginal).

Transdermal administration can be accomplished, for example, through use of a transdermal patch containing active ingredient(s) and a carrier that is non-toxic to the skin, and allows the delivery of at least some of the active ingredient(s) for systemic absorption into the bloodstream via the skin. The carrier can take any number of forms such as creams and ointments, pastes, gels, and occlusive devices. Creams and ointments can be viscous liquid or semisolid emulsions of either the oil-in-water or water-in-oil type. Pastes including absorptive powders dispersed in petroleum or hydrophilic petroleum containing active ingredient(s) can also be suitable. A variety of occlusive devices can be used to release active ingredient(s) into the bloodstream such as a semipermeable membrane covering a reservoir containing the active ingredient(s) with or without a carrier, or a matrix containing the active ingredient.

Suppository formulations can be made from traditional materials, including cocoa butter, with or without the addition of waxes to alter the suppository's melting point, and glycerin. Water soluble suppository bases, such as polyethylene glycols of various molecular weights, can also be used.

Materials and methods for producing various formulations are known in the art and can be adapted for practicing the subject invention.

A. Encapsulating Agents

In some embodiments, compositions provided by the present invention include one or more encapsulating agents. In general, an encapsulating agent can be any physiologically tolerable agent that can be used to entrap an entity such as a chlorotoxin agent or a moiety. By "entrapped" it is meant that the encapsulating agent can encircle or enclose the entity, or an "entrapped" entity can be embedded partially or wholly within the material including the encapsulating agent.

In some embodiments, the encapsulating agent is part of the moiety (such as therapeutic moiety), and a chlorotoxin polypeptide is conjugated to the encapsulating agent. In some such embodiments, a chlorotoxin polypeptide is conjugated to the outer surface of the encapsulating agent. In some such embodiments, a chlorotoxin polypeptide is exposed on the environment external to the encapsulating agent. A chlorotoxin polypeptide can be conjugated to the encapsulating agent by a direct interaction (which can be non-covalent or covalent), or it can be conjugated to the encapsulating agent via a linker.

In some embodiments, the chlorotoxin agent including a chlorotoxin polypeptide and a moiety (e.g., therapeutic moiety) is enclosed by the encapsulating agent. The chlorotoxin agent can be enclosed partially or wholly within a space or environment (for example, an aqueous environment) defined and/or created by the encapsulating agent. In some embodiments, the chlorotoxin agent is at least partially embedded within the encapsulating agent. For example, if the encapsulating agent includes lipid membranes, the conjugate can be at least partially embedded within or among lipid molecules in the membrane. In some embodiments, the conjugate is wholly embedded within the encapsulating agent.

A variety of types of encapsulating agents are known in the art, as are methods of using such agents to entrap drugs, biomolecules, and the like. In certain embodiments, the encapsulating agent includes a small particle having a core and a surface. Such encapsulating agents include, but are not limited to, liposomes, micelles, microparticles, nanoparticles, etc.

Liposomes are typically approximately spherically shaped bilayer structures or vesicles and are made up of, at least in part, natural or synthetic phospholipid membranes. Liposomes can further include other membrane components such as cholesterol and protein. The interior core of liposomes typically contain an aqueous solution. Therapeutic moieties and/or chlorotoxin agents can be dissolved in the aqueous solution. Therapeutic moieties and chlorotoxin agents can be embedded within the membrane of the liposome. Liposomes can be especially useful for delivering agents such as nucleic acid agents (such as those described herein), including inhibitory RNAs such as siRNAs.

Micelles are similar to liposomes, except they generally form from a single layer of phospholipids and lack an internal aqueous solution. Reverse micelles that are made to include internal aqueous solution can also be used in accordance with the present invention.

In some embodiments, the particle is a microparticle, at least one dimension of which averages to be smaller than about 1 μm. For example, the smallest dimension of the particles can average about 100 nm, about 120 nm, about 140 nm, about 160 nm, about 180 nm, about 200 nm, about 220 nm, about 240 nm, about 260 nm, about 280 nm, about 300 nm, about 320 nm, about 340 nm, about 360 nm, about 380 nm, about 400 nm, about 420 nm, about 440 nm, about 460 nm, about 480 nm, about 500 nm, about 550 nm, about 600 nm, about 650 nm, about 700 nm, about 750 nm, about 800 nm, about 850 nm, about 900 nm, or about 950 nm.

In some embodiments, the particle is a nanoparticle, at least one dimension of which averages to be smaller than about 100 nm. For example, the smallest dimension of the particles can average about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 22 nm, about 24 nm, about 26 nm, about 28 nm, about 30 nm, about 32 nm, about 34 nm, about 36 nm, about 38 nm, about 40 nm, about 42 nm, about 44 nm, about 46 nm, about 48 nm, about 50 nm, about 55 nm, about 60 nm, about 65 nm, about 70 nm, about 75 nm, about 80 nm, about 85 nm, about 90 nm, about 95 nm, or about 99 nm.

In some embodiments, the core of the particle includes a material having magnetic resonance activity, which can be advantageous in detection and/or therapeutic applications. Materials having magnetic resonance activity include metals and their oxides, such as aluminum-cobalt-, indium-, iron-, copper-, germanium-, manganese-, nickel-, tin-, titanium-, palladium-, platinum-, selenium-, silicon-, silver-, zinc-, etc. containing metals.

In some embodiments, therapeutic moieties include nucleic acids. Nucleic acids can be enclosed wholly within the encapsulating agent. In some embodiments, nucleic acid agents are embedded within the encapsulating agent. For example, the encapsulating agent can be a liposome and the nucleic agent can be enclosed within the liposome. The nucleic acid agent can be at least partially embedded within the lipid molecules of the liposome.

B. Pharmaceutical Packs or Kits

In another aspect, the present invention provides a pharmaceutical pack or kit including one or more containers (e.g., vials, ampoules, test tubes, flasks or bottles) containing one or more ingredients of a pharmaceutical composition as described herein, allowing administration of a chlorotoxin conjugate for use in the present invention.

Using Chlorotoxin Agents

In certain embodiments, the present disclosure provides various technologies related to use of chlorotoxin agents as described herein, including for example, methods that involve administration and/or delivery to one or more cells, tissues, or organisms (and specifically including humans). In some embodiments, a chlorotoxin agent may be modified or metabolized upon administration or delivery. For example, in some embodiments, administration of a chlorotoxin agent comprising a payload ultimately achieves (e.g., upon delivery to a particular site) separation of the payload from the chlorotoxin polypeptide and/or other modification or metabolism of one or both of the payload moiety and the chlorotoxin polypeptide moiety. Without wishing to be bound by any particular theory, Applicant proposes that, in some embodiments, release of payload from a chlorotoxin polypeptide may facilitate or otherwise be involved in or achieve delivery of the payload to a cell, and/or into an interior of a cell. Also without wishing to be bound by any particular theory, Applicant proposes that a particular site at which metabolism or modification (e.g., release of payload from) of a chlorotoxin agent as described herein may occur may, in some embodiments, be or comprise a tumor microenvironment.

In some embodiments, administration of a chlorotoxin agent as described herein may be particularly useful in detection of one or more particular cells, cell types, or components thereof. Alternatively or additionally, in some embodiments, administration achieves delivery of the chlorotoxin agent (and/or any payload that may be included in or otherwise associated with such agent) to a particular target site, cell, tissue, etc. In some embodiments, such delivery may involve binding between a chlorotoxin polypeptide and NRP1, e.g., at the site, cell, tissue, etc.

In some embodiments, provided technologies may comprise administration and/or delivery to a subject (and/or to a cell or tissue thereof) suffering from or susceptible to cancer. In some embodiments, a subject has (or, in some embodiments, may be suspected of having) at least one tumor. In some embodiments, administration of a chlorotoxin agent to a subject having a tumor (and/or to a system comprising one or more tumor cells) achieves specific binding by the chlorotoxin agent (or of a component or metabolite thereof) to tumor cells. In some embodiments, administration and/or deliver to a subject (and/or to a cell or tissue thereof) suffering from or susceptible to caner may be useful in treatment and/or detection or characterization (e.g., imaging, classification, diagnosis, etc) of cancer.

In some embodiments, treatment of cancer may be or comprise reducing likelihood that a subject (or population) will develop a tumor, that one or more tumors in the individual will increase in size, that one or more tumors in the individual will metastasize, and/or that ane or more tumors will progress by any other measure (such as clinical stage).

In some embodiments, detection may include, for example, recovering information relevant to identification or determination of the volume, dimensions, location, orientation, source, stage, type, class, number, distribution, metastasis, organ involvement, tissue involvement, growth or remission rate, growth or remission direction, treatment progress, and/or amenability to treatment of one or more cancers. Detection can be, for example, in a sample, in vitro, or in vivo. Detection can be, for example, pre-operative, inter-operative, post-operative, diagnostic, prior to a treatment or initiation of treatment regimen, during treatment or in the course of a treatment regimen, after cessation of a treatment or treatment regimen, or in the course of routine examination.

Imaging includes a method or use of detection that includes recovering information relevant to identification or determination of the volume, dimensions, location, orientation, source, stage, type, class, number, distribution, metastasis, organ involvement, tissue involvement, growth or remission rate, growth or remission direction, treatment progress, and/or amenability to treatment of one or more cancers via indicia that are observable (e.g., through the use of one or more fluorescent or otherwise observable labels as described herein or otherwise known in the art).

Characterization includes a method or use of detection that includes recovering information relevant to identification or determination of the volume, dimensions, location, orientation, source, stage, type, class, number, distribution, metastasis, organ involvement, tissue involvement, growth or remission rate, growth or remission direction, treatment progress, and/or amenability to treatment of one or more cancers, and further includes identifying or determining the volume, dimensions, location, orientation, source, stage, type, class, number, distribution, metastasis, organ involvement, tissue involvement, growth or remission rate, growth or remission direction, treatment progress, and/or amenability to treatment of one or more cancers.

Diagnosis includes a method or use of detection that provides information relevant to identifying the presence or absence of a cancer. Diagnosis includes a method or use of detection that provides information relevant to identifying a cancer as a cancer of one or more possible types. Diagnosis includes a method or use of detection that provides information relevant to identifying a cancer as a cancer of one or more possible stages. Diagnosis includes a method or use of detection that provides information relevant to a determination of a cancer prognosis. Diagnosis includes a method or use of detection that provides information relevant to identifying a cancer as metstatic or non-metastatic. Diagnosis includes a method or use of detection that provides information relevant to identifying a cancer as benign or non-benign. Diagnosis can result in the identification of one or more features or qualities of one or more cancers. Diagnosis may, in some embodiments or instances, not reveal one or more features or qualities of one or more cancers.

In certain embodiments, methods for use in the present invention include a step of administering a composition that includes a chlorotoxin agent as described herein to an individual having or suspected of having a disease or condition characterized by aberrant angiogenesis, such that the chlorotoxin agent reduces extent of angiogenesis. In some embodiments, the chlorotoxin agent prevents the formation of neovasculature. In some embodiments, the chlorotoxin agent causes existing neovasculature to regress.

A. Dosages and Administration

Chlorotoxin agents, or pharmaceutical compositions thereof, can be administered using any administration route effective for achieving a desired effect (e.g., therapeutic benefit, detection, or other uses discussed herein). Administration can be local or systemic.

In certain embodiments of the invention, chlorotoxin agents (or pharmaceutical compositions thereof) are delivered systemically. Systemic routes of administration include, but are not limited to, intramuscular, intravenous, pulmonary, and oral routes. In certain embodiments, administration is by injection, which injection can be subcutaneous, intravenous, intramuscular, intratumoral, intraperitoneal, or the like. In particular embodiments, a chlorotoxin agent is administered intravenously (IV). Systemic administration can also be performed, for example, by infusion or bolus injection, or by absorption through epithelial or mucocutaneous linings (e.g., oral mucosa, rectal mucosa, intestinal mucosa, etc.).

In certain embodiments, the chlorotoxin agent is administered by a route selected from intracranial (including intracavitary), intraocular, periocular, topical, dermal, intradermal, intranasal, or epidural. In particular embodiments, a chlorotoxin agent can be administered by intracavitary administration.

In certain embodiments, it can be desirable to administer a cytotoxic chlorotoxin conjugate locally to an area in need of treatment. For example, systemic administration of chemotherapeutic agents to treat brain tumors is often limited by the blood brain barrier impenetrability. As a result, effective therapeutic concentrations are difficult to achieve in the brain without causing systemic adverse effects. Thus, in certain embodiments where the tumor to be treated is located in the brain, the cytotoxic chlorotoxin conjugate is administered locally.

Local administration to the brain (or to a specific region of the brain) can be achieved, for example, and not by way of limitation, by local infusion (e.g., during surgery), by injection (e.g., intracerebro ventricular injection), by means of a catheter, or by means of a ventricular reservoir or pump placed in the tumor cavity during surgery or implanted subcutaneously in the scalp and connected to the brain via an outlet catheter. Alternatively or additionally, local administration can be achieved via the use of an implant device (e.g., a wafer implant containing the active ingredient) or a drug depot that can be placed locally during surgery. Such systems provide sustained drug release.

As discussed below, it can be desirable to utilize a chlorotoxin agent as described herein to reduce extent of angiogenesis in ocular neovascularization diseases. In some embodiments, chlorotoxin agents can be delivered to the eye. Delivery to the eye can be achieved, for example, using intraocular and/or periocular routes such as intravitreal injection, subjunctival injection, etc. Topical application of chlorotoxin agents to the eye can also be achieved, for example, using eye drops.

Ocular routes of administration can be particularly useful for detection and/or treatment of ocular neovascularization diseases such as macular degeneration.

Chlorotoxin agent compositions according to the present invention can be administered according to a regimen consisting of a single dose or a plurality of doses over a period of time.

Administration can be once daily, multiple times per day, multiple times per week, at some other hourly, multiple hour, daily, or multiple day interval, or on an intermittent schedule. For example, a composition can be administered one or more times per day on a weekly basis for a period of weeks (e.g., 4-10 weeks). Alternatively, a composition can be administered daily for a period of days (e.g., 1-10 days) following by a period of days (e.g., 1-30 days) without administration, with that cycle repeated a given number of times (e.g., 2-10 cycles). In some embodiments, at least two, at least three, at least four, at least five, or at least six doses are administered. In some embodiments, the composition is administered weekly for at least two weeks, three weeks, four weeks, five weeks, or six weeks.

Depending on the route of administration, effective doses can be calculated according to the organ function, body weight, or body surface area of the subject to be treated. Optimization of the appropriate dosages can readily be made by one skilled in the art in light of pharmacokinetic data observed in human clinical trials. Final dosage regimen can be determined by the attending physician, considering various factors that modify the action of the drugs, e.g., the drug's specific activity, the severity of the damage and the responsiveness of the patient, the age, condition, body weight, sex and diet of the patient, the severity of any present infection, time of administration, the use (or not) of concomitant therapies, and other clinical factors.

Typical dosages range from about 1.0 pg/kg body weight to about 100 mg/kg body weight. (Dosages are presented herein in terms of the weight of a chlorotoxin polypeptide component of the chlorotoxin agent.)

For example, for systemic administration, typical dosages range from about 100.0 ng/kg body weight to about 10.0 mg/kg body weight. For example, in certain embodiments where a chlorotoxin agent is administered intravenously, dosing of the agent can include administration of one or more doses including about 0.001 mg/kg to about 5 mg/kg, e.g., from about 0.001 mg/kg to about 5 mg/kg, from about 0.01 mg/kg to about 4 mg/kg, from about 0.02 mg/kg to about 3 mg/kg, from about 0.03 mg/kg to about 2 mg/kg or from about 0.03 mg/kg to about 1.5 mg/kg of chlorotoxin agent. For example, in some embodiments, one or more doses of chlorotoxin agent can be administered that each contains about 0.002 mg/kg, about 0.004 mg/kg, about 0.006 mg/kg, about 0.008 mg/kg, about 0.009 mg/kg, about 0.01 mg/kg, about 0.02 mg/kg or more than 0.02 mg/kg of chlorotoxin agent. In some embodiments, one or more doses of chlorotoxin agent can be administered that each contains about 0.03 mg/kg, about 0.04 mg/kg, about 0.05 mg/kg, about 0.06 mg/kg, about 0.07 mg/kg, about 0.09 mg/kg, about 1.0 mg/kg or more than 1.0 mg/kg of chlorotoxin agent. In some embodiments, one or more doses of chlorotoxin agent can be administered that each contains about 0.05 mg/kg, about 0.10 mg/kg, about 0.15 mg/kg, about 0.20 mg/kg, about 0.25 mg/kg, about 0.30 mg/kg, about 0.35 mg/kg, about 0.40 mg/kg, about 0.45 mg/kg, about 0.50 mg/kg, about 0.55 mg/kg, about 0.60 mg/kg, about 0.65 mg/kg, about 0.70 mg/kg, about 0.75 mg/kg, about 0.80 mg/kg, about 0.85 mg/kg, about 0.90 mg/kg, about 0.95 mg/kg, about 1.0 mg/kg, or more than about 1 mg/kg of chlorotoxin agent. In yet other embodiments, one or more doses of chlorotoxin agent can be administered that each contains about 1.0 mg/kg, about 1.05 mg/kg, about 1.10 mg/kg, about 1.15 mg/kg, about 1.20 mg/kg, about 1.25 mg/kg, about 1.3 mg/kg, about 1.35 mg/kg, about 1.40 mg/kg, about 1.45 mg/kg, about 1.50 mg/kg, or more than about 1.50 mg/kg of chlorotoxin agent. In such embodiments, detection and/or treatment can include administration of a single dose of chlorotoxin agent or administration of 2 doses, 3 doses, 4 doses, 5 doses, 6 doses or more than 6 doses. Two consecutive doses can be administered at 1 day interval, 2 days interval, 3 days interval, 4 days interval, 5 days interval, 6 days interval, 7 days interval, or more than 7 days interval (e.g., 10 days, 2 weeks, or more than 2 weeks).

For direct administration to the site via microinfusion, typical dosages range from about 1 ng/kg body weight to about 1 mg/kg body weight.

In certain embodiments where the chlorotoxin agent is administered locally, in particular in cases of intracavitary administration to the brain, dosing of the chlorotoxin agent can include administration of one or more doses including about 0.01 mg to about 100 mg of chlorotoxin agent, e.g., from about 0.05 to about 50 mg, from about 0.1 mg to about 25 mg, from about 0.1 mg to about 10 mg, from about 0.1 mg to about 5 mg, or from about 0.1 mg to about 1.0 mg. For example, in certain embodiments, one or more doses of chlorotoxin agent can be administered that each contains about 1 mg, about 1.5 mg, about 2 mg, about 2.5 mg, about 3 mg, about 3.5 mg, about 4 mg, about 4.5 mg or about 5 mg of chlorotoxin agent, chlorotoxin polypeptide. In some embodiments, one or more doses of chlorotoxin agent can be administered that each contains about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg or about 1 mg of chlorotoxin polypeptide. In some embodiments, detection and/or treatment can include administration of a single dose of chlorotoxin agent or administration of 2 doses, 3 doses, 4 doses, 5 doses, 6 doses or more than 6 doses. Two consecutive doses can be administered at 1 day interval, 2 days interval, 3 days interval, 4 days interval, 5 days interval, 6 days interval, 7 days interval, or more than 7 days interval (e.g., 10 days, 2 weeks, or more than 2 weeks). In some embodiments, multiple doses are administered, and the amount of chlorotoxin polypeptide administered is not the same for every dose. For example, in some embodiments, doses can be adjusted (e.g., escalated or reduced) from one dose to another as determined by the attending clinician.

It will be appreciated that pharmaceutical combinations for use in the present invention can be employed in combination with additional therapies (i.e., administration for detection and/or treatment according to the present invention can be concurrent with, prior to, or subsequent to one or more desired therapeutics or medical procedures). The particular combination of therapies or medical procedures (therapeutics and/or procedures) to employ in such a combination regimen will take into account compatibility of the desired therapeutics and/or procedures and desired therapeutic effects to be achieved.

For example, methods and compositions for use in the present invention can be employed together with other procedures including surgery, radiotherapy (e.g., .gamma.-radiation, proton beam radiotherapy, electron beam radiotherapy, proton therapy, brachytherapy, and systemic radioactive isotopes), endocrine therapy, hyperthermia and cryotherapy.

Alternatively or additionally, methods and compositions for use in the present invention can be employed together with other agents to attenuate any adverse effects (e.g., antiemetics), and/or with other approved chemotherapeutic drugs, including, but not limited to, alkylating drugs (mechlorethamine, chlorambucil, cyclophosphamide, melphalan, ifosfamide), antimetabolites (methotrexate), purine antagonists and pyrimidine antagonists (6 mercaptopurine, 5 fluorouracil, cytarabile, gemcitabine), spindle poisons (vinblastine, vincristine, vinorelbine, paclitaxel), podophyllotoxins (etoposide, irinotecan, topotecan), antibiotics (doxorubicin, bleomycin, mitomycin), nitrosoureas (carmustine, lomustine), inorganic ions (cisplatin, carboplatin), enzymes (asparaginase), and hormones (tamoxifen, leuprolide, flutamide, and megestrol), to name a few. For a more comprehensive discussion of updated cancer therapies see <www.cancer.gov/about-cancer/treatment/drugs> and The Merck Manual, Seventeenth Ed. 1999, the entire contents of each of which are hereby incorporated by reference.

Methods and compositions for use in the present invention can also be employed together with one or more further combinations of cytotoxic agents as part of a detection and/or treatment regimen. In some embodiments, the further combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, pro carbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); Ch1VPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylprediso-lone, high-dose cytaribine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

B. Indications

Compositions and methods for use in the present invention can be used in a variety of antiproliferative and/or antiangiogenic contexts to treat and/or detect diseases or conditions.

1. NRP1 Associated Conditions

NRP1 expression has been detected in connection with a number of known diseases, conditions, disorders, cancers, and tumor types, and in a number of cell types. The present invention provides, among other things, the detection and/or treatment of such NRP1-associated diseases, conditions, disorders, cancers, tumor types, and cell types by administration of a chlorotoxin agent. The present invention provides, among other things, detection of a NRP1-expressing cells of an NRP-associated disease, condition, disorder, cancer, tumor type, or cell type using a chlorotoxin agent.

Diseases, conditions, and disorders associated with expression of NRP1 include eye diseases, neovascular eye disease, Age-related macular degeneration (AMD), macular oedema in ischemic retinopathies, oxygen-induced retinopathy, liver fibrosis, Charcot-Marie-Tooth disease, cardiovascular disease, and various cancers (e.g., various tumors).

Cancer (e.g., tumors) associated with expression of NRP1 include, for example, melanoma, breast cancer, liver cancer, prostate cancer, lung cancer, brain cancer, carcinoma, colon carcinoma, pancreatic cancer, astrocytoma, glioblastoma, and neuroblastoma.

Cell types associated with expression of NRP1 include, for example, stromal cells, including fibroblasts, endothelial and immune cells NRP1-associated disease-related processes include angiogenesis, cancer angiogenesis, inflammation, axon guidance, immune responses, metastasis, cancer invasiveness, melanoma invasiveness, cancer progression, cancer aggressiveness, advanced cancer disease stage, poor cancer prognosis, metastatic potential (e.g., in melanoma and breast cancer), epithelial-mesenchymal transition in cancer invasion.

In various embodiments, the invention includes a step of determining whether a cancer expresses NRP1. Determination of whether a cancer expresses NRP1 can be determined from a sample present in or derived from cancer or subject, such as a tissue, protein, plasma, nucleic acid sample, or other biological sample. Techniques for determining whether a cancer expresses NRP1, e.g., by analysis of a sample, are known in the art and include, for example, proteomic analysis, mRNA analysis, and antibody-based methods.

2. Anti-Proliferative Contexts

In certain embodiments, compositions and methods for use in the present invention are used to treat and/or detect conditions involving uncontrolled cell proliferation, such as primary and/or metastatic cancers, and other cancerous conditions. For example, compositions and methods for use in the present invention should be useful for reducing size of solid tumors, inhibiting cancer growth or metastasis, treating various lymphatic cancers, and/or prolonging the survival time of mammals (including humans) suffering from these diseases.

Examples of cancers and cancer conditions that can be treated and/or detected according to the present invention include, but are not limited to, cancers of the brain and central nervous system (e.g., tumors of the meninges, brain, spinal cord, cranial nerves and other parts of the CNS, such as glioblastomas or medulloblastomas); head and/or neck cancer, breast cancers, cancers of the circulatory system (e.g., heart, mediastinum and pleura, and other intrathoracic organs, vascular cancers, and tumor-associated vascular tissue); cancers of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, haematopoietic and related tissues, such as diffuse large cell lymphoma, T-cell lymphoma or cutaneous T-cell lymphoma); cancers of the excretory system (e.g., kidney, renal pelvis, ureter, bladder, and other urinary organs); cancers of the gastrointestinal tract (e.g., esophagus, stomach, small intestine, colon, colorectal, rectosigmoid junction, rectum, anus, and anal canal); cancers involving the liver and intrahepatic bile ducts, gall bladder, and other parts of the biliary tract, pancreas, and other digestive organs; cancers of the oral cavity (e.g., lip, tongue, gum, floor of mouth, palate, parotid gland, salivary glands, tonsil, oropharynx, nasopharynx, puriform sinus, hypopharynx, and other sites of the oral cavity); cancers of the reproductive system (e.g., vulva, vagina, Cervix uteri, uterus, ovary, and other sites associated with female genital organs, placenta, penis, prostate, testis, and other sites associated with male genital organs); cancers of the respiratory tract (e.g., nasal cavity, middle ear, accessory sinuses, larynx, trachea, bronchus and lung, such as small cell lung cancer and non-small cell lung cancer); cancers of the skeletal system (e.g., bone and articular cartilage of limbs, bone articular cartilage and other sites); cancers of the skin (e.g., malignant melanoma of the skin, non-melanoma skin cancer, basal cell carcinoma of skin, squamous cell carcinoma of skin, mesothelioma, Kaposi's sarcoma); and cancers involving other tissues including peripheral nerves and autonomic nervous system, connective and soft tissue, retroperitoneum and peritoneum, eye and adnexa, thyroid, adrenal gland, and other endocrine glands and related structures, secondary and unspecified malignant neoplasms of lymph nodes, secondary malignant neoplasm of respiratory and digestive systems and secondary malignant neoplasms of other sites.

In some embodiments, cancer is cutaneous or intraocular melanoma. In some embodiments, the cancer is metastatic melanoma. In some embodiments, the cancer is non-small cell lung cancer. In some embodiments, the cancer is colon or colorectal cancer, e.g., metastatic colon or colorectal cancer.

In some embodiments, compositions and methods are useful in the treatment and/or detection of neuroectodermal cancers (See, e.g., U.S. Pat. No. 6,667,156; the entire contents of which are herein incorporated by reference). In some embodiments, the neuroectodermal tumor is glioma (See, e.g., U.S. Pat. Nos. 5,905,027; 6,028,174; 6,319,891; 6,429,187; and 6,870,029; and International Patent Application publications WO 03/101475, WO 09/021,136, and WO 2009/140599; the entire contents of each of which are herein incorporated by reference). Types of glioma for which compositions and methods of the invention are useful include, but are not limited to, glioblastoma multiformes (WHO grad IV), anaplastic astrocytomas (WHO grade III), low grade gliomas (WHO grade II), pliocytic astrocytomas (WHO grade I), oligodendrogliomas, gangliomas, meningiomas, and ependymomas. In some embodiments, the neuroectodermal tumor is selected from the group consisting of medulloblastomas, neuroblastomas, pheochromocytomas, melanomas, peripheral primitive neuroectodermal cancers, small cell carcinoma of the lung, Ewing's sarcoma, and metastatic cancers in the brain.

In certain embodiments of an invention described herein, compositions and methods are used in the treatment and/or detection of sarcomas. In some embodiments, compositions and methods for use in the present invention are used in the treatment and/or detection of bladder cancer, breast cancer, chronic lymphoma leukemia, head and neck cancer, endometrial cancer, Non-Hodgkin's lymphoma, non-small cell lung cancer, ovarian cancer, pancreatic cancer, kidney cancer, and prostate cancer. In some embodiments, the sarcoma is selected from the group consisting of prostate cancer or breast cancer (See, e.g., International Patent Application publications WO 03/101474A1, WO 03/10475A2, and WO 2009/140599, the entire contents of each of which are herein incorporated by reference). In some embodiments, the sarcoma is pancreatic cancer.

In certain embodiments of an invention described herein, compositions and methods are useful in the treatment and/or detection of myeloproliferative disorders (e.g., tumors of myeloid origin) and/or lymphoproliferative disorders (e.g., tumors of lymphoid origin) (See, e.g., International Patent Application publication WO 05/099774, the entire contents of which are herein incorporated by reference).

Types of myeloproliferative disorders for which compositions and methods for use in the present invention are useful include, but are not limited to, polycythemia vera (PV), essential thrombocythemia (ET), agnogenic myeloid metaplasia (AMM) (also referred to as idiopathic myelofibrosis (IMF)), and chronic myelogenous leukemia (CML).

In some embodiments, compositions and methods for use in the present invention are used to treat and/or detect (e.g., image or diagnose) a lymphoproliferative disorder. In some embodiments, the lymphoproliferative disorder is a non-Hodgkin's lymphoma. In some embodiments, the lymphoproliferative disorder is a B cell neoplasm, such as, for example, a precursor B-cell lymphoblastic leukemia/lymphoma or a mature B cell neoplasm. Non-limiting types of mature B cell neoplasms include B cell chronic lymphocytic leukemia/small lymphocytic lymphoma, B cell prolymphocytic leukemia, lymphoplasmacytic lymphoma, splenic marginal zone B cell lymphoma, hairy cell leukemia, extranodal marginal zone B cell lymphoma, mantle cell lymphoma, follicular lymphoma, nodal marginal zone lymphoma, diffuse large B cell lymphoma, Burkitt's lymphoma, plasmacytoma, and plasma cell myeloma.

In some embodiments, compositions and methods for use in the present invention are used to treat a T cell neoplasm. Non-limiting types of T cell neoplasms include T cell prolymphocytic leukemia, T cell large granular lymphocytic leukemia, NK cell leukemia, extranodal NK/T cell lymphoma, mycosis fungoides, primary cutaneous anaplastic large cell lymphoma, subcutaneous panniculitis-like T cell lymphoma, enteropathy-type intestinal T cell lymphoma, hepatosplenic gamma-delta T cell lymphoma, angioimmunoblastic T cell lymphoma, peripheral T cell lymphoma, anaplastic large cell lymphoma, and adult T cell lymphoma.

Cancers that can be treated using compositions and methods for use in the present invention can be refractory to detection and/or treatment with other chemotherapeutics. The term "refractory," when used herein in reference to treatment of a cancer means that the cancer (and/or metastases thereof), upon treatment with at least one chemotherapeutic other than an inventive composition, shows no or only weak anti-proliferative response (i.e., no or only weak inhibition of cancer growth) after the treatment of such a chemotherapeutic moiety—that is, a cancer that cannot be treated at all or only with unsatisfying results with other (preferably standard) chemotherapeutics. The present invention, where treatment of refractory cancers and the like is mentioned, is to be understood to encompass not only (i) cancers where one or more chemotherapeutics have already failed during treatment of a patient, but also (ii) cancers that can be shown to be refractory by other means, e.g., biopsy and culture in the presence of chemotherapeutics.

Cancers that can be treated by administration of composition for use in the present invention or according to a method for use in the present invention include, for example, cancers of the following types or tissues: accessory sinuses, acute leukemia, acute lymphoblastic leukemia, acute lymphocytic leukemia, adnexa, adrenal gland, adrenal mass neuroblastoma, adrenal pheochromocytoma, adult T cell lymphoma, agnogenic myeloid metaplasia (AMM) (IMF), AIDS-related lymphomas, anal canal, anal region, anaplastic astrocytoma, anaplastic ependymoma of the occipital lobe, anaplastic ependymoma of the parietal lobe, anaplastic large cell lymphoma, anaplastic oligodendroglioma, angioimmunoblastic T cell lymphoma, anus, articular cartilage of limbs, astrocytoma, astrocytoma of the parietal lobe, autonomic nervous system, B cell chronic lymphocytic leukemia/small lymphocytic lymphoma, B cell neoplasm, B cell prolymphocytic leukemia, basal cell carcinoma of skin, benign prostatic hyperplasia, biliary tract, bladder, bladder (metastatic), blastoma, blood, bone, brain, breast, breast (metastatic), breast cancer metastasized to bone, breast cancer metastasized to lung, bronchus, Burkitt's lymphoma, cancer expressing phosphatidylinositol phospholipid, carcinoma, carcinoma of the cervix, carcinoma of the endometrium, carcinoma of the fallopian tubes, carcinoma of the renal pelvis, carcinoma of the sexual and reproductive organs, carcinoma of the vagina, carcinoma of the vulva, cell prolymphocytic leukemia, central nervous system, Cervix uteri, chronic leukemia, chronic lymphocytic leukemia, chronic lymphoma leukemia, chronic myeloid leukemia, circulatory system, CNS, CNS lymphoma, colon, colon (metastatic), colon cancer metastasized to liver, colorectal, conditions involving choroidal neovascularization, connective tissue, cranial nerves, cutaneous melanoma, cutaneous T-cell lymphoma, desembryoplastic neuroepithelial tumor, desmoid tumors, desmoplastic medulloblastoma of the cerebellum, diabetic retinopathy, diffuse large B cell lymphoma, digestive organs, endocrine system, endometrial cancer, endometrial carcinoma, enteropathy-type intestinal T cell lymphoma, ependymoma, epidermoid cysts in brain, epilepsy, esophagus, essential thrombocythemia (ET), Ewing's sarcoma, excretory system, extranodal marginal zone B cell lymphoma, extranodal NK/T cell lymphoma, eye, female genital organs, fibrillary astrocytoma, floor of mouth, follicular lymphoma, G26 cells, gall bladder, ganglioglioma, ganglioma, ganglioneuroma, gastrointestinal tract, glial-derived tumor, glioblastoma, glioblastoma multiforme, glioblastoma multiforme (recurrent), glioblastoma multiforme of the cerebellopontine, glioblastoma multiforme of the frontal lobe, glioblastoma multiforme of the suprasellar intraventricular, glioblastoma multiforme of the temporal lobe, glioma, glioma (recurrent, metastatic), gliosarcoma, gliosis, gum, haematopoietic and related tissues, hairy cell leukemia, head or neck, heart, hepatosplenic gamma-delta T cell lymphoma, high grade glioma, high-grade glioma (recurrent), Hodgkin's disease, hypertrophy, hypopharynx, idiopathic myelofibrosis (IMF) (AMM), inflammatory diseases, intermediate/high-grade lymphomas, intracranial glioblastoma, intrahepatic bile ducts, intraocular melanoma, intrathoracic organs, Kaposi's sarcoma, Kidney (binding to healthy cortex), kidney, kidney cancer, larynx, leukemia, lip, liver, liver tumor, low grade astrocytoma (WHO Grade II), low grade glioma (WHO grade I or II), low grade gliomas (WHO grade II), low grade primary brain tumor (WHO grade II), lower part of the brain, lung, lymphatic system, lymphocytic lymphomas, lymphoid, lymphoid leukemia, lymphoma, lymphoplasmacytic lymphoma, lymphoproliferative disorders, male genital organ, malignant (anaplastic) astrocytoma of the periventricular occipital, malignant glioma, malignant immunoproliferative diseases, malignant melanoma of the skin, malignant plasma cell neoplasms, mantle cell lymphoma, mature B cell neoplasm, mediastinum, medulla blastomas, medullary thyroid, medulloblastoma, medulloblastoma of the posterior fossa, melanoma, melanoma (metastatic), melanoma (primary), melanoma metastasized to brain, melanoma metastasized to CNS, melanoma metastasized to lung, meninges, meningioma, meningioma-derived neoplastic tumor tissue, mesothelioma, metastatic tumor of neuroectodermal origin in the brain, metastatic tumors in brain, middle ear, mixed glioma, monocytic leukemia, multiple myeloma, mycosis fungoides, myeloid, myeloid leukemia, myeloproliferative disorders, nasal cavity, nasopharynx, neoplasms of the central nervous system (CNS), neoplastic disease cells, neuroblastoma, neuroectodermal cancer, neuroectodermally-derived cancers, NK cell leukemia, nodal marginal zone lymphoma, Non-Hodgkin's Lymphoma, non-melanoma skin cancer, non-small cell lung cancer, non-small cell lung cancer (metastatic), non-small cell lung carcinoma, ocular neovascularization, ocular trauma, oesophagus, oligodendroglioma, oral cavity, oropharynx, ovarian, ovarian carcinoma, palate, pancreas, pancreatic cancer (metastatic), pancreatic carcinoma, papilloma (ventricular), paraganglioma (metastatic), paraganglioma (metastic), parathyroid gland, parotid gland, penis, peripheral nerves, peripheral primitive neuroectodermal tumor, peripheral T cell lymphoma, peritoneum, pheochromocytoma, pilocytic astrocytoma, pilocytic astrocytoma of the cerebellum, pilocytic astrocytoma of the hypothalamus, pilocytic astrocytoma of the posterior fossa, pilocytic astrocytoma of the temporal lobe, pilocytic astrocytoma of the thalamus, pituitary, pituitary adenoma, placenta, plasma cell myeloma, plasma cell myeloma T cell neoplasms, plasmacytoma, pleomorphic xanthoastrocytoma, pleura, pliocytic astrocytoma, polycythemia vera (PV), precursor B-cell lymphoblastic leukemia/lymphoma, primary cutaneous anaplastic large cell lymphoma, primary neuroectodermal tumors (PNET), prostate, prostate cancer (metastatic), prostate cancer metastasized to bone, prostate carcinoma, pseudoxanthoma elasticum, psoriasis, puriform sinus, rectosigmoid junction, rectum, renal cell carcinoma, renal pelvis, reproductive system, respiratory tract, restenosis, retroperitoneum, salivary glands, sarcoma, sarcoma (metastatic), sarcoma of soft tissue, schwannoma, secondary and unspecified malignant neoplasms of lymph nodes, secondary malignant neoplasm of digestive system, secondary malignant neoplasm of respiratory system, secondary malignant neoplasms, skeletal system, skin, skin cancer, small cell lung cancer, small cell lung cancer (metastatic), small cell lung carcinoma, small intestine, soft tissue, spinal axis tumors, spinal cord, splenic marginal zone B cell lymphoma, squamous cell carcinoma of skin, stomach, stomach cancer metastasized to ovary, stroke, subcutaneous nodule on right leg, subcutaneous panniculitis-like T cell lymphoma, subependymalgiant cell astrocytoma of the frontal lobe, superficial bladder cancer, supratentorial, T cell large granular lymphocytic leukemia, T cell neoplasm, T cell prolymphocytic leukemia, T-cell lymphoma, testis, thrombocythemia (ET), thyroid, tongue, tonsil, trachea, transitional cell carcinoma, transitional cell carcinoma (metastatic), tumor of neuroectodermal origin, tumor of neuroectodermal origin (metastatic), ungraded gliomas, unspecified malignant neoplasms of lymphoid, upper part of the brain, ureter, urethra, urinary organs, uterine, vagina, vascular cancers, and/or vulva.

Cancer cell types can be treated, or that can be representative of certain cancers that can be treated, by administration of a composition for use in the present invention or according to a method for use in the present invention, include for example, cancers of the following cell types: 1299 human non-small cell lung cells, 2LMP human metastatic breast cancer cells, 9L rat glioma cells, A172 cells, A27 non-small cell lung carcinoma cells, A427 human lung carcinoma cells, A459 lung epithelial carcinoma cells, A549 human lung carcinoma cells, ACHN human renal cell adenocarcinoma cells, BABc 3T3 mouse fibroblast cell line, BT474 human breast carcinoma, C6 rat glioma cells, Caco-2 human colon carcinoma cells, Caki-1 human clear cell renal carcinoma cells, CCD986SK human skin fibroblast, CH-235MG GBM cells, COS-2 monkey kidney cell line, Crl:CD-1®(ICR)BR mice, D54-MG human glioma cells, Daudi human lymphoma cells, DU 145 human prostate cancer cells, DY3672 human breast cancer cells, E54-MG/SCID mouse model, GL2g1 mouse glioma cells, H1299 human non-small cell carcinoma cells, H1466 cells, H460 human lung adenocarcinoma cells, HCN-2 human neuronal cells, HCT116 human colon carcinoma cells, HeLa human cervix carcinoma cells, HepG2 human hepatic cancer cells, HL-60 human acute promyelocytic leukemia, HS683 human non-invasive glioma, HT29 human colon carcinoma cells, human primary glioma cultures, IMR-32 rhabdomyosarcoma cells, LCC6 human breast cancer cells, LNCaP human prostate cancer cells, Malme 3M human metastatic melanoma cells, MCF-10A breast cells, MCF-7 human breast cancer cells, MDA-MB-231 human breast adenocarcinoma cells, MDA-MB-453 human breast cancer cells, MDA-MB-468 human breast adenocarcinoma cells, Molt-4 T lymphoblasts from acute lymphoblastic leukemia, mouse CNV model, NCI-H187 human small cell lung carcinoma cells, NIH-H1466 human lung adenocarcinoma cells, PaCa-2 human pancreatic cancer cells, Panc-1 human pancreatic cancer cells, PC-3 human prostate cancer cells, PFSK-1 human primitive neuroectodermal cells, Raji human lymphoma cells, SH-N-MC human neuroblastoma cells, SH-SY5Y human neuroblastoma cells, SK-BR-3 human breast adenocarcinoma cells, SKM28 melanoma cells, SKMEL-28 human melanoma cells, SKMEL-31 human melanoma cells, SK-MG-1 GBM cells, SK-N-SH rhabdomyosarcoma cells, STTG1 astrocytoma cells, SW948 colorectal cancer cells, T98G cells, TE671 rhabdomyosarcoma cells, U105MG GBM cells, U138MG cells, U251 glioblastoma cells, U373 human glioblastoma cells, U87 human glioma cells, UAB12983 low-grade astrocytoma cells, UAB4613 pilocytic astrocytoma cells, UAB4630 GBM cells, UAB4663 pilocytic astrocytoma cells, UAB4720 anaplastic ependymoma cells, UAB485923 medulloblastoma cells, UAB8553 GBM cells, and/or W62 human lung cancer cells.

In certain embodiments, a chlorotoxin agent for use in the present invention is used to treat a cancer having been detected by a chlorotoxin agent in accordance with the present invention.

In some embodiments, chlorotoxin agents as described herein, and particularly those that are or comprise a C-terminal arginine chlorotoxin polypeptide (including, e.g., a C-terminal arginine chlorotoxin polypeptide fragment) may be particularly useful for administration and/or delivery to CNS tissue and/or cells.

Other indications that can be treated by administration of a composition as used in the present invention, or according to a method as used in the present invention, include without limitation, the following: age-related macular degeneration, Alzheimer's brain (no binding), arthritis, dry macular degeneration, juvenile macular degeneration, macular degeneration, myopia, rheumatoid arthritis, and/or wet macular degeneration.

3. Anti-Angiogenic Contexts

Chlorotoxin has been shown to exert anti-angiogenic properties. See, e.g., International Patent Application publication WO 2009/117018, the entire contents of which are herein incorporated by reference. In certain embodiments, compositions and methods for use in the present invention are used to treat, detect (e.g., image, diagnose, or characterize), and/or ameliorate a disease or condition such as, for example cancer (including metastatic cancer, as described herein), ocular neovascularization (such as macular degeneration), inflammatory diseases (such as arthritis), etc. In some embodiments, the condition or disease is characterized by choroidal neovascularization. Examples of such conditions or diseases include, but are not limited to, macular degeneration (including wet macular degeneration, age-related macular degeneration, etc.), myopia, ocular trauma, pseudoxanthoma elasticum, and combinations thereof.

Macular degeneration is the leading cause of vision loss and blindness in Americans aged 65 and older. Macular degeneration typically occurs in the age-related form (often called AMD or ARMD), though juvenile macular degeneration occurs as well. In AMD/ARMD, the macula—the part of the retina that is responsible for sharp, central vision—degenerates. Macular degeneration is typically diagnosed as either dry (non-neovascular) or wet (neovascular).

In dry macular degeneration, yellowish spots known as drusen begin to accumulate from deposits or debris from deteriorating tissue from mostly around the macula. Central vision less usually occurs gradually and is not as severe as vision loss in wet macular degeneration.

Wet macular degeneration, as the "neovascular" designation suggests, is characterized by new blood vessels growing aberrantly, e.g., on the macula. Such new blood vessels can grow beneath the retina, leaking blood and fluid. Such leakage causes permanent damage to light-sensitive retinal cells, which die and create blind spots in central vision. Wet macular degeneration can be further grouped into two categories. In the occult form of wet macular degeneration, new blood vessel growth beneath the retina is not as pronounced and leakage is less evident, typically resulting in less severe vision less. In the classic form of wet macular degeneration, blood vessel growth and scarring have very clear, delineated outlines that are observable beneath the retina. Classic wet macular degeneration is also known as classic choroidal neovascularization and usually results in more severe vision loss.

Given the role of angiogenesis in wet macular degeneration, which includes many AMD/ARMD cases, inventive compositions and methods can be useful in treating, detecting (e.g., imaging or diagnosing), and/or ameliorating such disorders. Current therapies for wet macular degeneration involve angiogenesis inhibitors such as LUCENTIS™, MACUGEN™ and/or VISUDYNE™, optionally combined with photodynamic therapy (PDT) to target drugs to specific cells. Photocoagulation, in which a high energy laser beam is used to create small burns in areas of the retina with abnormal blood vessels, is also used to treat wet macular degeneration.

In some embodiments, chlorotoxin agents (or a pharmaceutical composition thereof) are administered to a subject suffering from wet macular degeneration and/or age-related macular degeneration. Among subjects suffering from wet macular degeneration, subjects can suffer from the occult or the classic form. In some embodiments, chlorotoxin agents cause regression of existing neovasculature. In some embodiments, chlorotoxin agents prevent sprouting of new vessels. In certain embodiments, chlorotoxin agents are combined with other treatments for wet macular degeneration, such as photocoagulation, treatment with other angiogenesis inhibitors, photodynamic therapy, etc.

In some embodiments, chlorotoxin agents as described herein are administered in combination with or as part of a therapeutic regimen with one or more therapeutic regimens recommended for treatment of a disease, disorder, or condition associated with angiogenesis. Without wising to be bound by any particular scientific theory, it is hypothesized that a chlorotoxin agent, chlorotoxin polypeptide, or chlorotoxin fragment can, in some embodiments, disrupt interaction vascular endothelial growth factor (VEGF), which stimulates the formation of blood vessels, and NRP1.

C. Combination therapies

In various embodiments, chlorotoxin agents for use in the present invention can be administered to a subject in a course of treatment that further includes administration of one or more additional therapeutic agents or therapies that are not chlorotoxin agents. In certain embodiments, a chlorotoxin agent as described herein can be administered together with an additional agent or therapy. In certain embodiments, a chlorotoxin agent of the present can be administered separately from an additional agent or therapy. In certain embodiments, administration of a chlorotoxin agent can be to a subject having previously received, scheduled to receive, or in the course of a treatment regimen including an additional anti-cancer therapy. Administration of a chlorotoxin can, in some instances, improve delivery or efficacy of an agent or therapy used in combination with chlorotoxin agent, e.g., via interaction with NRP1.

An agent or therapy used in combination with chlorotoxin agent can be administered in a single therapeutic composition or dose together with chlorotoxin agent, at the same time as chlorotoxin agent in the form of a separate composition, or in a manner temporally distinct from the administration of chlorotoxin agent. When a chlorotoxin agent is to be used in combination with an additional agent, the chlorotoxin agent can be co-formulated with the additional agent or the chlorotoxin agent can be formulated separately from the additional agent formulation. For example, the respective chlorotoxin agent and additional agent compositions can be, e.g., mixed shortly prior to administration and administered together, or can be administered separately, e.g., at the same or at different times. In various embodiments, an additional agent or therapy administered in combination with a chlorotoxin agent as described herein can be administered at the same time as chlorotoxin agent, on the same day as chlorotoxin agent, or in the same week as chlorotoxin agent. In various embodiments, an additional agent or therapy administered in combination with a chlorotoxin agent as described herein can be administered such that administration of the chlorotoxin agent and the additional agent or therapy are separated by one or more hours before or after, one or more days before or after, one or more weeks before or after, or one or more months before or after administration of chlorotoxin agent. In various embodiments, the administration frequency of one or more additional agents can be the same as, similar to, or different from the administration frequency of a chlorotoxin agent.

The administration regimen, e.g. timing and dosage, of a chlorotoxin agent and that of any of one or more additional agents or therapies can be determined independently and administered independently, while in certain circumstances dosages can be co-modulated, interdependent, co-administered, or have any other relationship known to those of skill in the art. It is contemplated that chlorotoxin agent combination therapies can demonstrate synergy between chlorotoxin agent and one or more additional agents or therapies, and can in some embodiments demonstrate greater-than-additive effects. A chlorotoxin agent can be administered in any effective amount as determined independently or as determined by the joint action of chlorotoxin agent and any of one or more additional agents or therapies administered.

Administration of the chlorotoxin agent may, in some embodiments, reduce the therapeutically effective dosage, required dosage, or administered dosage of the additional agent or therapy relative to a reference regimen for administration of additional agent or therapy or therapy absent the chlorotoxin agent. In certain embodiment, a composition described herein can replace or augment other previously or currently administered therapy. For example, upon treating with chlorotoxin agent, administration of one or more additional agents or therapies can cease or diminish, e.g., be administered at lower levels.

Encompassed within combination therapy is the a treatment regimen that includes administration of two distinct chlorotoxin agents as described herein and/or a treatment regimen that includes administration of a chlorotoxin agent as described herein by a plurality of formulations and/or routes of administration.

In certain embodiments, a method of treating cancer can include administration of a chlorotoxin agent as described herein and administration of an anti-cancer agent or therapy that is not a chlorotoxin agent. Various agents and therapies are known in the art or described herein for the treatment of cancer. In particular embodiments, agents and therapies used in the treatment of patients having cancer include, for example, ABRAXANE®, BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomysin, tamoxifen, flutamide, leuprolide, goserelin, aminogluthimide, anastrozole, amsacrine, asparaginase, mitoxantrone, mitotane, amifostine, and a combination thereof, and others described herein or known in the art. Anti-cancer agents for use in the present invention include biologics and/or antibody therapies including, without limitation, Arzerra (Ofatumumab), Avastin (Bevacizumab), Bexxar (Tositumomab), Campath (Alemtuzumab), Erbitux (Cetuximab), Herceptin (Trastuzumab), Mylotarg (Gemtuzumab ozogamicin), Rituxan (Rituximab), Vectibix (Panitumumab), and Zevalin (Ibritumomab tiuxetan). Anti-cancer agents for use in the present invention further include cancer immunotherapy agents. Examples of recommended treatments of cancer can be found at <www.cancer.gov/about-cancer/treatment/drugs>. Treatment regimens can include chemotherapy, surgery, and/or radiation therapy. In some embodiments, chlorotoxin agents as described herein are administered as part of a method of detection of a cancer.

In certain embodiments, a method of treating macular degeneration can include administration of a chlorotoxin agent as described herein and administration of a macular degeneration treating agent or therapy that is not a chlorotoxin agent. Various agents and therapies are known in the art or described herein for the treatment of macular degeneration. In particular embodiments, agents or therapies used in the treatment of patients having macular degeneration include, for example, ranibizumab, bevacizumab, pegaptanib, aflibercept, verteporfin, laser treatment, implantable devices, and others described herein or known in the art. In particular embodiments, agents or therapies used in the treatment of patients having macular degeneration include, for example, anti-VEGF therapy.

In certain embodiments, a method of treating an inflammatory condition such as arthritis can include administration of a chlorotoxin agent as described herein and administration of a macular degeneration treating agent or therapy that is not a chlorotoxin agent. Various agents and therapies are known in the art or described herein for the treatment of an inflammatory condition such as arthritis. In particular embodiments, agents or therapies used in the treatment of patients having arthritis include, for example, analgesics, nonsteroidal anti-inflammatory drugs (NSAIDs), counterirritants, disease-modifying antirheumatic drugs (DMARDs), biologic response modifiers, corticosteroids, joint repair, joint replacement, joint fusion, acupuncture, glucosomaine, yoga, tai chi, massage, and others described herein or known in the art.

EXAMPLES

The following Examples illustrate, among other things, that a chlorotoxin agent can deliver a payload to an NRP1-expressing cancer or tumor. The Examples illustrate that a chlorotoxin agent as described herein can effectively treat cancer. The Examples further illustrate that chlorotoxin polypeptide fragments as described herein, particularly chlorotoxin polypeptide fragments including a carboxylated C-terminal arginine residue, bind NRP1 and can contribute to treatment of cancer. The Examples therefore demonstrate that chlorotoxin agents (e.g., chlorotoxin polypeptides, chlorotoxin polypeptide fragments, reduced lysine chlorotoxin polypeptides, and reduced lysine chlorotoxin polypeptide fragments, optionally conjugated to a payload such as a payload moiety) can be useful in a method of treating cancer.

Without wishing to be bound by any particular scientific theory, various data described herein support a hypothesis that chlorotoxin polypeptide is metabolized in tumor microenvironment to peptide fragments including carboxylate C-terminal arginine, which peptides bind to NRP1, where binding to NRP1 on tumor cells can enhance uptake of a therapeutic agent administered separately from a chlorotoxin agent or as a chlorotoxin conjugate.

As used in the present Examples and Figures, "CTX" (TM601) refers to a chlorotoxin polypeptide having the amino acid sequence of SEQ ID NO: 1 and amidated C-terminal arginine. "CTX-Cryptophycin" (ER-1135472) refers to a conjugate including a chlorotoxin polypeptide according to SEQ ID NO: 1 associated with a cryptophycin payload via a disulphide linker. "Cryptophycin Metabolite 1" (ER-1143077) refers to an active S-methyl cryptophycin metabolite of CTX-Cryptophycin. "Cryptophycin Metabolite 2" (ER-1143083) refers to a Glutathione-SS-cryptophycin metabolite of CTX-Cryptophycin. "Cryptophycin Metabolite 3" (ER-1143080) refers to a cysteine-SS-cryptophycin metabolite of CTX-Cryptophycin. "Carboxylated CTX-Cryptophycin" refers to a conjugate including a chlorotoxin polypeptide according to SEQ ID NO: 1 and a cryptophycin payload, where the chlorotoxin polypeptide has a carboxylated C terminal arginine residue (C-termR—COOH). "Cryptophycin Payload" refers to cryptophycin payload molecule alone (not conjugated to chlorotoxin), which payload molecule includes cryptophycin and a disulphide linker.

Example 1: Antitumor Activity of CTX-Cryptophycin in a Subcutaneous Human Pancreatic Cancer MIA PaCa-2 Xenograft Model The present Example describes work assessing the response of MIA PaCa-2 human pancreatic cancer cells to a chlorotoxin (SEQ ID NO: 1)-cryptophycin conjugate (CTX-Cryptophycin). MIA PaCa-2 human pancreatic cancer cells (ATCC® CRL-1420™) were grown in RPMI-1640 medium supplemented with 10% FBS. Immune-compromised NU/NU nude female mice, approximately 6 weeks old (Charles River Labs), were each inoculated with $5 \times 10^6$ MIA PaCa-2 cancer cells. Cancer cells were injected subcutaneously into mice near the right axillary area using a 27-gauge needle in a volume of 0.1 mL. Tumors were measured at least twice weekly using calipers and mice were randomized into treatment groups based on tumor size.

All treatments were initiated 14 days after tumor inoculation, when the average tumor size was approximately 400 $mm^3$. The experiment included six mice treated with a dosage of 1.25 mg/kg CTX-Cryptophycin, six mice treated with a dosage of 2.5 mg/kg CTX-Cryptophycin, and six vehicle-treated control mice. Animals were treated intravenously every four days for three treatments (Q4Dx3 schedule). All drugs were administered in the following vehicle: 10% EtOH, 5% Tween80 and 85% saline. Tumor size and body weight were measured twice a week.

Treatment with CTX-Cryptophycin at a dosage of 2.5 mg/kg resulted in tumor regression and led to durable cures of tumors in all mice (FIG. 1). Tumors did not re-grow during the monitoring period of greater than 3 weeks following the final treatment injection. No significant body weight loss or other signs of toxicity were observed in study animals.

Antitumor activity observed in these experiments was dose-responsive. Tumor regression and tumor cures at a dosage of 2.5 mg/kg were significantly different from comparatively minimal tumor growth inhibition at a dosage of 1.25 mg/kg.

Example 2: Antitumor Activity of CTX-Cryptophycin in a Subcutaneous Human Pancreatic Cancer BxPC3-Red-FLuc Xenograft Model The present Example describes work assessing the response of BxPC3-Red-FLuc human pancreatic cancer cells to CTX-Cryptophycin. BxPC3-Red-FLuc human pancreatic cancer cells (Perkin Elmer Cat. No. 125058 Parental cells ATCC® CRL-1678™) were grown in RPMI-1640 medium supplemented with 10% FBS. Immune-compromised NU/NU nude female mice, approximately 6 weeks old (Charles River Labs), were each inoculated with $5 \times 10^6$ BxPC3-Red-FLuc cancer cells. Cancer cells were injected subcutaneously into mice near the right axillary area using a 27-gauge needle in a volume of 0.1 mL. Tumors were measured at least twice weekly using calipers and mice were randomized into treatment groups based on tumor size.

All treatments were initiated 8 days after tumor inoculation when the average tumor size was approximately 200 $mm^3$. The experiment included six mice treated with a dosage of 2.3 mg/kg CTX-Cryptophycin, six mice treated with a dosage of 1.2 mg/kg CTX-Cryptophycin, and six vehicle-treated control mice. Animals were treated intravenously every four days for three treatments (Q4Dx3 schedule). All drugs were administered in the following vehicle: 10% EtOH, 5% Tween80 and 85% saline. Tumor size and body weight were measured twice a week.

Figure 2:
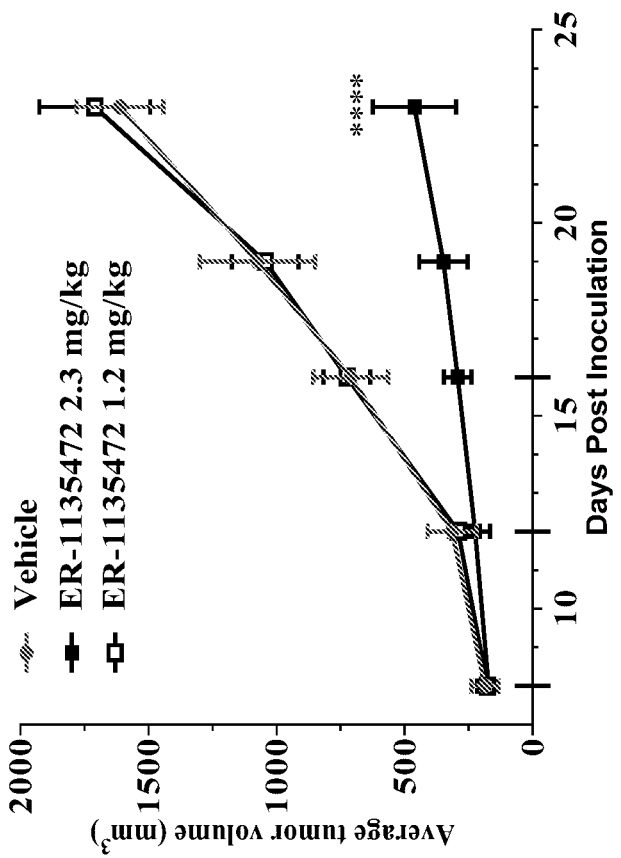
FIG. 2 is a chart showing the average tumor volume of BxPC3-Red-FLuc human pancreatic cancer cell xenograft mouse tumor following treatment with a dosage of 2.3 mg/kg CTX-Cryptophycin, a dosage of 1.2 mg/kg CTX-Cryptophycin, or vehicle control mice by intravenous administration every four days for three treatments (Q4Dx3 schedule).

Treatment with CTX-Cryptophycin at 2.3 mg/kg resulted in statistically significant tumor growth inhibition (P<0.0001 on Day 23, 1 way ANOVA, Bonferroni multiple comparison; FIG. 2). No antitumor activity was observed when CTX-Cryptophycin was administered at the 1.2 mg/kg dose (½ MTD). No significant body weight loss or other signs of toxicity were observed in any study animals.

Example 3: Antitumor Activity of CTX-Cryptophycin in a Subcutaneous Human Prostate Cancer PC-3 Xenograft Model The present Example describes work assessing the response of PC-3 human prostate cancer cells to CTX-Cryptophycin. PC-3 human prostate cancer cells (ATCC CRL-1435) were grown in RPMI-1640 medium supplemented with 10% FBS. Immune-compromised NU/NU nude female mice, approximately 6 weeks (Charles River Labs), were each inoculated with 2×10$^6$ PC-3 cancer cells. Cancer cells were injected subcutaneously into mice near the right axillary area using a 27-gauge needle in a volume of 0.1 mL. Tumors were measured at least twice weekly using calipers and mice were randomized into treatment groups based on tumor size when the average tumor reached approximately 180 mm$^3$.

All treatments were initiated 13 days after tumor inoculation. The experiment included five mice treated with a dosage of 0.6 mg/kg CTX-Cryptophycin, five mice treated with a dosage of 1.2 mg/kg CTX-Cryptophycin, and five vehicle-treated control mice. Animals were treated intravenously every four days for three treatments (Q4Dx3 schedule). All drugs were administered in the following vehicle: 10% EtOH, 5% Tween80 and 85% saline. Tumor size and body weight were measured twice per week.

Figure 3:
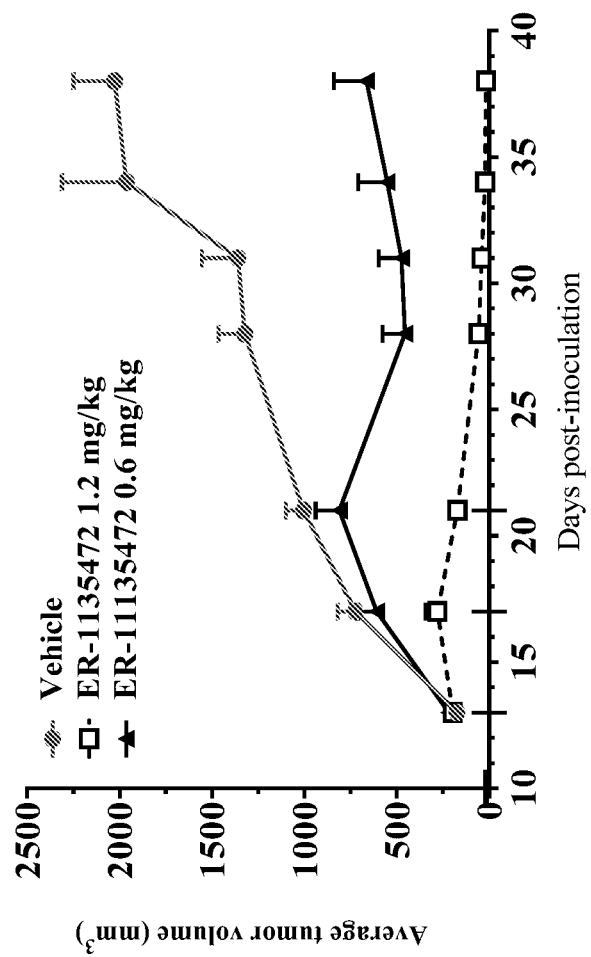
FIG. 3 is a chart showing the average tumor volume of PC-3 human prostate cancer cell xenograft mouse tumor following treatment with a dosage of 0.6 mg/kg CTX-Cryptophycin, a dosage of 1.2 mg/kg CTX-Cryptophycin, or vehicle control mice by intravenous administration every four days for three treatments (Q4Dx3 schedule).

CTX-Cryptophycin treatment resulted in dose-responsive anticancer activity. Tumor regression was observed at a dosage of 1.2 mg/kg, whereas inhibition of tumor growth occurred at the 0.6 mg/kg dose (FIG. 3).

A single tumor-free mouse was observed in each of the CTX-Cryptophycin treatment groups on day 38 of study. No significant body weight loss or other signs of toxicity were observed in any study animals.

Example 4: Biodistribution Studies Following Administration of Single CTX-Cryptophycin Dose to Human Xenografts: MIA PaCa-2, BxPC3-Red-FLuc and PC-3

The present Example describes work assessing concentrations of CTX-Cryptophycin and its active metabolite (Cryptophycin Metabolite 1) in plasma and select tissues. Data were collected following administration of a single dose of CTX-Cryptophycin to xenograft models of MIA PACa-2, BxPC3-Red-Fluc, and PC-3. Plasma and tumor tissue levels were compared.

MIA PaCa-2, BxPC3Red-FLuc, and PC-3 human cancer xenograft models were implanted as described in Examples 1-3, respectively, in female nude mice. When tumor size reached approx. 300 to 500 mm$^3$, a single 2.5 mg/kg dose of CTX-Cryptophycin was administered intravenously in the following vehicle: 10% EtOH, 5% Tween80 and 85% saline.

Mice were euthanized at predetermined time points from 5 min to 96 h after treatment (n=3 mice per time point). Whole blood (cardiac puncture) and select tissues (i.e. tumor, kidney, liver and/or brain) were harvested from euthanized mice.

Blood samples were centrifuged to obtain plasma and subsequently stored at −20° C. or lower pending analysis.

Tumor, kidney, liver and/or brain were harvested by removing each from surrounding tissues (only a portion of liver was removed). Tissues were immediately rinsed with normal saline solution, blotted dry, then weighed and stored at −20° C. or lower pending analysis. Tissues were cryofractured using the Covaris Cryoprep System (Covaris, Inc.). Once pulverized, samples were lysed in 3:1 (v:w) 1×PBS containing 1× Halt™ Protease Inhibitor Cocktail and 1× EDTA solution (Thermo Scientific, Product No. 78430).

Plasma and homogenized tissue samples were extracted via protein precipitation with 3:1 (v:v) methanol:acetonitrile 1:1 (v:v) containing 0.1% acetic acid.

Following extraction, concentrations of CTX-Cryptophycin and active S-methyl metabolite (Cryptophycin Metabolite 1) were quantified using LC-MS/MS analysis. Glutathione-SS- and cysteine-SS-cryptophycin metabolites (Cryptophycin Metabolite 2 and Cryptophycin Metabolite 3 respectively) were also quantified. Pharmacokinetic (PK) parameters were calculated using non-compartmental analysis in C3PO (a proprietary Eisai compound database and pharmacokinetic analysis tool). Mean plasma and tissue concentrations were used to calculate mean PK parameters.

As can be seen, plasma PK following administration of CTX-Cryptophycin was somewhat variable amongst the 3 tumor models and was below detection limits following the 4 or 8 h time point. CTX-Cryptophycin exposure of tumors was similar overall and highest in the MIA PaCa-2 model. Tissue penetration indexes were 1.59 for MIA PaCa-2, 0.923 for PC-3, and 0.426 for BxPC3-Red FLuc.

Figure 4:
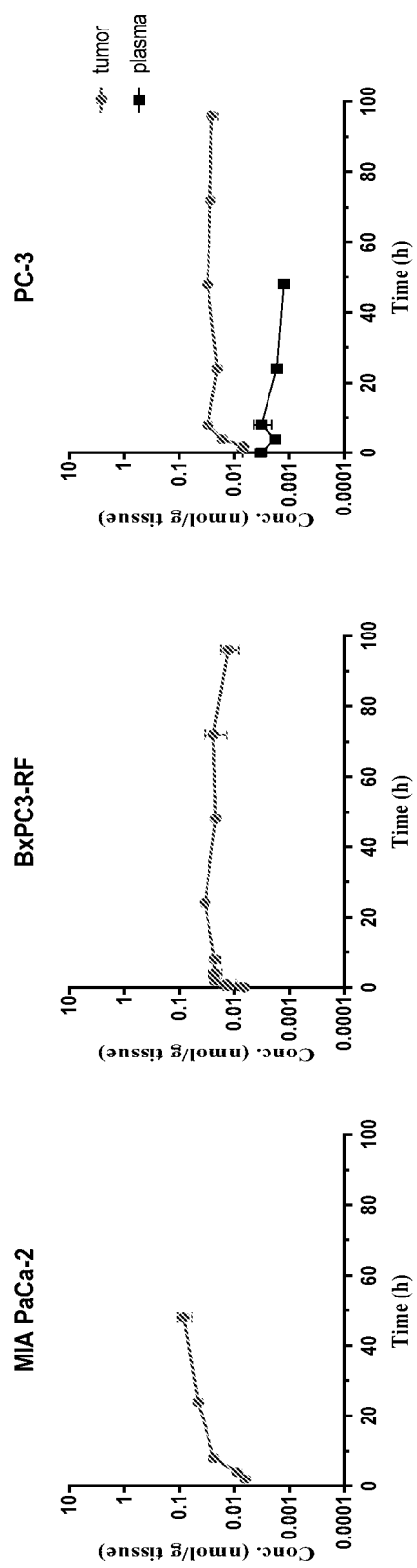
FIG. 4 is set of charts showing tumor and plasma concentrations of Cryptophycin Metabolite 1 (an active metabolite of CTX-Cryptophycin) following administration of a single dose of CTX-Cryptophycin to xenograft models of MIA PACa-2, BxPC3-Red-Fluc, and PC-3.
Figure 5:
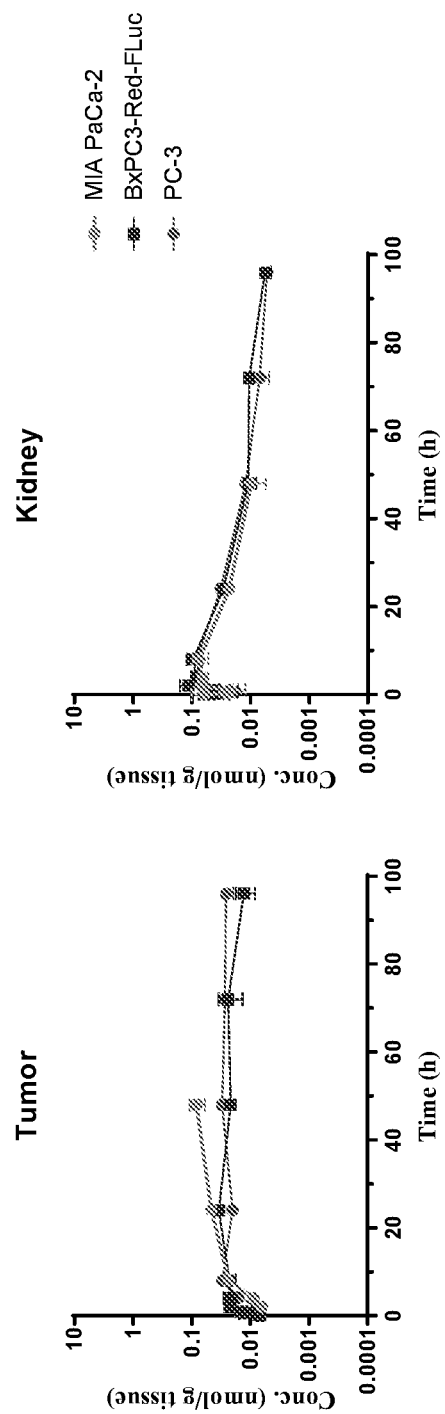
FIG. 5 is a set of charts showing tumor and kidney concentrations of Cryptophycin Metabolite 1 (an active metabolite of CTX-Cryptophycin) following administration of a single dose of CTX-Cryptophycin to xenograft models of MIA PACa-2, BxPC3-Red-Fluc, and PC-3.

FIGS. 4 and 5 show levels of S-methyl cryptophycin (Cryptophycin Metabolite 1) following a single administration of CTX-Cryptophycin to xenograft models of MIA PACa-2, BxPC3-Red-Fluc, and PC-3. Following administration of CTX-Cryptophycin, the tumor exposure (AUC$_{0-96\,h}$) of active S-methyl cryptophycin metabolite (Cryptophycin Metabolite 1), was found to be very similar amongst the different tumor models (MIA PaCa-2 (AUC$_{0-48\,h}$): 2202 pmol·h/g; BxPC-3-Red-FLuc: 2277 pmol·h/g and PC-3: 2463 pmol·h/g) (FIG. 4, left, center and right panels, respectively; see also the cumulative left panel of FIG. 5). A long half-life was observed: T$_{max}$ ranged from 24 to 48 hours.

Plasma Cryptophycin Metabolite 1 was only detected in the PC-3 model (AUC$_{0-48\,h}$=93.6 pmol·h/mL), indicating that approximately all (in MIA PaCa-2 and BxPC3-Red-Fluc) or the majority of (in PC-3) CTX-Cryptophycin metabolism to active metabolite occurs in tissue rather than plasma (FIG. 4).

Kidney Cryptophycin Metabolite 1 was almost identical in all 3 models (FIG. 5, right panel). Kidney half-life (T$_{max}$ of 2 to 8 h) was shorter than tumor half-life.

CTX-Cryptophycin has significantly more potent antitumor activity in PC-3 versus MIA PaCa-2 and BxPC3-Red-FLuc xenograft models. Increased potency is not a result of different agent metabolism in PC-3 tumors as very similar Cryptophycin Metabolite 1 tumor levels were observed in all three models.

Example 5: Levels of Neuropilin 1 (NRP1) mRNA Expression in Lysates of Ex Vivo Tumors from Human Xenografts: PC-3, BxPC3-Red-FLuc and MIA PaCa-2

The present Example describes work assessing NRP1 mRNA expression in lysates of PC-3, BxC3-Red-FLuc, and MIA PaCa-2 xenografts.

Tumors were harvested from PC-3, BxC3-Red-FLuc, and MIA PaCa-2 xenografts, flash frozen in liquid nitrogen, and stored at −80° C. RNA was extracted from ex vivo tumors (n=4) using the RNeasy Mini Kit (Qiagen, Germany) according to the manufacturer's protocol. 2 µg total RNA was converted to cDNA in a 20 µl reaction volume using SuperScript VILO MasterMix (Life Technologies, USA). These cDNAs were amplified using Applied Biosystems TaqMan expression assays using RNA-specific primers for NRP1 (Hs00826128_m1), GUSB (Hs99999908_m1), and HPRT1 (Hs00000009_m1). Quantitative PCR analysis was performed with TaqMan Fast Advanced Master Mix (Life Technologies, USA) on the Applied Biosystems 7900 Real-Time System, with an initial 2 min step at 50° C. followed by 95° C. for 2 s and 40 cycles of 95° C. for 1 s and 60° C. for 20 s.

Relative gene expression was calculated after normalization against the geomean of the two reference genes GUSB and HPRT1 using the using the 2-AACT method. Calculations were performed using the Applied Biosystems SDS 2.4 software and values with P<0.05 by Student's t test were considered statistically significant.

Figure 6:
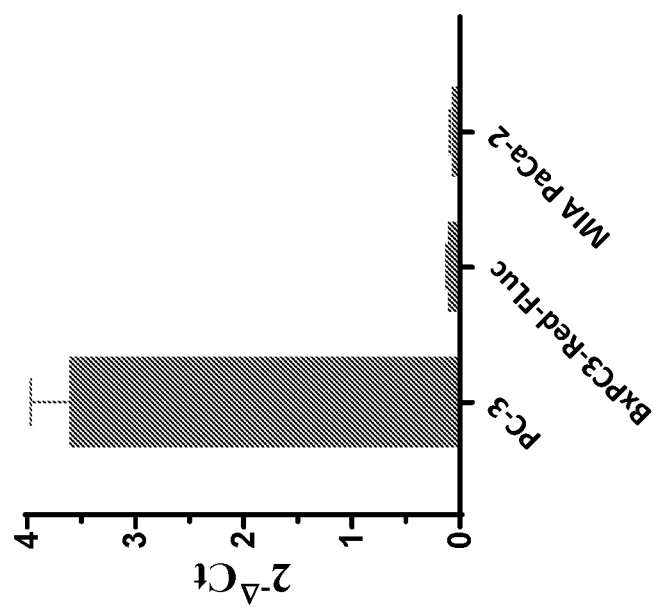
FIG. 6 is graph showing human NRP1 mRNA expression in lysates of PC-3, BxC3-Red-FLuc, and MIA PaCa-2 xenografts.

NRP1 mRNA was detected in all 3 tumor lysates (FIG. 6). Levels were low in both MIA PaCa-2 and BxPC3-Red-Fluc lysates; whereas significantly higher levels were found in PC-3 tumors (33 and 47 fold more respectively). Results suggest that PC-3 tumors express significantly higher levels of NRP1 mRNA than BxPC3-Ref-Fluc or MIA PaCa-2 tumors.

Example 6: Levels of Neuropilin 1 (NRP1) Protein Expression in Lysates of Ex Vivo Tumors from Human Xenografts: PC-3, BxPC3-Red-FLuc and MIA PaCa-2

The present Example describes work assessing NRP1 protein expression in lysates of PC-3, BxC3-Red-FLuc, and MIA PaCa-2 xenografts.

Tumors were harvested from PC-3, BxC3-Red-FLuc, and MIA PaCa-2 xenografts, flash frozen in liquid nitrogen and stored at −80° C. Tissue was cryofractured using the Covaris Cryoprep System (Covaris, Inc.). Once pulverized, samples were lysed in Covaris Extraction Buffer Super B. Lysates were centrifuged at 14,000 rpm for 10 min at 4° C. Supernatants from 5 like tumors were pooled and aliquots snap frozen; lysate protein concentration was assessed using the BCA assay (Thermo Fisher Scientific, Pierce). Lysates were heated in reducing and denaturing sample buffer for 3 min at 100° C.: 50 µg protein was loaded and resolved by electrophoresis on 8% Tris-Glycine Novex gels (Invitrogen). Recombinant Human NRP1, Phe22-Lys644 (R&D Systems) was included as a positive control. Protein was transferred to nitrocellulose using the iBlot™ (Invitrogen) apparatus. Following blocking with Odyssey PBS blocking buffer (LI-COR) the membrane was probed with rabbit monoclonal anti-NRP1 at 1:500 dilution (D62C6, Cat #3725, Cell Signaling Technology, or ab8132 Abcam) followed by anti-tubulin (Abcam, [YL1/2] ab6160). Immune complexes were visualized with appropriate IRDye 680RD and 800CW-agentd secondary antibodies (LI-COR Biosciences) using an Odyssey Infrared Imaging System (LI-COR Biosciences).

NRP1 full length is ~120 kDa, while extracellular domain (soluble NRP1) has a molecular weight of ~70-80 kDa (human recombinant NRP1). Tubulin is resolved at ~50 kDa.

Figure 7:
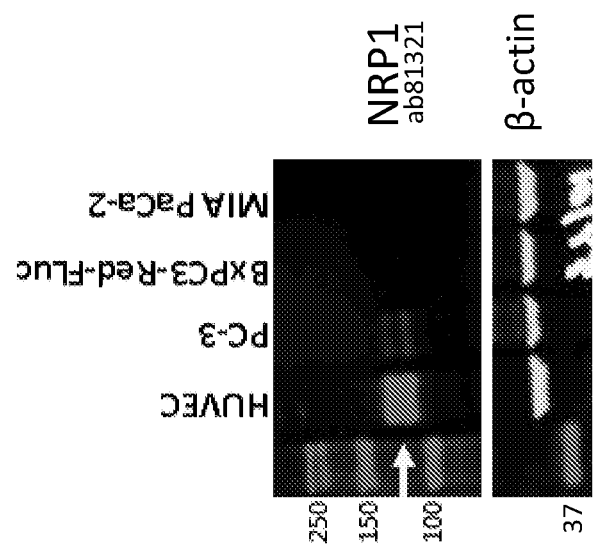
FIG. 7 is a blot showing NRP1 protein expression in lysates of PC-3, BxC3-Red-FLuc, and MIA PaCa-2 xenografts, as stained by an anti-NRP1 antibody directed against the cytoplasmic tail of NRP1 (ab8132).

Results showed an anti-NRP1 antibody directed against the cytoplasmic tail of NRP1 (ab8132) stains NRP1 bands of ~120 kDa in PC-3 tumor lysate (FIG. 7). No NRP1 was detected in MIA PaCa-2 or BxPC3-Red-FLuc tumor lysates using the same antibody.

Figure 8:
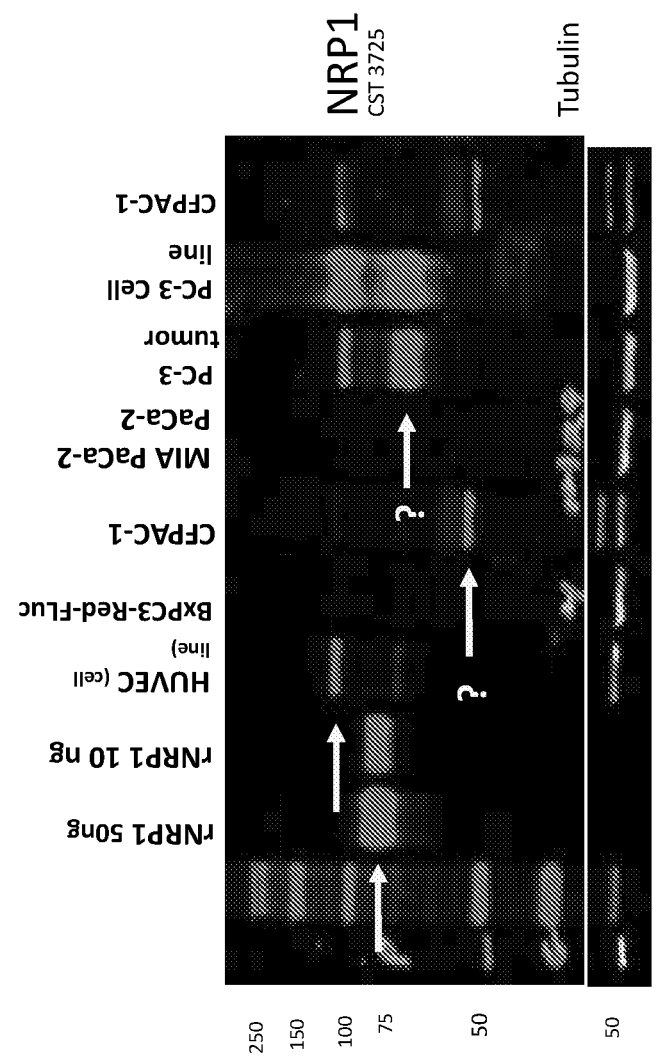
FIG. 8 is a blot showing NRP1 protein expression in lysates of PC-3, BxC3-Red-FLuc, and MIA PaCa-2 xenografts, as stained by a CST antibody directed against extracellular domain of NRP1 (Cat #3725).

Results showed a CST antibody directed against extracellular domain of NRP1 (Cat #3725) stains two NRP1 bands likely representing full length and soluble NRP1 (70-80 and 120 kDa respectively) in PC-3 lysate (FIG. 8). As with the ab8132 antibody, no NRP1 protein was detected in MIA PaCa-2 and BxPC3-Red-FLuc tumor lysates.

Thus, consistent with the mRNA expression results, significant NRP1 protein was observed in PC-3 tumor lysates whereas no NRP1 was observed in lysates of MIA PaCa-2 and BxPC3-Red-FLuc tumors.

Example 7: Trypsinization of CTX In Vitro Yields Peptides with C-Terminal Arginine Residues Examples 7-10 utilized the following reagents: CTX (CPC Scientific), Recombinant Chlorotoxin (Alomone; Cat #RTC-450), Trypsin (Promega; Cat #V5280), Streptavidin Dip and Read Biosensors (Forte Bio; Cat #18-5020), EZ-Link Biocytin (Thermo Scientific; Cat #28022); Recombinant human NRP1 with His Tag (Sino Biological Inc.; Cat #1001-H08H); Biotinylated recombinant Human VEGF165 (ACRO Biosystems; Cat #VE5-H8210), PBS (No Ca or Mg) (Corning; Cat #21-040-CV), BSA (Cell Signaling Technology; Cat #9998S), and Tween-20 (Boston BioProducts; Cat #P-934).

This Example analyzed trypsinization of CTX.

Trypsin digestion was performed with CTX in native folded conformation (4 disulphide bonds) and with linearized CTX where cysteine residues were reduced and capped.

Trypsin (~40 µg/mL) was added to CTX biotinylated at the N-terminus (10 mg/mL) and incubated for 24 h at 37° C., pH 8.5. Resulting peptide peaks were separated by preparative HPLC and peptide fragments were characterized by MALDI.

Figure 9:
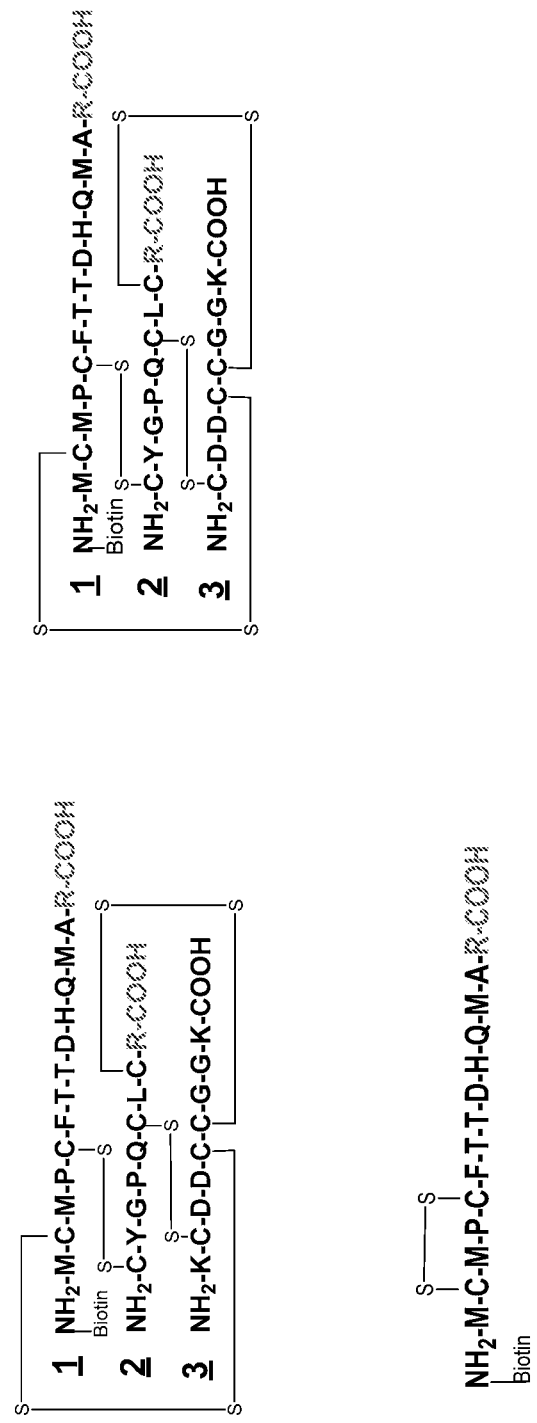
FIG. 9 is a diagram of peptide fragments produced by trypsin digestion of N-terminally biotinylated CTX.

Digestion of naturally folded CTX resulted in generation of tri-peptides held together by disulfide bonds, as well as linear peptides with disulfide bonds pairing different cysteines than those in the parent molecule (FIG. 9).

N-terminally biotinylated CTX was reduced with TCEP at pH 8 and thiols were capped using iodoacetamide. The resulting linear peptide was digested with trypsin. The mixture generated was separated and peptide fragments were identified by MALDI.

Figure 10:
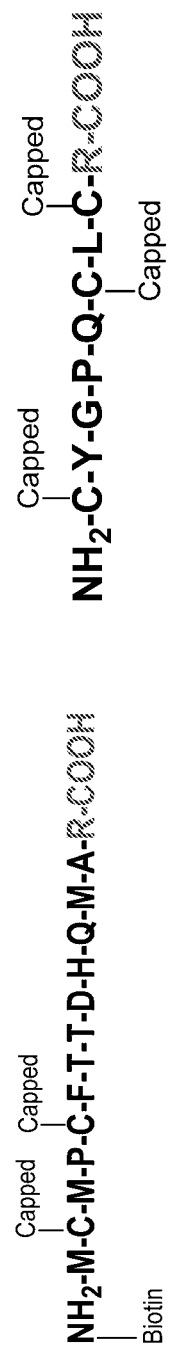
FIG. 10 is a diagram of 2 peptides with C-terminal arginine residues resulting from trypsin digestion of linearized N-terminally biotinylated CTX.
Figure 12:
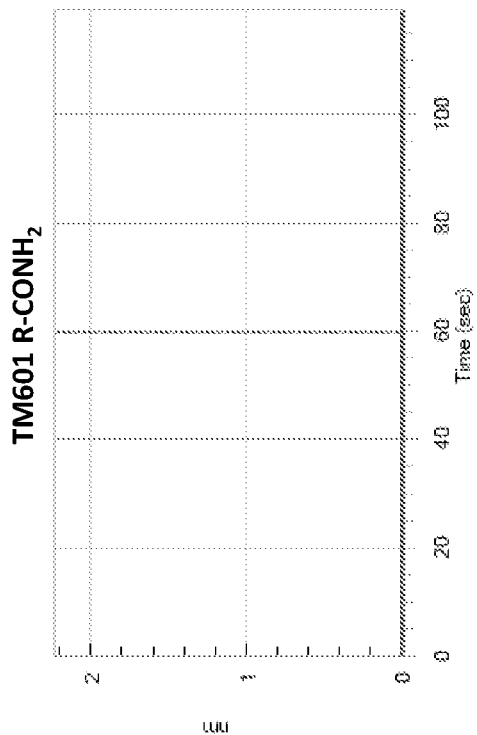
FIG. 12 is a graph showing the binding (or lack thereof) of reduced and capped CTX(R—$CONH_2$) NRP1 as measured in Example 9.
Figure 13:
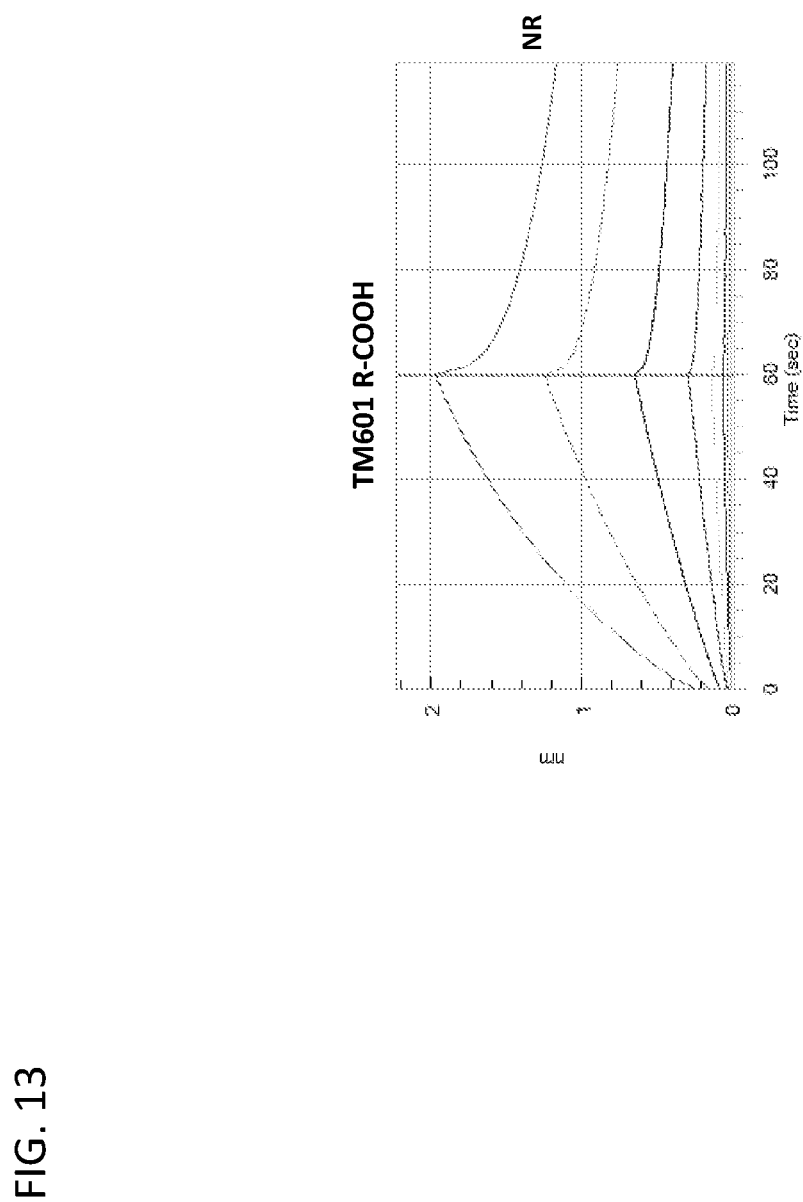
FIG. 13 is a graph showing the binding of CTX(R—COOH) to NRP1 as measured in Example 9.
Figure 14:
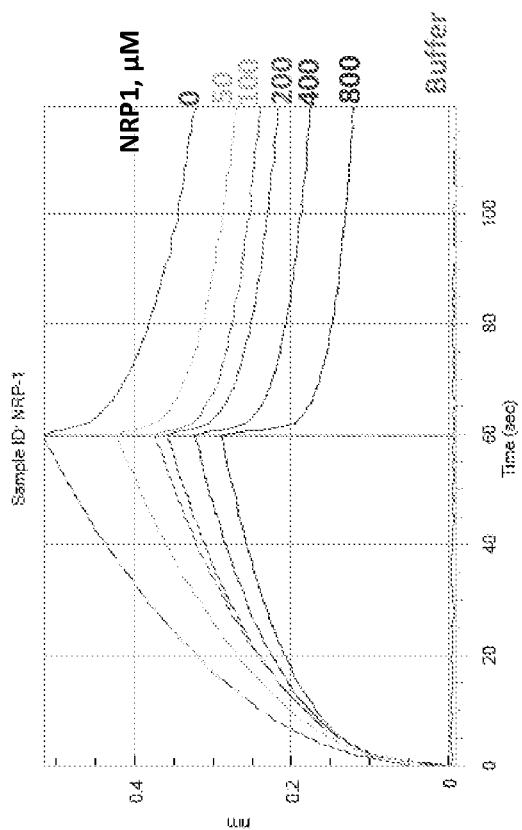
FIG. 14 is a graph showing inhibition of binding of biotinylated VEGF165 to NRP1 by CTX(R—COOH).
Figure 15:
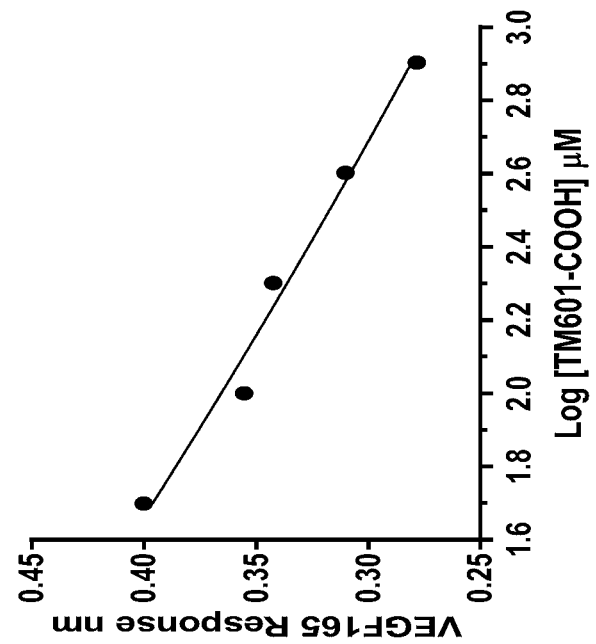
FIG. 15 is a graph showing a linear dose-dependent response in the inhibition of binding of biotinylated VEGF165 to NRP1 by CTX(R—COOH).

Trypsin digestion of linearized N-terminally biotinylated CTX resulted in identification of 2 peptides with C-terminal arginine residues (FIG. 10).

Inclusion of biotin allowed peptide fragments generated by trypsinization to be subsequently bound to streptavidin sensors for determination of binding to NRP1 on the Octet instrument.

As can be seen, trypsin-mediated digestion of CTX generated peptide fragments with C-terminal arginine residues. Without wishing to be bound by any particular scientific theory, such peptide fragments may have the potential for NRP1 binding.

Example 8: Binding of CTX-Derived Fragments to NRP1

The present Example describes work assessing the ability of CTX and derived peptide fragments to bind NRP1 using the Octet instrument. In the Octet Binding Assay, binding of CTX and derived peptides to NRP1 was assessed by Bio-Layer Interferometry (BLI) measurements on the Octet Red96 System (ForteBio, Pall). Binding of immobilized, biotinylated CTX on a streptavidin biosensor to NRP1 analyte in suspension was measured. Binding of analyte produces a change in optical thickness that results in a wavelength shift which is measured in nanometers.

Biotinylation of all peptide fragments to be assessed (see FIG. 11) was required for immobilization on the streptavidin sensor. Peptides for assay were generated either through trypsinization of biotinylated CTX or by de-novo peptide synthesis (see FIG. 11). Biotinylated CTX and derived fragments were captured on pre-wet Streptavidin (SA) Biosensors to saturation (1 min). Initially, a dose response loading curve was performed for each fragment to identify the dose which gave optimal and approximately equivalent loading conditions as recommended by Forte Bio. Assays for NRP1 binding were performed using the identified optimal peptide fragment loading conditions.

Following sensor loading with peptide fragments the sensors were quenched with EZ-Link Biocytin at 10 μg/mL for 2 min, and then washed in assay buffer (PBS, 1% BSA, 0.05% Tween20 for 1 min). Recombinant human NRP1 was added to wells in assay buffer at concentrations from 0 to 1750 nM. Binding to recombinant human NRP1 was assessed by association for 1 min followed by dissociation for 1 min in assay buffer on the Octet Red96 System. The NRP1 binding constant $K_D$ was assessed by measuring CTX binding over the range of NRP1 concentrations (Octet Data Analysis Software version 8.2).

As can be seen, full length CTX peptide, which has an amidated C-terminal arginine, did not bind to NRP1, as measured using the Octet instrument (see FIG. 11). No NRP1 binding was observed regardless of where biotin was located on CTX (see FIG. 11). Linearization of CTX through reduction and capping of cysteine bonds did not alter the negative NRP1 binding result.

Peptide fragments derived from CTX (by enzymatic digestion or synthesis) that possessed a free (carboxylated) C-terminal arginine residue did bind to NRP1. NRP1 binding affinities ($K_D$) ranged from 2.5 to 7 fold lower than that observed for VEGF165. Binding was specific. Binding occurred when the peptide's C-terminal amino acid was an arginine residue (carboxylated). No NRP1 binding was observed when the peptide C-terminal amino acid was lysine, leucine, or glutamic acid.

Results therefore showed that full length CTX peptide, which has an amidated C-terminal arginine, does not bind to NRP1, as measured using the Octet instrument. NRP1 binding was demonstrated for several CTX-derived peptides. Binding was specific and occurred when the peptide's C-terminal amino acid was an arginine residue (carboxylated).

Example 9: Full Length CTX with Carboxylated C-Terminal Arginine Binds to NRP1

The present Example describes work assessing full length CTX peptides having either a carboxylated or an amidated C-terminal arginine residue ($NH_2$-MCMPCFTTDHQMARKCDDCCGGKGRGKCYGPQCLCR(SEQ ID NO: 1)-$CONH_2$; $NH_2$-MCMPCFTTDHQMARKCDDCCGGKGRGKCYGPQCLCR(SEQ ID NO: 1)-COOH).

Recombinant CTX with C-terminal R—COOH from *Escherichia coli* (Alomone) was biotinylated using NHS-chemistry under basic conditions (pH=8.5). The resulting mixture of products was reduced with TCEP at pH 8 and thiols were capped using iodoacetamide. A similar synthetic sequence was used to prepare reduced and capped biotinylated CTX(R—$CONH_2$). Both derivatives (mono-biotinylated CTX) were purified on HPLC to remove excess reagents. Biotinylation occurred mostly at Lys 27 and at Lys 23; peptides were not further purified.

Biotinylated, reduced, and capped CTX(R—COOH) (UM 1936-039, 2.5 ug/ml) or R—$CONH_2$ (UM 1936-047, 1.25 ug/ml) was captured on pre-wet Streptavidin (SA) Biosensors to saturation (1 min). Sensors were quenched with EZ-Link Biocytin at 10 μg/mL for 2 min, and then washed in assay buffer (PBS, 1% BSA, 0.05% Tween20 for 1 min). A shaker speed of 1,000 rpm was used in all steps. Recombinant human NRP1 was added to wells in assay buffer at concentrations from 0 to 1750 nM. Binding to recombinant human NRP1 was assessed by association for 1 min followed by dissociation for 1 min in assay buffer on the Octet Red96 System. The NRP1 binding constant $K_D$ was assessed by measuring CTX binding over the range of NRP1 concentrations (Octet Data Analysis Software version 8.2).

As can be seen, no NRP1 binding was observed for reduced and capped CTX(R—$CONH_2$) whereas dose responsive NRP1 binding was observed for CTX(R—COOH) (FIGS. 12 and 13). The $K_D$ for NRP1 binding was calculated as 244 nM for CTX(R—COOH) ($R^2$ 0.9932) using Octet Data Analysis software. The observed $K_D$ was ~2.5 to 5 fold lower than that observed for positive control; NRP1 binding to biotinylated VEGF165 ($K_D$ 40 to 98 nM). Results therefore show that CTX peptide binds to NRP1 when its C-terminal arginine is carboxylated, but did not show NRP1 binding when C-terminal arginine is amidated. The affinity of CTX(R—COOH) binding to NRP1 is in a similar range to that observed for VEGF165.

Example 10: CTX(R—COOH) but not CTX(R—$CONH_2$) Competes with VEGF for Binding with NRP1

CTX peptides (C-terminal arginine-COOH or —$NH_2$) were assessed for their ability to compete with human recombinant VEGF165 for binding to NRP1 in an Octet binding assay. Biotinylated VEGF (5 ug/ml) was captured on pre-wet SA Biosensors (60 sec), quenched with EZ-link Biocytin (120 sec, 10 μg/ml), and washed in assay buffer (60 sec). CTX peptides with C-terminal arginine-COOH or —$NH_2$ were assessed for their ability to compete with sensor-bound biotinylated VEGF165 for binding to NRP1. Biosensors were submerged in wells containing 390 nM NRP1 in the presence of increasing concentrations of CTX peptide (0 to 800 M) and association (60 sec) was measured as response (nm). Maximum binding was quantified by averaging the binding response 5 seconds prior to switching probes to assay buffer for dissociation (60 sec). Octet Data Analysis Software version 8.2 and GraphPad Prism version 6.0 were used to analyze the data.

As can be seen, CTX(R—COOH) dose-dependently inhibited binding of biotinylated VEGF165 to NRP1 (FIG. 14). A linear response was observed (R2=0.98, linear regression in GraphPad Prism 6.0; FIG. 15). VEGF165 binding to NRP1 was not inhibited in the presence of increasing concentrations of CTX(R—$CONH_2$). Results therefore show that CTX peptide can compete with VEGF165 for NRP1 binding but only when its C-terminal arginine is carboxylated. Competition does not occur when the C-terminal arginine is amidated.

Example 11: Comparison, in Athymic Nude Mice, of Antitumor Effects of CTX-Cryptophycin Conjugates with Carboxylated or Amidated C-Terminal Arginine The present Example compared effects of CTX conjugate in which CTX C-terminal arginine is amidated (CTX-Cryptophycin) and CTX conjugate in which CTX C-terminal arginine is carboxylated (Carboxylated CTX-Cryptophycin) on growth of subcutaneous implanted human prostate cancer PC-3 cells in athymic NU/NU nude mice.

Treatment groups included 3 groups of CTX-cryptophycin in which the C-terminal arginine of CTX was amidated (CTX-Cryptophycin) (0.6, 1.2, 2.3 mg/kg) and 4 groups of CTX-cryptophycin in which the C-terminal arginine of CTX was carboxylated (Carboxylated CTX-Cryptophycin) (0.6, 1.2, 2.3, 3.0 mg/kg). CTX-Cryptophycin conjugates were intravenously administered once every 4 days, 3 times.

PC-3 cells (ATCC® CRL-1435™) were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and resuspended in ice-cold PBS. Female immunodeficient athymic mice were inoculated subcutaneously near the right axillary area with $2\times10^6$ PC-3 cancer cells in PBS using a 27-gauge needle in a volume of 0.1 mL. All treatments were initiated 14 days after tumor inoculation following randomization of animals into treatment groups and vehicle control group based on tumor size. The average tumor size was 180 $mm^3$.

Eighty mice were inoculated with PC-3 cells and on Day 14 following implantation, tumor volumes were measured and mice were randomized into the 8 treatment groups based on tumor volume (average of 180 $mm^3$). Following randomization, drug treatment was initiated (14 days after tumor inoculation).

In this Example, mice were treated with CTX-Cryptophycin (as a single agent, at 3 different dosages); Carboxylated CTX-Cryptophycin (as a single agent, at four different dosages); and with a vehicle control (Table 4). Conjugates were formulated in 10% EtOH, 5% Tween-80 and 85% saline (vehicle) and administered intravenously once every four days, 3 times. Doses were 0.6, 1.2, 2.3 and 3.0 mg/kg based on body weight at 0.1 mL per 10 g. The control group was treated with intravenous vehicle once every 4 days, 3 times. Each group was composed of 6 mice for a total of 48 mice on the first day of treatment.

General health of the mice was monitored and mortality recorded daily. Tumor volume was assessed by caliper (Mitutoyo, Aurora, IL) measurements (mm) using the formula $(l\times w^2)/2 = mm^3$, where l and w refer to the larger and smaller perpendicular dimensions collected at each measurement. Tumor dimensions were recorded twice per week starting at the initiation of drug treatment. Body weights were recorded twice per week starting on the first day of treatment. Relative body weight was calculated as follows: Relative body weight=(body weight on day of measurement/body weight on first day of treatment). The data generated included group mean tumor volumes and group mean body weights at each measurement. The mean±SEM for tumor volume and mean±SEM for relative body weight for each experimental group was calculated.

Dose-dependent and drug-related body weight loss was similarly observed upon treatment with both conjugates but reached only ~10% at maximum and was recovered upon completion of treatment. Body weight loss associated with increased disease severity was observed in vehicle treated animals on Day 36; mice were euthanized because of large tumors.

Animals whose tumor measurement reached ≥2 cm at the longest axis were euthanized prior to study termination. Mice in vehicle group were euthanized on Day 36 because of large tumors. One animal in the 2.3 mg/kg CTX-Cryptophycin treatment group was found dead after the second dose. Study was terminated on Day 42.

Statistical analysis was by a one way analysis of variance (ANOVA) for tumor volume followed by Dunnett's multiple comparison tests. The analysis was performed on Day 36 of the study (vehicle endpoint). Data represent the mean tumor volume±SEM. A value of P<0.05 was considered statistically significant under a two-sided hypothesis. All statistical analyses were performed using GraphPad Prism 6 software (Lake Forest, CA).

TABLE 4

Treatment Groups for Investigation of Effect of CTX-Cryptophycin Conjugates in PC-3 Human Prostate Cancer Xenografts in Athymic Mice

| Group Number | Treatment | Route | Schedule | No. of Animals |
|---|---|---|---|---|
| A | CTX-Cryptophycin 2.3 mg/kg | IV | Q4Dx3 | 6 |
| B | CTX-Cryptophycin 1.2 mg/kg | IV | Q4Dx3 | 6 |
| C | CTX-Cryptophycin 0.6 mg/kg | IV | Q4Dx3 | 6 |
| D | Carboxylated CTX-Cryptophycin 3.0 mg/kg | IV | Q4Dx3 | 6 |
| E | Carboxylated CTX-Cryptophycin 2.3 mg/kg | IV | Q4Dx3 | 6 |
| F | Carboxylated CTX-Cryptophycin 1.2 mg/kg | IV | Q4Dx3 | 6 |
| G | Carboxylated CTX-Cryptophycin 0.6 mg/kg | IV | Q4Dx3 | 6 |
| H | Vehicle (10% EtOH, 5% Tween-80 and 85% saline) | IV | Q4Dx3 | 6 |

Figure 16:
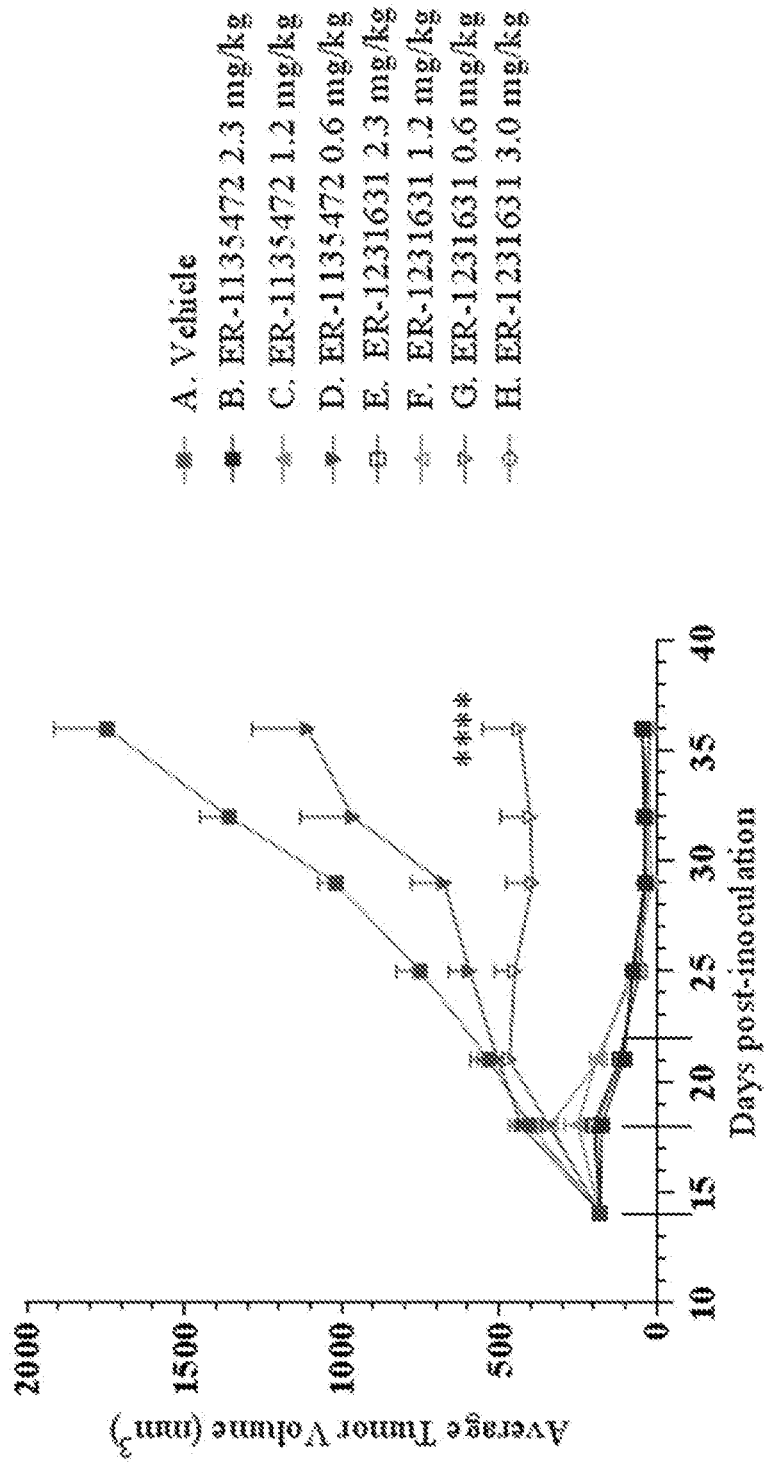
FIG. 16 is a graph showing average tumor volume over days post inoculation for treatments including CTX-Cryptophycin or Carboxylated CTX-Cryptophycin.
Figure 17:
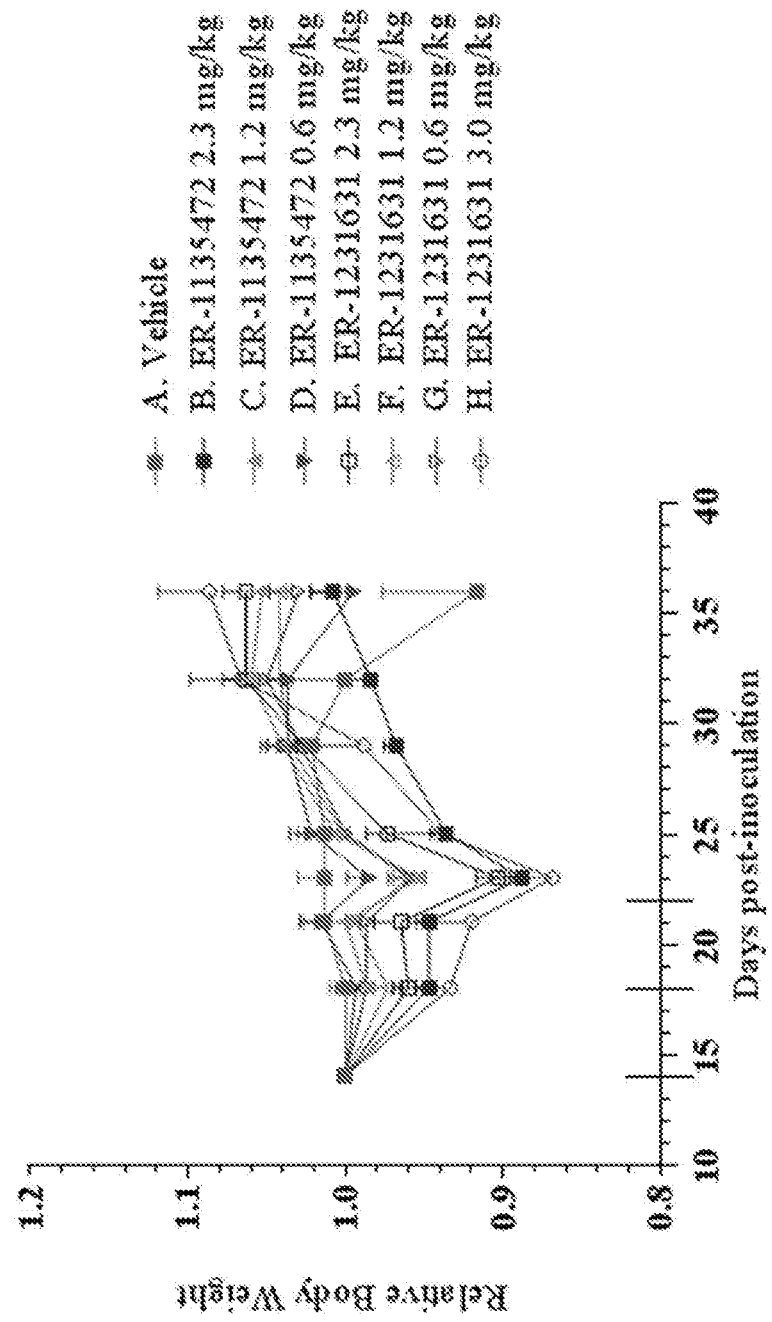
FIG. 17 is a graph showing relative body weight over days post inoculation for treatments including CTX-Cryptophycin or Carboxylated CTX-Cryptophycin.

As can be seen, treatment with CTX-Cryptophycin and Carboxylated CTX-Cryptophycin at doses of 1.2 mg/kg, 2.3 mg/kg, and 3.0 mg/kg all resulted in complete tumor regression (FIG. 16). At the 0.6 mg/kg dosage, statistically significant tumor growth inhibition was observed for both conjugates, and carboxylated CTX-Cryptophycin proved more efficacious at reducing tumor growth than CTX-Cryptophycin at that dosage (P<0.0001, Day 36). Based on body weight loss, the conjugates appeared equally well tolerated (FIG. 17). Thus, at the lower 0.6 mg/kg (¼ MTD) dose, carboxylated CTX-Cryptophycin conjugate in which CTX peptide C-terminal arginine is carboxylated and readily able to bind NRP1 was more effective in inhibiting tumor growth than CTX-Cryptophycin with amidated C-terminal arginine.

Example 12: Comparison, in NOD SCID Mice, of Antitumor Effects of CTX-Cryptophycin Conjugates with Carboxylated or Amidated C-Terminal Arginine This Example compared effects of CTX-cryptophycin conjugates on growth of subcutaneously implanted human prostate cancer PC-3 cells (ATCC® CRL-1435TM), engineered at WuXi AppTec to be wild type (WT; PC-3-sg1-4 WT cells: from WuXi AppTec) or knockout (KO; 1. PC-3-sg1-9 KO cells: from WuXi AppTec) for NRP1, in NOD SCID mice.

NRP1 isogenic PC-3 cells were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and re-suspended in ice-cold PBS. Female immunodeficient NOD.SCID mice (~6 week old, immune compromised NOD. SCID from Charles River laboratories) were inoculated subcutaneously near the right axillary area with $5\times10^6$ PC-3 cancer cells in PBS:matrigel (1:1 dilution) using a 26-gauge needle in a volume of 0.1 mL. A total of 30 mice per model were implanted with PC-3 cells. Treatments were initiated 13 or 17 days after tumor inoculation in the NRP1 KO and WT PC-3 models respectively following randomization of animals into treatment groups and vehicle control group based on tumor size; the average tumor size was 250-300 mm$^3$.

Side-by-side studies were performed in the two isogenic cell lines for treatment groups including: (a) 0.6 mg/kg (which represents ¼ MTD) of CTX-Cryptophycin CTX cryptophycin conjugate including a C-termR—NH$_2$ (i.e., CTX(R—CONH$_2$)); (b) 1.2 mg/kg (which (represents ½ MTD) of CTX-Cryptophycin; (c) 0.6 mg/kg (which (represents ¼ MTD) of Carboxylated CTX-Cryptophycin CTX cryptophycin conjugate including a C-termR—COOH (i.e., CTX(R—COOH)); (d) 1.2 mg/kg (which represents ½ MTD) of Carboxylated CTX-Cryptophycin); and (e) vehicle (see Table 5). Conjugates were formulated in 10% EtOH, 5% Tween-80 and 85% saline (vehicle) and administered intravenously once every four days, 3 times. Doses were based on body weight and administered at a concentration of at 0.1 mL per 10 g. The control group was treated with intravenous vehicle once every 4 days, 3 times. In the PC-3 NRP1 WT study, each group was composed of 5 mice for a total of 25 mice on the first day of treatment. In the PC-3 NRP1 KO study each group was composed of 6 mice for a total of 30 mice on the first day of treatment.

TABLE 5

Treatment Groups for Investigation of Effect of CTX-Cryptophycin Conjugates in NRP1 isogenic PC-3 Human Prostate Cancer Xenografts in NOD.SCID Mice

| Group | Treatment | Route | Schedule | No. of Animals* |
|---|---|---|---|---|
| A | Vehicle (10% EtOH, 5% Tween-80 and 85% saline) | IV | Q4Dx3 | 5 or 6 |
| B | CTX-Cryptophycin 1.2 mg/kg | IV | Q4Dx3 | 5 or 6 |
| C | CTX-Cryptophycin 0.6 mg/kg | IV | Q4Dx3 | 5 or 6 |
| D | Carboxylated CTX-Cryptophycin 1.2 mg/kg | IV | Q4Dx3 | 5 or 6 |
| E | Carboxylated CTX-Cryptophycin 0.6 mg/kg | IV | Q4Dx3 | 5 or 6 |

*5 in WT and 6 in KO NRP1 PC-3 models

General health of the mice was monitored and mortality recorded daily. Tumor volume was assessed by caliper (Mitutoyo, Aurora, IL) measurements (mm) using the formula $(l \times w^2)/2 = mm^3$, where 1 and w refer to the larger and smaller perpendicular dimensions collected at each measurement. Tumor dimensions were recorded twice per week starting at the initiation of drug treatment. Body weights were recorded twice per week starting on the first day of treatment. Relative body weight was calculated as follows: Relative body weight=(body weight on day of measurement/body weight on first day of treatment). Data generated included group mean tumor volumes and group mean body weights at each measurement. The mean±SEM for tumor volume and mean±SEM for relative body weight for each experimental group was calculated. Animals whose tumor measurement reached ≥2 cm at the longest axis were euthanized prior to study termination. Statistical analysis was performed on Day 34 when vehicle groups were euthanized due to large tumors.

Statistical analysis was performed using two way analysis of variance (ANOVA) for tumor volume followed by Tukey's multiple comparison tests. The analysis was performed on Day 34 of the study (vehicle endpoint). A value of $P < 0.05$ was considered statistically significant under a two-sided hypothesis. All statistical analyses were performed using GraphPad Prism 6 software (Lake Forest, CA).

Figure 18:
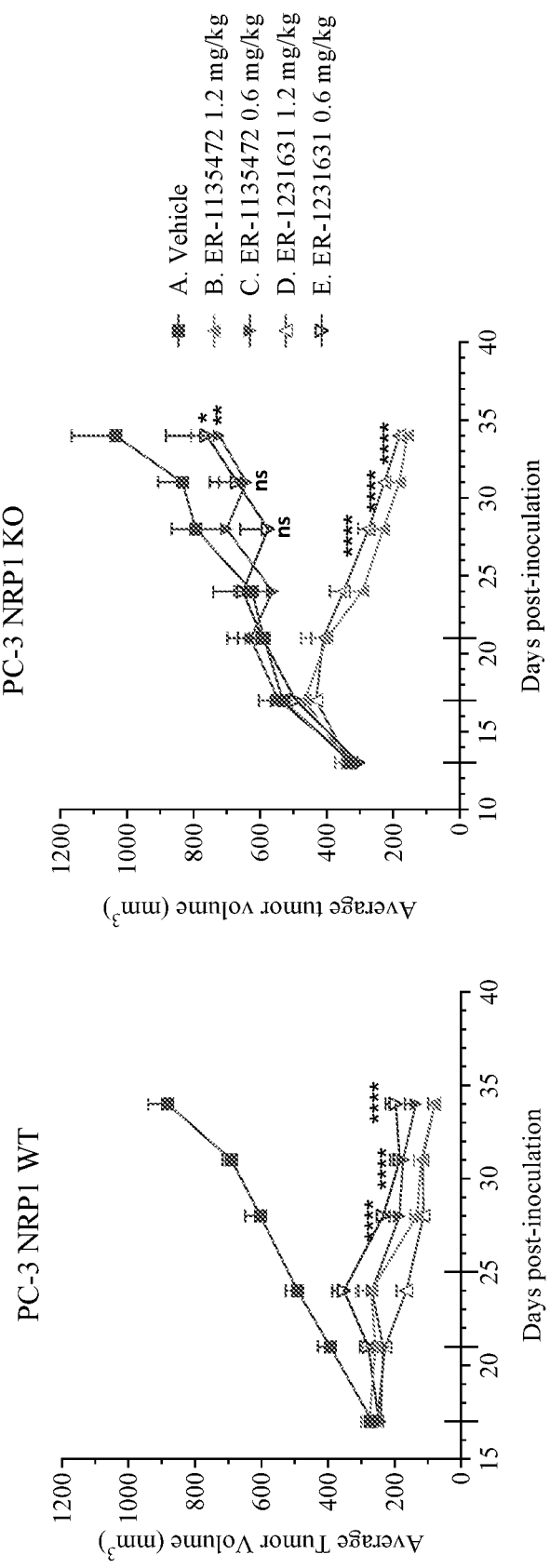
FIG. 18 is a pair of graphs showing tumor volume following CTX-Cryptophycin or Carboxylated CTX-Cryptophycin treatment in PC-3 human prostate xenografts WT or KO for NRP1 in SCID mice.

FIG. 18 shows effects of CTX-Cryptophycin and Carboxylated CTX-Cryptophycin on PC-3 human prostate xenografts WT or KO for NRP1 in SCID mice. Data represent the mean tumor volume±SEM. A similar tumor growth rate was observed for NRP1 KO and WT PC-3 implanted cells with tumors reaching an average tumor volume of 250-300 mm$^3$ by Day 13 in KO and Day 17 in WT PC-3 models. Mice in the vehicle group from both studies were euthanized on Day 34 because of large tumors.

As can be seen, treatment with CTX-Cryptophycin and Carboxylated CTX-Cryptophycin, either conjugate at the 1.2 mg/kg dose resulted in complete tumor regression in both models (i.e., independent of presence or absence of NRP1). However, at 0.6 mg/kg, tumor regression was only observed in the NRP1 WT model; only minimal effects on tumor growth in the NRP1 KO model. No significant body weight loss or other signs of acute or delayed toxicity were observed in any study animals.

In the experiments depicted in FIG. 18, similar effects on tumor regression were observed with both the CTX-Cryptophycin (i.e., CTX(R—CONH$_2$)) and the Carboxylated CTX-Cryptophycin (i.e., CTX(R—COOH)) conjugates. In Example 11, where NU/NU nude mice were used rather than SCID mice, Carboxylated CTX-Cryptophycin (i.e., CTX (R—COOH)) conjugate showed significantly greater efficacy in tumor regression than did the CTX-Cryptophycin (i.e., CTX(R—CONH$_2$)), when dosed at 0.6 mg/ml. Without wishing to be bound by any particular theory, we note that one possible explanation for the different results observed in SCID vs. nude mice might reflect a difference between strains, e.g., that CTX-Cryptophycin might be converted into Carboxylated CTX-Cryptophycin in the more immune-compromised SCID strain.

Taken together, our findings suggest that NRP1 plays a role in the antitumor activity of CTX-cryptophycin conjugates, and furthermore suggest that CTX(R—COOH) may interact more effectively with NRP1 than does CTX(R—CONH$_2$). Without wishing to be bound by any particular theory, we propose that CTX may bind to NRP1 may mediate, or at least facilitate, cellular uptake, thus achieving delivery of payload, with antitumor effect.

Example 13: Comparison, in NOD SCID, Mice of Antitumor Effects of CTX-Cryptophycin Conjugates with Carboxylated or Amidated C-Terminal Arginine The present Example describes work assessing antitumor effects of CTX-Cryptophycin, Carboxylated CTX-Cryptophycin, and Cryptophycin Payload alone (cryptophycin with a disuplphide linker) in NRP1 WT and KO PC-3 isogenic xenografts in SCID mice.

Figure 19:
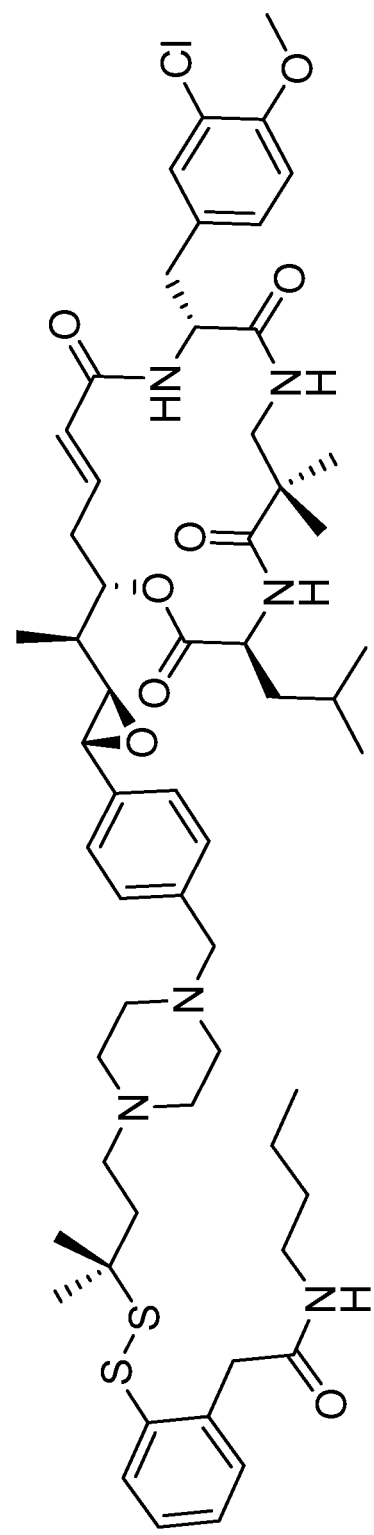
FIG. 19 is a diagram showing Cryptophycin Payload alone, including cryptophycin and a disulphide linker.

This Example included CTX-Cryptophycin, Carboxylated CTX-Cryptophycin, Cryptophycin Payload, and vehicle control treated groups (n=6; see Table 6)). Cryptophycin Payload (FIG. 19) was generated to closely mimic all aspects of CTX-Cryptophycin, removing CTX. Cryptophycin Payload is therefore comprised of cryptophycin with the disulfide linker used in CTX-Cryptophycin. Identical experiments were performed side by side in NRP1 WT and KO PC-3 isogenic xenografts.

NRP1 isogenic PC-3 cells were maintained in monolayer cultures in RPMI-1640 growth medium supplemented with 10% fetal bovine serum at 37° C. in a 5% CO$_2$ humidified incubator. On the day of inoculation, cells were harvested by trypsinization, washed, and re-suspended in ice-cold PBS. Female immunodeficient NOD.SCID mice (~6 week old, immune compromised NOD. SCID from Charles River laboratories) were inoculated subcutaneously near the right axillary area with $5 \times 10^6$ PC-3 cancer cells in PBS:matrigel (1:1 dilution) using a 26-gauge needle in a volume of 0.1 mL. Treatments were initiated 14 or 17 days after tumor inoculation in the KO and WT models respectively following randomization of animals into treatment groups and vehicle control group based on tumor size. The average tumor size was 150-200 mm$^3$. A total of 40 mice per model were implanted with PC-3 cells.

Each group was composed of 6 mice for a total of 30 mice on the first day of treatment. Conjugates and Payload were formulated in 10% EtOH, 5% Tween-80 and 85% saline (vehicle) and administered intravenously once every four days, 3 times. Doses were 0.6 mg/kg (conjugate) or 0.2 (cryptophycin), based on body weight at 0.1 mL per 10 g. The control group was treated with intravenous vehicle once every 4 days, 3 times. Animals were treated intravenously on a Q4Dx3 schedule. Tumor size and body weight were measured twice per week.

General health of the mice was monitored and mortality recorded daily. Tumor volume was assessed by caliper (Mitutoyo, Aurora, IL) measurements (mm) using the formula $(l \times w^2)/2 = mm^3$, where l and w refer to the larger and smaller perpendicular dimensions collected at each measurement. Tumor dimensions were recorded twice per week starting at the initiation of drug treatment. Body weights were recorded twice per week starting on the first day of treatment. Relative body weight was calculated as follows: Relative body weight=(body weight on day of measurement/body weight on first day of treatment). Data generated include group mean tumor volumes and group mean body weights at each measurement. The mean±SEM for tumor volume and mean±SEM for relative body weight for each experimental group was calculated. Animals whose tumor measurement reached ≥2 cm at the longest axis were euthanized prior to study termination.

TABLE 6

Treatment Groups for Investigation of Effects of CTX-Cryptophycin Conjugates and Cryptophycin Payload alone in NRP1 isogenic PC-3 Human Prostate Cancer Xenografts in NOD.SCID Mice

| Group | Treatment | Route | Schedule | No. of Animals |
|---|---|---|---|---|
| A | Vehicle (10% EtOH, 5% Tween-80 and 85% saline) | IV | Q4Dx3 | 6 |
| B | CTX-Cryptophycin 0.6 mg/kg | IV | Q4Dx3 | 6 |
| C | Carboxylated CTX-Cryptophycin 0.6 mg/kg | IV | Q4Dx3 | 6 |
| D | Cryptophycin Payload 0.2 mg/kg | IV | Q4Dx3 | 6 |

Figure 20:
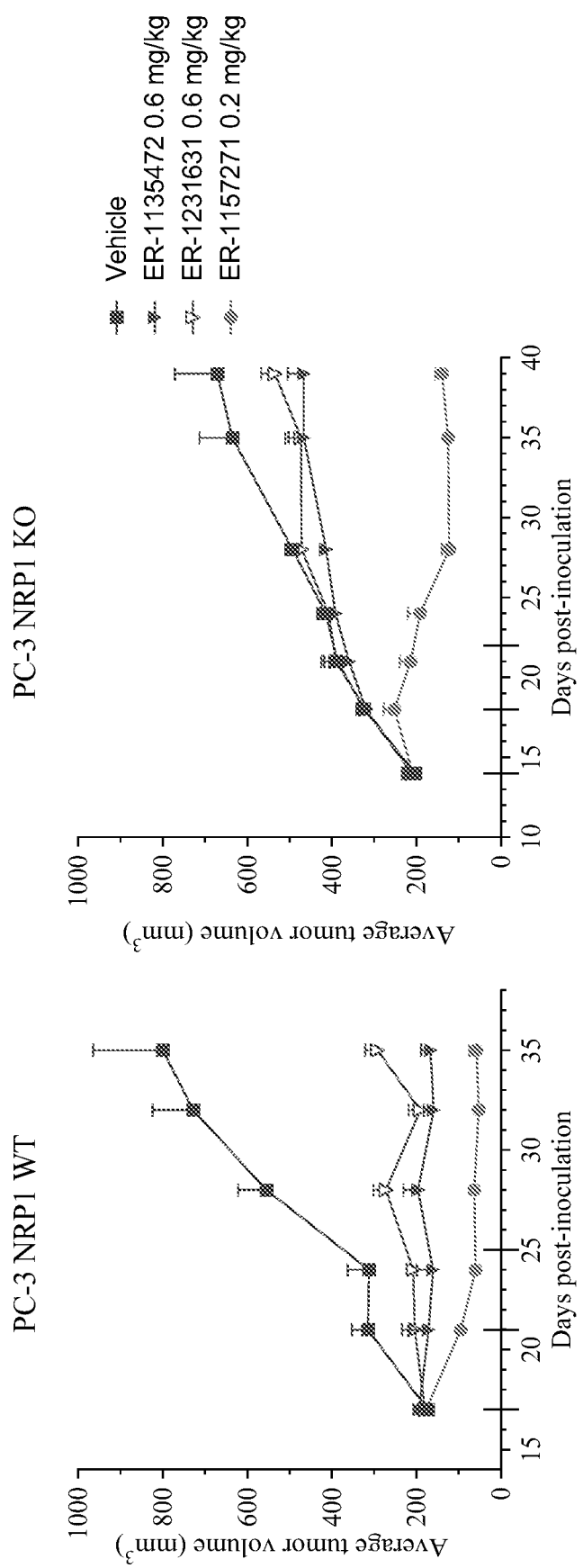
FIG. 20 is a pair of graphs showing tumor volume over days post inoculation for treatment of NRP1 WT or KO tumors, the treatments including administration of CTX-Cryptophycin, Carboxylated CTX-Cryptophycin, or Cryptophycin Payload.

FIG. 20 shows effects of CTX-Cryptophycin and Carboxylated CTX-Cryptophycin in PC-3 human prostate xenografts, WT or KO for NRP1 in SCID mice. Data represent the mean tumor volume±SEM. Treatment with either conjugate at 0.6 mg/kg (equivalent to ¼ MTD) resulted in significant antitumor effects in the NRP1 WT model, but not in the NRP1 KO model. In contrast, treatment with Cryptophycin Payload alone yielded similar antitumor effects in both models.

Without wishing to be bound by any particular theory, we note that one possible explanation for the different results observed in SCID vs. NU/NU nude mice (as used in Example 11) might reflect a difference between strains, e.g., that CTX-Cryptophycin might be converted into Carboxylated CTX-Cryptophycin in the more immune-compromised SCID strain.

Taken together these data support a role for NRP1 in the antitumor efficacy of CTX-cryptophycin conjugates.

Example 14: Bioactivity Assay of Chlorotoxin Peptides in Crayfish

CTX peptides were assessed for ability to induce paralysis in crayfish, where paralysis is indicative of bioactivity. The assay can be used, for example, in quality control testing of peptide batches. In this study CTX peptides having either an amidated or carboxylated C-terminal arginine residue, and in either native confirmation or in a reduced and alkylated form, were compared for ability to induce paralysis upon injection into crayfish.

Figure 21:
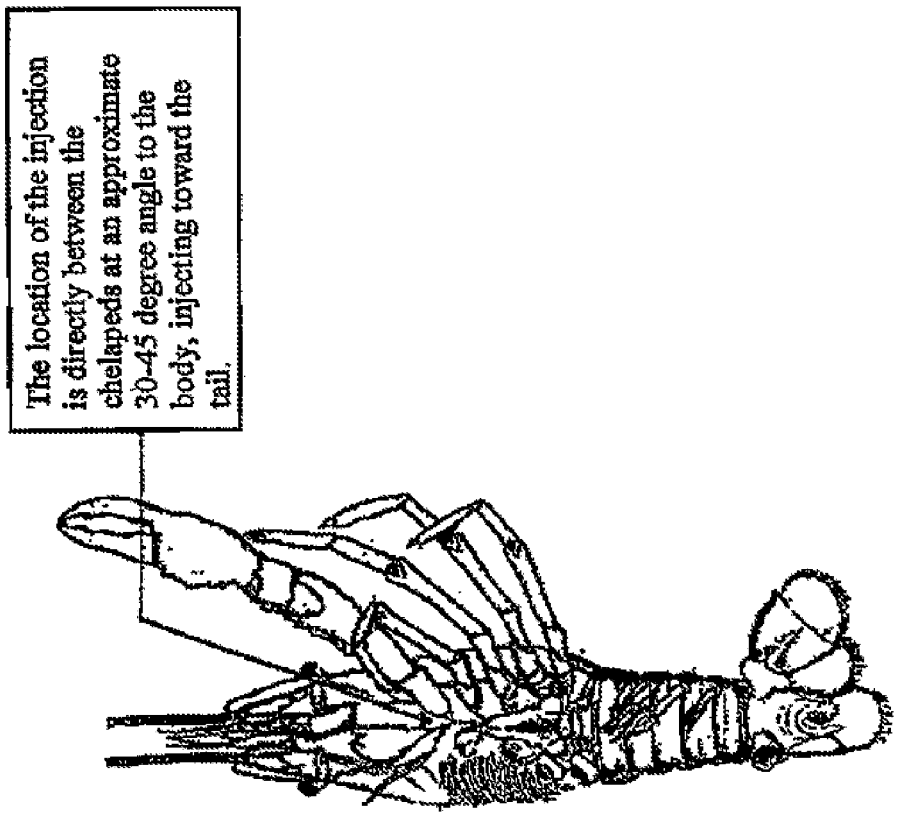
FIG. 21 is diagram showing a crayfish injection location.

The crayfish assay to assess bioactivity of CTX peptide and various conjugates was performed at ABC Labs in Missouri. CTX peptides were formulated at 1 mg/mL in sterile water; shipped, and stored at 4° C. until use. Crayfish were injected with 20 µg peptide (50 µL) using a 26-gauge needle through the ventral surface of the thorax in the region of the sub esophageal ganglion. Injections were made directly between the chelapeds at an approximate 30 to 45 degree angle to the body, injecting towards the tail ~5 to 10 mm deep (see FIG. 21, showing crayfish injection location).

In each trial of the present Example, 10 crayfish per group were injected and crayfish response to physical challenge was assessed over time. Physical challenge is defined as multiple, continuous, gentle prods in random parts of the body from head to tail. The response is based on avoidance, ability to right itself, and clasping with chelae in a defensive manner. The time from injection to total incapacitance was recorded, where total incapacitance is defined as a state in which a tested crayfish is not responsive when physically challenged. Total incapacitance is not total paralysis, as there may still be movement of the appendages, but a crayfish at total incapacitance is not able to move in response to or in defense of physical challenge. Animals were monitored for 6 minutes (360 seconds) post-injection for their response.

Time to total incapacitance data were subjected to Kaplan-Meier survival analysis (GraphPad Prism) and median time was reported for each group (following removal of fastest and slowest responder (n=8 final). A median time to incapacitance of ≤150 seconds was selected as the criteria for qualifying CTX as biologically active.

In the first crayfish study, (a) CTX peptides chemically synthesized and obtained from various commercial sources (CPC Scientific, CBL, Bachem) and having C-terminal arginine-amide, (b) clinical grade, e.g., chemically synthesized, CTX, and (c) recombinant chlorotoxin polypeptide (from *Escherichia coli*, Alomone) having a carboxylated C-terminal arginine, were compared. Native CTX (C-terminal arginine amidated) was reduced with TCEP at pH 8 and thiols were capped using iodoacetamide. Reduced and linearized CTX was compared with native peptide for its ability to induce total incapacitance in crayfish assay.

Figure 22:
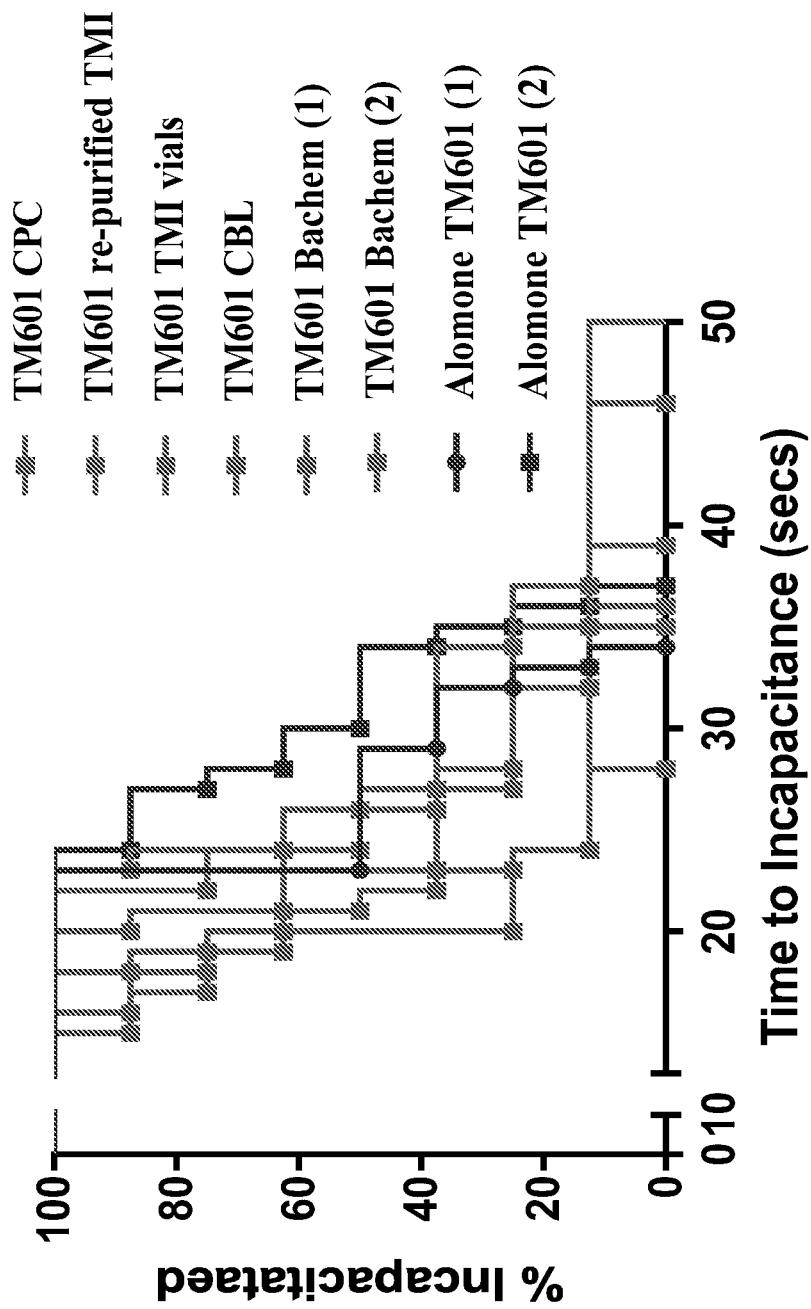
FIG. 22 is a graph showing incapacitation over time.

As can be seen, all chlorotoxin polypeptides tested induced incapacitance in crayfish and were deemed bioactive. Overall, total incapacitance was induced within a narrow time range (15 to 63 seconds) with a median time of ~25 seconds (Table 7, FIG. 22). CTX from varied sources behaved similarly in the assay. No difference in paralysis induction was observed for peptide with C-terminal amidated (CPC, CBL, TMI, Bachem) or carboxylated arginine (Alomone, Cat #RTC-450).

TABLE 7

| CTX source | Time to Incapacitance (sec) |
| --- | --- |
| CPC | 26.5 |
| CBL | 25 |
| Bachem | 26.5 |
|  | 23 |
| TMI, clinical grade | 20 |
| TMI, clinical grade | 21.5 |
| Alomone* | 26 |
|  | 32 |

*Recombinant CTX has carboxylated C-terminal arginine

Figure 23:
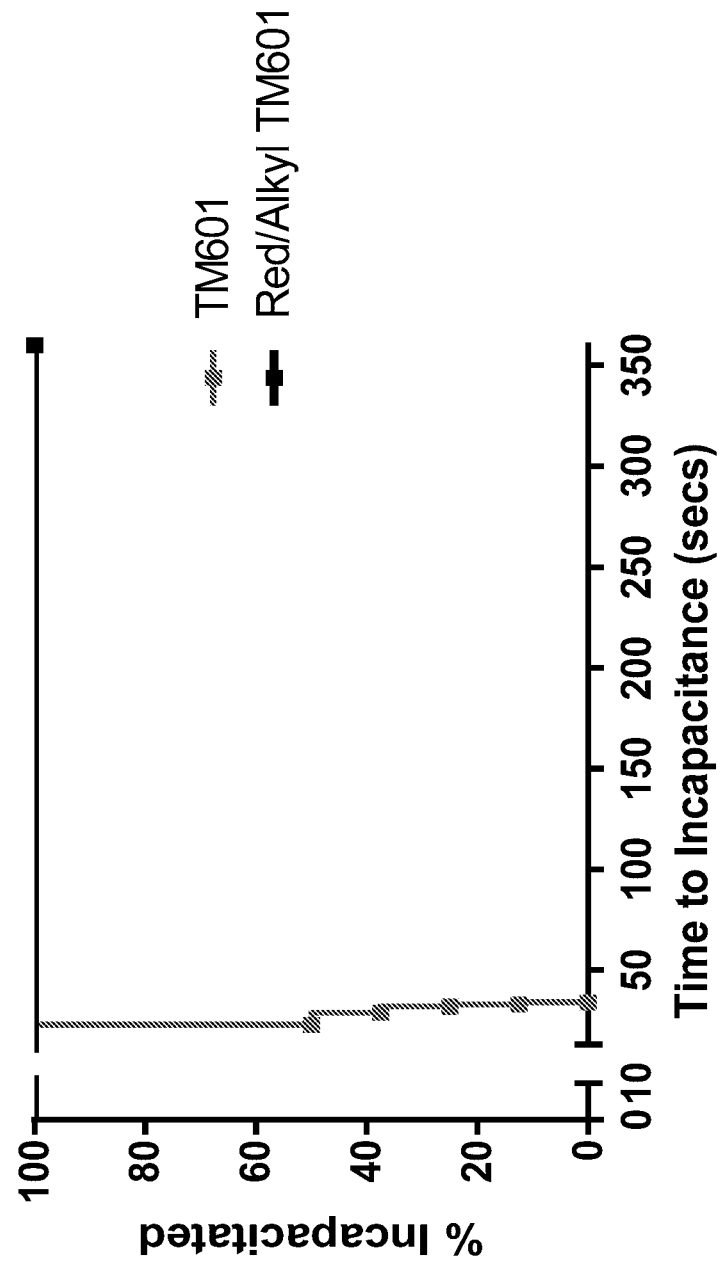
FIG. 23 is a graph showing incapacitation over time.

Chlorotoxin polypeptide that was reduced and alkylated did not induce paralysis (monitored for >6 min after injection) in assays where native Chlorotoxin polypeptide proved active (Table 8, FIG. 23) with a median time to incapacitance of 26 seconds.

TABLE 8

| Peptide | Time to Incapacitance (sec) |
| --- | --- |
| CTX | 26 |
| Reduced & alkylated CTX | >360 |

Results therefore showed that chlorotoxin polypeptide induces incapacitance in crayfish within a very short time period of the injection. The status of the chlorotoxin polypeptide C-terminal arginine residue (amidated versus carboxylated) does not affect the peptides ability to induce incapacitance. This is in contrast to the finding that carboxylated C-terminal arginine contributes to, and may be necessary for binding of chlorotoxin polypeptide to NRP1. Linearized chlorotoxin polypeptide was unable to induce paralysis, which may imply that one or more features of the 3D structure of the peptide may be required to induce paralysis. Again, this deviates from the finding that linearized chlorotoxin polypeptide binds to NRP1 as long as the C-terminal arginine is carboxylated. In sum, this data establishes that the toxin-related function of the peptide appears to be separable from its ability to bind NRP1.

Example 15: Biodistribution of Carboxylated CTX-Cryptophycin and Cryptophycin Metabolite 1 Following Administration of Carboxylated CTX-Cryptophycin to NRP1 WT or KO Isogenic PC-3 Xenografts in SCID Mice Plasma and tumor tissue concentrations of CTX-Cryptophycin conjugate, Carboxylated CTX-Cryptophycin, and its active S-methyl cryptophycin metabolite (Cryptophycin Metabolite 1) were measured and compared following a single dose of conjugate in isogenic PC-3 tumors WT or KO for NRP1 in SCID mice.

Cells used were human prostate cancer cells, PC-3 (ATCC® CRL-1435™) engineered at WuXi AppTec to generate an isogenic pair of cell lines WT (PC-3-sg1-4 WT cells) and KO (PC-3-sg1-9 KO cells) for NRP1. Mice used were female, ~6 week old, immune compromised NOD. SCID from Charles River laboratories. Identical experiments were performed side by side in the isogenic xenograft models. Drug administration was performed when tumor size reached ~300 to 500 mm³. A single dose of Carboxylated CTX-Cryptophycin at 0.6 mg/kg was administered (to mimic dose where differential efficacy was observed) intravenously in the following vehicle: 10% EtOH, 5% Tween80 and 85% saline. Animals were euthanized and whole blood (cardiac puncture) and tumor tissues harvested at predetermined time points from 5 min to 96 h post-dose (n=3 mice per time point). Blood samples were centrifuged to obtain plasma and subsequently stored at −20° C. or lower pending analysis. Tumors were harvested by removing the entire specimen from surrounding tissues. Specimens were immediately rinsed with normal saline solution, blotted dry, then weighed and stored at −20° C. or lower pending analysis. Tumor tissue was cryofractured using the Covaris Cryoprep System (Covaris, Inc.). Once pulverized, samples were lysed in 3:1 (v:w) 1×PBS containing 1× Halt™ Protease Inhibitor Cocktail and 1×EDTA solution (Thermo Scientific, Product No. 78430). Plasma and homogenized tissue samples were extracted via protein precipitation with 3:1 (v:v) methanol: acetonitrile 1:1 (v:v) containing 0.1% acetic acid. Following extraction, concentrations of conjugate (Carboxylated CTX-Cryptophycin) and active S-methyl metabolite (Cryptophycin Metabolite 1) were quantified using LC-MS/MS analysis. Pharmacokinetic (PK) parameters were calculated using non-compartmental analysis in C3PO (a proprietary Eisai compound database and pharmacokinetic analysis tool). Mean plasma and tissue concentrations were used to calculate mean PK parameters.

Figure 24:
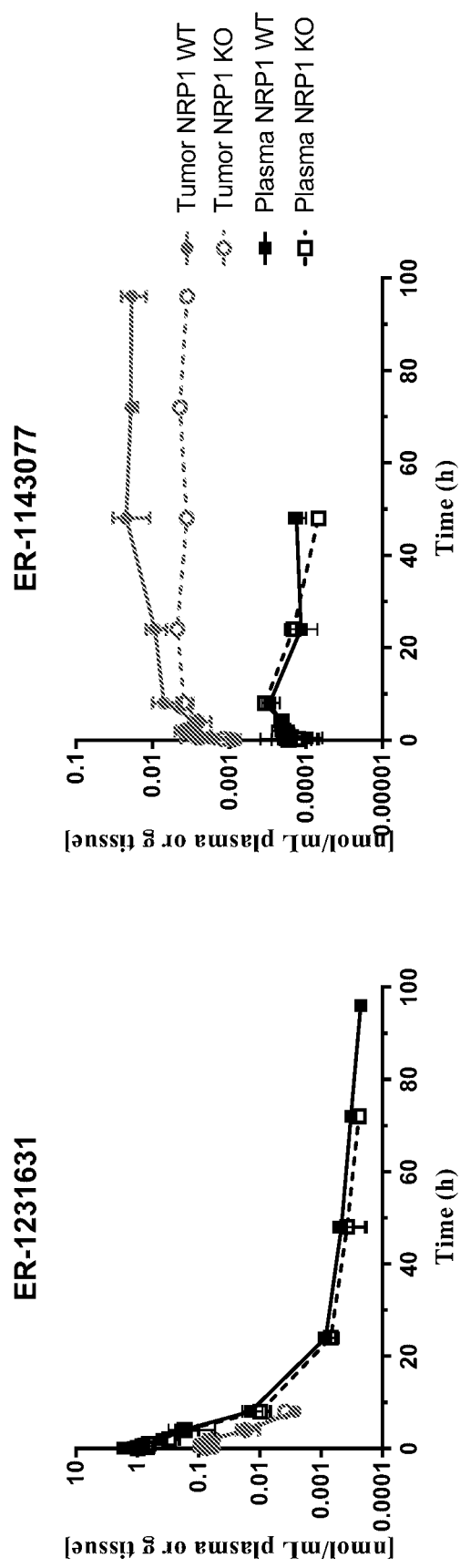
FIG. 24 is a pair of graphs showing nmol/mL plasma or g tissue over time for Carboxylated CTX-Cryptophycin and Cryptophycin Metabolite 1 in NRP1 WT or KO tumor tissue.

As can be seen, levels of Carboxylated CTX-Cryptophycin conjugate detected in plasma and tumor were almost identical in the isogenic NRP1 WT and KO models. In both models conjugate had a long plasma elimination half-life, a slow mean clearance and limited volume of distribution, as well as low distribution to tumor. Similar low levels of S-methyl cryptophycin, (Cryptophycin Metabolite 1, active metabolite generated from conjugate) was measured in the plasma of both models. However, significantly higher levels of active metabolite Cryptophycin Metabolite 1 were observed in NRP1 WT versus KO tumor tissue. Mean level of active metabolite ($AUC_{0-96\ h}$) was measured to be 1494 or 385 pmol·h/g in NRP1 WT and KO tumors respectively. Mean $C_{max}$ was measured to be 22.1 pmol/g at $t_{max}$ 48 hours in NRP1 WT versus mean $C_{max}$ of 4.75 pmol/g at $t_{max}$ 24 hours in NRP1 KO tumors. (FIG. 24)

Overall, the plasma PK and tumor distribution results were highly comparable for Carboxylated CTX-Cryptophycin in NRP1 WT and KO xenograft models with $AUC_{WT}/AUC_{KO}$ ratios close to 1. Plasma level of the active metabolite Cryptophycin Metabolite 1 was also very similar in the 2 models. In contrast, a ~4 fold difference in tumor levels of active metabolite of Cryptophycin Metabolite 1 was observed ($AUC_{WT}/AUC_{KO}$=3.9); i.e. knockout of NRP1 in PC-3 tumors led to a ~4 fold decrease in level of active metabolite Cryptophycin Metabolite 1. This decreased exposure of NRP1 KO tumors to active metabolite may be responsible for reduced antitumor activity observed for conjugate in efficacy studies when compared in NRP1 WT tumors.

Example 16: Effects of Anti-Human and Anti-Mouse NRP1 Blocking Antibody on the Antitumor Efficacy of CTX-Cryptophycin Conjugates in Human Prostate Cancer PC-3 Xenografts The present Example describes work assessing effects of anti-NRP1 antibody pretreatment on the antitumor effects of CTX-Cryptophycin on subcutaneously implanted human prostate cancer PC-3 cells (ATCC® CRL-1435™ human prostate cancer cells) in athymic mice. Experiments included a vehicle group, an CTX-Cryptophycin group, a group pre-treated with control antibodies 30 mins prior to administration of CTX-Cryptophycin, and a group pre-treated with anti-NRP1 antibodies 30 mins prior to administration of CTX-Cryptophycin. All drugs were administered in the following vehicle: 10% EtOH, 5% Tween-80 and 85% saline. Animals were treated intravenously on a Q4Dx3 schedule. Tumor size and body weight were measured twice per week.

PC-3 cells were maintained in monolayer cultures in RPMI-1640 growth medium supplemented with 10% fetal bovine serum at 37° C. in a 5% $CO_2$ humidified incubator. On the day of inoculation, cells were harvested by trypsinization, washed, and re-suspended in ice-cold PBS. Female immunodeficient athymic mice (~6 week old, immune compromised NU/NU nude mice, from Charles River Laboratories) were inoculated subcutaneously near the right axillary area with $2 \times 10^6$ PC-3 cancer cells in PBS using a 27-gauge needle in a volume of 0.1 mL. Treatment was initiated 20 days after tumor inoculation following randomization of animals into treatment groups and vehicle control group based on tumor size; the average tumor size was ~500 $mm^3$.

In this Example, mice were treated with (a) CTX-Cryptophycin alone; (b) CTX-Cryptophycin following an anti-NRP1 IgG antibody pretreatment; (c) CTX-Cryptophycin following an IgG antibody control treatment; and (d) vehicle (Table 9). CTX-Cryptophycin was administered as single agent at 0.9 mg/kg, either alone or 30 minutes after administration antibody (anti-NRP1 antibody or control antibody). Conjugates were formulated in 10% EtOH, 5% Tween-80 and 85% saline (vehicle) and administered intravenously once every four days, 3 times. CTX-Cryptophycin doses were 0.9 mg/kg based on body weight at 0.1 mL per 10 g. For anti-NRP1 antibody treatment, polyclonal goat IgG anti-human NRP1 and polyclonal sheep IgG anti-mouse NRP1 were mixed in equal amounts (20 µg anti-human NRP-1 antibodyantibody; 20 g anti-mouse NRP1 antibody: Cat #AF566), and a total of 40 µg anti-NRP1 antibody mixture was administered 30 minutes prior to the CTX-Cryptophycin. For control antibody, 20 µg goat and 20 µg sheep IgG were mixed, and a total of 40 µg was administered 30 minutes prior to the CTX-Cryptophycin for the control group. The vehicle control group was treated with intravenous vehicle once every 4 days, 3 times.

TABLE 9

| Group | Treatment | Schedule |
|---|---|---|
| A | CTX-Cryptophycin 0.9 mg/kg | Q4Dx3 |
| B | Anti-NRP1 (20 µg anti-human and 20 µg anti-mouse) followed 30 mins later by CTX-Cryptophycin 0.9 mg/kg | Q4Dx3 |
| C | Control IgG (20 µg goat and 20 µg sheep): followed 30 mins later by CTX-Cryptophycin 0.9 mg/kg | Q4Dx3 |
| D | Vehicle (10% EtOH, 5% Tween-80 and 85% saline) | Q4Dx3 |

General health of the mice was monitored and mortality recorded daily. Tumor volume was assessed by caliper (Mitutoyo, Aurora, IL) measurements (mm) using the formula $(1 \times w^2)/2 = mm^3$, where 1 and w refer to the larger and smaller perpendicular dimensions collected at each measurement. Tumor dimensions were recorded twice per week starting at the initiation of drug treatment. Body weights were recorded twice per week starting on the first day of treatment. The data generated include group mean tumor volumes±SEM and group mean body weights±SEM at each measurement. Animals whose tumor measurement reached ≥2 cm at the longest axis were euthanized prior to study termination. Statistical analysis was performed on Day 35 when vehicle-treated animals were euthanized due to large tumors.

Statistical analysis was by one way analysis of variance (ANOVA) for tumor volume followed by Dunnett's multiple comparison tests. The analysis was performed on Day 35 of the study (vehicle endpoint). A value of P<0.05 was considered statistically significant under a two-sided hypothesis. All statistical analyses were performed using GraphPad Prism 6 software (Lake Forest, CA).

Figure 25:
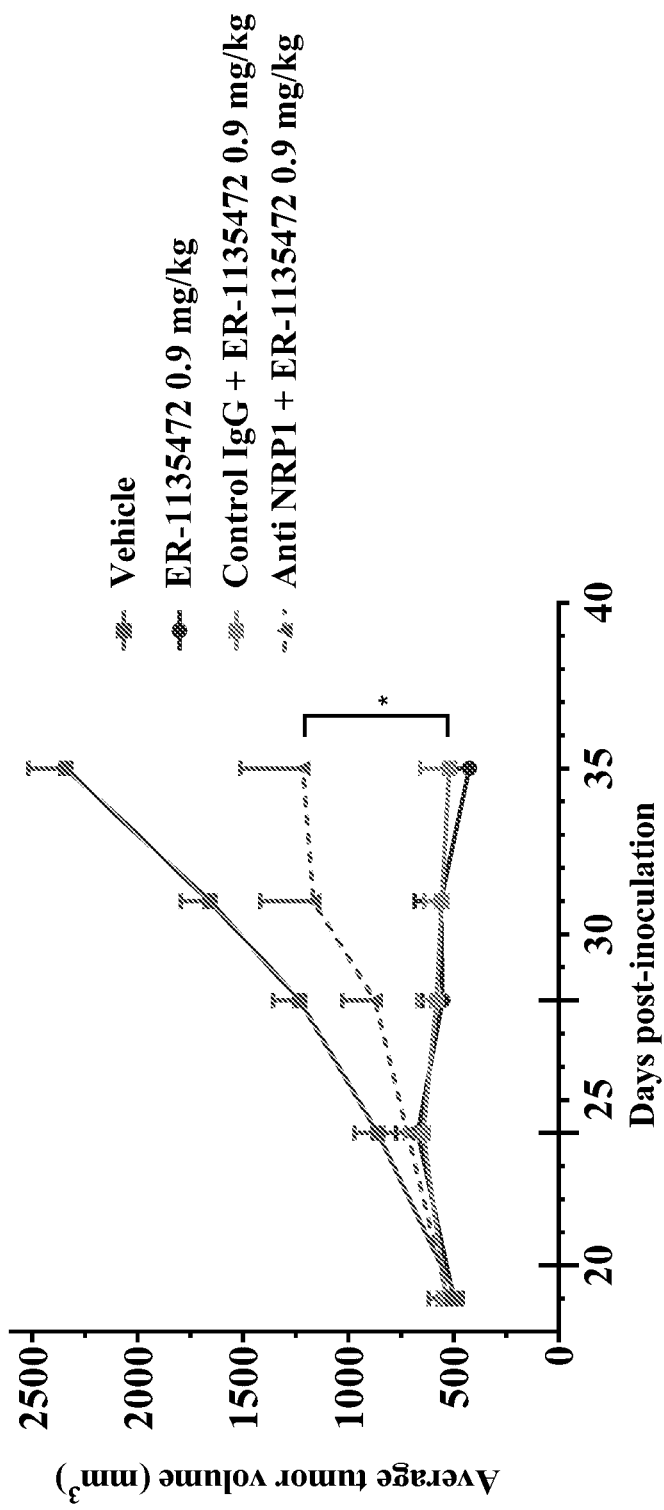
FIG. 25 is a graph showing average tumor volume over days post inoculation for treatments including CTX-Cryptophycin alone or following treatment with anti-NRP1 or control IgG antibody.

Data shown in FIG. 25 demonstrate effects of CTX-Cryptophycin administration alone or following pretreatment with anti-NRP1 antibodies or control IgG, on tumor growth of PC-3 human prostate xenografts in athymic mice. Data represent mean tumor volume±SEM. Antitumor effects were observed in mice treated with CTX-Cryptophycin alone, and almost identical effects were observed in mice treated with CTX-Cryptophycin following pretreatment with control IgG. In contrast pretreatment of xenografts with anti-NRP1 antibodies resulted in blunting the efficacy of CTX-Cryptophycin and the difference in activity was statistically significant.

Thus, pretreatment of PC-3 xenografts with anti-NRP1 antibody resulted in blunting the antitumor activity of CTX-Cryptophycin. Without wishing to be bound by any particular scientific theory, these data suggest a role for NRP1 in the antitumor efficacy of CTX-cryptophycin conjugates and support a hypothesis that CTX binds NRP1 on tumor cells to increase uptake resulting in an enhanced antitumor effect.

Example 17: Effects of Anti-Human NRP1 Blocking Antibody on the Antitumor Efficacy of CTX-Cryptophycin Conjugates in Human Prostate Cancer PC-3 Xenografts The present Example describes work assessing ability of anti-human NRP1 Ab to blunt the efficacy of CTX-Cryptophycin conjugate on subcutaneously implanted human prostate cancer PC-3 cells in athymic mice and its reproducibility using a particular lot of anti-human NRP1 antibody.

The present experiment was conducted as described in Example 16, with 30 minute pretreatment of antibody or control IgG prior to administration of CTX-Cryptophycin at 0.9 mg/kg. Treatment was initiated 16 days after tumor inoculation. Antibody used was from the same bleed ("bleed 1") as anti-human NRP-1 antibody used in Example 16.

Figure 26:
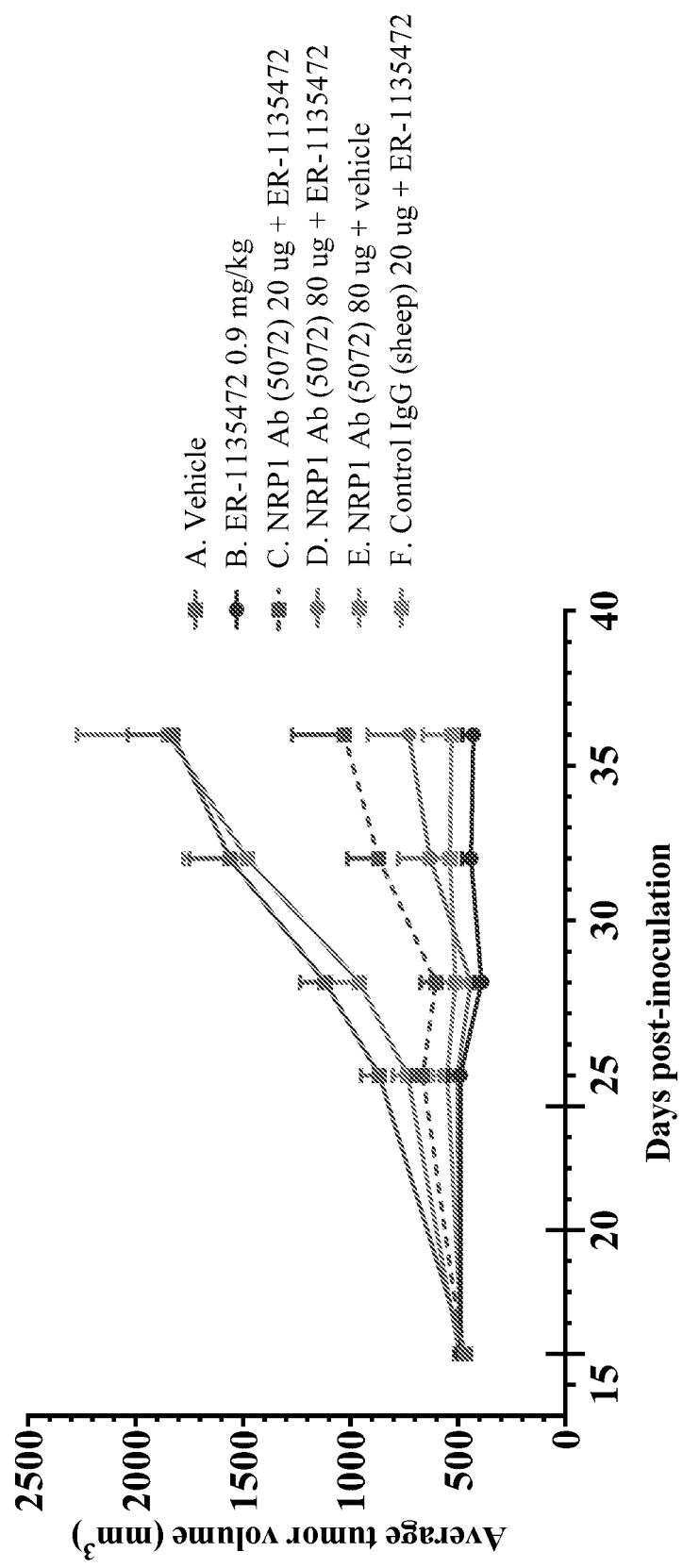
FIG. 26 is a graph showing average tumor volume over days post inoculation for treatments including CTX-Cryptophycin alone or in following treatment with anti-NRP1 IgG antibody.

Treatment with anti-human NRP1 antibody at 20 µg followed by CTX-Cryptophycin resulted in statistically significant lower antitumor activity than that of control IgG followed by CTX-Cryptophycin (FIG. 26). Blunting effects of the antibody were lost at the 80 g dose of anti-human NRP1 antibody. This data suggests that at certain doses anti-human NRP1 antibody blunts the activity of CTX-cryptophycin conjugates, which further suggests a role for NRP1 in mediating anti-tumor effects of CTX-cryptophycin conjugate.

Moreover, experiments conducted using a less potent lot of anti-human NRP1 IgG antibody failed to demonstrate blunting of CTX-Cryptophycin antitumor response (data not shown). This less potent lot was from a second bleed of the same animal from which "bleed 1" was taken, but was found to have ½ the potency in NRP1 blocking, as measured by ability to block VEGF binding to NRP1 in a cell based assay. These data from the less potent lot of anti-human NRP1 IgG suggest that antibody potency in a VEGF blocking assay is relevant to performance in vivo assays.

Overall, without wishing to be bound by any particular scientific theory, blunting of antitumor effects observed after anti-NRP1 antibody pretreatment support a hypothesis that NRP1 plays a role in the antitumor activity of CTX-cryptophycin conjugates.

Example 18: Co-Administration of Cryptophycin Payload with CTX in a Subcutaneous Human Prostate Cancer PC-3 Xenograft Model The tumor-penetrating peptide iRGD (CRGDK/RGPD/EC) (SEQ ID NO: 202), when chemically conjugated to, or co-administered with, a drug, can carry the drug deep into extravascular tumor tissue. Increased drug permeability is tumor-specific and NRP1-dependent. iRGD binds av integrins expressed tumor endothelial cells and is then proteolytically cleaved in the tumor to produce CRGDK/R (SEQ ID NO: 203). The truncated peptide loses much of its integrin-binding activity, but gains affinity for NRP1 because of the C-terminal exposure of a conditional C-end Rule (CendR) motif (R/KXXR/K) (SEQ ID NO: 251). NRP1 binding triggers tissue penetration, which is tumor-specific because cleavage requires earlier binding of the peptide to integrins. These features confer on iRGD a tumor-specific tissue penetration activity which enhances cancer drug delivery and activity when iRGD and drug are administered as separate components of a combination therapy. Truncated iRGD peptide (which lacks av integrin binding) also demonstrated tumor-specific enhanced uptake (Sugahara K N et al. 2010. Science 328: 1031-35).

Without wishing to be bound by any particular scientific theory, chlorotoxin and/or fragments thereof (at least when C-terminal arginine is carboxylic acid) may, like cleaved iRGD, bind NRP1 and thereby enhance drug penetration to NRP1-expressing tumors. The following CTX combination studies examined co-administration of CTX or iRGD and Cryptophycin Payload in PC-3 xenografts.

In this study, Cryptophycin Payload was evaluated alone (as a single agent with peptide vehicle control), in combination with iRGD peptide (CPC Scientific; Lot #CK-11-01042), or in combination with CTX. The experiment also included a vehicle-treated control group (Table 10). iRGD dose and administration schedule were based on those published in Sugahara K N et al. 2010. *Science* 328: 1031-35.

TABLE 10

Treatment Groups for Investigation of Effect of Cryptophycin Analog alone or in Combination with iRGD Versus CTX Peptide in PC-3 Human Prostate Cancer Xenografts in Athymic Mice

| Group | Treatment | Route | Schedule | No. of Animals |
|---|---|---|---|---|
| A | Vehicle (10% EtOH, 5% Tween-80 and 85% saline) | IV | Q2Dx3 | 5 |
| B | Cryptophycin Payload 0.4 mg/kg + Vehicle | IV | Q2Dx3 | 5 |
| C | Cryptophycin Payload 0.4 mg/kg + iRGD 3.8 mg/kg | IV | Q2Dx3 | 5 |
| D | Cryptophycin Payload 0.4 mg/kg + CTX 16 mg/kg | IV | Q2Dx3 | 5 |

PC-3 human prostate cancer cells (ATCC CRL-1435) were grown in RPMI-1640 medium supplemented with 10% FBS. For inoculation, $2\times10^6$ PC-3 cancer cells were injected subcutaneously into mice near the right axillary area using a 27-gauge needle in a volume of 0.1 mL. Mice were immune-compromised NU/NU nude females, approximately 6 weeks old from Charles River Labs. Tumors were measured at least twice weekly using calipers and mice were randomized into treatment groups based on tumor size when the average tumor reached approximately 180 mm³. All treatments were initiated 17 days after tumor inoculation. The experiment included a vehicle-treated group and drug-treated groups (n=5). CTX was dissolved in saline, Cryptophycin Payload was dissolved in vehicle (10% EtOH, 5% Tween80 and 85% saline), iRGD peptide was initially dissolved in 100% EtOH as a 10× stock solution and then saline was used for further dilution. For combination dosing, cryptophycin and peptides were first prepared as 2× stock solutions and then mixed together 1:1 (v/v) prior to administration. All drugs were administered intravenously on a Q2Dx3 schedule. Each group was composed of 5 mice; drugs were administered i.v. once every 2 days, 3 times. Doses were 0.4 mg/kg cryptophycin, 4 mg/kg iRGD and 16 mg/kg CTX (molar equivalent dose of iRGD peptide) based on body weight at 0.1 mL per 10 g.

General health of the mice was monitored and mortality recorded daily. Tumor volume was assessed by caliper (Mitutoyo, Aurora, IL) measurements (mm) using the formula $(1\times w^2)/2 = mm^3$, where 1 and w refer to the larger and smaller perpendicular dimensions collected at each measurement. Tumor dimensions were recorded twice per week starting at the initiation of drug treatment. Body weights were recorded twice per week starting on the first day of treatment. Relative body weight was calculated as follows: Relative body weight=(body weight on day of measurement/body weight on first day of treatment). The data generated include group mean tumor volumes and group mean body weights at each measurement. The mean±SEM for tumor volume and mean±SEM for relative body weight for each experimental group was calculated. Animals whose tumor measurement reached ≥2 cm at the longest axis were euthanized prior to study termination.

Statistical analysis was by one way analysis of variance (ANOVA) for tumor volume followed by Bonferroni's multiple comparison tests. Analysis was performed on Day 60 of the study. A value of $P<0.05$ was considered statistically significant under a two-sided hypothesis. All statistical analyses were performed using GraphPad Prism 6 software (Lake Forest, CA).

Figure 27:
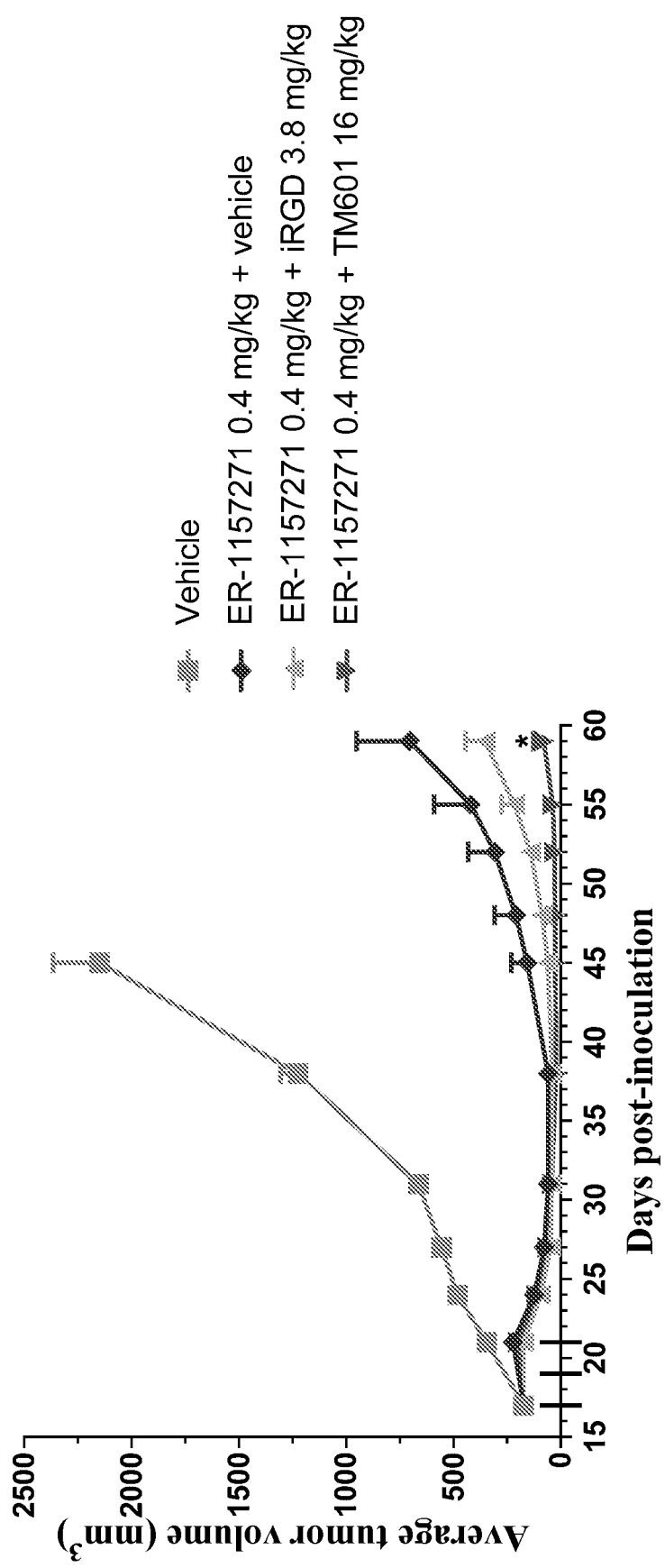
FIG. 27 is a graph showing average tumor volume over days post inoculation for treatments including Cryptophycin Payload alone or in combination with iRGD peptide or CTX peptide.

Results show that administration of Cryptophycin Payload at 0.4 mg/kg to PC-3 xenografts resulted in significant antitumor activity (FIG. 27). On Day 45 animals in the vehicle group were euthanized due to large tumor size while tumors remained very small in drug treated groups. Tumor regression was observed in all treatment groups; then at 3 to 4 weeks post-the last dose, tumors began to re-grow. Re-growth of tumors was delayed in both groups treated in combination with peptides. The delay in tumor re-growth was more pronounced and statistically significant for CTX combination, which appeared more effective than iRGD combination. These results were not reproduced when the protocol of the present Example was modified by lowering Cryptophycin Payload dosage to 0.2 mg/kg: at that dosage, re-growth of tumors was not shown to be significantly different between treatments of Cryptophycin Payload alone and Cryptophycin Payload with iRGD, or between treatments of Cryptophycin Payload alone and Cryptophycin Payload with CTX (data not shown).

Combination of cryptophycin with either iRGD or CTX peptide delayed tumor progression in PC-3 xenografts as compared to treatment with Cryptophycin Payload alone. The CTX/Payload combination resulted in slower tumor progression than with iRGD/Payload. Tumor size following CTX/Payload treatment, but not following iRGD/Payload treatment, was significantly different from tumor size following treatment with Cryptophycin Payload alone.

Example 19: Co-Administration of Cryptophycin Payload with Various Dosages CTX in a Subcutaneous Human Prostate Cancer PC-3 Xenograft Model The present Example describes work assessing multiple CTX doses for co-administration with a Cryptophycin Payload.

For the present experiment, materials, methods, drugs and model were as described in Example 18. PC-3 tumors were measured at least twice weekly using calipers and mice were randomized into treatment groups based on tumor size when the average tumor reached approximately 250 mm$^3$. All treatments were initiated 17 days after tumor inoculation. The experiment consisted of a vehicle-treated group and drug-treated groups (n=5). All drugs were administered intravenously on a Q2Dx3 schedule.

Cryptophycin Payload was evaluated as a single agent, in combination with iRGD peptide, and in combination with CTX peptide (Table 11). Each group included 5 mice. Treatments were administered intravenously once every 2 days, 3 times. Animals were dosed with 0.2 mg/kg cryptophycin in combination with 4 mg/kg iRGD, 16 mg/kg CTX (molar equivalent dose of iRGD peptide), or vehicle, based on body weight at 0.1 mL per 10 g. In addition, CTX administered at doses of 2, 4 and 64 mg/kg was assessed for potentiation of cryptophycin activity.

TABLE 11

Treatment Groups for Investigation of Effect of Cryptophycin Analog alone or in Combination with iRGD Versus CTX Peptide in PC-3 Human Prostate Cancer Xenografts in Athymic Mice

| Group | Treatment | Route | Schedule | No. of Animals |
|---|---|---|---|---|
| A | Vehicle (10% EtOH, 5% Tween-80 and 85% saline) | IV | Q2Dx3 | 5 |
| B | Cryptophycin Payload 0.4 mg/kg + Vehicle | IV | Q2Dx3 | 5 |
| C | Cryptophycin Payload 0.4 mg/kg + iRGD 3.8 mg/kg | IV | Q2Dx3 | 5 |
| D | Cryptophycin Payload 0.4 mg/kg + CTX 16 mg/kg | IV | Q2Dx3 | 5 |
| E | Cryptophycin Payload 0.4 mg/kg + CTX 64 mg/kg | IV | Q2Dx3 | 5 |
| F | Cryptophycin Payload 0.4 mg/kg + CTX 4 mg/kg | IV | Q2Dx3 | 5 |
| G | Cryptophycin Payload 0.4 mg/kg + CTX 2 mg/kg | IV | Q2Dx3 | 5 |

Figure 28:
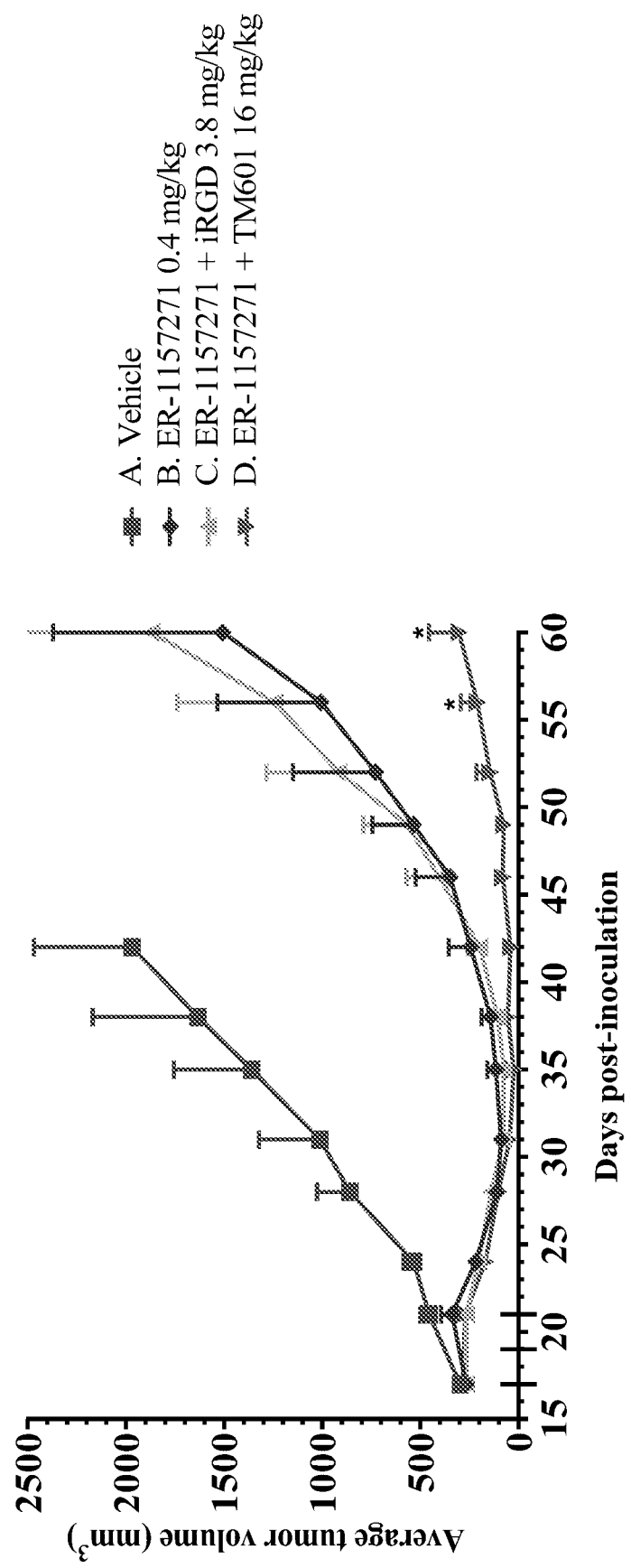
FIG. 28 is a graph showing average tumor volume over days post inoculation for treatments including Cryptophycin Payload alone or in combination with iRGD peptide or CTX.

Administration of Cryptophycin Payload alone at 0.4 mg/kg to PC-3 xenografts on a Q4Dx3 schedule resulted in significant antitumor activity (FIG. 28). On Day 42 animals in the vehicle group were euthanized due to large tumor size while tumors remained very small in drug treated groups. Tumor regression was observed in all treatment groups, and then tumors began to re-grow at 2-3 weeks post-last drug dose.

A statistically significant delay in re-growth of tumors was observed in group D treated with cryptophycin in combination with CTX at 16 mg/kg as compared to cryptophycin treatment alone (Group B, t-test P<0.05) (FIG. 28). Addition of iRGD to cryptophycin in this study had no discernable impact on the antitumor activity of cryptophycin (FIG. 28).

Figure 29:
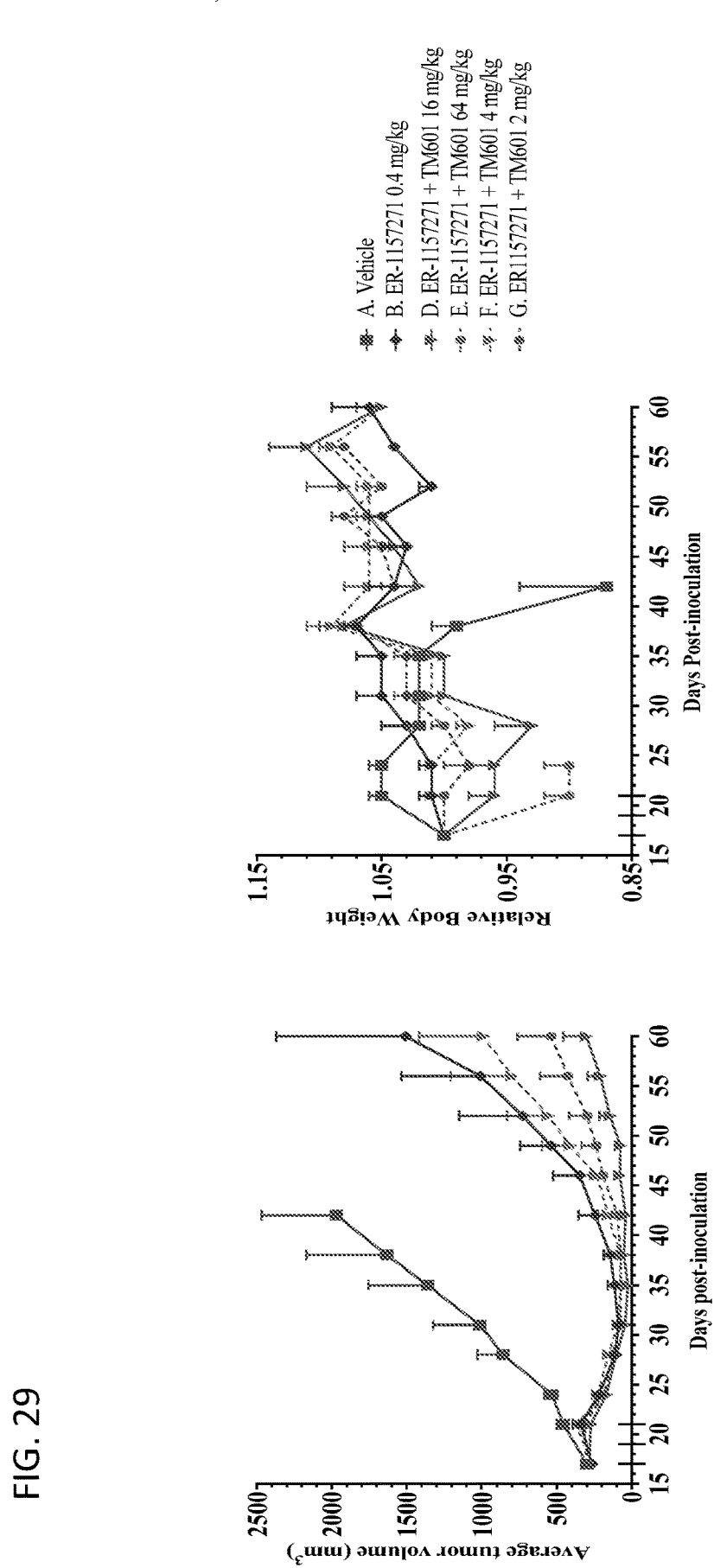
FIG. 29 is a pair of graphs showing average tumor volume and relative body weight over days post inoculation for Cryptophycin Payload alone or in combination with CTX peptide.

In contrast to combination with CTX at 16 mg/kg, dosages of 2 mg/kg CTX and 4 mg/kg CTX did not significantly delay tumor re-growth (FIG. 29). When a CTX dose of 64 mg/kg was administered with cryptophycin, significant body weight loss was observed and the animals were euthanized on Day 26. CTX alone is well tolerated by mice at much higher doses than the 64 mg/kg in this group. Therefore, the toxicity observed was likely due to potentiation of effects of cryptophycin. Prior to termination, these animals were also observed to suffer from neurological constipation (an established cryptophycin-induced side-effect), suggesting an increase in uptake of cryptophycin in tissues other than tumor. Overall, results support a finding that CTX potentiates the activity of cryptophycin.

Example 20: Co-Administration of CTX with Cryptophycin Payload in a Subcutaneous Human Prostate Cancer PC-3 Xenograft Model The present Example describes work assessing tissue distribution of cryptophycin and its active metabolite in a duplicate study. Concentrations of Cryptophycin Payload and its potential metabolite Cryptophycin Metabolite 1, were measured in plasma, liver, tumor, kidney, heart, brain, small intestine, skin and skeletal muscle following a single dose of Cryptophycin Payload alone, or in combination with CTX, in PC-3 xenografts.

For the present experiment, materials, methods, drugs and model were as described in Example 21. A single dose of Cryptophycin Payload was administered intravenously at 0.4 mg/kg with or without 16 mg/kg of CTX to the nude mice. Following intravenous administration, whole blood samples were collected at predetermined time points via cardiac puncture (n=3 mice per time point). Blood samples were centrifuged to obtain plasma and subsequently stored at ~20° C. or lower pending analysis. Additionally, at each time point, kidney, liver, small intestine, brain, heart, and tumor were harvested by removing entire specimen from surrounding tissues (only a portion of liver and small intestine were removed). After removal, tissues were rinsed with normal saline solution (contents of small intestine were emptied) and blotted dry with clean adsorptive tissue. Once dried, the specimens were weighed and stored at −20° C. or lower pending analysis. Following extraction, concentrations of Cryptophycin Payload and Cryptophycin Metabolite 1 were assessed in plasma and tissues using LC-MS/MS. Pharmacokinetic (PK) parameters were calculated. Mean plasma and tissue concentrations were used to calculate mean PK parameters. Skin and skeletal muscle which were not assessed due to difficulty of homogenization.

Vehicle for single dose group was 10% ethanol, 5% Tween 80, 85% saline. Vehicle for combination treatment was 5% ethanol, 2.5% Tween 80, 92.5% saline.

Observed concentrations of Cryptophycin Payload and Cryptophycin Metabolite 1 in plasma (ng/mL) and tissues (ng/g) and are shown in Tables 12-15. The PK parameters of Cryptophycin Payload and Cryptophycin Metabolite 1 following 0.4 mg/kg administration of Cryptophycin Payload as a single dose or a co-administration of 0.4 mg/kg of Cryptophycin Payload and 16 mg/kg of CTX are presented in Table 16 and Table 17.

Following single dose Cryptophycin Payload, Cryptophycin Payload had a mean plasma exposure ($AUC_{0-inf}$) of 154 ng·h/mL with a moderate half-life ($t_2$) of 1.13 hours, a moderate clearance (CL) of 2.60 L/h/kg, and a moderate $V_{ss}$ of 1.15 L/kg. The mean exposures of Cryptophycin Payload in liver ($AUC_{0-6\,h}$), tumor ($AUC_{0-inf}$), kidney ($AUC_{0-inf}$), heart ($AUC_{0-inf}$), brain ($AUC_{0-inf}$) and small intestine ($AUC_{0-6\,h}$) were measured to be 9.65, 28.8, 826, 38.9, 3.57 and 81.6 ng·h/g, respectively, with respective mean $C_{max}$ values of 6.02, 11.6, 533, 63.2, 8.32 and 53.3 ng/g at $t_{max}$ of 0.083 hours, respectively.

Following single dose Cryptophycin Payload, the mean exposure ($AUC_{0-inf}$) of the cryptophycin-S-methyl metabolite, Cryptophycin Metabolite 1, in plasma was 40.7 ng·h/mL with a mean $C_{max}$ of 23.6 ng/mL at $t_{max}$ of 0.083 hours. The mean exposures of Cryptophycin Metabolite 1 in liver ($AUC_{0-inf}$), tumor ($AUC_{0-24\,h}$), kidney ($AUC_{0-inf}$), heart ($AUC_{0-inf}$), brain ($AUC_{0-6\,h}$) and small intestine ($AUC_{0-inf}$) were measured to be 1870, 117, 1750, 396, 4.42 and 314 ng·h/g, respectively, with $C_{max}$ values of 2710, 5.33, 361, 87.1, 1.46 and 29.7 ng/g at $t_{max}$ of 0.08, 6.00, 0.50, 0.08, 0.08 and 0.50 hours, respectively.

Following single dose Cryptophycin Payload, a high to low tissue rank order of Cryptophycin Payload exposure of kidney>>small intestine>heart>tumor>liver>brain (TPI of 5.36, 0.268, 0.253, 0.187, 0.0631 and 0.0208 mL/g, respectively) was observed. Distribution of cryptophycin-S-methyl metabolite (Cryptophycin Metabolite 1) to tissues was, in high to low rank order of exposure, liver>kidney>heart>small intestine>tumor>brain.

Following co-administration of Cryptophycin Payload and CTX, Cryptophycin Payload had a mean plasma exposure ($AUC_{0-inf}$) of 129 ng·h/mL with a short half-life (t½) of 0.848 hours, a moderate clearance of 3.11 L/h/kg, and an extensive $V_{ss}$ of 2.28 L/kg. The mean exposures of Cryptophycin Payload in liver ($AUC_{0-6\,h}$), tumor ($AUC_{0-6\,h}$), kidney ($AUC_{0-inf}$), heart ($AUC_{0-inf}$), brain ($AUC_{0-2\,h}$) and small intestine ($AUC_{0-inf}$) were measured to be 15.1, 42.7, 1230, 62.0, 3.69 and 36.4 ng·h/g, respectively, with respective $C_{max}$ values of 7.13, 12.5, 411, 47.3, 3.97 and 19.8 ng/g at $t_{max}$ of 1.00, 0.08, 0.50, 0.08, 0.08 and 0.08 hours, respectively.

Following co-administration of Cryptophycin Payload and CTX, the mean exposure ($AUC_{0-inf}$) of Cryptophycin Metabolite 1, in plasma was 53.2 ng·h/mL with a $C_{max}$ of 12.4 ng/mL at $t_{max}$ 1.0 hour. The mean exposures of Cryptophycin Metabolite 1 in liver ($AUC_{0-inf}$), tumor ($AUC_{0-24\,h}$), kidney ($AUC_{0-24\,h}$), heart ($AUC_{0-inf}$), brain ($AUC_{0-6\,h}$) and small intestine ($AUC_{0-inf}$) were measured to be 2930, 259, 2720, 620, 5.38 and 316 ng·h/g, respectively, with respective $C_{max}$ values of 1540, 12.2, 370, 107, 1.09 and 26.9 ng/g at $t_{max}$ of 0.08, 6.00, 2.00, 0.08, 2.00 and 1.00 hours, respectively.

Following co-administration of Cryptophycin Payload and CTX, distribution of Cryptophycin Payload to tissues was high to low, with a rank order of exposure of kidney>>heart>tumor>small intestine>liver>brain with TPI of 9.53, 0.481, 0.334, 0.282, 0.118 and 0.0315 mL/g, respectively. Distribution of Cryptophycin Metabolite 1, to tissues was high to low, with a rank order of exposure of liver>kidney>heart>small intestine>tumor>brain.

Figure 30:
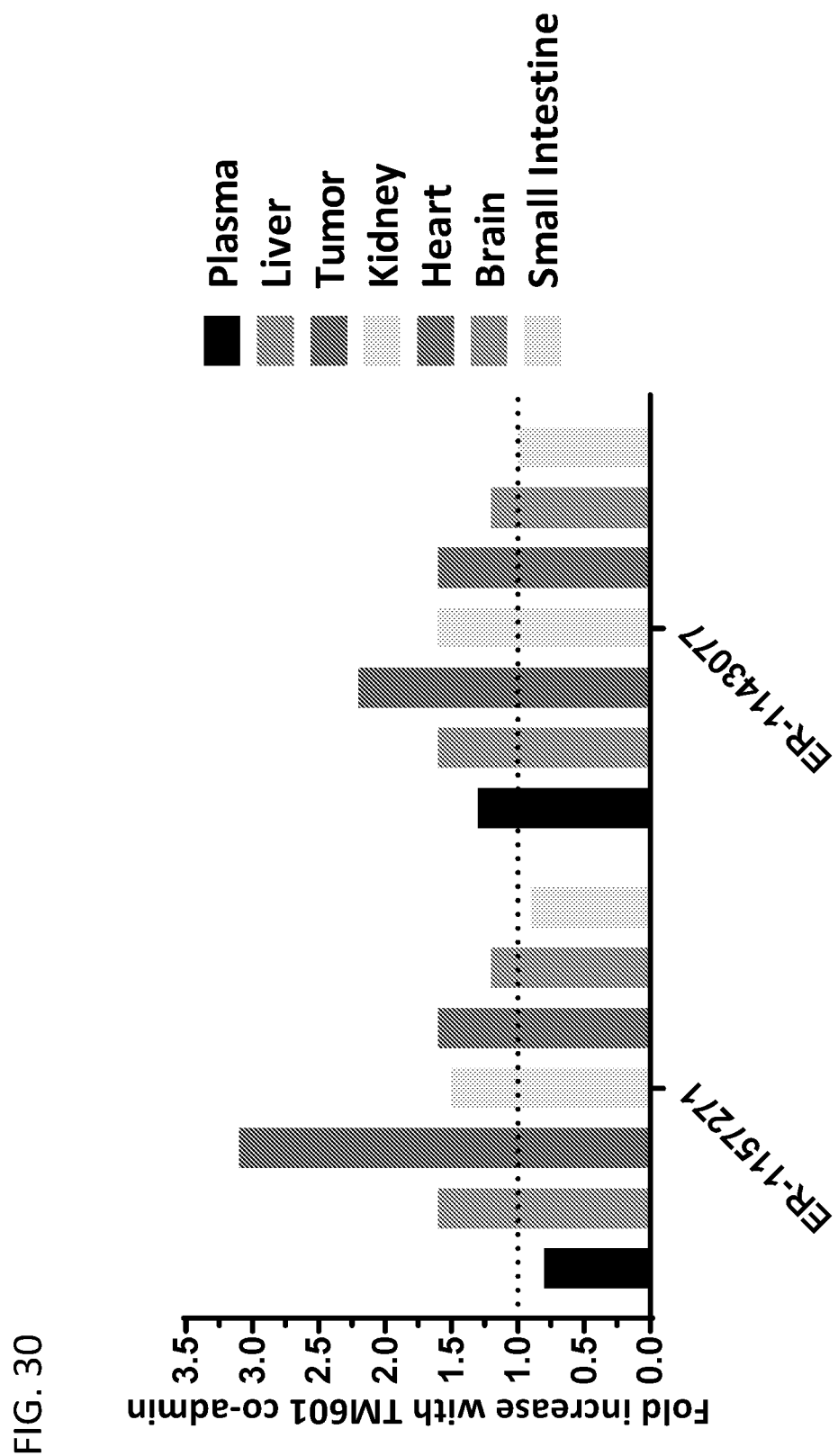
FIG. 30 is a chart showing show fold increase in Carboxylated CTX-Cryptophycin or Cryptophycin Metabolite 1 in various tissues following Cryptophycin Payload treatment alone or in combination with CTX peptide.

Fold change in tissue exposure following single dose Cryptophycin Payload versus combination treatment was calculated ($AUC_{Combo}/AUC_{Single\,agent}$) and plotted for each tissue (FIG. 30).

In general, an increase in Cryptophycin Payload and Cryptophycin Metabolite 1 was observed following the co-administration of Cryptophycin Payload with CTX compared to Cryptophycin Payload alone. The largest exposure increase was observed in tumor (i.e., 3.1- and 2.2-fold greater AUC, respectively, in tables 16 and 17).

Taken together, increased exposure (AUC) for parent Cryptophycin Payload and metabolite Cryptophycin Metabolite 1 was observed in all tissues, except small intestine, following co-administration of Cryptophycin Payload with CTX to PC-3 xenograft mice. Exposure ratios (combination/cryptophycin alone) for all tissues except tumor were between 1 to ~1.5, while mean plasma exposure remained close to 1 (0.8 and 1.3 fold for Cryptophycin Payload and Cryptophycin Metabolite 1 respectively). A significantly higher increase in exposure was observed in tumor tissue following for co-administration versus single agent with ratios of 3.1 and 2.2 fold for Cryptophycin Payload and Cryptophycin Metabolite 1, when CTX was present.

PC-3 tumors have high NRP1 expression. NRP1 binding by C-end rule peptides is reported to increase penetration of co-administered drugs deep into tissue (Sugahara K N et al. 2010. *Science* 328: 1031-35). CTX appeared to enhance delivery of cryptophycin in this study in a tumor-specific manner, lending weight to the theory that CTX binds to NRP1 in vivo. Without wishing to be bound by any particular scientific theory, these data also provide a possible mechanistic basis for enhanced efficacy observed for combination treatment of PC-3 xenografts.

TABLE 12

Mean Plasma and Tissue Concentrations of Cryptophycin Payload following a Single IV Dose of Cryptophycin Payload or of Cryptophycin Payload with CTX

| Dose | Time | Concentration of Cryptophycin Payload (ng/mL Plasma; ng/g Tissue) | | | | | |
|---|---|---|---|---|---|---|---|
| | | Plasma | | Liver | | Tumor | |
| (mg/kg) | (h) | Mean | SD | Mean | SD | Mean | SD |
| 0.4 mg/kg | 0.083 | 493 | 250 | 6.02 | 2.52 | 11.6 | 4.46 |
| ER-001157271 | 0.5 | 36.3 | 1.96 | 1.92 | 1.30 | 4.11 | 2.28 |
| | 1 | 11.0 | 3.05 | 3.32 | 2.95 | 2.14 | 0.929 |
| | 2 | 5.30 | 0.317 | 1.29 | NA[a] | 2.41 | 0.414 |
| | 6 | 0.492 | 0.135 | 0.948 | NA[a] | 1.03 | 0.365 |
| | 24 | BLQ | NA | BLQ | NA | 0.335 | 0.0854 |

TABLE 12-continued

Mean Plasma and Tissue Concentrations of Cryptophycin Payload following a
Single IV Dose of Cryptophycin Payload or of Cryptophycin Payload with CTX

| Dose | Time | Concentration of Cryptophycin Payload (ng/mL Plasma; ng/g Tissue) | | | | | |
|---|---|---|---|---|---|---|---|
| | | Plasma | | Liver | | Tumor | |
| (mg/kg) | (h) | Mean | SD | Mean | SD | Mean | SD |
| 0.4 mg/kg ER-001157271 + 16 mg/kg CTX | 0.083 | 268 | 119 | 3.89 | 2.83 | 12.5 | 9.22 |
| | 0.5 | 37.9 | 7.85 | 7.13 | 4.26 | 10.3 | 0.653 |
| | 1 | 43.8 | 29.9 | 7.13 | 1.47 | 9.46 | 1.28 |
| | 2 | 7.53 | 1.93 | 2.13 | 0.611 | 10.1 | 6.21 |
| | 6 | 0.537 | 0.293 | 0.632 | NA[a] | 2.80 | 0.937 |
| | 24 | BLQ | NA | BLQ | NA | BLQ | NA |

BLQ = below limit of quantification (<0.05 ng/mL plasma; <0.2 ng/g tissue).
IV = intravenous.
NA = not applicable.
[a] Standard deviation was not assessed as n = 2.

TABLE 13

Mean Plasma and Tissue Concentrations of Cryptophycin Payload following a
Single IV Dose of Cryptophycin Payload or of Cryptophycin Payload with CTX

| Dose | Time | Concentration of Cryptophycin Payload (ng/mL Plasma; ng/g Tissue) | | | | | | | |
|---|---|---|---|---|---|---|---|---|---|
| | | Kidney | | Heart | | Brain | | Small Intestine | |
| (mg/kg) | (h) | Mean | SD | Mean | SD | Mean | SD | Mean | SD |
| 0.4 mg/kg ER-001157271 | 0.083 | 533 | 45.4 | 63.2 | 25.1 | 8.32 | 4.09 | 53.3 | 46.5 |
| | 0.5 | 320 | 24.5 | 18.9 | 8.47 | 1.42 | 0.342 | 13.6 | 3.30 |
| | 1 | 158 | 15.5 | 7.91 | 1.79 | 0.673 | 0.106 | 6.55 | 1.10 |
| | 2 | 93.8 | 4.01 | 3.28 | 3.44 | 0.436 | 0.033 | 6.41 | 5.16 |
| | 6 | 20.4 | 2.43 | 0.885 | 0.170 | BLQ | NA | 2.17 | 0.859 |
| | 24 | 3.79 | 2.75 | BLQ | NA | BLQ | NA | 2.31 | 1.91 |
| 0.4 mg/kg ER-001157271 + 16 mg/kg CTX | 0.083 | 389 | 313 | 47.3 | 39.9 | 3.97 | 2.51 | 19.8 | 15.1 |
| | 0.5 | 411 | 50.0 | 41.3 | 12.7 | 2.09 | 0.074 | 13.4 | 3.63 |
| | 1 | 317 | 30.2 | 18.7 | 1.29 | 2.07 | 0.687 | 15.5 | 4.34 |
| | 2 | 179 | 28.2 | 6.37 | 2.14 | 0.703 | 0.202 | 5.66 | 2.87 |
| | 6 | 35.9 | 16.0 | 1.39 | 0.126 | BLQ | NA | 0.873 | 0.124 |
| | 24 | 3.39 | 0.621 | BLQ | NA | BLQ | NA | BLQ | NA |

BLQ = below limit of quantification (<0.05 ng/mL plasma; <0.2 ng/g tissue).
IV = intravenous.
NA = not applicable.
a: Standard deviation was not assessed as n = 2.

TABLE 14

Mean Plasma and Tissue Concentrations of Cryptophycin Metabolite 1 following
a Single IV Dose of Cryptophycin Payload or of Cryptophycin Payload with CTX

| Dose | Time | Concentration of Cryptophycin Metabolite 1 (ng/mL Plasma; ng/g Tissue) | | | | | |
|---|---|---|---|---|---|---|---|
| | | Plasma | | Liver | | Tumor | |
| (mg/kg) | (h) | Mean | SD | Mean | SD | Mean | SD |
| 0.4 mg/kg ER-001157271 | 0.083 | 23.6 | 7.36 | 2710 | 546 | 2.36 | 1.37 |
| | 0.5 | 8.37 | 2.66 | 499 | 235 | 3.27 | 3.09 |
| | 1 | 6.46 | 0.263 | 310 | 96.1 | 3.41 | 1.35 |
| | 2 | 4.32 | 0.749 | 194 | 38.6 | 4.01 | 2.14 |
| | 6 | 1.86 | 0.258 | 37.2 | 10.5 | 5.33 | 0.551 |
| | 24 | 0.141 | 0.0445 | 7.89 | 4.32 | 4.91 | 0.324 |
| 0.4 mg/kg ER-001157271 + 16 mg/kg | 0.083 | 10.8 | 10.6 | 1540 | 1560 | 2.61 | NA[a] |
| | 0.5 | 8.10 | 1.77 | 1000 | 274 | 2.69 | 0.260 |
| | 1 | 12.4 | 11.1 | 1370 | 1120 | 3.90 | 0.176 |

TABLE 14-continued

Mean Plasma and Tissue Concentrations of Cryptophycin Metabolite 1 following a Single IV Dose of Cryptophycin Payload or of Cryptophycin Payload with CTX

| | | Concentration of Cryptophycin Metabolite 1 (ng/mL Plasma; ng/g Tissue) | | | | | |
|---|---|---|---|---|---|---|---|
| Dose | Time | Plasma | | Liver | | Tumor | |
| (mg/kg) | (h) | Mean | SD | Mean | SD | Mean | SD |
| CTX | 2 | 5.12 | 0.491 | 335 | 166 | 9.66 | 5.88 |
| | 6 | 2.15 | 0.757 | 53.6 | 15.3 | 12.2 | 0.982 |
| | 24 | 0.384 | 0.146 | 5.15 | 0.729 | 10.8 | 2.16 |

BLQ = below limit of quantification (<0.05 ng/mL plasma; <0.2 ng/g tissue).
IV = intravenous.
NA = not applicable.
[a]Standard deviation was not assessed as n = 2.

TABLE 15

Mean Plasma and Tissue Concentrations of Cryptophycin Metabolite 1 following a Single IV Dose of Cryptophycin Payload or of Cryptophycin Payload with CTX

| | | Concentration of Cryptophycin Metabolite 1 (ng/mL Plasma; ng/g Tissue) | | | | | | | |
|---|---|---|---|---|---|---|---|---|---|
| Dose | Time | Kidney | | Heart | | Brain | | Small Intestine | |
| (mg/kg) | (h) | Mean | SD | Mean | SD | Mean | SD | Mean | SD |
| 0.4 mg/kg ER-001157271 | 0.083 | 225 | 59.3 | 87.1 | 40.6 | 1.46 | 0.879 | 22.2 | 12.4 |
| | 0.5 | 361 | 113 | 80.2 | 13.5 | 0.895 | 0.327 | 29.7 | 12.1 |
| | 1 | 294 | 49.2 | 70.3 | 21.8 | 0.983 | 0.282 | 24.3 | 6.20 |
| | 2 | 249 | 25.4 | 52.8 | 47.3 | 0.887 | 0.335 | 23.1 | 4.16 |
| | 6 | 91.2 | 2.72 | 25.4 | 2.87 | 0.412 | 0.085 | 26.1 | 8.54 |
| | 24 | 4.88 | 1.76 | 0.387 | 0.150 | BLQ | NA | 1.50 | 0.942 |
| 0.4 mg/kg ER-001157271 + 16 mg/kg CTX | 0.083 | 115 | 94.5 | 107 | 141 | 0.622 | NA[a] | 10.4 | 8.72 |
| | 0.5 | 252 | 13.2 | 94.9 | 35.1 | 0.641 | 0.183 | 18.5 | 5.09 |
| | 1 | 285 | 48.8 | 77.1 | 14.0 | 1.07 | 0.147 | 26.9 | 6.46 |
| | 2 | 370 | 37.1 | 87.9 | 19.0 | 1.09 | 0.174 | 21.8 | 1.72 |
| | 6 | 191 | 97.6 | 43.7 | 16.2 | 0.725 | 0.190 | 14.8 | 0.917 |
| | 24 | 9.65 | 1.77 | 0.763 | 0.467 | BLQ | NA | 4.02 | 1.87 |

BLQ = below limit of quantification (<0.05 ng/mL plasma; <0.2 ng/g tissue).
IV = intravenous.
NA = not applicable.
[a]Standard deviation was not assessed as n = 2.

TABLE 16

Mean Plasma and Tissue PK Parameters of Cryptophycin Payload following a Single Dose of Cryptophycin Payload or of Cryptophycin Payload with CTX

| Dose (mg/kg) | Matrix (Plasma) (Tissue) | $C_{max}$ (ng/mL) (ng/g) | $t_{max}$ (h) (h) | $t_{1/2}$ (h) (h) | $AUC_{(0-t)}$ (ng·h/mL) (ng·h/g) | $AUC_{(0-inf)}$ (ng·h/mL) (ng·h/g) | Vss (L/kg) (NA) | CL (L/hr/kg) (NA) | $TPI^a$ (NA) (mL/g) | $AUC_{Co\text{-}admin}/AUC_{Single\ Dose}^b$ (NA) (NA) |
|---|---|---|---|---|---|---|---|---|---|---|
| 0.4 mg/kg Cryptophycin Payload | Plasma | NA | NA | 1.13 | 153 | 154 | 1.15 | 2.60 | NA | NA |
| | Liver | 6.02 | 0.08 | NR | 9.65 | NR | NA | NA | 0.0631[c] | NA |
| | Tumor | 11.6 | 0.08 | 8.43 | 24.9 | 28.8 | NA | NA | 0.187 | NA |
| | Kidney | 533 | 0.08 | 4.70 | 804 | 826 | NA | NA | 5.36 | NA |
| | Heart | 63.2 | 0.08 | 1.71 | 36.8 | 38.9 | NA | NA | 0.253 | NA |
| | Brain | 8.32 | 0.08 | 0.941 | 3.02 | 3.57 | NA | NA | 0.0208[d] | NA |
| | Small Intestine | 53.3 | 0.08 | NR | 81.6 | NR | NA | NA | 0.268[c] | NA |
| 0.4 mg/kg Cryptophycin Payload + | Plasma | NA | NA | 0.848 | 128 | 129 | 2.28 | 3.11 | NA | 0.8 |
| | Liver | 7.13 | 1.00 | NC | 15.1 | NC | NA | NA | 0.118[c] | 1.6[e] |
| | Tumor | 12.5 | 0.08 | NR | 42.7 | NR | NA | NA | 0.334[c] | 3.1[e] |

TABLE 16-continued

Mean Plasma and Tissue PK Parameters of Cryptophycin Payload following a
Single Dose of Cryptophycin Payload or of Cryptophycin Payload with CTX

| Dose (mg/kg) | Matrix (Plasma) (Tissue) | $C_{max}$ (ng/mL) (ng/g) | $t_{max}$ (h) (h) | $t_{1/2}$ (h) (h) | $AUC_{(0-t)}$ (ng·h/mL) (ng·h/g) | $AUC_{(0-inf)}$ (ng·h/mL) (ng·h/g) | Vss (L/kg) (NA) | CL (L/hr/kg) (NA) | $TPI^a$ (NA) (mL/g) | $AUC_{Co-admin}/AUC_{Single\ Dose}{}^b$ (NA) (NA) |
|---|---|---|---|---|---|---|---|---|---|---|
| 16 mg/kg CTX | Kidney | 411 | 0.50 | 4.19 | 1210 | 1230 | NA | NA | 9.53 | 1.5 |
|  | Heart | 47.3 | 0.08 | 1.44 | 59.2 | 62.0 | NA | NA | 0.481 | 1.6 |
|  | Brain | 3.97 | 0.08 | NR | 3.69 | NR | NA | NA | $0.0315^d$ | $1.2^f$ |
|  | Small Intestine | 19.8 | 0.08 | 1.27 | 34.9 | 36.4 | NA | NA | 0.282 | $0.9^e$ |

IV = intravenous.
NA = not applicable.
NC = not calculated due to the poorly defined elimination phase.
NR = not reported due to greater than 20% extrapolation of the AUC0-inf.
$^a$TPI = AUC0-inf tissue/AUC0-inf plasma, unless otherwise noted.
$^b$AUC0-inf was used for ratio determination, unless otherwise noted.
$^c$TPI = AUC0-6 h tissue/AUC0-6 h plasma, where AUC0-6 h small intestine = 41.0 h · ng/g.
$^d$TPI = AUC0-2 h tissue/AUC0-2 h plasma, where AUC0-2 h plasma = 145 or 117 h · ng/mL for single dose and co-administration studies, respectively.
$^e$AUC0-6 h was used for ratio determination, where AUC0-6 h single dose = 14.0 and 41.0 ng · h/g for tumor and small intestine, respectively.
$^f$AUC0-2 h was used for ratio determination.

TABLE 17

Mean Plasma and Tissue PK Parameters of Cryptophycin Metabolite 1 following
a Single Dose of Cryptophycin Payload or of Cryptophycin Payload with CTX

| Dose (mg/kg) | Matrix (Plasma) (Tissue) | $C_{max}$ (ng/mL) (ng/g) | $t_{max}$ (h) (h) | $t_{1/2}$ (h) (h) | $AUC_{(0-t)}$ (ng·h/mL) (ng·h/g) | $AUC_{(0-inf)}$ (ng·h/mL) (ng·h/g) | Vss (L/kg) (NA) | CL (L/hr/kg) (NA) | $TPI^a$ (NA) (mL/g) | $AUC_{Co-admin}/AUC_{Single\ Dose}{}^b$ (NA) (NA) |
|---|---|---|---|---|---|---|---|---|---|---|
| 0.4 mg/kg Cryptophycin Payload | Plasma | 23.6 | 0.08 | 4.57 | 39.8 | 40.7 | NA | NA | NA | NA |
|  | Liver | 2710 | 0.08 | 4.77 | 1820 | 1870 | NA | NA | NA | NA |
|  | Tumor | 5.33 | 6.00 | NC | 117 | NC | NA | NA | NA | NA |
|  | Kidney | 361 | 0.50 | 3.99 | 1720 | 1750 | NA | NA | NA | NA |
|  | Heart | 87.1 | 0.08 | 3.06 | 394 | 396 | NA | NA | NA | NA |
|  | Brain | 1.46 | 0.08 | NR | 4.42 | NR | NA | NA | NA | NA |
|  | Small Intestine | 29.7 | 0.50 | 5.15 | 302 | 314 | NA | NA | NA | NA |
| 0.4 mg/kg Cryptophycin Payload + 16 mg/kg CTX | Plasma | 12.4 | 1.00 | 6.24 | 49.9 | 53.2 | NA | NA | NA | 1.3 |
|  | Liver | 1540 | 0.08 | 4.04 | 2900 | 2930 | NA | NA | NA | $1.6^c$ |
|  | Tumor | 12.2 | 6.00 | NC | 259 | NC | NA | NA | NA | $2.2^c$ |
|  | Kidney | 370 | 2.00 | NC | 2720 | NC | NA | NA | NA | $1.6^c$ |
|  | Heart | 107 | 0.08 | 3.17 | 616 | 620 | NA | NA | NA | 1.6 |
|  | Brain | 1.09 | 2.00 | NC | 5.38 | NC | NA | NA | NA | $1.2^d$ |
|  | Small Intestine | 26.9 | 1.00 | 9.18 | 263 | 316 | NA | NA | NA | 1.0 |

IV = intravenous.
NA = not applicable.
NC = not calculated due to the poorly defined elimination phase.
NR = not reported due to greater than 20% extrapolation of the AUC0-inf.
$^a$TPI = AUC0-inf tissue/AUC0-inf plasma, unless otherwise noted.
$^b$AUC0-inf was used for ratio determination, unless otherwise noted.
$^c$AUC0-24 h was used for ratio determination.
$^d$AUC0-6 h was used for ratio determination, where AUC0-6 h single dose = 14.0 and 41.0 ng · h/g for tumor and small intestine, respectively.

Example 21: NRP1 mRNA Expression in Xenograft Models

Tumors can vary in sensitivity to treatment with CTX-cryptophycin conjugate. In particular, a significantly wider therapeutic window was observed for CTX-Cryptophycin in a PC-3 xenograft model (MTD, ½ MTD, ¼ MTD) than in MIA PaCa-2 and BxPC3-Red-FLuc xenograft models (activity only observed at the MTD). PC-3 tumors have high NRP1 expression. Without wishing to be bound by any particular scientific theory, NRP1 may contribute to a CTX-dependent increase in uptake of conjugate in the presence of CTX, thereby contributing to enhanced antitumor activity. Both MIA PaCa-2 and BxPC3-Red-FLuc tumor lysates had low, almost undetectable levels of NRP1. To further evaluate correlation between therapeutic window and NRP1 expression level, several additional xenograft models were assessed for NRP1 expression level and for sensitivity CTX-Cryptophycin treatment.

Xenograft tumors with a range of NRP1 expression can be useful in the assessment of CTX-Cryptophycin conjugate antitumor activity. NRP1 gene expression values from the cancer cell line encyclopedia (CCLE, a database of compiled gene expression, chromosomal copy number and sequencing data from 947 human cancer cell lines) were used to select models of interest.

Once established, tumors were harvested from xenograft models (n=3 to 7) and subjected to quantitative PCR of NRP1 mRNA. Human and mouse NRP1 mRNA levels were measured in harvested tumors using species-specific primers; reflecting expression in tumor cells and tumor vasculature respectively.

NRP1 expression data in CCLE cell lines was downloaded using the H3B proprietary software; expression data for cell lines of interest were graphed using GraphPad Prism 6 software. Multiple tumors were harvested from various xenograft models (Table 18) and immediately flash frozen in liquid nitrogen, prior to storing at −80° C. Frozen tumor tissue was ground using a mortar and pestle and RNA was isolated using an RNeasy Mini Kit (Qiagen). cDNA was generated from total mRNA using SuperScript VILO Master Mix (Thermo Fisher Scientific). TaqMan™ quantitative PCR assays were performed for human and mouse NRP1 (hS00826128_m1, mm00435379_m1), while GUSB (hs99999908_m1, mm0046953_m1) and HPRT1 (hS000000000_m1, mm00446968_m1) were included as endogenous controls. Data analysis was performed using RQ Manager software (Thermo Fisher Scientific). Raw data was exported into DataAssist™ software for generation of $2^{-\Delta\Delta CT}$ values. Human NRP1 data was normalized to endogenous human controls and mouse NRP1 data to mouse endogenous controls; mean gene expression levels were exported for graphing into GraphPad Prism 6 software.

TABLE 18

| Xenograft Model | Fresh Frozen Tumors # |
|---|---|
| MIA PaCa-2 | 4 |
| BxPC3-Red-FLuc | 4 |
| PC-3 | 4 |
| SK-N-MC | 5 |
| TC-71 | 4 |
| MDA-MB-231 | 4 |
| HT-1080 | |
| U-87 MG | |
| COLO 320DM | 4 |
| Hs 695T | 7 |
| CFPAC-1 | 6 |
| LOX IMVI | 3 |
| HCT 116 | 3 |

Figure 31:
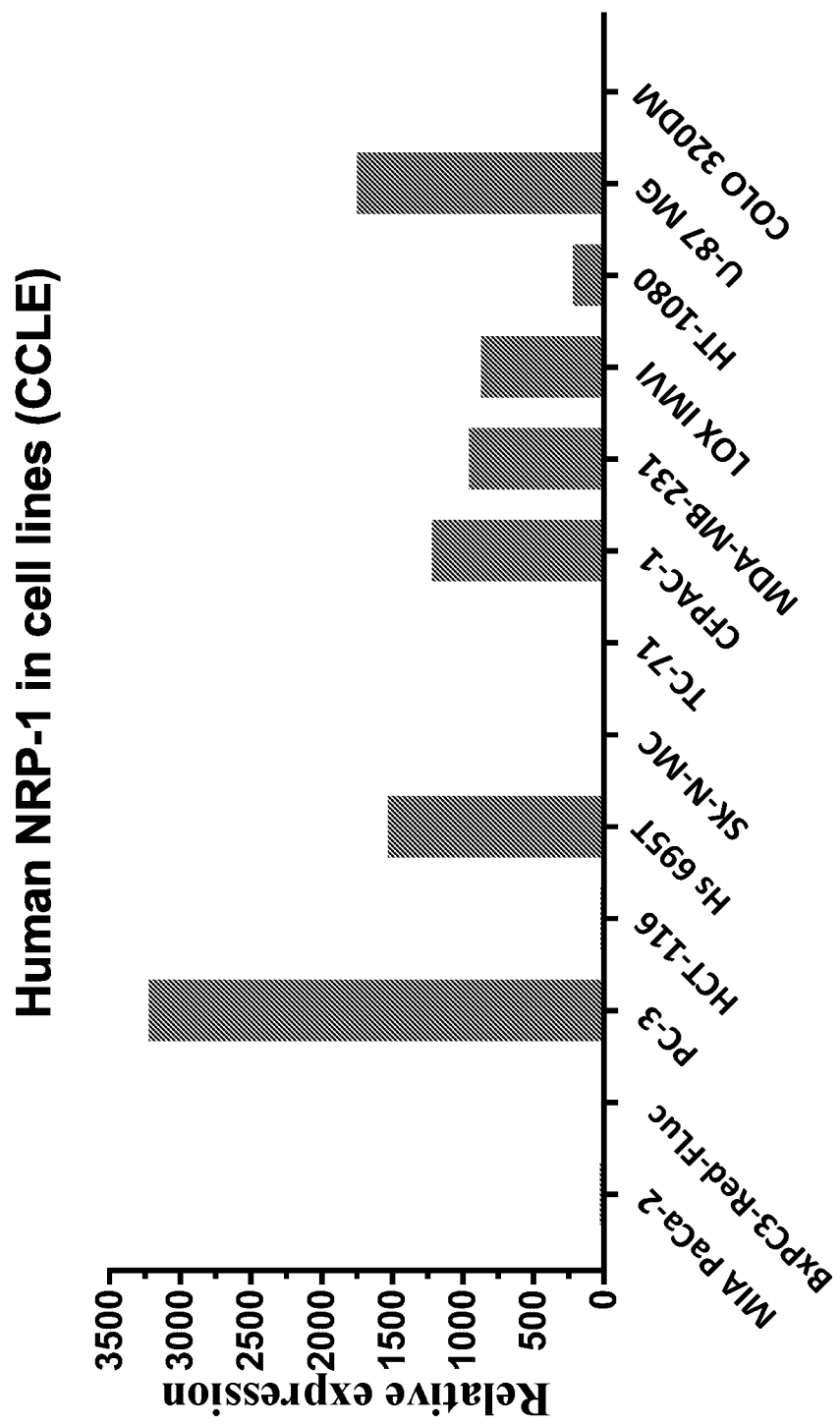
FIG. 31 is a chart showing human NRP1 expression levels in selected cell lines from the CCLE database
Figure 32:
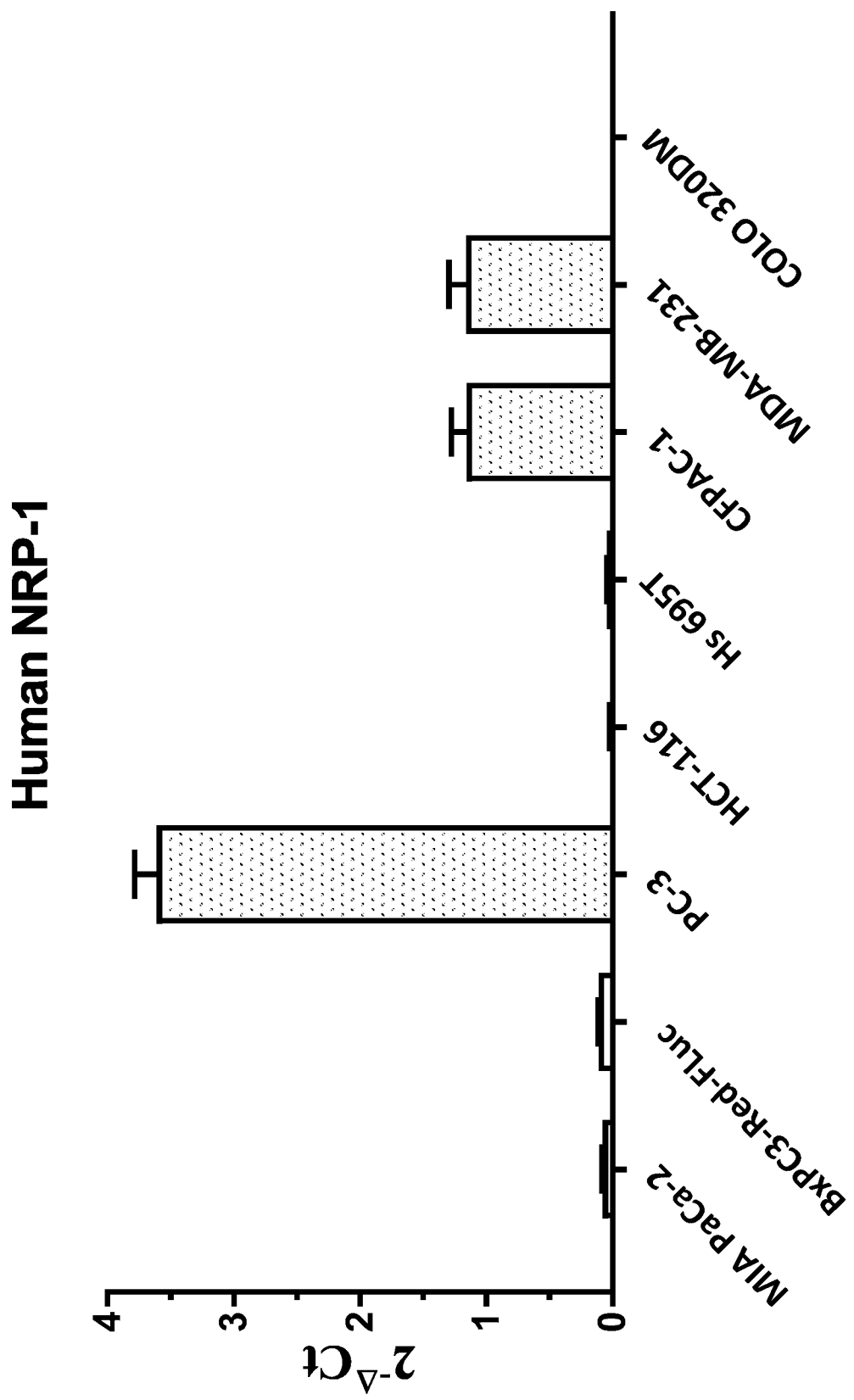
FIG. 32 is a chart showing human NRP1 expression in tumor lysates.
Figure 33:
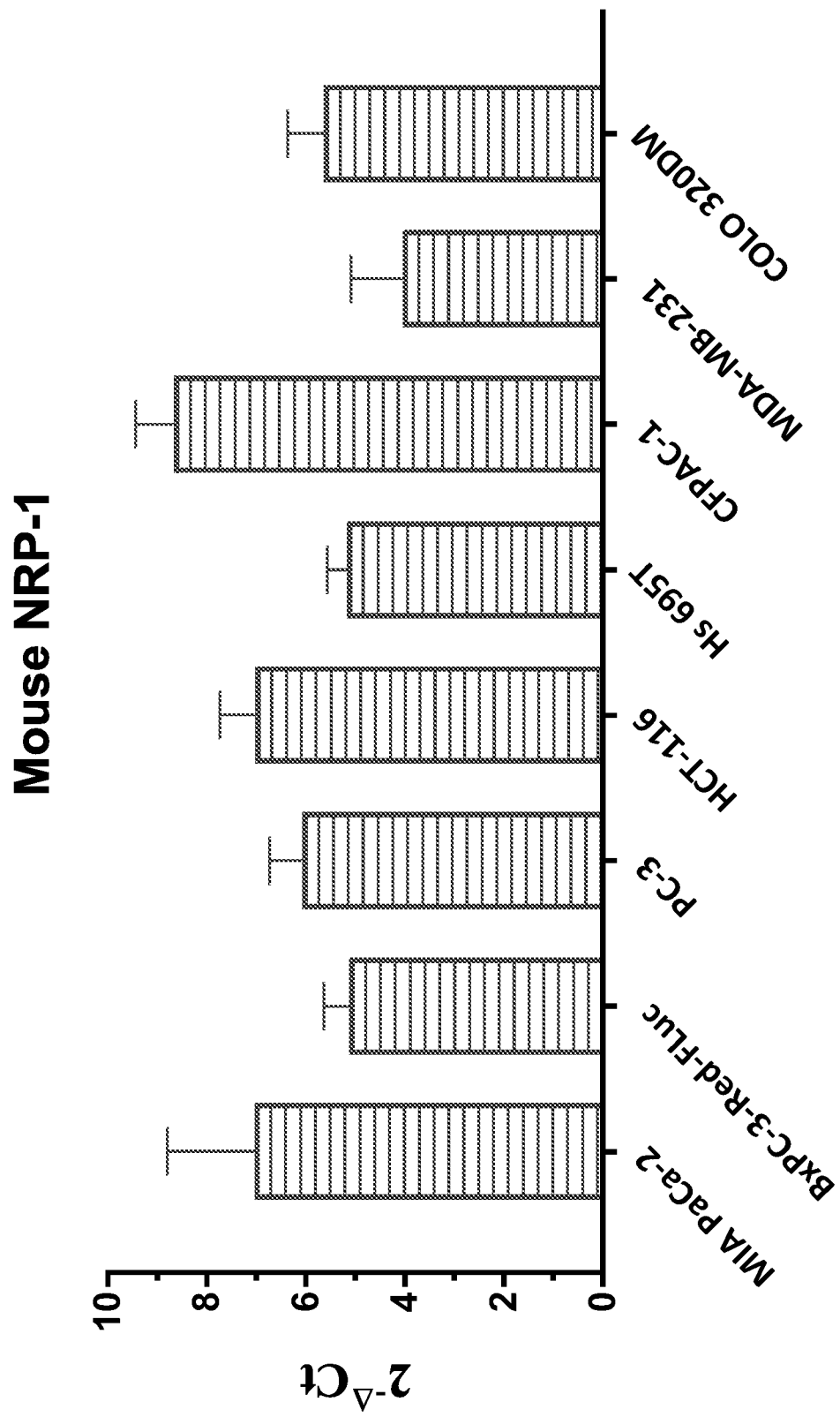
FIG. 33 is a chart showing mouse NRP1 expression in tumor lysates.

Human NRP1 expression levels in select cell lines from the CCLE database are represented in FIG. 31. The cell lines were chosen for their wide range of NRP1 expression. PC-3 has one of the highest NRP1 expression levels in the CCLE, while 6 of the 13 cell lines have low or no NRP1 expression. NRP1 mRNA expression levels were measured in tumors harvested from xenograft models used to assess CTX-cryptophycin antitumor activity. Comparable to CCLE cell line data, a wide range of human NRP1 expression was observed in tumor lysates (FIG. 32). These data reflect the NRP1 levels on the tumor cells. Expression levels closely correlate with CCLE data with one exception: in Hs 695T tumors very low NRP1 was detected, but reasonably high expression of NRP1 was reported for this cell line in the CCLE. Levels of mouse NRP1 were much more uniform with comparable levels observed across all xenografts (FIG. 33). NRP1 detected with mouse-specific probes likely represents the NRP1 expressed on mouse endothelial cells of the tumor vasculature, which is broadly consistent across all xenografts assessed. Human and mouse NRP1 mRNA levels were not assessed for SK-N-MC, TC-71, LOX IMVI, HT-1080 and U-87 MG tumors.

As can be seen, human cell lines and tumor xenografts established using these cells have a wide range of NRP1 levels, as detected by mRNA expression. Differential NRP1 expression reflects the human NRP1 expression on tumor cells whereas mouse NRP1 on endothelial cells in vasculature was expressed at similar levels across all models. The wide NRP1 expression range in xenograft models enables testing for correlation with efficacy. High NRP1 expressing models include PC-3 prostate cancer, CFPAC-1 pancreatic cancer, MDA-MB-231 breast cancer, LOX IMVI melanoma, HT-1080 fibrosarcoma and U-87 MG glioblastoma. Low or no NRP1 expression was observed in MIA PaCa-2 and BxPC3-Red-Fluc pancreatic cancers, HCT-116 and COLO 320DM colon cancers, Hs 695T melanoma, and SK-N-MC and TC-71 Ewing's sarcoma models.

Example 22: NRP1 Protein Expression in Xenograft Models

The present Example describes work assessing NRP1 protein levels in xenograft models. Tumors were harvested from xenografts (3-5 animals from each study) and immediately flash frozen in liquid nitrogen and stored at −80° until lysis. Frozen tumor tissue was cryofractured using the Covaris Cryoprep System (Covaris, Inc.). Once pulverized, samples were lysed in Super B protein extraction buffer (Covaris) or cell lysis buffer (Cell Signaling Technology, Cat #9803: Super B protein extraction buffer, Covaris Cat #520112, cell lysis buffer) on ice, in the presence of protease inhibitors. Lysates were centrifuged at 14,000 rpm for 10 min at 4° C. Supernatants from 3-5 tumors per study were pooled and aliquots snap frozen; lysate protein concentration was assessed using the BCA assay (Pierce; Thermo Fisher Scientific, Cat #23225). Lysates were heated in reducing and denaturing sample buffer for 3 min at 100° C.: 50 μg protein was loaded and resolved by electrophoresis on 8% Tris-Glycine Novex gels (Invitrogen; Thermo Fisher Scientific, Cat #EC6015BOX). Recombinant Human NRP1, Phe22-Lys644 (R&D Systems Cat #3870-N1: Phe22-Lys644, no oligomerization, transmembrane or cytoplasmic domains) and cell lysate from HUVECs (Human Umbilical Vein Endothelial Cells, pooled donor; Lonza, Cat #C2519A); endothelial cells with high NRP1 expression were included on gels as a positive control. Protein was transferred to nitrocellulose using the iBlot™ (Invitrogen) apparatus. Following blocking with Odyssey PBS blocking buffer (LI-COR) the membrane was probed with rabbit monoclonal anti-NRP1 antibodies at 1:500 or 1:1000 dilution (D62C6, Cat #3725, Cell Signaling Technology followed by anti-tubulin antibody (Abcam, [YL1/2] Abcam ab6160). Antibodies utilized in the present experiment included Abcam Rabbit mAb (EPR3113, Cat #ab81321, produced using a synthetic peptide immunogen corresponding to human NRP1 amino acid 900 through NRP1 (intracellular) C-terminus, thus directed against cytoplasmic region of NRP). The Abcam anti-NRP1 antibody reacts with human and mouse NRP1, and does not recognize recombinant NRP1 lacking oligomerization, transmembrane and cytoplasmic domains. Antibodies utilized in the present experiment also included Cell Signaling Technology (CST) rabbit mAb (D62C6, Cat #3725, produced by immunizing animals with a GST-fusion protein corresponding to residues of mouse NRP1). The CST anti-NRP1 antibody binds to NRP1 extracellular domain and therefore recognizes recombinant NRP1. The CST anti-NRP1 antibody reacts with human and mouse NRP1.

Figure 34:
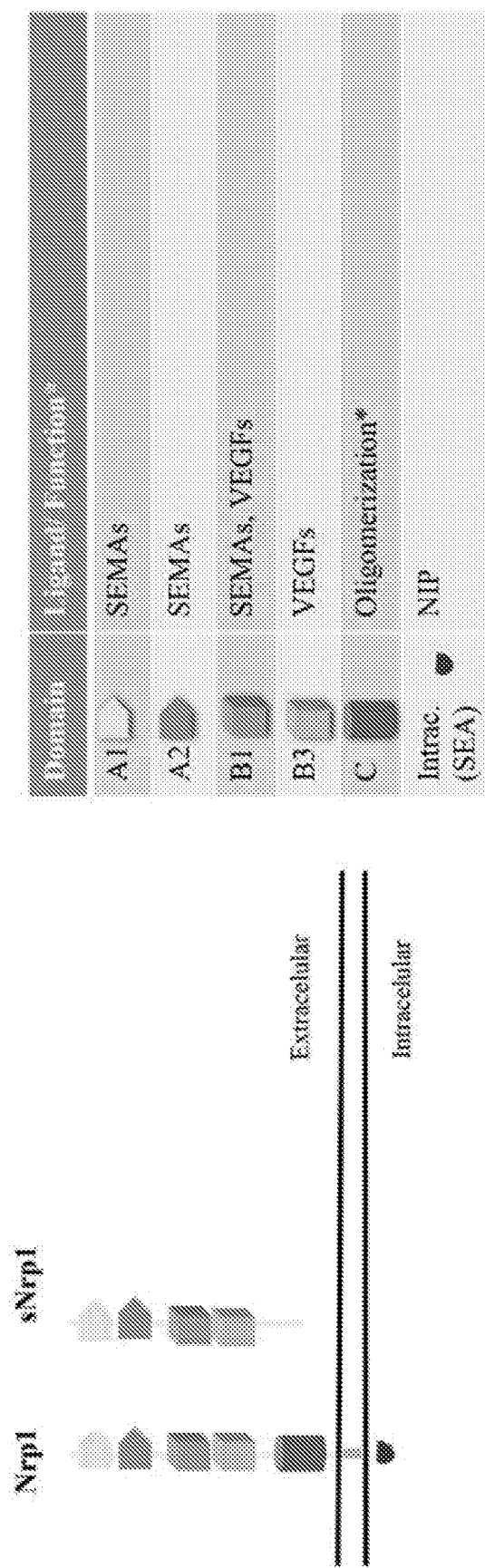
FIG. 34 is schematic showing a full length NRP1 and a soluble NRP1.

Immune complexes were visualized with appropriate IRDye 680RD and 800CW-conjugated secondary antibodies (LI-COR Biosciences) using an Odyssey Infrared Imaging System (LI-COR Biosciences). Full length NRP1 is ~120 kDa, while extracellular domain (soluble NRP1) has a molecular weight of ~70-80 kDa (human recombinant NRP1) (FIG. 34). Tubulin is resolved at ~50 kDa.

Figure 35:
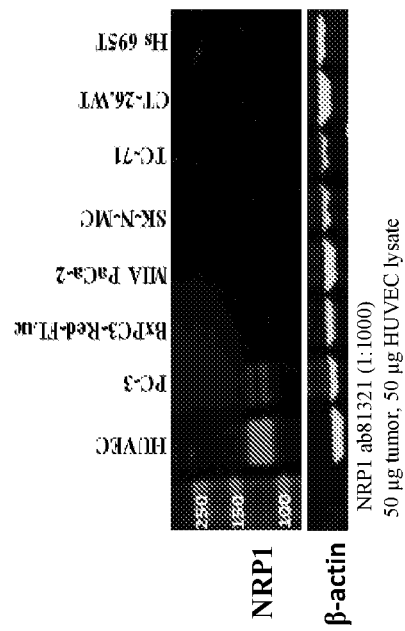
FIG. 35 is a western blot showing detection of NRP1 in cell or tumor lysates.
Figure 36:
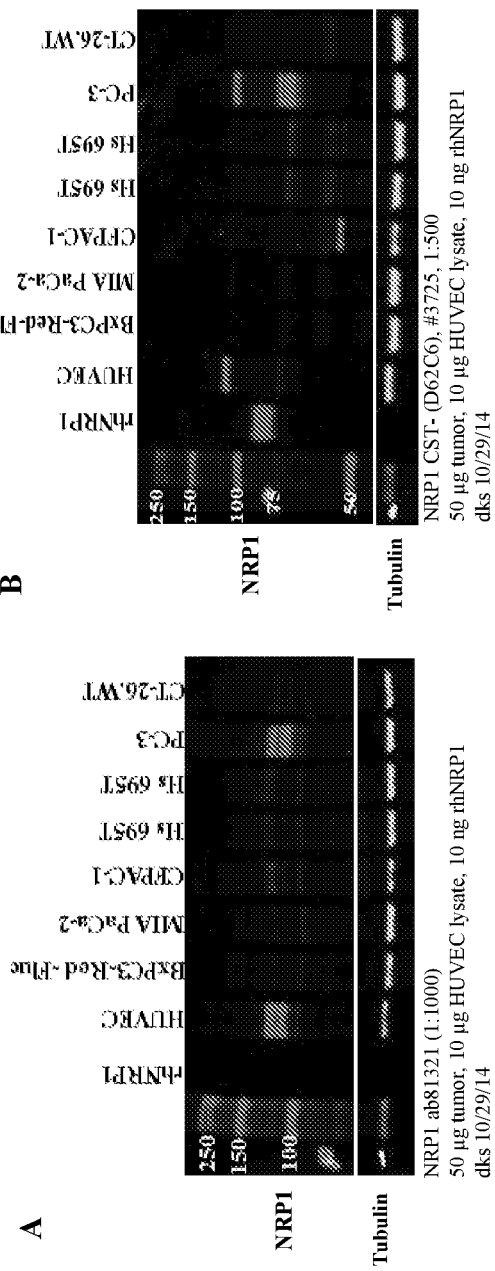
FIG. 36 is a pair of western blots showing detection of NRP1 in cell or tumor lysates with Abcam or CST antibody, respectively.
Figure 37:
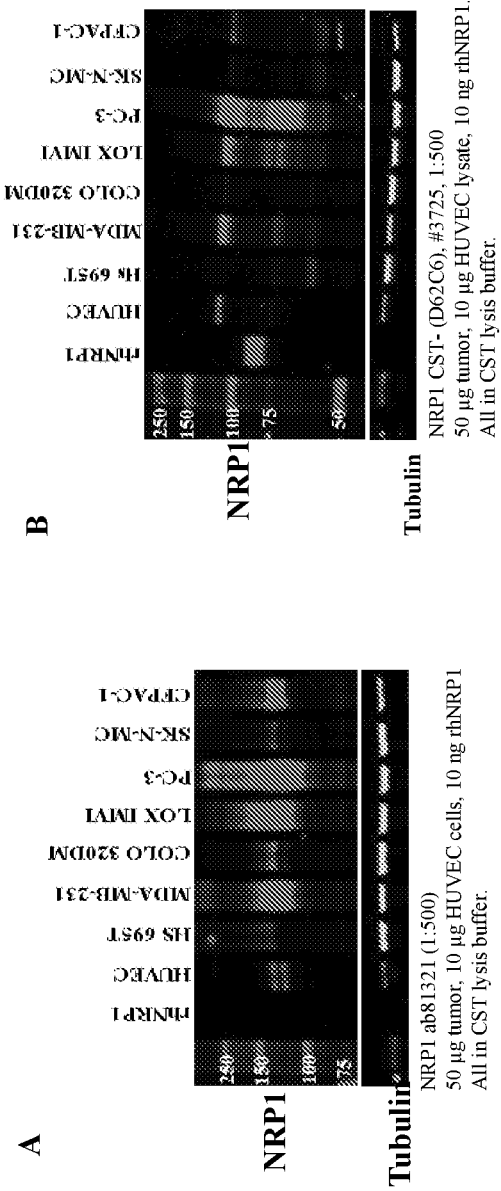
FIG. 37 is a pair of western blots showing detection of NRP1 in cell or tumor lysates with Abcam or CST antibody, respectively.
Figure 38:
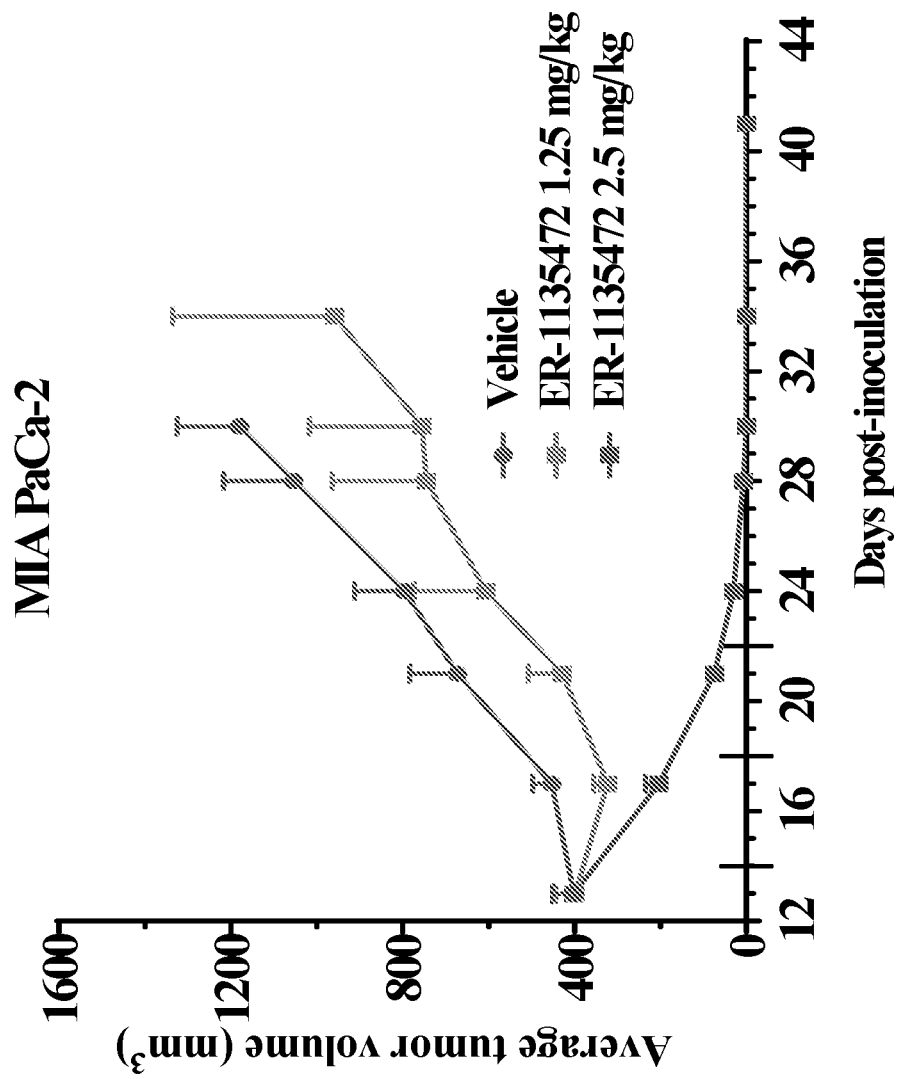
FIG. 38 is a graph showing average tumor volume over days post inoculation for treatment with various doses of CTX-Cryptophycin in a MIA PaCa-2 xenograft model.
Figure 39:
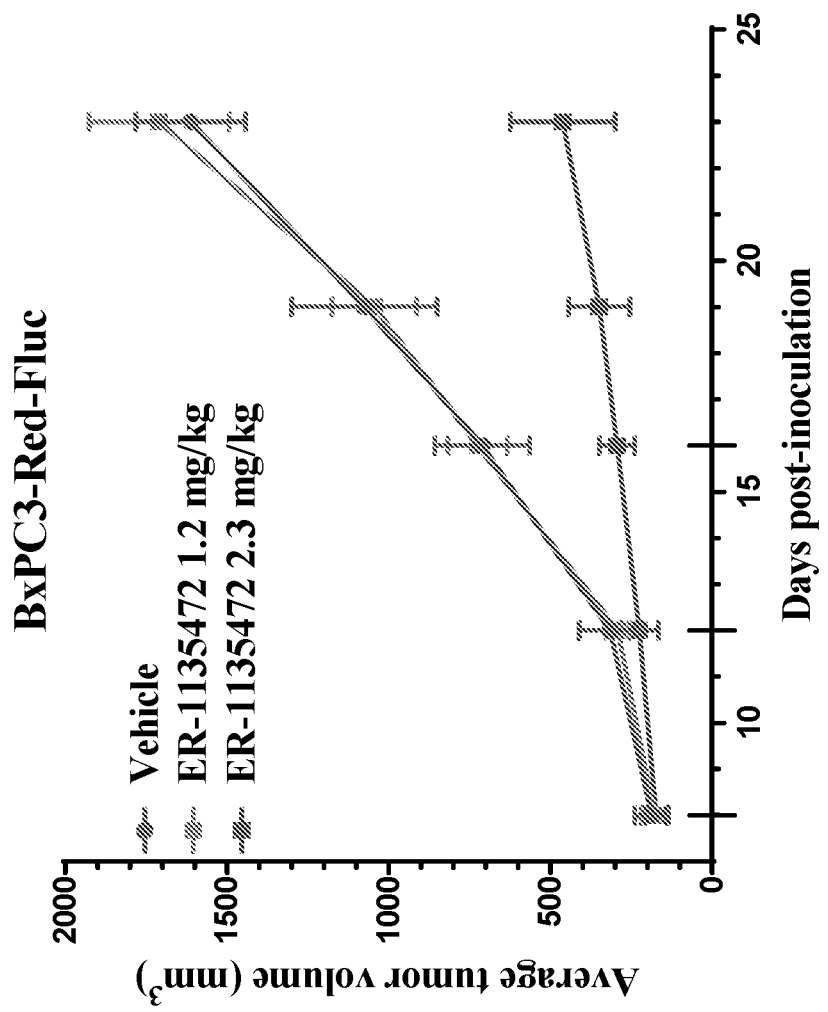
FIG. 39 is a graph showing average tumor volume over days post inoculation for treatments including CTX-Cryptophycinin a BxPC3-Red-FLuc xenograft model.
Figure 40:
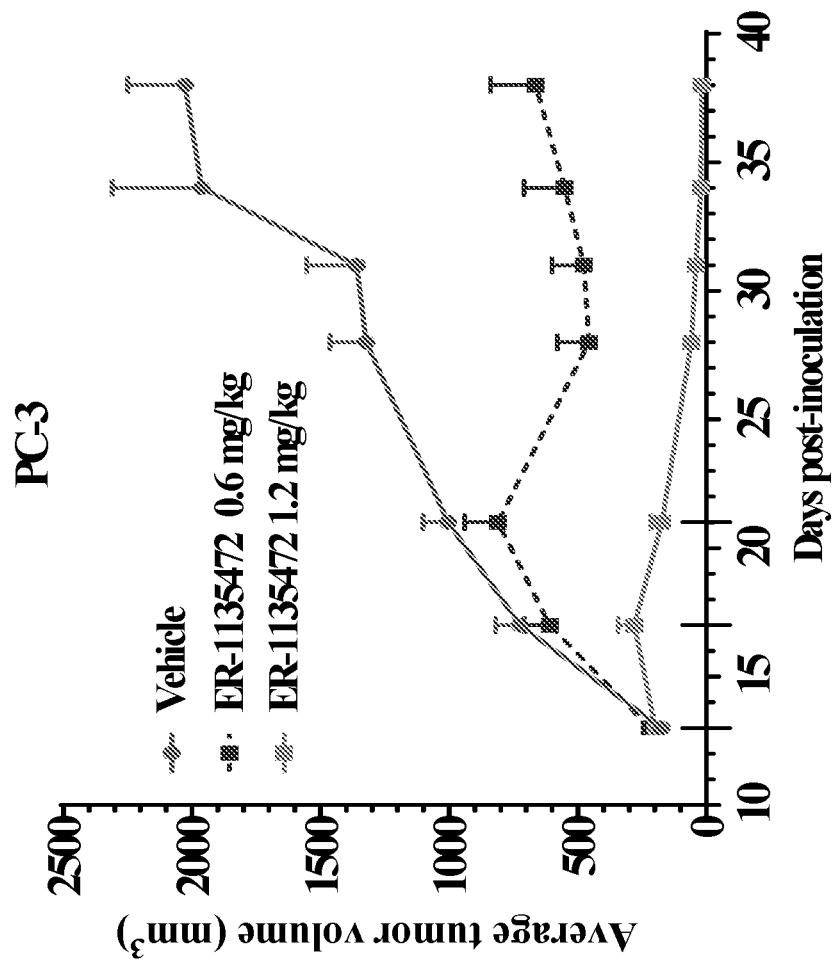
FIG. 40 is a graph showing average tumor volume over days post inoculation for treatments including CTX-Cryptophycinin a PC-3 xenograft model.
Figure 41:
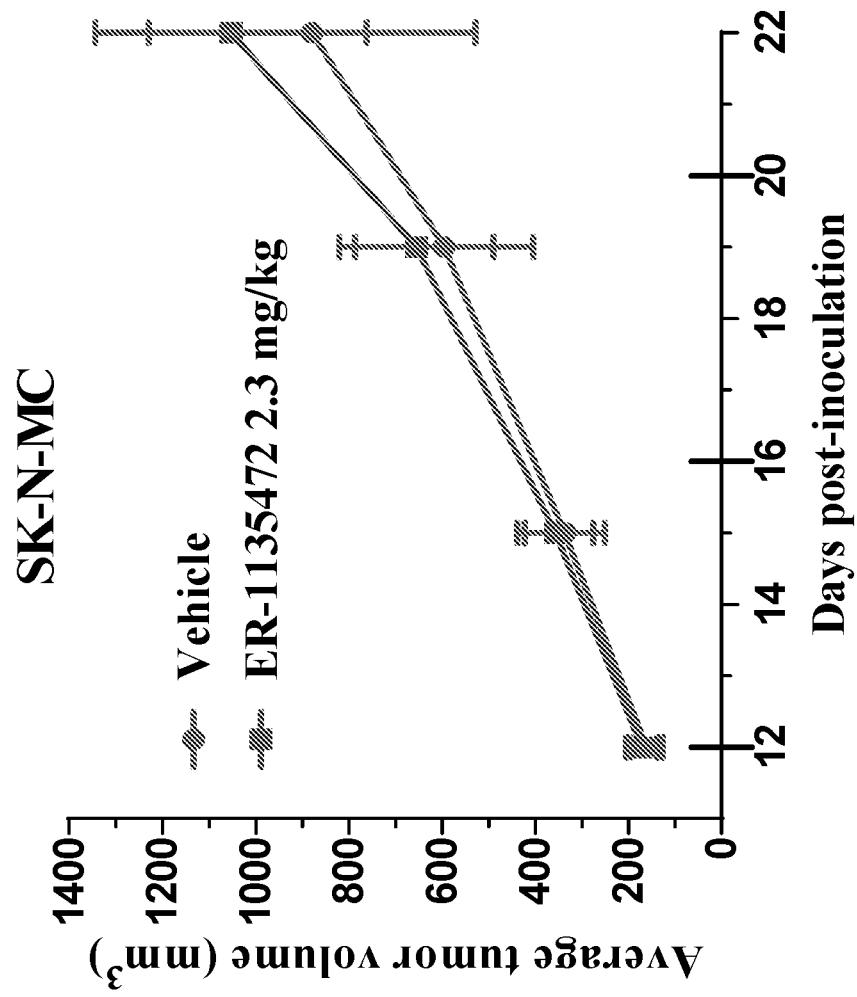
FIG. 41 is a graph showing average tumor volume over days post inoculation for treatments including CTX-Cryptophycinin a SK-N-MC xenograft model.
Figure 42:
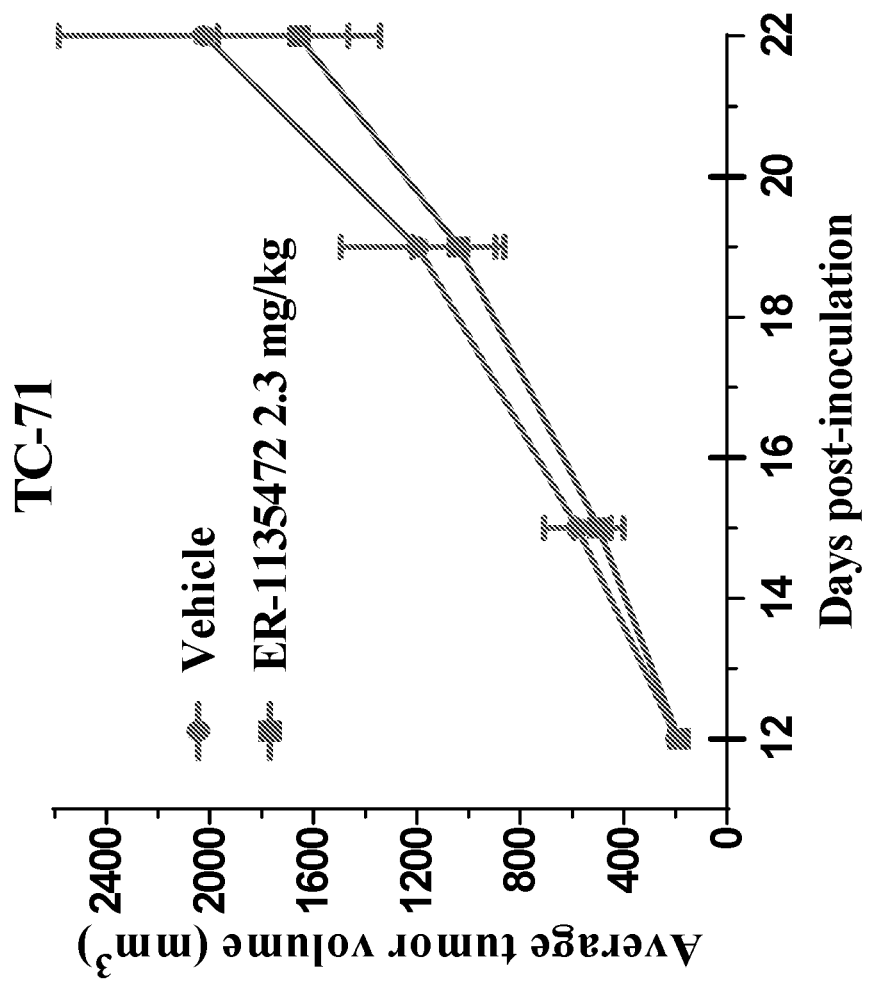
FIG. 42 is a graph showing average tumor volume over days post inoculation for treatments including CTX-Cryptophycinin a TC-71 xenograft model.
Figure 43:
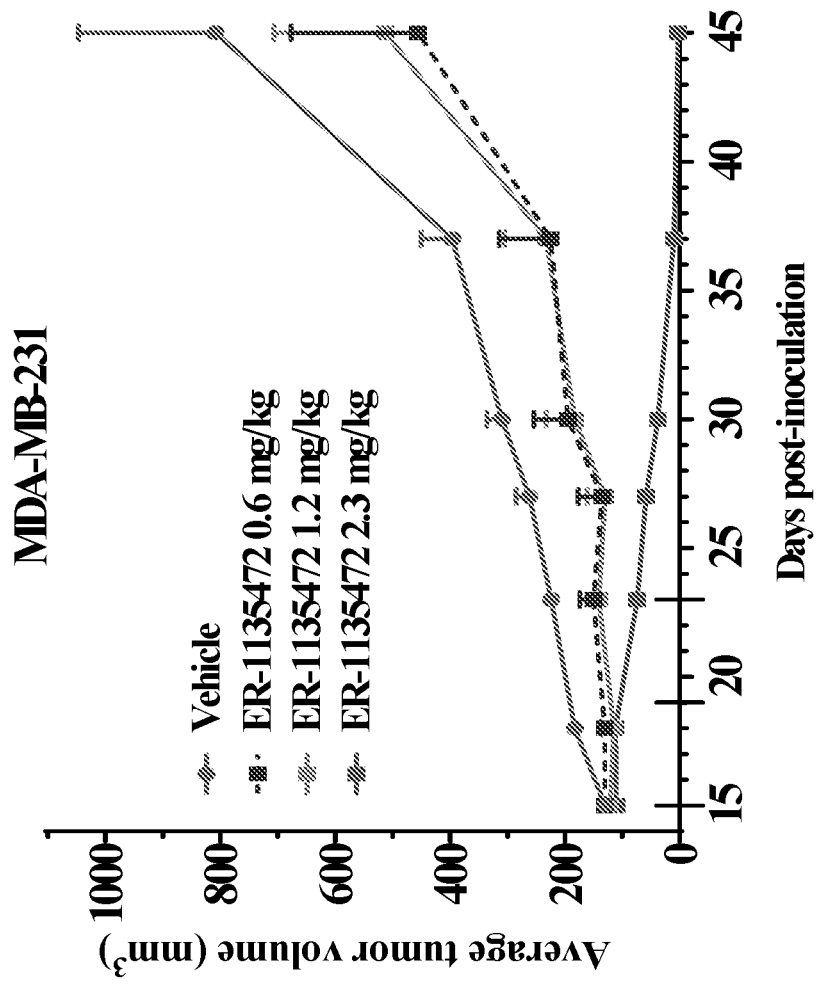
FIG. 43 is a graph showing average tumor volume over days post inoculation for treatments including CTX-Cryptophycinin a MDA-MB-231 xenograft model.
Figure 44:
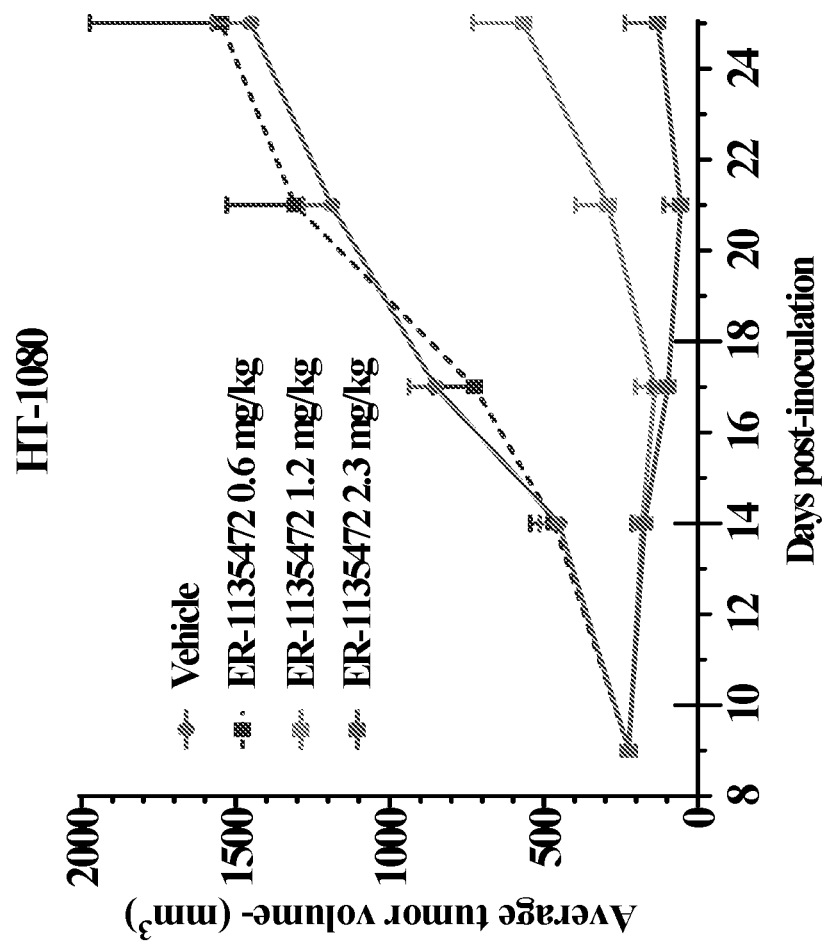
FIG. 44 is a graph showing average tumor volume over days post inoculation for treatments including CTX-Cryptophycinin a HT-1080 xenograft model.
Figure 45:
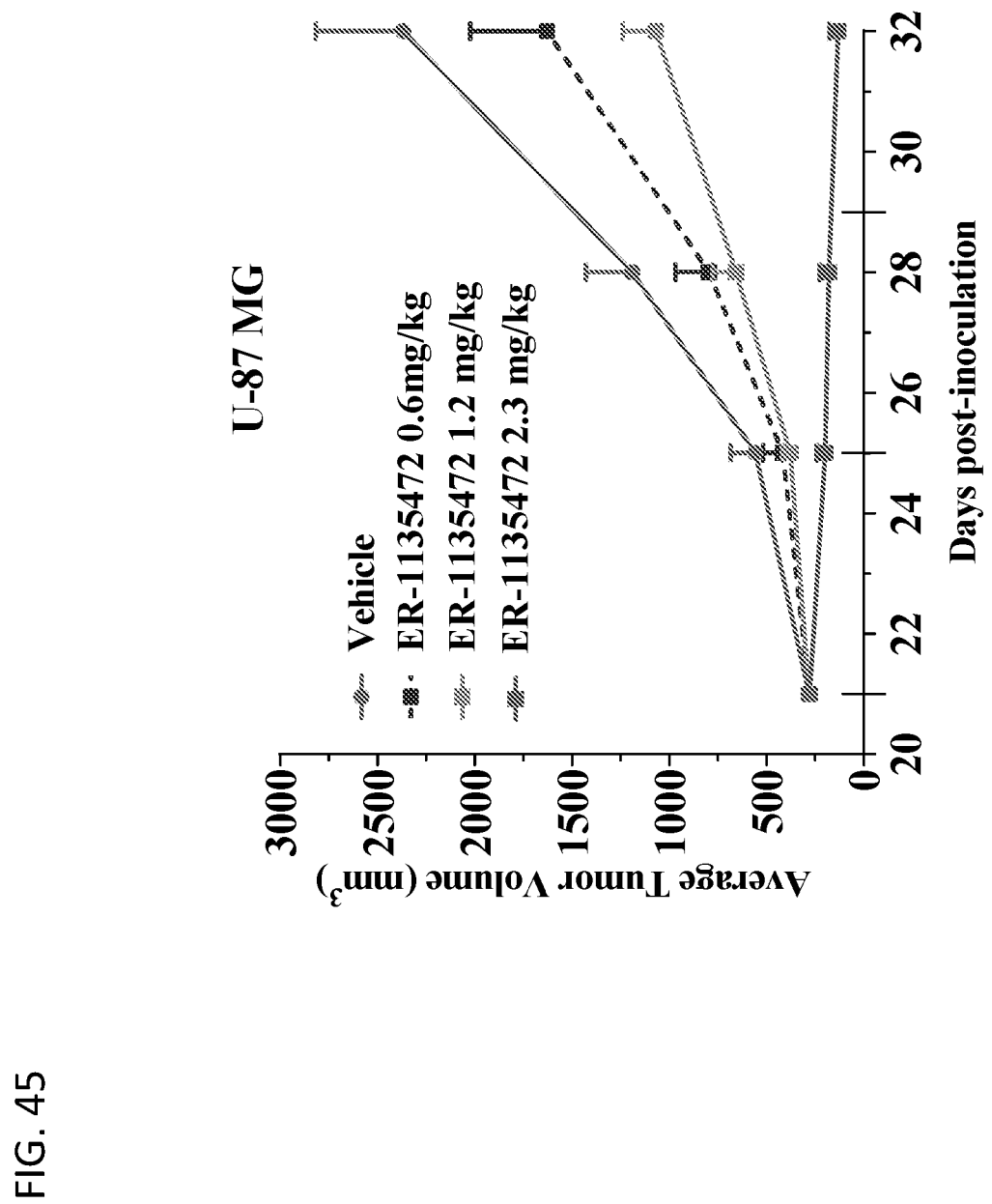
FIG. 45 is a graph showing average tumor volume over days post inoculation for treatments including CTX-Cryptophycinin a U-87 MG xenograft model.
Figure 46:
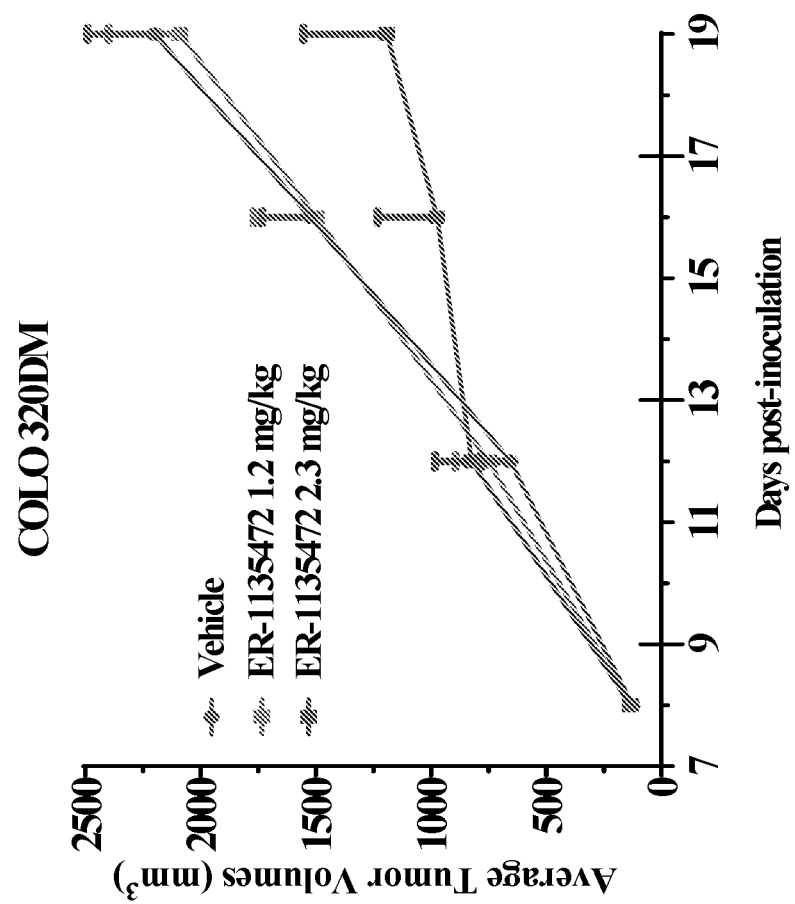
FIG. 46 is a graph showing average tumor volume over days post inoculation for treatments including CTX-Cryptophycinin a COLO 320DM xenograft model.
Figure 47:
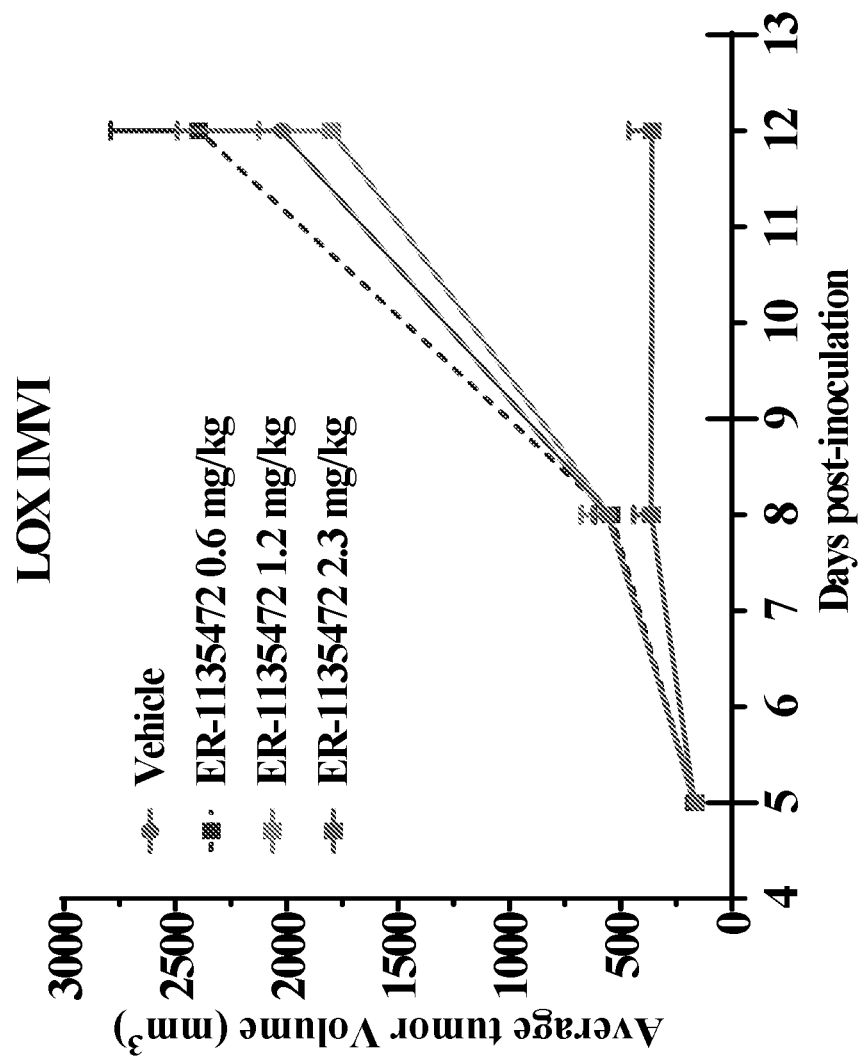
FIG. 47 is a graph showing average tumor volume over days post inoculation for treatments including CTX-Cryptophycinin a LOX IMVI xenograft model.
Figure 48:
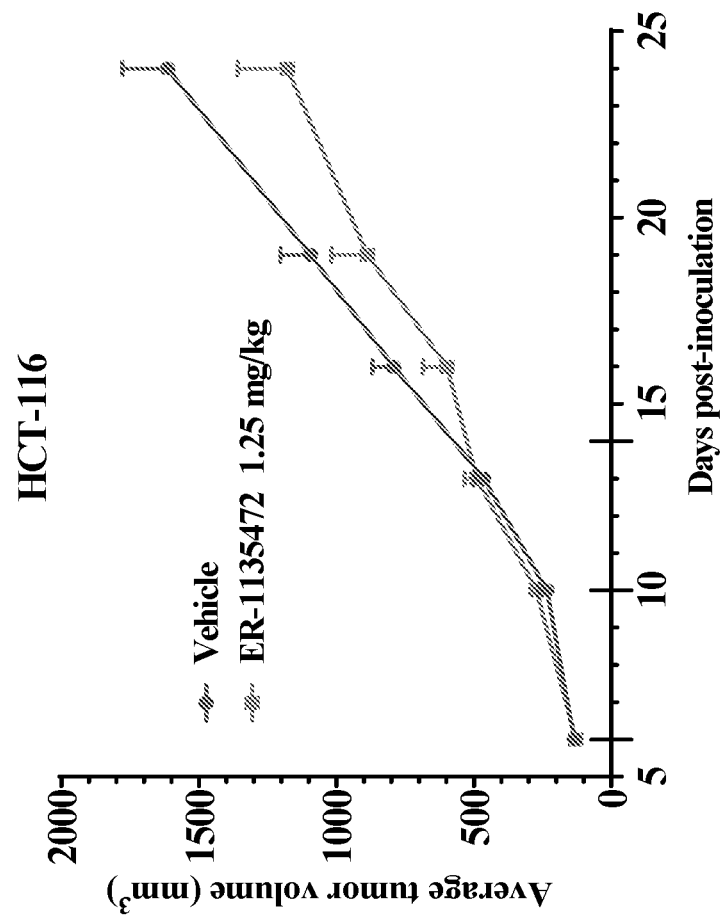
FIG. 48 is a graph showing average tumor volume over days post inoculation for treatments including CTX-Cryptophycinin a HCT 116 xenograft model.
Figure 49:
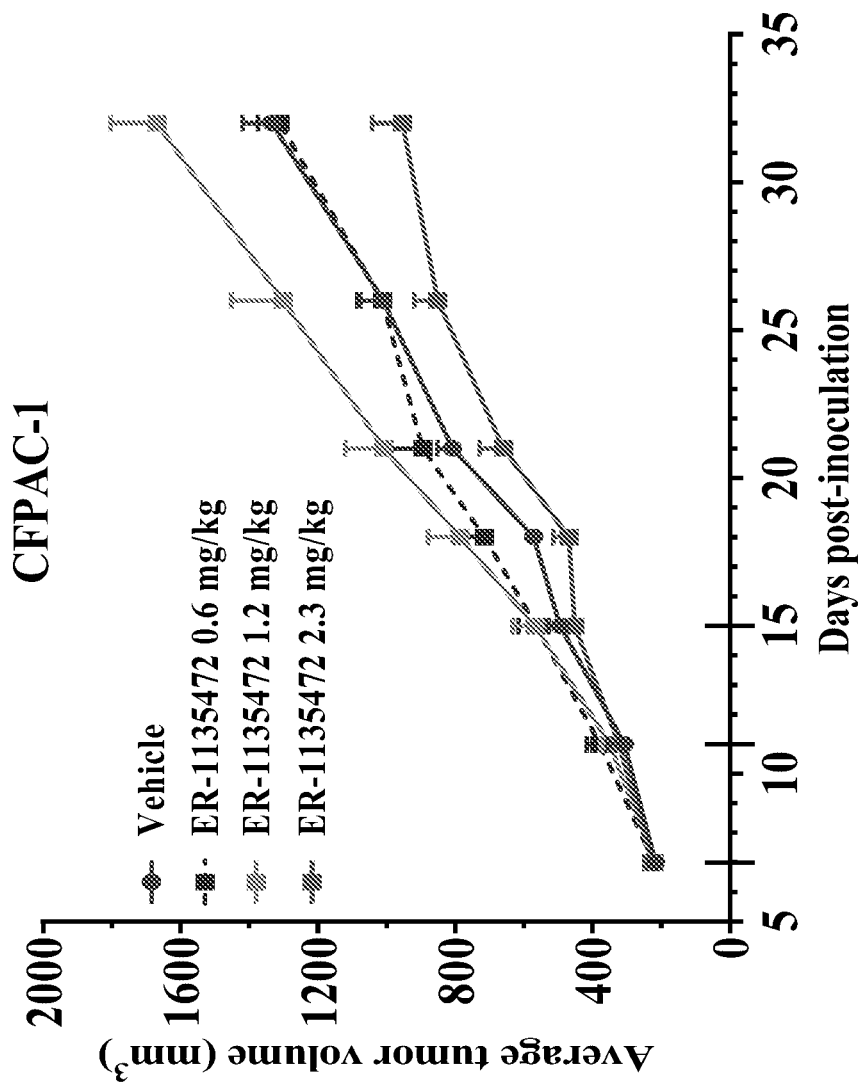
FIG. 49 is a graph showing average tumor volume over days post inoculation for treatments including CTX-Cryptophycinin a CFPAC-1 xenograft model.

As can be seen, NRP1 was detected in HUVEC cell lysates and specific tumor lysates with both Abcam and CST anti-NRP1 antibodies. A doublet or smear of ~120 to 140 kDa was detected with the Abcam antibody, representing full length NRP1. With the CST antibody, bands were detected at ~120 kDa as well as ~70 to 80 kDa, the smaller of which correspond to the soluble form of NRP1. Recombinant NRP1 was observed only with the CST Ab, at ~80 kDa, i.e. soluble/extracellular domain NRP1. Representative western blots are shown in FIGS. 35-37 (Panels A and B of FIGS. 36 and 37 represent detection with Abcam and CST antibody, respectively).

Of all lysates examined, highest NRP1 levels were detected in PC-3 tumors. Low or no NRP1 was found in lysates from BxPC3-Red-FLuc, MIA PaCa-2, SK-N-MC, TC-71, Hs 695T, and COLO 320 DM tumors. High NRP1 expression was also observed in MDA-MB-231, LOX IMVI and CFPAC-1 tumor lysates (FIGS. 35, 36 panel A, 36 panel B, 37 panel A, and 37 panel B). A summary of NRP1 expression in Table 19. Of note, full length NRP1 at ~120 kDa was observed in CFPAC-1 tumor lysates as well as a prominent band of ~55 kDa (CST Ab) whose identity is unknown.

TABLE 19

| Xenograft Model | NRP1 expression |
| --- | --- |
| MIA PaCa-2 | − |
| BxPC3-Red-FLuc | − |
| PC-3 | ++++ |
| SK-N-MC | − |
| TC-71 | − |
| MDA-MB-231 | ++ |
| HT-1080 | nd |
| U-87 MG | nd |
| COLO 320DM | +/− |
| Hs 695T | +/− |
| CFPAC-1 | + * |
| LOX IMVI | ++ |
| HCT 116 | nd | nd = not assessed
* In addition to full length, band ~55 kDa with CST Ab

Taken together, protein expression data showed a wide range of NRP1 expression in tumor lysates from tumor models. NRP1 expression on tumor cells closely correlates with mRNA expression data. Both antibodies in the study react with human and mouse NRP1.

Western data suggest that human NRP1 is present at significantly greater levels on tumor cells (when expressed) than mouse NRP1 in vasculature.

Mouse NRP1 mRNA was expressed at similar levels across all models (while ~50% of tumors have low or no expression of mouse NRP1 by western blot).

The wide expression range of human NRP1 protein in xenograft models allows examination of correlation between NRP1 expression and tumor treatment efficacy. Tumors with high NRP1 protein levels include PC-3, MDA-MB-231, LOX IMVI and CFPAC-1; high NRP1 protein corresponds to the mRNA data. Low or no NRP1 expression was observed in MIA PaCa-2, BxPC3-Red-FLuc, HCT-116, COLO 320DM, SK-N-MC and TC-71 tumor lysates, also corresponding to expression data. Detection of NRP1 protein was low in Hs 695T lysates, consistent with tumor mRNA data, but not with cell line or CCLE data.

Example 23: Antitumor Effects of CTX-Cryptophycin Conjugate in Xenograft Models

The present Example describes work assessing CTX-cryptophycin conjugate sensitivity of xenograft tumors with a range of NRP1 expression.

Xenograft cell types, the source of each cell type, and tissue type are described in Table 20. Materials, methods, drugs and establishment of model were similar to those described in Examples 1-3. Cells were cultured in the recommended medium. For inoculation, cancer cells were injected subcutaneously into mice near the right axillary area using a 27-gauge needle in a volume of 0.1 mL. Cell numbers for inoculation, mice strain, and additional details to establish xenograft models are described in Table 21. Tumors were measured at least twice weekly using calipers and mice were randomized into treatment groups based on tumor size. Treatments were initiated when the average tumor size was approximately 200 mm$^3$; see Table 21 for first day of dosing in each model (days post-cell inoculation). In each model the experiment consisted of a vehicle-treated group and drug-treated groups (n=5 or 6, Table 21). All drugs were administered in the following vehicle: 10% EtOH, 5% Tween80 and 85% saline. Animals were treated intravenously on a Q4Dx3 schedule. Tumor size and body weight were measured twice a week.

TABLE 20

| Xenograft Model | Cancer type | Cell Line Source | | | |
| --- | --- | --- | --- | --- | --- |
| | | ATCC® | Perkin Elmer | NCI | DSMZ |
| MIA PaCa-2 | Pancreatic | CRL-1420™ | | | |
| BxPC3-Red-FLuc | Pancreatic | | BW125058 | | |
| PC-3 | Prostate | CRL-1435™ | | | |
| SK-N-MC | Ewing's Sarcoma | HTB-10™ | | | |
| TC-71 | Ewing's Sarcoma | | | | ACC 516 |
| MDA-MB-231 | Breast | HTB-26™ | | | |
| HT-1080 | Fibrosarcoma | CCL-121™ | | | |
| U-87 MG | Glioblastoma | HTB-14™ | | | |
| COLO 320DM | Colon | CCL220™ | | | |
| Hs 695T | Melanoma | HTB-137™ | | | |
| CFPAC-1 | Pancreatic | CRL-1918™ | | | |
| LOX IMVI | Melanoma | | | NCI | |
| HCT 116 | Colon | CCL247™ | | | |

TABLE 21

| Xenograft Model | Cell # for inoculation | Mice Strain*, Source | Study ID | Study ID | n |
| --- | --- | --- | --- | --- | --- |
| MIA PaCa-2 | 5 × 10$^6$ | Nu/Nu, CRL | JW1142 | Day 14 | 6 |
| BxPC3-Red-FLuc | 5 × 10$^6$ | Nu/Nu, CRL | JE0002 | Day 8 | 6 |
| PC-3 | 2 × 10$^6$ | Nu/Nu, CRL | JW1147 | Day 13 | 5 |
| SK-N-MC | 5 × 10$^6$ | Nu/Nu, CRL | JE0010 | Day 19 | 5 |
| TC-71 | 5 × 10$^6$ | Nu/Nu, CRL | JE0011 | Day 12 | 5 |
| MDA-MB-231 | 5 × 10$^6$ + Matrigel | Nu/Nu, CRL | JW1158 | Day 15 | 5 |

TABLE 21-continued

| Xenograft Model | Cell # for inoculation | Mice Strain*, Source | Study ID | Study ID | n |
|---|---|---|---|---|---|
| HT-1080 | 1 × 10⁶ + Matrigel | C.B.17-SCID, CRL | JW1175 | Day 10 | 6 |
| U-87 MG | 5 × 10⁶ + Matrigel | NCr, CRL | KCH270 | Day 20 | 6 |
| COLO 320DM | 5 × 10⁶ | NOD SCID, CRL | JW1146 | Day 9 | 6 |
| COLO 320DM | 5 × 10⁶ | NOD SCID, CRL | JE0009 | Day 7 | 6 |
| Hs 695T | 5 × 10⁶ | Nu/Nu, CRL | JW1152 | Day 27 | 5 |
| Hs 695T | 5 × 10⁶ | NOD SCID, CRL | JW1154 | Day 13 | 5 |
| CFPAC-1 | 10 × 10⁶ | Nu/Nu, CRL | JW1157 | Day 7 | 6 |
| LOX IMVI | 2 × 10⁶ | Nu/Nu, CRL | JW1160 | Day 5 | 5 |
| HCT 116 | 2 × 10⁶ | Nu/Nu, CRL | JW1135 | Day 6 | 5 |

*all mice female, age 6 to 8 weeks on receipt
CRL, Charles River Laboratories

A summary of antitumor activity of CTX-Cryptophycin in various xenograft models is provided in Table 22, with individual data shown in FIGS. 38-50. Conjugate activity was assessed at various doses including 0.6, 1.2, and 2.3 mg/kg, equivalent to ¼ MTD, ½ MTD and MTD (with the exception of dosing in MIA PaCa-2 model, with respect to which doses of 2.5 and 1.25 mg/kg were administered). Data represent the mean tumor volume±SEM.

In many cases administration of CTX-Cryptophycin at or close to the 2.3 mg/kg MTD dose resulted in robust antitumor activity (tumor stasis or regression) with tumor-free mice observed for long durations in several models (MIA PaCa-2, PC-3, MDA-MB-231, U-87 MG and Hs 695T). In contrast, minimal antitumor effects were observed at MTD in SK-N-MC, TC-71, COLO 320DM and CFPAC-1 xenografts (dose not tested in HCT-116 xenografts). In MIA PaCa-2, BxPC3-Red-Fluc and LOX IMVI models CTX-Cryptophycin at MTD was active but no antitumor activity was observed at ½ MTD dose (0.6 mg/kg). In contrast, for PC-3, MDA-MB-231, HT-1080, U-87 MG and Hs 6095T models statistically significant antitumor activity was observed for the ½ MTD dose. Additionally, the ¼ MTD dose was active in PC-3, Hs 695T, MDA-MB-231 and U-87 MG demonstrating a wide therapeutic window for the conjugate in these models.

TABLE 22

| | Antitumor Activity, Conjugate Dose | | |
|---|---|---|---|
| Xenograft Model | MTD | ½ MTD | ¼ MTD |
| MIA PaCa-2 | ++++ | – | nd |
| BxPC3-Red-FLuc | ++ | – | nd |
| PC-3 | ++++ | ++++ | ++ |
| SK-N-MC | – | nd | nd |
| TC-71 | – | nd | nd |
| MDA-MB-231 | ++++ | + | + |
| HT-1080 | +++ | ++ | – |
| U-87 MG | +++ | ++ | +/– |
| COLO 320DM | +/– | – | nd |
| Hs 695T | ++++ | +++ | + |
| CFPAC-1 | + | – | – |
| LOX IMVI | ++ | – | – |
| HCT 116 | nd | – | nd | nd = not assessed

Example 24: Correlation of CTX-Cryptophycin Conjugate Antitumor Activity and NRP1 Expression in Various Xenograft Models Correlation of NRP1 expression and therapeutic activity for 13 xenografts is presented in Table 23. A positive correlation with NRP1 expression and therapeutic activity was observed for 10 of the 13 models (77%). Results demonstrate that when tumor NRP1 expression was moderate to high, a wide therapeutic window was observed for conjugate antitumor activity. Low NRP1 expression was associated with a narrow therapeutic window or a lack of conjugate antitumor activity. Without wishing to be bound by any particular scientific theory, these data lend weight to the possibility that CTX-mediated cryptophycin uptake in tumors and subsequent efficacy is impacted by the level of NRP1 expression on tumor cells.

Correlation of NRP1 expression and CTX-Cryptophycin antitumor activity was observed for 10 of the 13 models, but not for Hs 695T, CFPAC-1 and LOX IMVI. The 3 models which deviated from this trend (Hs 695T, CFPAC-1, and LOX IMVI) are discussed in detail below.

TABLE 23

| Xenograft Model | Antitumor Activity | | | Human NRP1 Expression | Correlation Efficacy to NRP1 |
|---|---|---|---|---|---|
| | MTD | ½ MTD | ¼ MTD | | |
| MIA PaCa-2 | ++++ | – | | nd | low | yes |
| BxPC3-Red-FLuc | ++ | – | | nd | low | yes |
| PC-3 | ++++ | ++++ | ++ | high | yes |
| SK-N-MC | – | nd | nd | low | yes |
| TC-71 | – | nd | nd | low | yes |
| MDA-MB-231 | ++++ | + | + | high | yes |
| HT-1080 | +++ | ++ | – | high | yes |
| U-87 MG | +++ | ++ | +/– | high | yes |
| COLO 320DM | +/– | – | nd | low | yes |
| Hs 695T | ++++ | +++ | + | low[a] | no[a] |
| CFPAC-1 | + | – | – | high[b] | no[b] |
| LOX IMVI | ++ | – | – | high | no[c] |
| HCT 116 | nd | – | nd | low | yes |

Hs 695T

Figure 50:
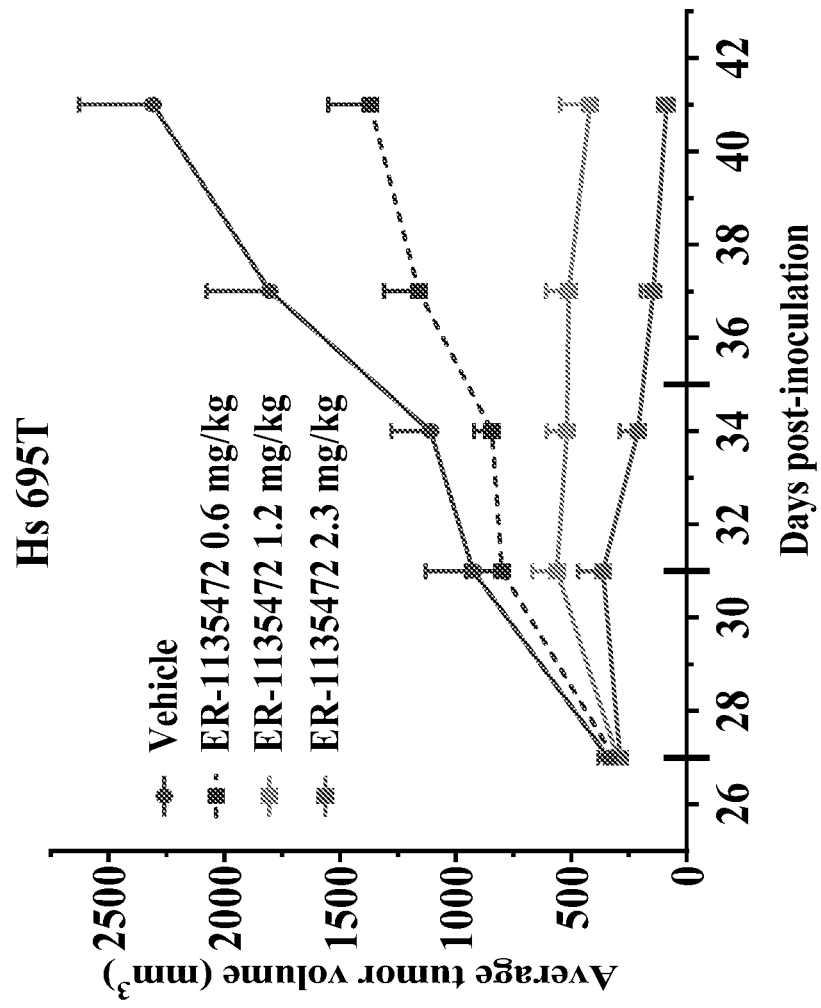
FIG. 50 is a graph showing average tumor volume over days post inoculation for treatments including CTX-Cryptophycinin a Hs 695T xenograft model.
Figure 51:
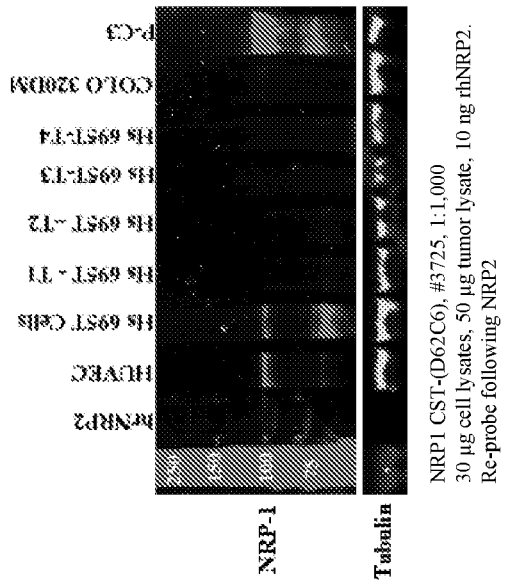
FIG. 51 is a western blot showing NRP1 expression in cells and tumor lysates, including Hs 695T cells and tumor lysates.

A wide therapeutic window was observed for CTX-Cryptophycin in the Hs 695T model but only a low level of NRP1 expression was detected in tumor lysates. This Hs 695T model was chosen based on high NRP1 expression in the CCLE cell line database. The cell line culture for inoculation into models also expressed NRP1 at high levels but expression appeared to less in tumors as compared to cell line culture (FIGS. 50 and 51). Tumors were harvested at various times post-implantation (Day 21 to 35) and ranged in size from 240 to ~1,000 mm³ so it seemed that NRP1 expression was lost early in the tumors growth in mice and was likely not expressed at time points when CTX-Cryptophycin was administered. Based on this data, NRP1 appears to have no clear role in the wide window of therapeutic activity observed in Hs 695T. The reason for the unexpected antitumor activity is unknown.

CFPAC-1

Figure 52:
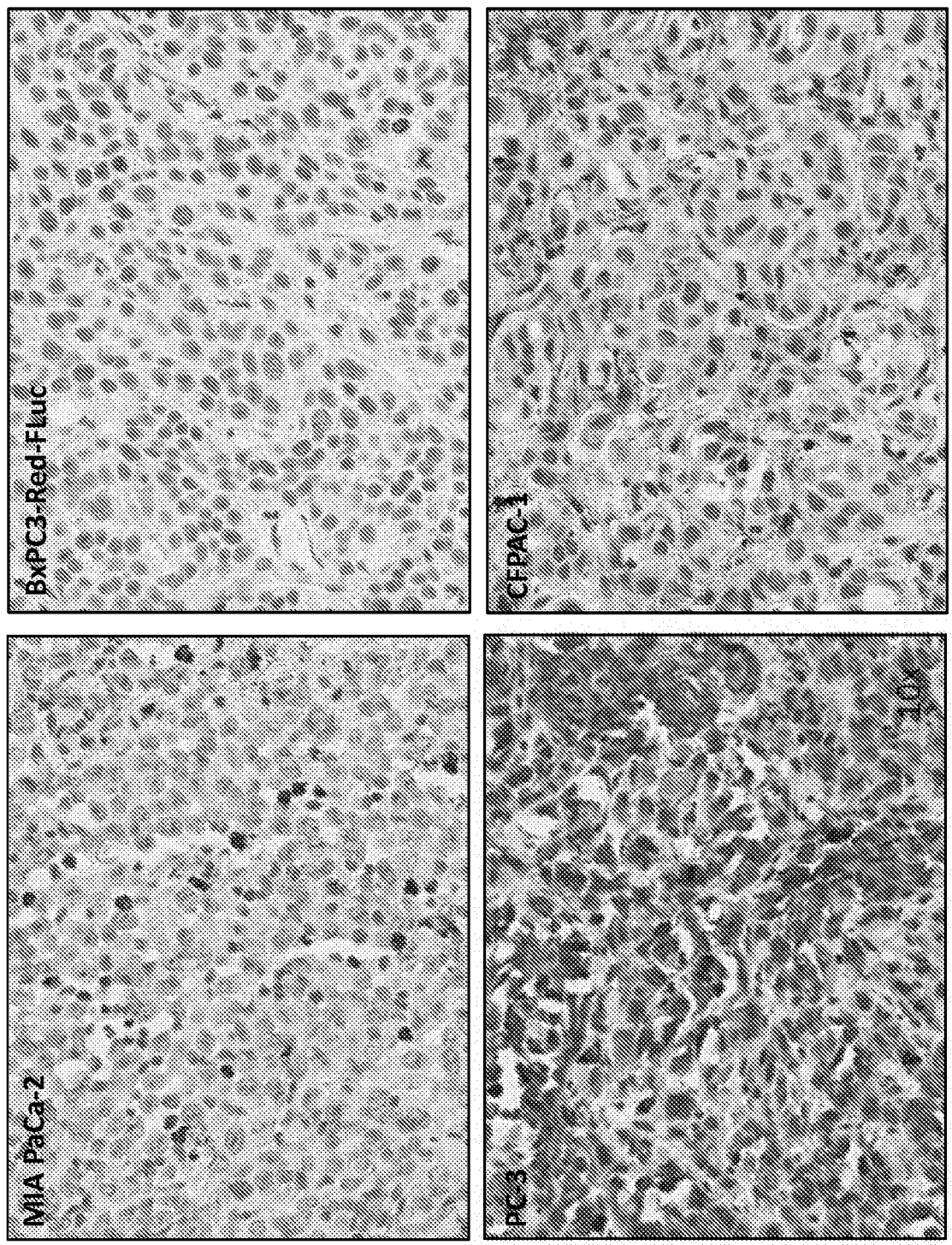
FIG. 52 is a series of images of NRP1 staining by IHC of, paraffin-embedded tumor sections from selected tumors.

Despite reasonable levels of NRP1 expression in CFPAC-1 tumor lysates, poor antitumor activity was observed for CTX-Cryptophycin. Only modest activity was observed at MTD, and none at lower doses (see FIG. 49). As noted herein, CST anti-NRP1 Ab identified a smaller strongly reacting band of ~50 kDa, observed in addition to full length NRP1 band (see FIG. 37). The identity of this smaller protein and its relationship to NRP1 are unknown. To further examine NRP1 expression in tumors, IHC was performed on paraffin-embedded tumor sections from a subset of tumors, including CFPAC-1 (FIG. 52). In contrast to PC-3 tumors where NRP1 was detected throughout the tumor section, strong NRP1 staining was only observed in stromal cells in the CFPAC-1 sections. This stromal cell NRP1 likely makes up the majority of the NRP1 protein observed in tumor lysates by western blot. The lack of tumor cell NRP1 expression may account for the poor antitumor activity observed for conjugate. Conjugate uptake would likely be increased into the stromal cells through NRP1-CTX interaction; however cryptophycin activity is cell proliferation dependent and if not actively cycling will have minimal effect.

NRP1 protein levels detected by western blot from CFPAC-1 tumor lysate appear to be of stromal origin. CFPAC-1 cells have very low NRP1 expression which may explain the poor therapeutic index of CTX-Cryptophycin.

LOX IMVI

Despite reasonable levels of NRP1 expression in LOX IMVI tumor lysates, poor antitumor activity was observed for CTX-Cryptophycin. Some activity was observed for CTX-Cryptophycin at MTD but none at lower doses. This model was highly aggressive and vehicle-treated tumors had already reached ~2000 mm$^3$ in size prior to administration of the 3' CTX-Cryptophycin dose. In the absence of another explanation it may be that this model was too aggressive and fast growing for the conjugate to act, despite significant NRP1 levels. Additional studies with lower cell inoculation into and earlier drug administration will be necessary to confirm.

Example 25: CTX Fragments in Tumor Lysates of CTX-Treated Mice

Without wishing to be bound by any particular scientific theory, CTX or fragments thereof may bind NRP-1 on the surface of tumor cells. In the present study, PC-3 xenograft tumors were cryofractured and tumor lysates were analyzed by HPLC and MS to identify CTX-related peptides.

Results from animals treated with CTX were compared to results from animals treated with vehicle control in order to identify CTX peptide assignments unique to CTX treatment. CTX Normally has an amidated C-terminus but can be deamidated in vivo.

Figure 53:
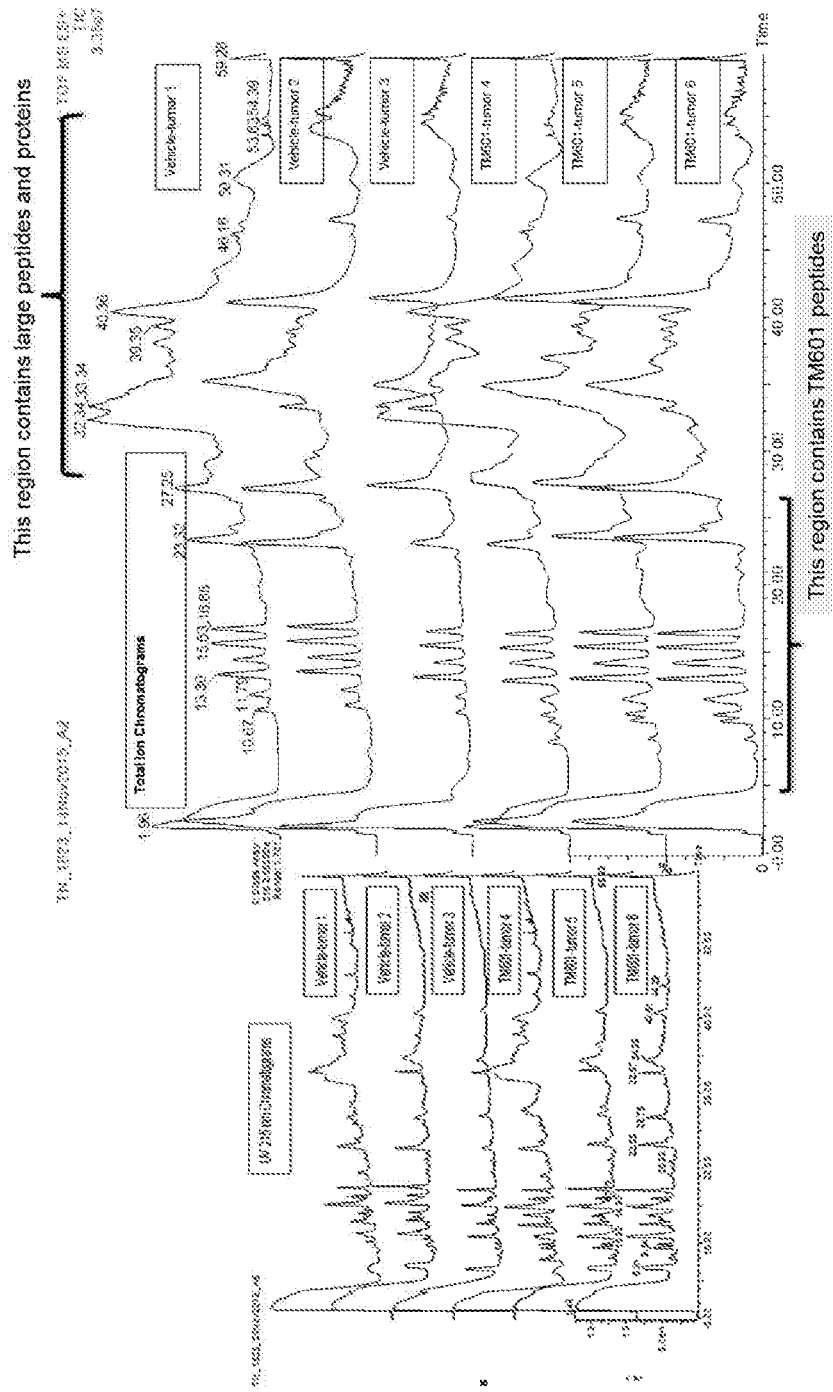
FIG. 53 is a pair of graphs showing total ion (TIC) and UV (215 nm) chromatograms of tumor lysate preparations.

Total ion (TIC) and UV (215 nm) chromatograms of the tumor lysate preparations are shown and compared in FIG. 53. The UV and TIC chromatograms were slightly different between the Vehicle-treated mouse tumors and the tumors from CTX-treated mice.

CTX-related peptides unique to the tumor lysates from CTX-treated mice are shown in FIGS. 54-56. FIG. 54-56 each respectively show the 20 most MS-intense CTX-related peptides unique to a tumor lysate of a tumor from a CTX-treated mouse, as compared to a tumor from control-treated mouse. Each of FIGS. 54-56 represents results from a different particular tumor, which tumors can be referred to as tumors 4, 5, and 6, respectively.

Figure 57:
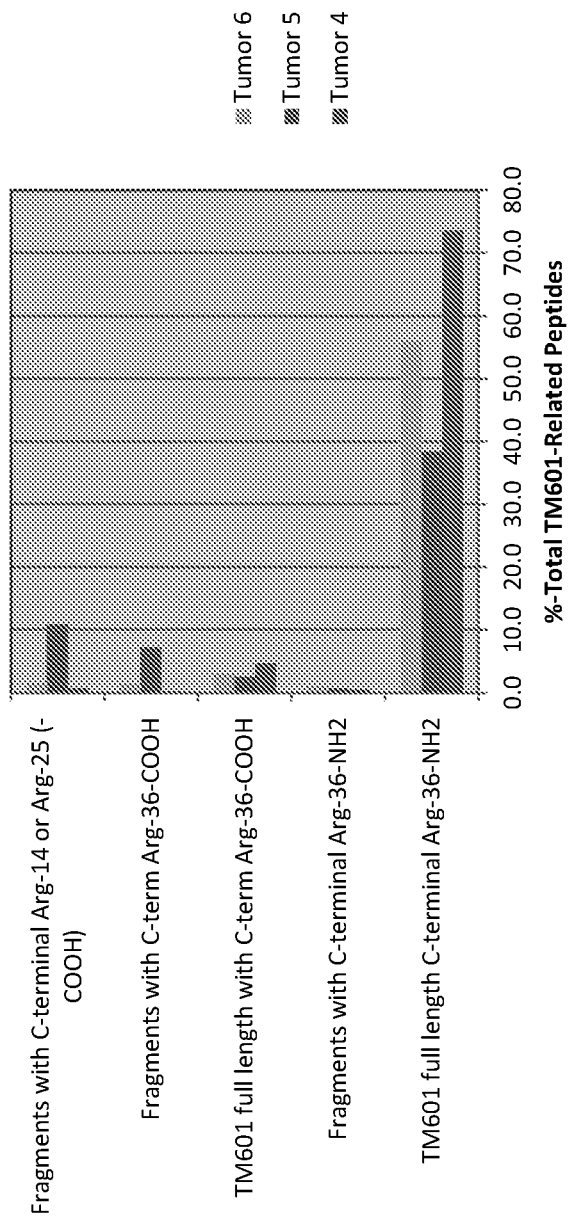
FIG. 57 is a graph characterizing CTX-related peptides unique to tumor lysates from CTX-treated mice.

FIG. 57 further graphs the relative intensities of CTX-related peptides unique to CTX-treated mice, grouped into particular classes. The majority of CTX-peptides observed were full-length with C-terminal amidation (35% to 74% of Total). Approximately 5% of peptides were full length containing C-terminal carboxyls (deamidated). Fragments with C-terminal Arg-14 and Arg-25 were also observed.

Example 26: Further Examples of R-End Peptides that Bind NRP1 and were Found in Tumors Following CTX Administration In the present Example, 150 mg/kg CTX or vehicle was administered to mice and tumors were harvested 1 hour thereafter. A selection of CTX-related peptides with C-terminal Arg residues identified in tumor lysates of CTX-treated mice include, in order of abundance, those shown in Table 24.

TABLE 24

| SEQ ID NO: | Peptide |
|---|---|
| 1 | MCMPCFTTDHQMARKCDDCCGGKGRGKCYGPQCLCR (residues 1-36; C-terminal-amidated) |
| 199 | CMPCFTTDHQMARKCDDCCGGKGRGKCYGPQCLCR (residues 2-36 C-terminal-deamidated) |
| 1 | MCMPCFTTDHQMARKCDDCCGGKGRGKCYGPQCLCR (residues 1-36 C-terminal-deamidated) |
| 199 | CMPCFTTDHQMARKCDDCCGGKGRGKCYGPQCLCR (residues 2-36 C-terminal-amidated) |
| 200 | CMPCFTTDHQMARKCDDCCGGKGR (residues 2-25) |
| 201 | PCFTTDHQMARKCDDCCGGKGRGKCYGPQCLCR (residues 4-36 C-terminal-deamidated) |
| 201 | PCFTTDHQMARKCDDCCGGKGRGKCYGPQCLCR (4-36 C-terminal-amidated) |

Figure 59:
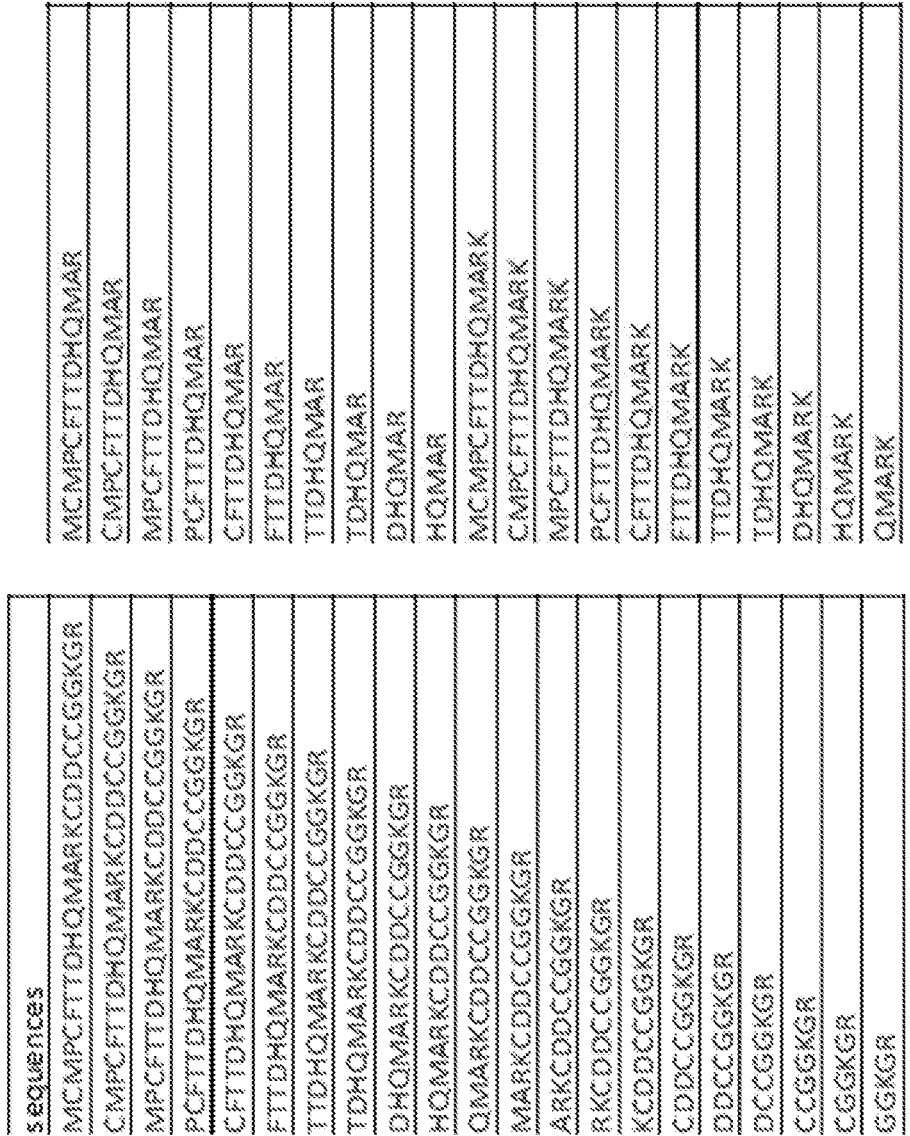
FIG. 59 is a table showing selected CTX peptides identified in tumor lysates of CTX-treated mice.

Additional CTX-related peptides are show in FIGS. 58 and 59.

Example 27: Antiangiogenic Activity of Chlorotoxin and Role of NRP1

Various findings indicate that CTX has anti-angiogenic properties. For instance, CTX inhibited angiogenesis stimulated by many factors and potentiates anti-angiogenic effects of bevacizumab. CTX bound proliferating vascular endothelial cells, decreased human umbilical vein endothelial cell (HUVEC) invasion, and reducing secretion of IMMIP-2. CTX inhibited angiogenesis stimulated by 8 proangiogeni c factors using the chick chorioallantoi c membrane assay (CAM). When CTX was co-administered with bevacizumab, the combination was significantly more potent than a ten-fold increase in bevacizumnab dose. CTX did not alter tumor or vascular endothelial cell growth in vitro, but CTX treatment of tumors grown on the CAM decreased tumor growth and intra-tumoral hemoglobin levels. Intravenously injected CTX was shown to significantly decrease new blood vessel growth in mice in a matrigel plug assay.

NRP1 is a multi-functional receptor that contributes to the development of both the nervous and vascular systems. During embryogenesis, NRP1 binds the semaphorin 3A ligand in the CNS, acting with plexin co-receptors to regulate axon guidance. Concurrently, NRP1 binds members of the VEGF ligand family, including VEGF and P1GF, to mediate angiogenesis. Loss of NRP1 function results in vascular remodeling and branching defects. NRP1 is highly expressed on endothelial cells and plays a key role in modulating EC motility. Blocking NRP1 function can enhance the ability of anti-VEGF to block tumor growth, thus identifying NRP1 as a target for antitumor therapy in combination with anti-VEGF. NRP1 may also be expressed on tumor cells and has also been reported as a direct tumor target, possibly regulating tumor cell survival and proliferation. MNRP1685A (Genentech, Inc.) a first-in-class, recombinant human IgG1 monoclonal antibody that targets NRP1 was tested in clinical trials as an anti-angiogenic agent (Weekes et al. 2014. A phase I study of the human monocloncal anti-NRP1 antibody MNRP1685A in patients with advanced solid tumors. *Invest New Drugs* 32:653-660).

The selective binding properties of CTX to glioma cells and other tumors of neuroectodermal origin, but not to normal non-transformed cells and tissues, was initially described by Lyons et al (Lyons S A, O'Neal J and Sontheimer H. 2002. Chlorotoxin, a scorpion derived peptide, specifically binds to gliomas and tumors of neuroectodermal origin. *Glia* 39: 162-173). Further, more than 15 normal human tissues were shown to be negative for chlorotoxin binding, except for vascular endothelial cells.

Certain evidence indicates activity of CTX in Ocular neovascularization. When administered by intraocular injection, intravenous injections, or periocular injections, CTX significantly suppressed the development of choroidal NV at rupture sites in Bruch's membrane. Treatment of established choroidal NV with CTX caused apoptosis of endothelial cells and regression of the NV. CTX suppressed ischemia-induced and VEGF-induced retinal NV and reduced excess vascular permeability induced by VEGF.

CTX, through suppression and regression of ocular NV and reduction of vascular leakage may provide a new treatment for blinding diseases such as neovascular age-related macular degeneration and diabetic retinopathy. Without wishing to be bound by any particular scientific theory, anti-angiogenic properties of CTX may be explained by binding of CTX to NRP1, which could block VEGF binding and thereby suppress NRP1 function in angiogenesis. It is conceivable that high dose of CTX (C-term R—COOH) competes with VEGF for NRP1 signaling and thus reduces angiogenic signaling. Such CTX activity may require a C-terminal R—COOH (which can be generated from R—NH$_2$ in vivo).

ADDITIONAL REFERENCES

1. Jacoby D B et al. 2010. Potent pleiotropic anti-angiogenic effects of CTX, a synthetic chlorotoxin peptide. *Anticancer Res* 30:37-46.
2. Lima e Silva R, et al. 2010. Agents that bind annexin A2 suppress ocular neovascularization. *J Cell Physiol* 225 (3):855-64
3. Pan Q, et al. 2007. Blocking Neuropilin-1 Function Has an Additive Effect with Anti-VEGF to Inhibit Tumor Growth. *Cancer Cell* 11, 53-67

Example 28: Chlorotoxin, Damage/Wound Healing, and Role of NRP1

CTX uptake or increased antitumor activity of a CTX-conjugate was observed following damage, by either physical means or by chemotherapy. These data suggest an up-regulation of the NRP1 target in response to damage, which in turn leads to more uptake or activity. NRP1 is a key player in angiogenesis and thus, likely to be very important in response to any damage. Without wishing to be bound by any particular scientific theory, increase in NRP1 is likely associated with damage and/or present in damage models, and would in turn lead to increased uptake of CTX.

OTHER EMBODIMENTS

While we have described a number of embodiments of this invention, it is apparent that our basic disclosure and examples can be altered to provide other embodiments that utilize the compounds and methods of this invention. Therefore, it will be appreciated that the scope of this invention is to be defined by the appended claims rather than by the specific embodiments that have been represented by way of example.

All references cited herein are hereby incorporated by reference.

---

What is claimed is:

1. A method for treating a tumor that expresses Neuropilin 1 comprising steps of:
   determining expression of Neuropilin 1 in a tumor sample from a subject, and
   administering to the subject having the tumor determined to express Neuropilin 1 a chlorotoxin agent,
   wherein the chlorotoxin agent comprises a chlorotoxin polypeptide having an amino acid sequence at least 85% identical to SEQ ID NO: 1,
   wherein the chlorotoxin polypeptide comprises a carboxylated C-terminal arginine residue, and
   wherein the chlorotoxin polypeptide is characterized as binding Neuropilin 1.

2. The method of claim 1, wherein the chlorotoxin polypeptide has not more than one lysine available as a site for conjugation.

3. The method of claim 1, wherein the chlorotoxin agent is associated with a payload.

4. The method of claim 3, wherein the payload is or comprises a therapeutic moiety.

5. The method of claim 4, wherein the therapeutic moiety is or comprises an anti-cancer agent.

6. The method of claim 5, wherein the anti-cancer agent is selected from the group consisting of:
   BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomysin, tamoxifen, flutamide, leuprolide, goserelin, aminogluthimide, anastrozole, amsacrine, asparaginase, mitoxantrone, mitotane, amifostine, ofatumumab, bevacizumab, tositumomab, alemtuzumab, cetuximab, trastuzumab, gemtuzumab ozogamicin, rituximab, panitumumab, ibritumomab tiuxetan, and a combination thereof.

7. The method of claim 5, wherein the anti-cancer agent is a member of the group consisting of anti-cancer agents that exhibits poor selectivity/specificity for cancer cells; anti-cancer agents that exhibit poor uptake by cancer cells; anti-cancer agents that exhibit poor retention in cancer cells; anti-cancer agents that exhibit poor water solubility; anti-cancer agents that undergo premature inactivation in cancer cells; anti-cancer agents that undergo impaired activation in cancer cells; anti-cancer agents that undergo extensive cellular degradation; and anti-cancer agents associated with drug resistance.

8. The method of claim 3, wherein the payload is or comprises a targeting moiety.

9. The method of claim 8, wherein the targeting moiety comprises an antibody or antibody fragment.

10. The method of claim 3, wherein the payload is or comprises an imaging moiety or a detectable moiety.

11. The method of claim 10, wherein the imaging moiety or a detectable moiety is selected from the group consisting of a fluorescent label, a radioactive or paramagnetic isotope or ion, a ligand, a chemiluminescent agent, a bioluminescent agent, a photosensitizer, a quantum dot, a microparticle, a metal nanoparticle, a nanocluster, an enzyme, a colorimetric label, a hapten, a molecular beacon, an aptamer beacon, biotin, and dioxigenin.

12. The method of claim 10, wherein the imaging moiety or a detectable moiety is or comprises a fluorescent label selected from the group consisting of a fluorescein dye, a rhodamine dye, a coumarin dye, a cyanine dye, a styryl dye, an oxonol dye, a carbocyanine, merocyanine, phycoerythrin, erythrosin, eosin, an infrared dye, and a boron dipyrromethene dye.

13. The method of claim 10, the method comprising at least one of (a) imaging a tissue imagable by chlorotoxin; (b) diagnosing a cancer detectable by chlorotoxin; (c) detecting a tissue detectable by chlorotoxin and removing the cancerous tissue detected by the chlorotoxin agent; and (d) detecting a tumor during surgery.

14. The method of claim 1, wherein the method further comprises administering a chemotherapeutic agent.

15. The method of claim 1, wherein the chlorotoxin polypeptide is characterized as binding Neuropilin 1 in that the chlorotoxin polypeptide binds Neuropilin 1 in an in vitro binding assay.

\* \* \* \* \*